(12) United States Patent
Zask et al.

(10) Patent No.: US 6,429,214 B1
(45) Date of Patent: Aug. 6, 2002

(54) BICYCLIC ANTAGONISTS SELECTIVE FOR THE $\alpha_v\beta_3$ INTEGRIN

(75) Inventors: Arie Zask, New York, NY (US); Diane Barbara Hauze, St. Davids; Kenneth Lewis Kees, Glenmoore, both of PA (US); Richard Dale Coghlan, Freehold, NJ (US); John Yardley, King of Prussia, PA (US)

(73) Assignee: Wyeth, Madison, NJ (US)

( * ) Notice: Subject to any disclaimer, the term of this patent is extended or adjusted under 35 U.S.C. 154(b) by 12 days.

(21) Appl. No.: 09/620,381

(22) Filed: Jul. 20, 2000

Related U.S. Application Data

(60) Provisional application No. 60/172,238, filed on Jul. 21, 1999.

(51) Int. Cl.[7] .................. A61K 31/47; C07D 215/16
(52) U.S. Cl. ........................ 514/312; 546/158
(58) Field of Search .................. 544/328, 331; 546/163, 157, 165, 158; 514/309, 312

(56) References Cited

U.S. PATENT DOCUMENTS

| | | | |
|---|---|---|---|
| 5,312,828 A | | 5/1994 | Finkelstein et al. |
| 5,371,226 A | * | 12/1994 | Mederski et al. |
| 5,473,092 A | | 12/1995 | Talley |
| 5,565,449 A | | 10/1996 | Blackburn et al. |
| 5,602,145 A | | 2/1997 | Samanen |
| 5,618,843 A | | 4/1997 | Fisher et al. |
| 5,629,321 A | | 5/1997 | Okumura et al. |
| 5,693,636 A | | 12/1997 | Bondinell et al. |
| 5,719,145 A | | 2/1998 | Yamashita et al. |
| 5,731,324 A | | 3/1998 | Fisher et al. |
| 5,760,028 A | | 6/1998 | Jadhav et al. |

FOREIGN PATENT DOCUMENTS

| | | |
|---|---|---|
| CA | 2199923 | 3/1997 |
| DE | 1423495 | 6/1974 |
| DE | 2621604 | 5/1976 |
| DE | 2621605 | 5/1976 |
| DE | 2918160 | 5/1979 |
| DE | 2918162 | 5/1979 |
| EP | 456835 A1 | 12/1990 |
| EP | 528586 A1 | 8/1992 |
| EP | 528587 A1 | 8/1992 |
| EP | 540334 A1 | 10/1992 |
| EP | 635492 A1 | 7/1994 |
| EP | 655439 A2 | 5/1995 |
| EP | 709370 A1 | 5/1996 |
| EP | 760364 A2 | 8/1996 |
| WO | 9429273 | 12/1994 |
| WO | 9532710 | 12/1995 |
| WO | 9606087 | 2/1996 |
| WO | 9618602 | 6/1996 |
| WO | 9622288 | 7/1996 |
| WO | 9626190 | 8/1996 |
| WO | 9637492 | 11/1996 |
| WO | 9701540 | 1/1997 |
| WO | 9706791 | 2/1997 |
| WO | 796855 A1 | 3/1997 |
| WO | 9708145 | 3/1997 |
| WO | 9723480 | 3/1997 |
| WO | 9733887 | 9/1997 |
| WO | 9724119 | 10/1997 |
| WO | 9724122 | 10/1997 |
| WO | 9724124 | 10/1997 |
| WO | 9736862 | 10/1997 |
| WO | 9737655 | 10/1997 |
| WO | 9815278 | 4/1998 |
| WO | 9823608 | 6/1998 |

OTHER PUBLICATIONS

Ca 114:81622, "Preparation of carbostyril derivatives as inotropic cardiotonics and their forumulations", Tanaka, Vo. 114, p. 715, 1991.*
E. Schwenk et al., J. Am. Chem. Soc., 70, 3626–3627 (1948).
N. Allinger et al., J. Org. Chem., 27, 70–76 (1962).
N. Allinger et al., J. Org. Chem., 30, 2165–2169 (1965).
M. Gibson et al., Angew. Chem. Int'l. Edit., 7, 919–930 (1968).
P. Shanmugam et al., Proc. Indian Acad. Sci., Section A., 96–101 (1972).
D. Evans et al., J. Org. Chem., 39,914 (1974).
M. Lennon et al., J.C.S. Perkins 1, 622–626 (1975).

(List continued on next page.)

*Primary Examiner*—Alan L. Rotman
*Assistant Examiner*—Binta Robinson
(74) *Attorney, Agent, or Firm*—Arnold S. Milowsky

(57) ABSTRACT

This invention provides novel bicyclic compounds of Formula (I):

Formula (I)

wherein u, v, m, Y, G, A—B, $R^1$, $R^{1a}$, $R^2$, $R^4$, $R^5$, $R^{5a}$, and $R^{5b}$ are defined in the specification which compounds exhibit activity as inhibitors of bone resorption and compounds of Formula (II)

Formula (II)

wherein u, v, m, Y, G, D, A—B, $R^1$, $R^{1a}$, $R^2$, $R^3$, $R^4$, $R^5$, $R^{5a}$, and $R^{5b}$ are defined in the specification which compounds exhibit activity as inhibitors of bone resorption.

20 Claims, No Drawings

OTHER PUBLICATIONS

Y. Kashman et al., J. Org. Chem., 43(8), 1538–1540 (1978).
N. Narashimhan et al., Synthesis, 903–906 (1979).
M. Demuynck et al., J. Org. Chem. 44(26), 4863–4866 (1979).
O. Meth–Cohn et al., Tetrahedron Letters, 33, 3111–3114 (1979).
L. Garanti, et al., et al., J. Org. Chem., 45, 4767–4769 (1980).
O. Mitsunobu, Synthesis, 1–28 (1981).
O. Meth–Cohn et al., J. Chem. Soc., Perkins I., 2509–2517 (1981).
O. Meth–Cohn et al., J. C. S. Perkins, 1520–1530 (1981).
O. Meth–Cohn et al., J.C.S. Perkins, I., 1537–1543 (1981).
S. B. Kadin et al., J. Org. Chem., 49, 4999–5000 (1984).
P. Baraldi et al., J. Chem. Soc. Perkin Trans. I., 2501–2505 (1984).
J. Davies et al., J. Cell Biology, 109, 1817–1876 (1989).
R. J. Murrills et al., Bone, 11, 333–344 (1990).
S. Uemura et al., J. Chem. Soc. Perkin Trans I., 1697–1701 (1990).
M. Takeuchi et al., Abstract #53, $199^{th}$ American Chemical Society Meeting, Boston, MA (1990).
M. Horton et al., Experimental Cell Research, 195, 368–375 (1991).
M. Gurrath et al. Eur. J. Biochem 210, 911–922 (1992).
M. Helfrich et al., Journal of Bone and Mineral Research, 7(3) 335–343 (1992).
R. Seftor et al., Proc. Natl. Acad. Scie., 89, 1557–1561 (1992).
R. Hynes, Cell, 69, 11–25 (1992).
S. Nesbitt et al., Analytical Biochemistry, 206, 267–272 (1992).
J. White, Current Biology, 3(9) 596–599 (1993).
S. Copinga et al., Journal Med. Chem., 36, 2891–2898 (1993).
G. Pandey et al., Tetrahedron Letters, 34(41), 6631–6634 (1993).
M. Foster et al., Thrombosis Research, 72, 231–245 (1993).
D. Ramjit et al., Journal of Pharmacology and Experimental Therapeutics, 266(3), 1501–1511 (1993).
Doulut et al., J. Med. Chem., 36, 1369–1379 (1993).
M. Alami et al., Tetrahedron Letters 34(40), 6403–6406 (1993).
A. Adamis et al., American Journal of Ophthalmology, 118, 445–450 (1994).
E. Choi et al., J. Vasc. Surg., 19(1) 125–134 (1994).
H. Matsuno et al., Circulation, 90(5) 2203–2206 (1994).
A. Montgomery et al., Proc. Natl. Acad. Sci., 91, 8856–8860 (1994).
M. Walters et al., J. Org. Chem., 59, 2645–2647 (1994).
P. Brooks et al., Cell. 79, 1157–1164 (1994).
P. Brooks et al, Science, 264, 569–571 (1994).
A. Cordi et al., Journal Med. Chem., 38, 4056–4069 (1995).
K. Hattori et al., Biorganic & Medicinal Chemistry Letters 5(23), 2821–2824 (1995).
J. Samanen, Annual Reports in Medicinal Chemistry, Chapter 10, 91–100 (1996).
J. Stubbs, Connective Tissue Research, 35(1–4) 393–399 (1996).
M Frielander et al., Proc. Natl. Acad. Sci., 93, 9764–9769 (1996).
H. P. Hammes et al., National Medicine, 2(5), 529–533 (1996).
Z. Yun et al., Cer. Research, 56, 3103–3111 (1996).
E. Ruoslahti Annual Reviews Biochem., 57, 375–413 (1998).
H. Dauben et al., Org. Syn., Coll. vol. 4, 221.
A. Kalir., Organic Synthesis, Col. vol. 5, 825–828.
K. Ichikawa, et al., 31, 447–452 (1966).
A. Blaschette, et al., Angew. Chem. Int'l. Edit., 8, 450–451 (1969).
P. Dowd et al., Syn. Comm, 11, 935–941 (1981).
S. Uemura et al., J. Chem. Soc. Chem. Comm., 111–112 (1988).

* cited by examiner

BICYCLIC ANTAGONISTS SELECTIVE FOR THE $\alpha_v\beta_3$ INTEGRIN

This application claims the benefit of U.S. Provisional Application No. 60/172,238 which was converted from U.S. patent application Ser. No. 09/358,035 filed Jul. 21, 1999, pursuant to a petition filed under 37 C.F.R. 1.53(c)(2) on Oct. 5, 1999.

FIELD OF THE INVENTION

This invention relates to a series of tetrahydro- and dihydroquinoline, tetrahydronaphthalene and tetrahydro-5H-benzocycloheptene bicyclic compounds of Formulae (I) and (II) and non-toxic salts thereof, which selectively antagonize the $\alpha_v\beta_3$ integrin while minimally inhibiting platelet aggregation mediated by $\alpha_{IIb}\beta_3$ integrin and are useful as bone antiresorptive agents.

BACKGROUND OF THE INVENTION

The present invention relates to fused bicyclic derivatives which exhibit activity as bone antiresorptive agents by inhibition of the osteoclast vitronectin receptor($\alpha_v\beta_3$). The integrin $\alpha_v\beta_3$ has been shown to mediate the invasion of cancerous melanoma cells into healthy tissue (Seftor et al., Proc. Natl. Acad. Sci, USA, 1992, 89, 1557–1561) and to protect these cells against natural cell death cycle (apoptosis) (Montgomery et al., Proc. Natl. Acad. Sci. USA, 1994, 91, 8856–8860). Vitronectin receptor ($\alpha_v\beta_3$) antagonists have been shown to inhibit the growth of various solid tumors of human origin (Brooks et al., Cell, 1994, 79, 1157–1164). More recently, $\alpha_v\beta_3$ has been shown to be involved in liver metastasis (Yun et al., Cancer Res., 1996, 56, 3103–3111). Although angiogenesis is an important and natural process in growth and wound healing, it is now appreciated that a variety of clinically relevent conditions are pathologically related to these processes, and that the integrin $\alpha_v\beta_3$ is involved. For example, $\alpha_v\beta_3$ was shown to be expressed on human wound tissue but not on normal skin (Brooks, et al., Science, 1994, 264, 569–571) and is preferentially expressed on angiogenic blood vessels, such as those feeding a growing/invading tumor. It has also been shown that antagonists of $\alpha_v\beta_3$ promote tumor regression by inducing apoptosis of the tumor cells (Brooks et al., Cell, 1994, 79, 1157–1164). The process of neovascularization (new blood vessel growth, angiogenesis), which is critical for tumor growth and metastasis, is also an important event in occular tissue, leading to diabetic retinopathy, glaucoma and blindness (Adamis et al., Am. J. Ophthal., 118, 445–450 (1994); Hammes et al., Nature Med., 1996, 2,529–533; Friedlander, et al., Natl. Acad. Sci. U.S.A., 1996, 93, 9764–9769) and in joints, promoting rheumatoid arthritis (Peacock et al., J. Exp. Med., 1992, 175, 1135–1138). $\alpha_v\beta_3$ has been shown to play a pivotal role in the proliferation and migration of smooth muscle and vascular endothetial cells, a pathological process leading to restenosis after balloon angioplasty (Choi et al., J. Vasc. Surgery, 1994, 19, 125–134; Matsuno et al., Circulation, 1994, 90, 2203–2206). At least one type of virus (adenovirus) has been shown to utilizeo $\alpha_v\beta_3$ for entering host cells (White et al., Current Biology, 1993, 596–599).

Various bone diseases involve bone resorption, the dissolution of bone matter, which is mediated by only one known class of cells, the osteoclasts. When activated for resorption, these motile cells initially bind to bone, a process well known to be mediated by $\alpha_v\beta_3$ (Davies et al., J. Cell. Biol., 1989 109, 1817–1826; Helfrich et al., J Bone Mineral Res., 1992, 7, 335–343). It is also well known that blockade of $\alpha_v\beta_3$ with antibodies or peptides containing the sequence arginine-glycine-aspartic acid (RGD) blocks osteoclast cell adhesion and bone resorption in vitro (Horton et al., Exp. Cell Res. 1991, 195, 368–375) and that echistatin, an RGD containing protein, inhibits bone resorption in vivo (Fisher et al., Endocrinolog. y, 1993, 132, 1411–1413). More recently, an RGD peptidomimetic has likewise been shown to inhibit osteoclasts in vitro and, by iv administration prevents osteoporosis in vivo (Engleman et al., J. Clin. Invest., 1997, 99, 2284–2292).

A series of bicyclic compounds having a nucleus formed of two fused six-membered rings which include isoquinoline, isoquinolone, tetrahydronaphthalene, dihydronaphthalene or tetralone substituted with both basic and acidic functionality and which are useful in inhibition of platelet aggregation are disclosed in EP 0635492, WO96/22288, U.S. Pat Nos. 5,618,843 and 5,731,324 and are described by Formula I

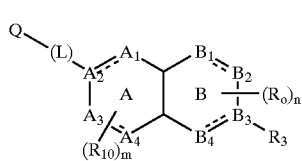

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia and the result of glucocorticoid treatment.

All these conditions are characterized by bone loss, resulting from an imbalance between bone resorption (breakdown) and bone formation, which continues throughout life at the rate of about 14% per year on the average. However, the rate of bone turnover differs from site to site, for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

There are currently 20 million people with detectable fractures of the vertebrae due to osteoporosis in the United States. In addition, there are 250,000 hip fractures per year attributed to osteoporosis. This clinical situation is associated with a 12% mortality rate within the first two years, while 30% of the patients require nursing home care after the fracture.

The minimal inhibition of platelet aggregation mediated by $\alpha_{IIb}\beta_3$ integrin while selectively antagonizing the $\alpha_v\beta_3$ integrin and thus being available as bone antiresorptive agents is an important benefit of compounds of the invention and is important in mammals, especially man.

BRIEF SUMMARY OF THE INVENTION

Accordingly, the present invention discloses bicyclic compounds represented by general Formula (I):

Formula (I)

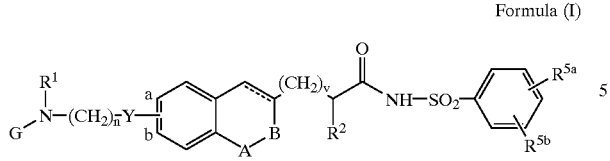

wherein:

— — — represents the presence of an optional double bond;
n is an integer of 2 to 5;
v is an integer of 0 or 1;
A—B is a diradical of the formulae:

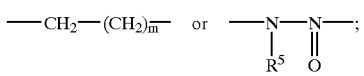

m is an integer of 1 or 2;
Y is selected from the group consisting of —O—, —CH$_2$—CH$_2$—, —CH=CH—,

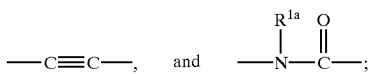

$R^1$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms; heterocyclylalkyl, wherein the alkyl moiety is a straight chain alkyl of 1 to 6 carbon atoms and the heterocyclyl moiety is selected from a 5- or 6-membered heterocyclic ring which contains 1 to 3 heteroatoms which may be the same or different, selected from nitrogen, oxygen and sulfur optionally substituted with one or more substituents which may be the same or different, and are selected from hydroxy, amino, halogen, straight chain alkyl of 1 to 6 carbon atoms, cyano and nitro;

$R^{1a}$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

$R^2$ is hydrogen, —NHR$^1$, or —OR$^1$; aryl of 6 to 12 carbon atoms optionally substituted with one or more substituents selected from straight chain alkyl of 1 to 6 carbon atoms, alkoxy of 1 to 6 carbon atoms, —S-alkyl of 1 to 6 carbon atoms, cyano, nitro, halogen and phenyl; the heterocyclyl moiety is selected from a 5- or 6-membered heterocyclic ring which contains 1 to 3 heteroatoms which may be the same or different, selected from nitrogen, oxygen and sulfur optionally substituted with one or more substituents which may be the same or different, and are selected from hydroxy, amino, halogen, straight chain alkyl of 1 to 6 carbon atoms, cyano and nitro; phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms; heterocyclylalkyl, wherein the alkyl moiety is a straight chain alkyl of 1 to 6 carbon atoms and the heterocyclyl moiety is selected from a 5- or 6-membered heterocyclic ring which contains 1 to 3 heteroatoms which may be the same or different, selected from nitrogen, oxygen and sulfur optionally substituted with one or more substituents which may be the same or different, and are selected from hydroxy, amino, halogen, straight chain alkyl of 1 to 6 carbon atoms, cyano and nitro;

G is a moiety selected from the group consisting of:

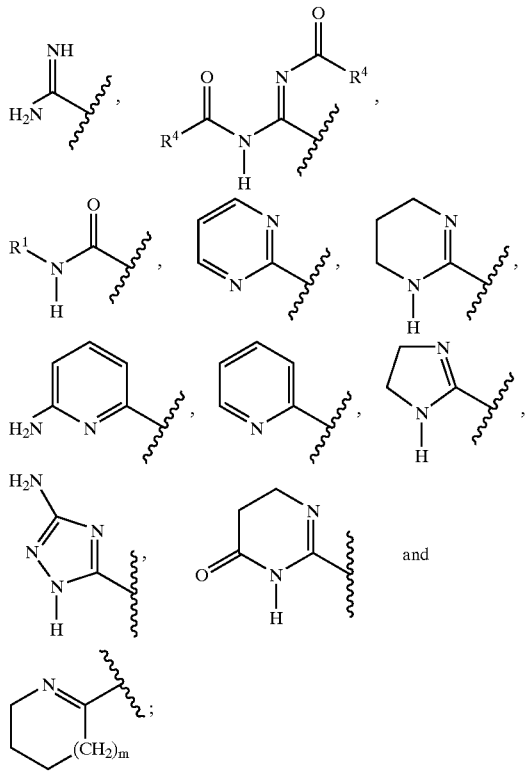

u is an integer of 0 or 1;
$R^4$ is straight chain alkyl of 1 to 6 carbon atoms, branched chain alkyl of 3 to 7 carbon atoms, alkoxy, or phenylalkyloxy wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

$R^5$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

$R^{5a}$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

$R^{5b}$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

provided that the optional double bond — — — is a single bond when A—B is the diradical —CH$_2$—(CH$_2$)$_m$—;

or a pharmaceutically acceptable salt thereof.

Among the preferred groups of compounds of Formula (I) of this invention including pharmaceutically acceptable salts thereof are those in the subgroups wherein:

a)
n is an integer of 2 to 4;
the moiety

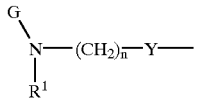

is located at the a or b position of the bicyclic nucleus;

$R^1$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or two substituents which may be the same or different and are selected from halogen, straight chain alkyl of 1 to 6 carbon atoms, and nitro; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl optionally substituted with one or two, substituents which may be the same or different, and are selected from halogen, straight chain alkyl of 1 to 6 carbon atoms, and nitro;

$R^2$ is hydrogen; aryl of 6 to 12 carbon atoms optionally substituted with one or more substituents selected from straight chain alkyl of 1 to 6 carbon atoms, alkoxy of 1 to 6 carbon atoms, nitro, and halogen; the heterocyclyl moiety is selected from 2- or 3-furyl, 2- or 3-thienyl, and 2-, 3- or 4-pyridyl; phenylalkyl wherein the alkyl moiety is a straight chain alkyl of 1 to 6 carbon atoms and the phenyl moiety is optionally substituted with one or more substituents which may be the same or different and are selected from halogen, straight chain alkyl of 1 to 6 carbon atoms, and nitro; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl;

the optional double bond — — — is a single bond;
where m, u, v, G, Y, A—B, $R^{1a}$, $R^4$, $R^{5a}$, and $R^{5b}$ are hereinbefore defined;

b)
n is an integer of 2 to 4;
the moiety

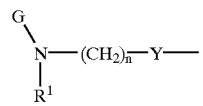

is located at the a or b position of the bicyclic nucleus; A—B is the diradical —CH$_2$—(CH$_2$)$_m$—;

$R^1$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or two substituents which may be the same or different and are selected from halogen, straight chain alkyl of 1 to 6 carbon atoms, and nitro; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl optionally substituted with one or two, substituents which may be the same or different, and are selected from halogen, straight chain alkyl of 1 to 6 carbon atoms, and nitro;

$R^2$ is hydrogen; aryl of 6 to 12 carbon atoms optionally substituted with one or more substituents selected from straight chain alkyl of 1 to 6 carbon atoms, alkoxy of 1 to 6 carbon atoms, —NO$_2$, and halogen; the heterocyclyl moiety is selected from 2- or 3-furyl, 2- or 3-thienyl, and 2-, 3- or 4-pyridyl; phenylalkyl wherein the alkyl moiety is a straight chain alkyl of 1 to 6 carbon atoms and the phenyl moiety is optionally substituted with one or more substituents which may be the same or different and are selected from halogen, straight chain alkyl of 1 to 6 carbon atoms, and nitro; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl;

the optional double bond — — — is a single bond;
where m, u, v, G, Y, $R^{1a}$, $R^4$, $R^{5a}$, and $R^{5b}$ are hereinbefore defined;

c)
n is an integer of 2 to 4;
the moiety

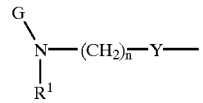

is located at the a or b position of the bicyclic nucleus;
$R^1$ is H;
$R^2$ is H;

$R^5$ is H;

the optional double bond — — — is a single bond;

where m, u, v, G, Y, A—B, $R^{1a}$, $R^4$, $R^{5a}$, and $R^{5b}$ are hereinbefore defined;

Among the more preferred groups of compounds of Formula (I) of this invention including pharmaceutically acceptable salts thereof are those in the subgroups wherein:

a)
n is an integer of 2 to 4;
m is an integer of 1;
v is an integer of 0;
the moiety

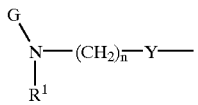

is located at the a or b position of the bicyclic nucleus;
Y is —O—;
$R^1$ is H;
$R^2$ is H;
$R^5$ is H;
the optional double bond — — — is a single bond;
where u, G, A—B, $R^{1a}$, $R^4$, $R^{5a}$, and $R^{5b}$ are hereinbefore defined;

b)
n is an integer of 2 to 4;
the moiety

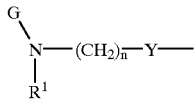

is located at the a or b position of the bicyclic nucleus;
$R^1$ is H;
$R^2$ is H;
$R^5$ is H;
G is a moiety selected from the group consisting of:

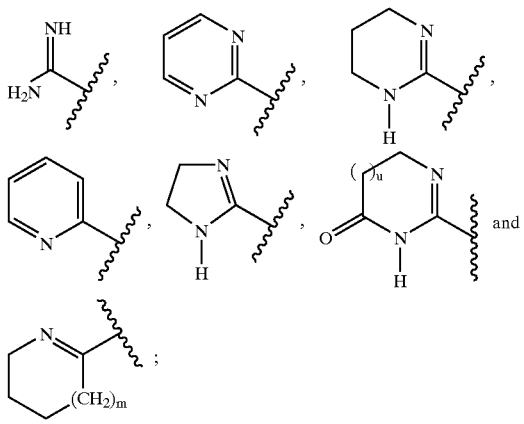

where — — —, u, v, m, D, Y, $R^{1a}$, $R^4$, A—B, $R^{5a}$, and $R^{5b}$ are hereinbefore defined;

c)
n is an integer of 2 to 4;

the moiety

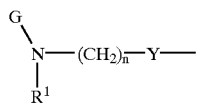

is located at the a or b-position of the bicyclic nucleus;
$R^1$ is H;
$R^2$ is H;
$R^5$ is H;
Y is —O—;
G is a moiety selected from the group consisting of:

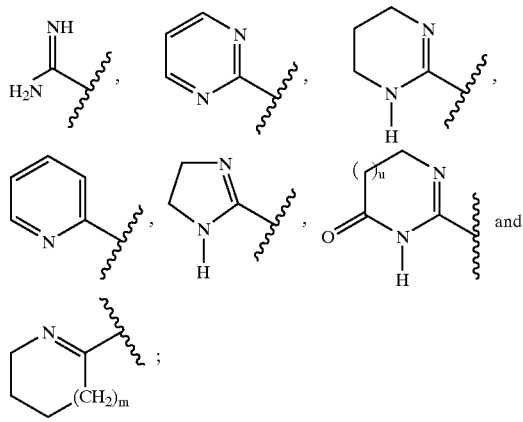

where — — —, u, V, m, D, $R^{1a}$, $R^4$, A—B, $R^{5a}$, and $R^{5b}$ are hereinbefore defined;

d)
n is an integer of 2 to 4;
the moiety

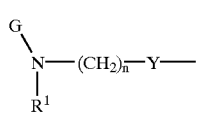

is located at the b-position of the bicyclic nucleus;
$R^1$ is H;
$R^2$ is H;
$R^5$ is H;
G is a moiety selected from the group consisting of:

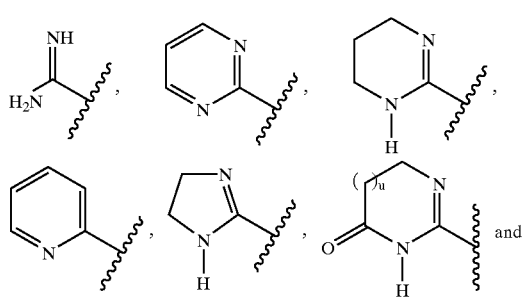

-continued

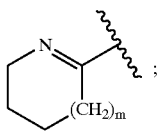

where ————, u, v, m, D, Y, $R^{1a}$, $R^4$, A—B, $R^{5a}$, and $R^{5b}$ are hereinbefore defined;

e)
n is an integer of 2 to 4;

the moiety

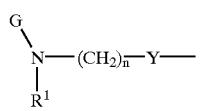

is located at the b-position of the bicyclic nucleus;

G is a moiety selected from the group consisting of:

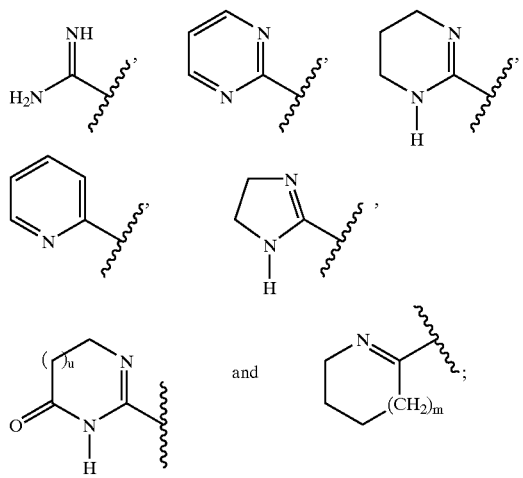

where ————, u, v, m, Y, $R^1$, $R^{1a}$, $R^2$, $R^4$, $R^5$, A—B, $R^{5a}$, and $R^{5b}$ are hereinbefore defined;

f)
n is an integer of 2 to 4;
$R^1$ is H;
$R^2$ is H;
$R^5$ is H;

A—B is the diradical —$CH_2$—$(CH_2)_m$—;

the moiety

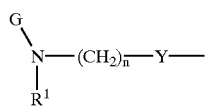

is located at the a or b-position of the bicyclic nucleus;

G is a moiety selected from the group consisting of:

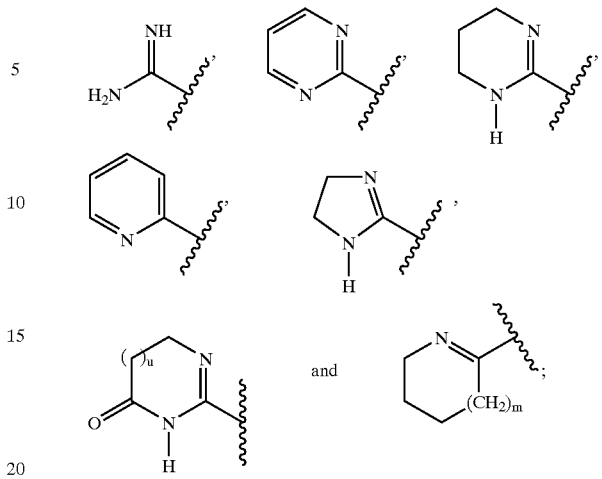

the optional double bond ———— is a single bond;
where u, v, m, Y, $R^{1a}$, $R^4$, $R^{5a}$, and $R^{5b}$ are hereinbefore defined;

Among the specifically preferred compounds of Formula (I) of this invention including pharmaceutically acceptable salts thereof are those set forth below:

4-Methyl-N-({6-[3-(1,4,5,6-tetrahydro-pyrimidin-2-ylamino)-propoxyl]1,2,3,4-tetrahydro-naphthalen-2-yl}-acetyl)-benzenesulfonamide, trifluoroacetic acid salt, and 4-Methyl-N-{[7-(3-guanidino-propoxy)-2-oxo-1,2,3,4-tetrahydro-quinolin-3-yl]-acetyl}-benzenesulfonamide.

In particular, the present invention also provides a method of treatment of diseases characterized by bone resorption of mineralized tissue and by bone loss, resulting from an imbalance between bone resorption and bone formation such as osteoporosis, hypercalcemia of malignancy, osteopenia due to bone metastases, periodontal disease, hyperparathyroidism, periarticular erosions in rheumatoid arthritis, Paget's disease, immobilization-induced osteopenia and the result of glucocorticoid treatment in warm-blooded animals in need thereof, which comprises administering to said warm-blooded animals, preferably mammals, most preferably humans, an effective amount of a compound of Formulae (I) or (II) or a pharmaceutically acceptable salt thereof.

In addition the present invention also provides a method of blocking or inhibiting bone resorption by antagonizing the $\alpha_v\beta_3$ integrin receptor mediated binding of an osteoclast to a bone matrix which comprises administering to warm-blooded animals, preferably mammals, most preferably humans, an effective amount of a compound of general Formulae (I) or (II) or a pharmaceutically acceptable salt thereof.

Formula (II)

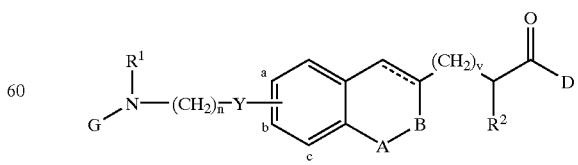

wherein:
———— represents the presence of an optional double bond;

n is an integer of 2 to 5;
v is an integer of 0 or 1;
A—B is a diradical of the formulae:

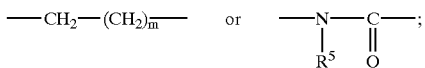

m is an integer of 1 or 2;
D is a moiety selected from the group consisting of:

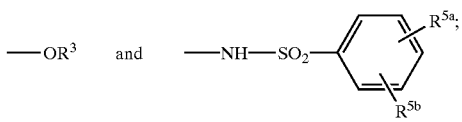

Y is selected from the group consisting of —O—, —CH$_2$—CH$_2$—, —CH=CH—,

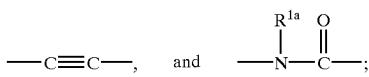

$R^1$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms; heterocyclylalkyl, wherein the alkyl moiety is a straight chain alkyl of 1 to 6 carbon atoms and the heterocyclyl moiety is selected from a 5- or 6-membered heterocyclic ring which contains 1 to 3 heteroatoms which may be the same or different, selected from nitrogen, oxygen and sulfur optionally substituted with one or more substituents which may be the same or different, and are selected from hydroxy, amino, halogen, straight chain alkyl of 1 to 6 carbon atoms, cyano and nitro;

$R^{1a}$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

$R^2$ is hydrogen, —NHR$^1$, or —OR$^1$; aryl of 6 to 12 carbon atoms optionally substituted with one or more substituents selected from straight chain alkyl of 1 to 6 carbon atoms, alkoxy of 1 to 6 carbon atoms, —S-alkyl of 1 to 6 carbon atoms, cyano, nitro, halogen and phenyl; the heterocyclyl moiety is selected from a 5- or 6-membered heterocyclic ring which contains 1 to 3 heteroatoms which may be the same or different, selected from nitrogen, oxygen and sulfur optionally substituted with one or more substituents which may be the same or different, and are selected from hydroxy, amino, halogen, straight chain alkyl of 1 to 6 carbon atoms, cyano and nitro; phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms; heterocyclylalkyl, wherein the alkyl moiety is a straight chain alkyl of 1 to 6 carbon atoms and the heterocyclyl moiety is selected from a 5- or 6-membered heterocyclic ring which contains 1 to 3 heteroatoms which may be the same or different, selected from nitrogen, oxygen and sulfur optionally substituted with one or more substituents which may be the same or different, and are selected from hydroxy, amino, halogen, straight chain alkyl of 1 to 6 carbon atoms, cyano and nitro;

$R^3$ is H, straight chain alkyl of 1 to 6 carbon atoms optionally substituted with a group selected from amino, hydroxyl and carboxyl or branched chain alkyl of 3 to 7 carbon atoms optionally substituted with a group selected from amino, hydroxyl and carboxyl;

G is a moiety selected from the group consisting of:

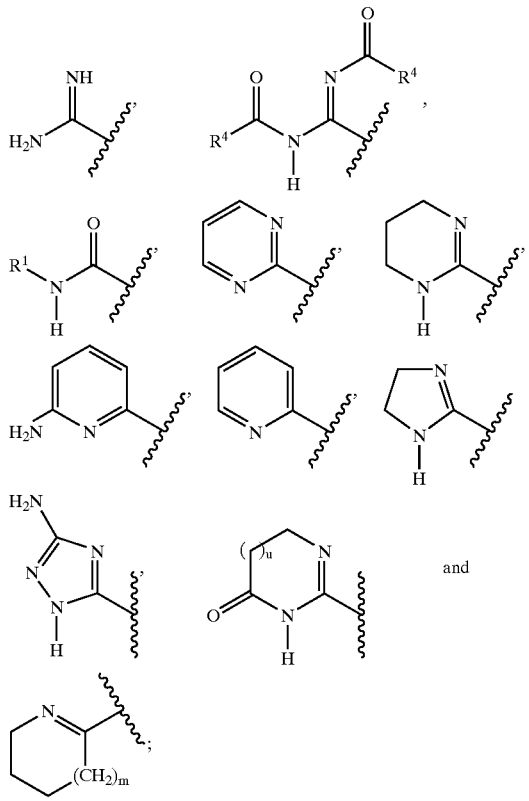

u is an integer of 0 or 1;

$R^4$ is straight chain alkyl of 1 to 6 carbon atoms, branched chain alkyl of 3 to 7 carbon atoms, alkoxy, or phenylalkyloxy wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

$R^5$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

$R^{5a}$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

$R^{5b}$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

with the proviso that Y is not O; n is not 3 or 4; $R^1$, $R^2$, $R^3$ and $R^5$ are not H; D is not —$OR^3$; G is not

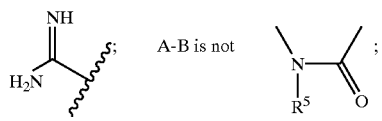   A-B is not 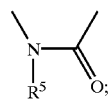

— — — is not a single bond;

a) when v is 0 and substitution is at position a;

with the additional proviso that n is not 2,3 or 4; G is not

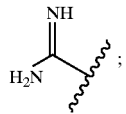

— — — is not a single bond; v is not 1; A—B is not

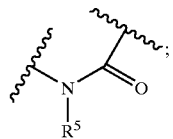

D is not —$OR^3$;

a) when Y is —O—; $R^1$, $R^2$, $R^3$ and $R^5$ are H; and substitution is at position a;

with the still further proviso that when A—B is the moiety

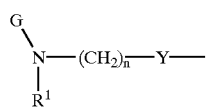

the moiety

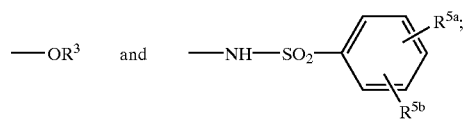

is located at the a,b or c positions of the bicyclic nucleus; and with the additional proviso that the optional double bond — — — — is a single bond when A—B is the diradical —$CH_2$—$(CH_2)_m$—;

or a pharmaceutically acceptable salt thereof.

For the compounds defined for Formulae (I) or (II) above and referred to herein, unless otherwise noted, the following terms are defined:

The term halogen may be selected from fluorine, chlorine, bromine and iodine, unless otherwise specified.

Phenyl as used herein refers to a 6-membered aromatic ring.

The term alkoxy means an alkyl group having a straight chain alkyl group attached through an oxygen bridge and including for example methoxy, ethoxy, n-propoxy, n-butoxy, and the like.

The term aryl when used alone means a homocyclic aromatic radical, whether or not fused, having 6 to 10 carbon atoms. Preferred aryl groups include phenyl, alpha-naphthyl and beta-naphthyl and the like optionally substituted.

The term heterocyclyl means an optionally substituted monocyclic heteroaromatic ring. Preferred are 2- or 3-furyl, 2- or 3-thienyl, 2-, 3- or 4-pyridyl.

The range of carbon atoms defines the total number of carbon atoms in the substituent group.

The compounds of Formulae (I) or (II) of the present invention can be used in the form of salts derived from pharmaceutically or physiologically acceptable acids or bases. These salts include, but are not limited to, the following: salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium or with organic bases. The compounds can also be used in the form of esters, carbamates and other conventional "pro-drug" forms, which, when administered in such form, convert to the active moiety in vivo.

Among the preferred groups of compounds of Formula (II) of this invention including pharmaceutically acceptable salts thereof are those in the subgroups wherein:

a)
D is the moiety $R^3$ is H;
where — — — —, n, m, u, v, G, Y, $R^1$, $R^{1a}$, $R^2$, $R^4$, $R^{5a}$, and $R^{5b}$ are hereinbefore defined;

b)
  n is an integer of 2 to 4;
  v is an integer of 0;
the moiety

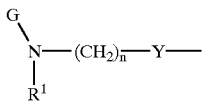

is located at the a or b position of the bicyclic nucleus;
  $R^1$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or two substituents which may be the same or different and are selected from halogen, straight chain alkyl of 1 to 6 carbon atoms, and nitro; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl optionally substituted with one or two, substituents which may be the same or different, and are selected from halogen, straight chain alkyl of 1 to 6 carbon atoms, and nitro;
  $R^2$ is hydrogen; aryl of 6 to 12 carbon atoms optionally substituted with one or more substituents selected from straight chain alkyl of 1 to 6 carbon atoms, alkoxy of 1 to 6 carbon atoms, nitro, and halogen; the heterocyclyl moiety is selected from 2- or 3-furyl, 2- or 3-thienyl, and 2-, 3- or 4-pyridyl; phenylalkyl wherein the alkyl moiety is a straight chain alkyl of 1 to 6 carbon atoms and the phenyl moiety is optionally substituted with one or more substituents which may be the same or different and are selected from halogen, straight chain alkyl of 1 to 6 carbon atoms, and nitro; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl;
the optional double bond — — — is a single bond;
where m, u, G, Y, D, $R^{1a}$, $R^3$, $R^4$, $R^{5a}$, and $R^{5b}$ are hereinbefore defined;
  c)
    n is an integer of 2 to 4;
    v is an integer of 0;
  the moiety

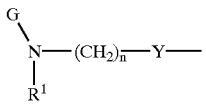

is located at the a or b position of the bicyclic nucleus;
A—B is the diradical —$CH_2$—$(CH_2)_m$—;
  $R^1$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or two substituents which may be the same or different and are selected from halogen, straight chain alkyl of 1 to 6 carbon atoms, and nitro; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl optionally substituted with one or two, substituents which may be the same or different, and are selected from halogen, straight chain alkyl of 1 to 6 carbon atoms, and nitro;
  $R^2$ is hydrogen; aryl of 6 to 12 carbon atoms optionally substituted with one or more substituents selected from straight chain alkyl of 1 to 6 carbon atoms, alkoxy of 1 to 6 carbon atoms, —$NO_2$, and halogen; the heterocyclyl moiety is selected from 2- or 3-furyl, 2- or 3-thienyl, and 2-, 3- or 4-pyridyl; phenylalkyl wherein the alkyl moiety is a straight chain alkyl of 1 to 6 carbon atoms and the phenyl moiety is optionally substituted with one or more substituents which may be the same or different and are selected from halogen, straight chain alkyl of 1 to 6 carbon atoms, and nitro; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl;
the optional double bond — — — is a single bond;
where m, u, G, Y, D, $R^{1a}$, $R^3$, $R^4$, $R^{5a}$, and $R^{5b}$ are hereinbefore defined;
  d)
    n is an integer of 2 to 4;
    v is an integer of 0;
  the moiety

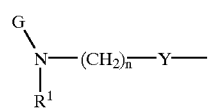

is located at the a or b position of the bicyclic nucleus;
    $R^1$ is H;
    $R^2$ is H;
    $R^5$ is H;
    the optional double bond — — — is a single bond;
    where m, u, G, Y, A—B, D, $R^{1a}$, $R^3$, $R^4$, $R^{5a}$, and $R^{5b}$ are hereinbefore defined;
  e)
    n is an integer of 2 to 4;
    v is an integer of 0;
  the moiety

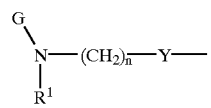

is located at the a or b position of the bicyclic nucleus;
    $R^1$ is H;
    $R^2$ is H;
    A—B is the diradical —$CH_2$—$(CH_2)_m$—;
    Y is —O—;
    the optional double bond — — — is a single bond;
    where m, u, D, G, $R^{1a}$, $R^3$, $R^4$, $R^{5a}$, and $R^{5b}$ are hereinbefore defined;
  f)
    n is an integer of 2 to 4;
    v is an integer of 0;

the moiety

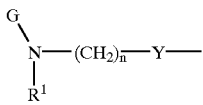

is located at the a or b position of the bicyclic nucleus;
 $R^1$ is H;
 $R^2$ is H;
 $R^5$ is H;
 Y is —O—;
 where ———, u, G, D, A—B, $R^{1a}$, $R^3$, $R^4$, $R^{5a}$, and $R^{5b}$ are hereinbefore defined;

Among the more preferred groups of compounds of Formula (II) of this invention including pharmaceutically acceptable salts thereof are those in the subgroups wherein:
a)
 n is an integer of 2 to 4;
 m is an integer of 1;
 v is an integer of 0;
the moiety

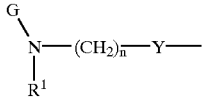

is located at the a or b position of the bicyclic nucleus;
 Y is —O—;
 $R^1$ is H;
 $R^2$ is H;
 $R^5$ is H;
 the optional double bond — — — is a single bond;
 where u, G, D, A—B, $R^{1a}$, $R^3$, $R^4$, $R^{5a}$, and $R^{5b}$ are hereinbefore defined;
b)
 n is an integer of 2 to 4;
 m is an integer of 2;
 v is an integer of 0;
the moiety

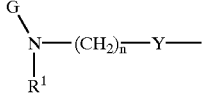

is located at the a or b position of the bicyclic nucleus;
 Y is —O—;
 $R^1$ is H;
 $R^2$ is H;
 $R^5$ is H;
 the optional double bond — — — is a single bond;
 where u, G, D, A—B, $R^{1a}$, $R^3$, $R^4$, $R^{5a}$, and $R^{5b}$ are hereinbefore defined;

Among the particularly preferred groups of compounds of Formula (II) of this invention including pharmaceutically acceptable salts thereof are those in the subgroups wherein:
a)
 n is an integer of 2 to 4;
 v is an integer of 0;

the moiety

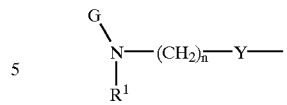

is located at the a or b position of the bicyclic nucleus;
 $R^1$ is H;
 $R^2$ is H;
 $R^5$ is H;
 G is a moiety selected from the group consisting of:

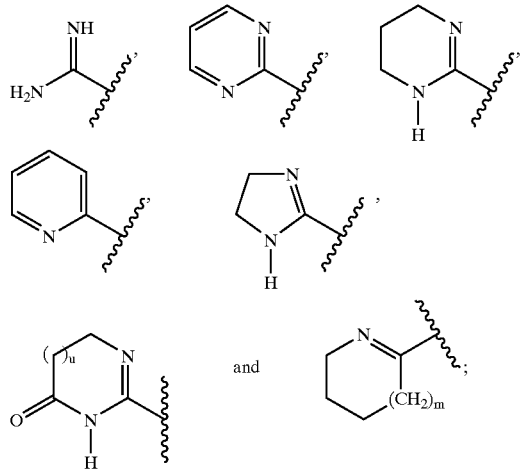

where ———, u, m, D, Y, $R^{1a}$, $R^3$, $R^4$, A—B, $R^{5a}$, and $R^{5b}$ are hereinbefore defined;
b)
 n is an integer of 2 to 4;
 v is an integer of 0;
the moiety

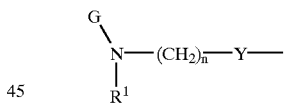

is located at the a or b-position of the bicyclic nucleus;
 $R^1$ is H;
 $R^2$ is H;
 $R^5$ is H;
 Y is —O—;
 G is a moiety selected from the group consisting of:

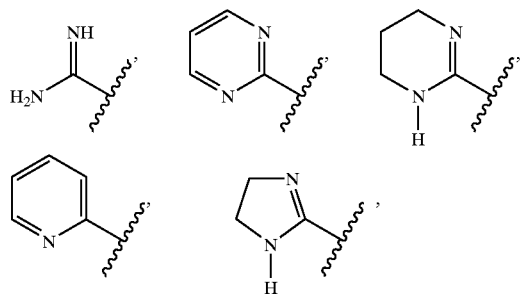

-continued

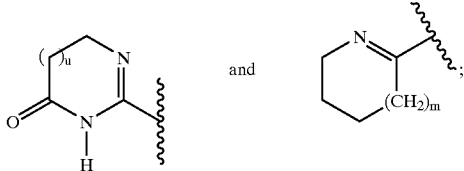

where ———, u, m, D, $R^{1a}$, $R^3$, $R^4$, A—B, $R^{5a}$, and $R^{5b}$ are hereinbefore defined;

c)
  n is an integer of 2 to 4;
  v is an integer of 0;

the moiety

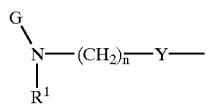

is located at the b-position of the bicyclic nucleus;

$R^1$ is H;
$R^2$ is H;
$R^5$ is H;

G is a moiety selected from the group consisting of:

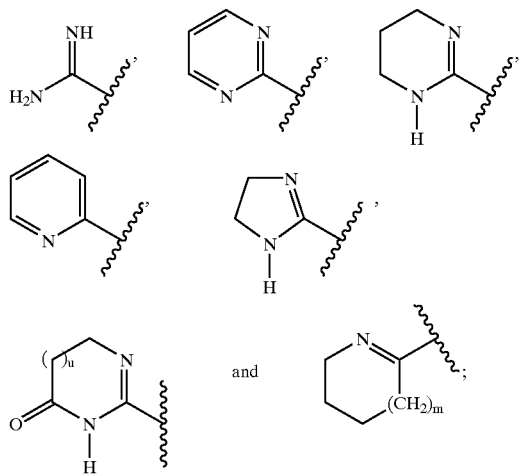

where ———, u, m, D, Y, $R^{1a}$, $R^3$, $R^4$, A—B, $R^{5a}$, and $R^{5b}$ are hereinbefore defined;

d)
  n is an integer of 2 to 4;

the moiety

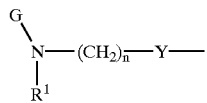

is located at the a or b-position of the bicyclic nucleus;

G is a moiety selected from the group consisting of:

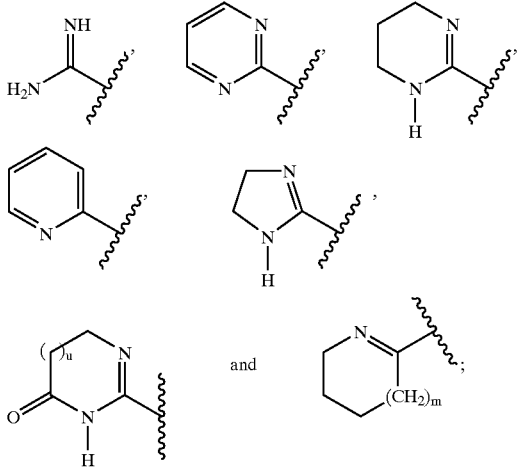

D is moiety

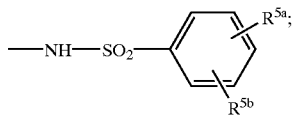

where ———, u, v, m, Y, $R^1$, $R^{1a}$, $R^2$, $R^4$, $R^5$, A—B, $R^{5a}$, and $R^{5b}$ are hereinbefore defined;

e)
  n is an integer of 2 to 4;

the moiety

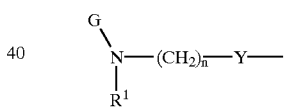

is located at the b-position of the bicyclic nucleus;

G is a moiety selected from the group consisting of:

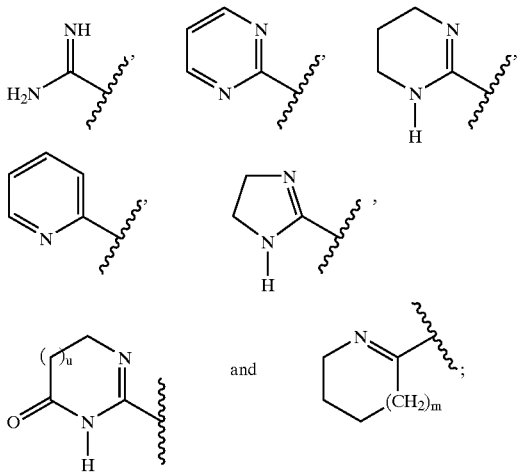

D is a moiety

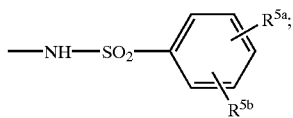

where — — —, u, v, m, Y, $R^1$, $R^{1a}$, $R^2$, $R^4$, $R^5$, A—B, $R^{5a}$, and $R^{5b}$ are hereinbefore defined;

f)
n is an integer of 2 to 4;
$R^1$ is H;
$R^2$ is H;
$R^5$ is H;
A—B is the diradical —$CH_2$—$(CH_2)_m$—;
the moiety

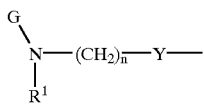

is located at the a or b-position of the bicyclic nucleus;
G is a moiety selected from the group consisting of:

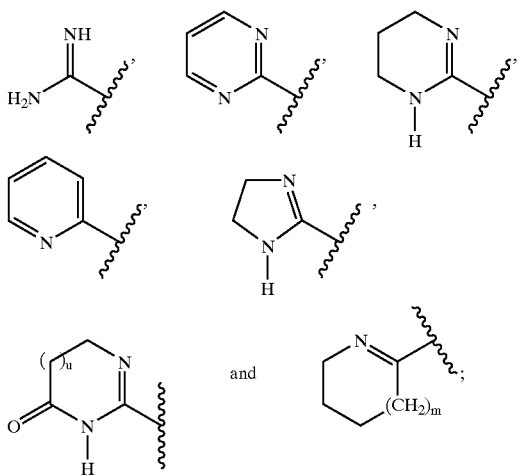

D is a moiety

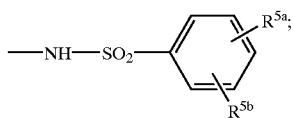

the optional double bond — — — is a single bond;
where u, v, m, Y, $R^{1a}$, $R^4$, $R^{5a}$, and $R^{5b}$ are hereinbefore defined;

g)
n is an integer of 2 to 4;
the moiety

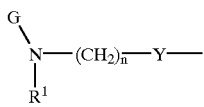

is located at the a or b-position of the bicyclic nucleus;

G is a moiety selected from the group consisting of:

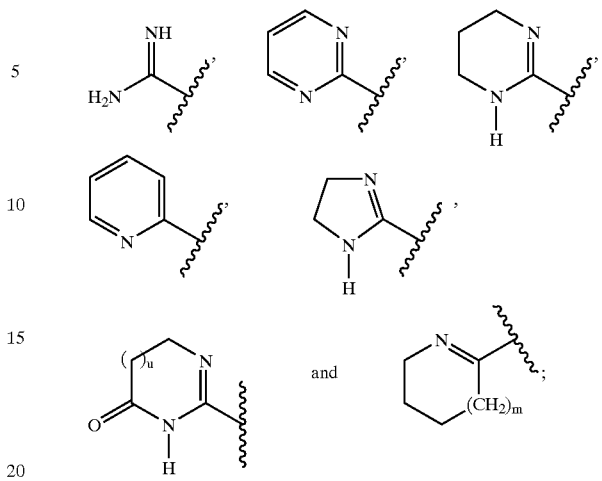

D is a moiety —OR3;
$R^3$ is H;
where — — —, u, v, m, Y, $R^1$, $R^{1a}$, $R^2$, $R^4$, $R^5$, A—B, $R^{5a}$, and $R^{5b}$ are hereinbefore defined;

Among the specifically preferred compounds of Formula (II) of this invention including pharmaceutically acceptable salts thereof are those set forth below:

[6-(3-Guanidinopropoxy)-1,2,3,4-tetrahydro-napthalen-2-yl]-acetic acid ethyl ester,

[6-(3-Guanidino-propoxy)-1,2,3,4-tetrahydro-napthalen-2-yl]-acetic acid trifluoroacetate,

[7-(3-Guanidino-propoxy)-1,2,3,4-tetrahydro-napthalen-2-yl]-acetic acid trifluoroacetate,

[2-(2-Guanidino-ethoxy)-6,7,8,9-tetrahydro-5H-benzocyclohepten-6-yl]-acetic acid hydrochloride,

[2-(3-Guanidino-propoxy)-6,7,8,9-tetrahydro-5H-benzocyclohepten-6-yl]-acetic acid trifluoroacetate,

[2-(4-Guanidino-butoxy)-6,7,8,9-tetrahydro-5H-benzocyclohepten-6-yl]-acetic acid trifluoroacetate,

[7-(4-Guanidino-butoxy)-2-oxo-1,2,3,4-tetrahydro-quinolin-3-yl]-acetic acid trifluoroacetate,

[6-(4-Guanidino-butoxy)-2-oxo-1,2,3,4-tetrahydro-quinolin-3-yl]-acetic acid trifluoroacetate,

[7-(2-Guanidino-ethoxy)-2-oxo-1,2,3,4-tetrahydro-quinolin-3-yl]-acetic acid Hydrochloride,

[7-(3-Guanidino-propoxy)-2-oxo-1,2,3,4-tetrahydro-quinolin-3-yl]-acetic acid Hydrochloride,

[7-(4-Guanidino-but-1-ynyl)-2-oxo-1,2,3,4-tetrahydro-quinolin-3-yl]-acetic acid Hydrochloride,

[7-(5-Guanidino-pent-1-ynyl)-2-oxo-1,2,3,4-tetrahydro-quinolin-3-yl]-acetic acid Trifluoroacetate,

[7-(4-Guanidino-but-1-enyl)-2-oxo-1,2,3,4-tetrahydro-quinolin-3-yl]-acetic acid Trifluoroacetate, {6-[3-(Pyrimidin-2-ylamino)-propoxy]-1,2,3,4-tetrahydro-naphthalen-2-yl}-acetic acid, {6-[3-(1,4,5,6-Tetrahydro-pyrimidin-2-ylamino)-propoxy]-1,2,3,4-tetrahydro-naphthalen-2-yl}-acetic acid, {6-[3-(1,4,5,6-Tetrahydro-pyrimidin-2-ylamino)-propoxy]-1,2,3,4-tetrahydro-naphthalen-2-yl}-acetic acid methyl ester bis(hydrochloride), {6-[3-(1,4,5,6-Tetrahydro-pyrimidin-2-ylamino)-propoxy]-1,2,3,4-tetrahydro-naphthalen-2-yl}-acetic acid ethyl ester, acetic acid salt, 4-Methyl-N-({6-[3-(1,4,5,6-tetrahydro-pyrimidin-2-ylamino)-propoxyl]1,2,3,4-tetrahydro-naphthalen-2-yl]-acetyl)-benzenesulfonamide, trifluoroacetic acid salt,

[6-(3-Guanidino-propoxy)-2-oxo-1,2,3,4-tetrahydro-quinolin-3-yl]-acetic acid,
3-[7-(2-Guanidino-ethoxy)-2-oxo-1,2,3,4-tetrahydro-quinolin-3-yl]-propionic acid,
3-[7-(3-Guanidino-propoxy)-2-oxo-1,2,3,4-tetrahydro-quinolin-3-yl]-propionic acid,
[8-(3-Guanidino-propoxy)-2-oxo-1,2,3,4-tetrahydro-quinolin-3-yl]-acetic acid,
[8-(4-Guanidino-butoxy)-2-oxo-1,2,3,4-tetrahydro-quinolin-3-yl]-acetic acid,
[1-Benzyl-7-(3-guanidino-propoxy)-2-oxo-1,2-dihydro-quinolin-3-yl]-acetic acid Trifluoroacetate,
[7-(5-Guanidino-pent-1-enyl)-2-oxo-1,2,3,4-tetrahydro-quinolin-3-yl]-acetic acid Trifluoroacetate,
[7-(4-Guanidino-butyl)-2-oxo-1,2,3,4-tetrahydro-quinolin-3-yl]-acetic acid Trifluoroacetate,
[7-(5-Guanidino-pentyl)-2-oxo-1,2,3,4-tetrahydro-quinolin-3-yl]-acetic acid Trifluoroacetate,
[1-Ethyl-7-(3-guanidino-propoxy)-2-oxo-1,2-dihydro-quinolin-3-yl]-acetic acid Trifluoroacetate
[1-Benzyl-7-(3-guanidino-propoxy)-2-oxo-1,2-dihydro-quinolin-3-yl]-acetic acid
[1-Ethyl-7-(3-guanidino-propoxy)-2-oxo-1,2,3,,4-tetrahydro-quinolin-3-yl]-acetic acid Trifluoroacetate,
[1-Benzyl-7-(3-guanidino-propoxy)-2-oxo-1,2,3,4-tetrahydro-quinolin-3-yl]-acetic acid,
[7-(4-Guanidino-butoxy)-2-oxo-1,2-dihydro-quinolin-3-yl]-acetic acid Hydrochloride,
[7-(2-Guanidino-ethoxy)-2-oxo-1,2-dihydro-quinolin-3-yl]-acetic acid,
[7-(3-Guanidino-propoxy)-2-oxo-1,2-dihydro-quinolin-3-yl]-acetic acid Trifluoroacetate,
[7-(2-Guanidino-ethylcarbamoyl)-2-oxo-1,2,3,4-tetrahydro-quinolin-3-yl]-acetic acid Hydrochloride,
[7-(3-Guanidino-propylcarbamoyl)-2-oxo-1,2,3,4-tetrahydro-quinolin-3-yl]-acetic acid Hydrochloride,
{6-[3-(Pyrimidin-2-ylamino)-propoxy]-1,2,3,4-tetrahydro-naphthalen-2-yl}-acetic acid methyl ester,
3-[7-(2-Guanidino-ethoxy)-2-oxo-1,2-dihydro-quinolin-3-yl]propionic acid nitric acid salt,
4-Methyl-N-{[7-(3-guanidino-propoxy)-2-oxo-1,2,3,4-tetrahydro-quinolin-3-yl]-acetyl}-benzenesulfonamide and
[8-(5-Guanidino-pentoxy)-2-oxo-1,2,3,4-tetrahydro-quinolin-3-yl]-acetic acid.

Some of the compounds of the hereinafter described schemes have centers of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

The present invention accordingly provides a pharmaceutical composition which comprises a compound of Formulae (I) or (II) of this invention in combination or association with a pharmaceutically acceptable carrier. In particular, the present invention provides a pharmaceutical composition which comprises an effective amount of a compound of this invention and a pharmaceutically acceptable carrier.

DETAILED DESCRIPTION OF THE INVENTION

The compounds of the present invention may be prepared according to the following reaction schemes.

In Scheme I, bicyclic ketone 1 where Y is —O—, A—B is the diradical —$CH_2$—$(CH_2)_m$—, and m is 1 or 2 is reacted with tri($C_1$–$C_6$)alkyl phosphonoacetate 2 where v and $R^2$ are hereinbefore defined in the presence of potassium tert-butoxide to give olefin 3. Tri($C_1$–$C_6$)alkyl phosphonoacetate 2 may be prepared using the conditions as described in U.S. Pat. Nos. 5,312,828 and 5,473,092. Bicyclic ketone 1 where m is 1 can be prepared from dimethoxynaphthalene as described by S. Copinga et al., J. Med. Chem., 36, 2891–2898 (1993) or as described by A. Cordi et al, J.Med.Chem., 38, 4056–4069(1995) and where m is 1 or 2 as described in G. Pandey et al., Tetrahedron Lett. 1993, 34, 6631–6634. Catalytic hydrogenation of olefin 3 in the presence of palladium-on-carbon affords ester 4. Treating ester 4 with boron tribromide in methylene chloride at 0° C. gives phenol 5 where Y is —O—, A—B is the diradical —$CH_2$—$(CH_2)_m$, and v, m and $R^2$ are hereinbefore defined. Alkylation of ester 4 where v is 0 or 1 with $R^2X$ where $R^2$ is hereinbefore defined provided $R^2$ is not H, in the presence of a base such as sodium methoxide and where X is a leaving group which includes but is not limited to —Cl, —Br, —I and methanesulfonyl gives ester 6. Treating ester 6 with boron tribromide in methylene chloride at 0° C. gives phenol 7 where Y is —O—, $R^2$ is hereinbefore defined excluding hydrogen, A—B is the diradical —$CH_2$—$(CH_2)_m$—, and v and m are hereinbefore defined.

SCHEME I

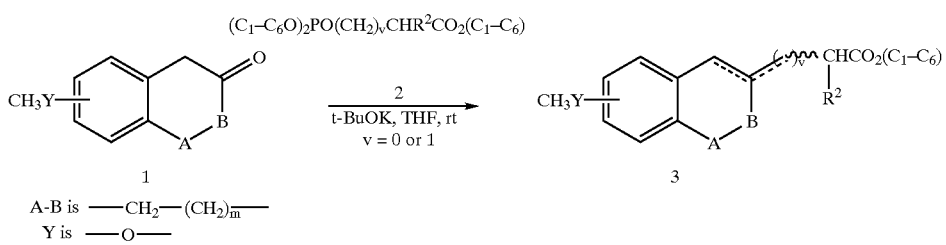

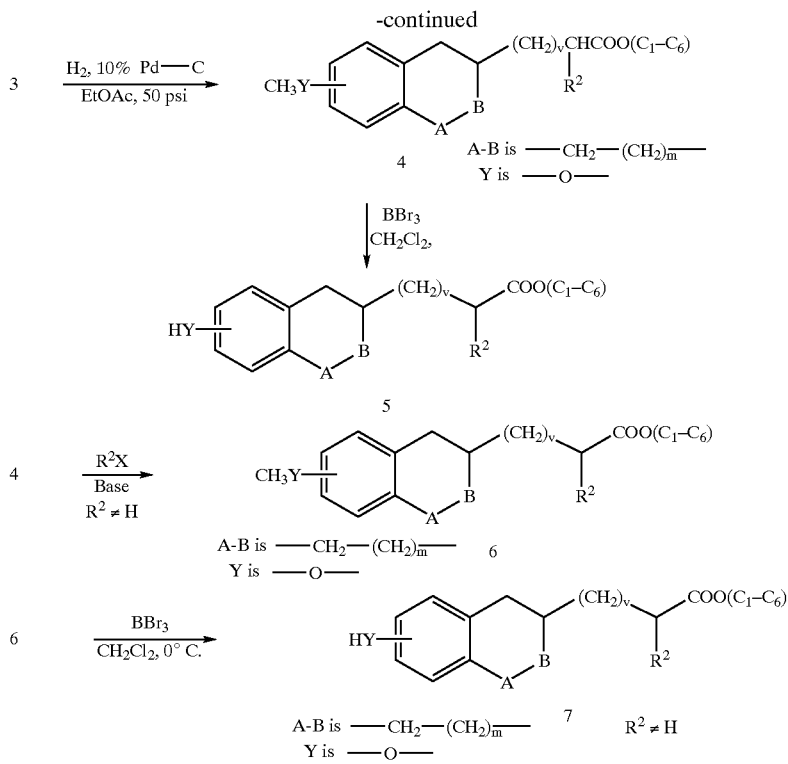

As described in Scheme II, nitrobenzaldehyde 8 where R is straight chain alkyl of 1 to 6 carbon atoms is reacted with diester 9, in acetic acid where v and $R^2$ are hereinbefore defined and W is a moiety

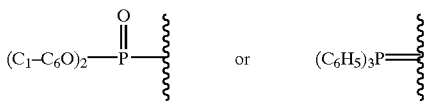

to give the corresponding diester 10 where R, $R^2$ and v are hereinbefore defined. Diester 9 where v is an integer of 0, $R^2$ is H and W is

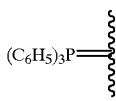

can be prepared in situ from a distraight chain lower alkyl of 1 to 6 carbon atoms maleate and triphenyl phosphine in acetic acid, according to the modified method of Kadin, S. B. and Lamphere, C. H., J. Org. Chem., 49, 4999 (1984), and in the case where v is an integer of 1 from ethyl α-bromoglutanate (E. Schwenk and D. Papa, J. Am. Chem. Soc., 70 3626–3627 (1948)). Diester 9 where v and $R^2$ are hereinbefore defined and W is

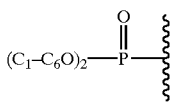

may be prepared using the conditions as described in P. G. Baraldi et al, J.Chem. Soc., Perkin Trans. I, 2501–2505 (1984) and GB1423495. Reduction of the nitro and olefinic groups of diester 10 by catalytic hydrogenation (10% Pd/C) followed by spontaneous cyclization gives tetrahydroquinolinone 11 where R, $R^2$ and v are hereinbefore defined and the moiety A—B is the diradical

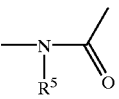

where $R^5$ is H. Reduction of the nitro group of diester 10 using zinc in 12N HCl-ethyl alcohol followed by spontaneous cyclization gives substituted (1,2-dihydro-3-yl) alkanoate ester 12 where R, $R^2$ and v are hereinbefore defined and $R^5$ is H. Alternatively, as also shown in Scheme II, substituted (1,2-dihydro-3-yl)alkanoate ester 12 where R is hereinbefore defined may be converted to phenol 13 by reaction with borontribromide followed by catalytic reduction in the presence of palladium-on-carbon to give phenol 14 where $R^2$ and v are hereinbefore defined and the moiety A—B is the diradical

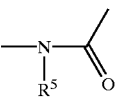

where $R^5$ is H. Catalytic reduction of substituted (1,2-dihydro-3-yl) alkanoate ester 12 where R, $R^2$ and v are hereinbefore defined and $R^5$ is H in the presence of palladium-on-carbon affords substituted tetrahydroquinolinone 11 where R, $R^2$ and v are hereinbefore defined and $R^5$ is H.

Again, referring to Scheme II, (1,2-dihydro-3-yl) alkanoate ester 12 where $R^5$ is H is alkylated with $R^5$ X where $R^5$ is hereinbefore defined excluding hydrogen and X is a leaving group which includes but is not limited to —Cl, —Br, —I and methanesulfonyl in the presence of potassium bis(trimethylsilyl)amide $(KN(TMS)_2)$ to give ester 16. Treating ester 16 with boron tribromide can afford phenol 13.

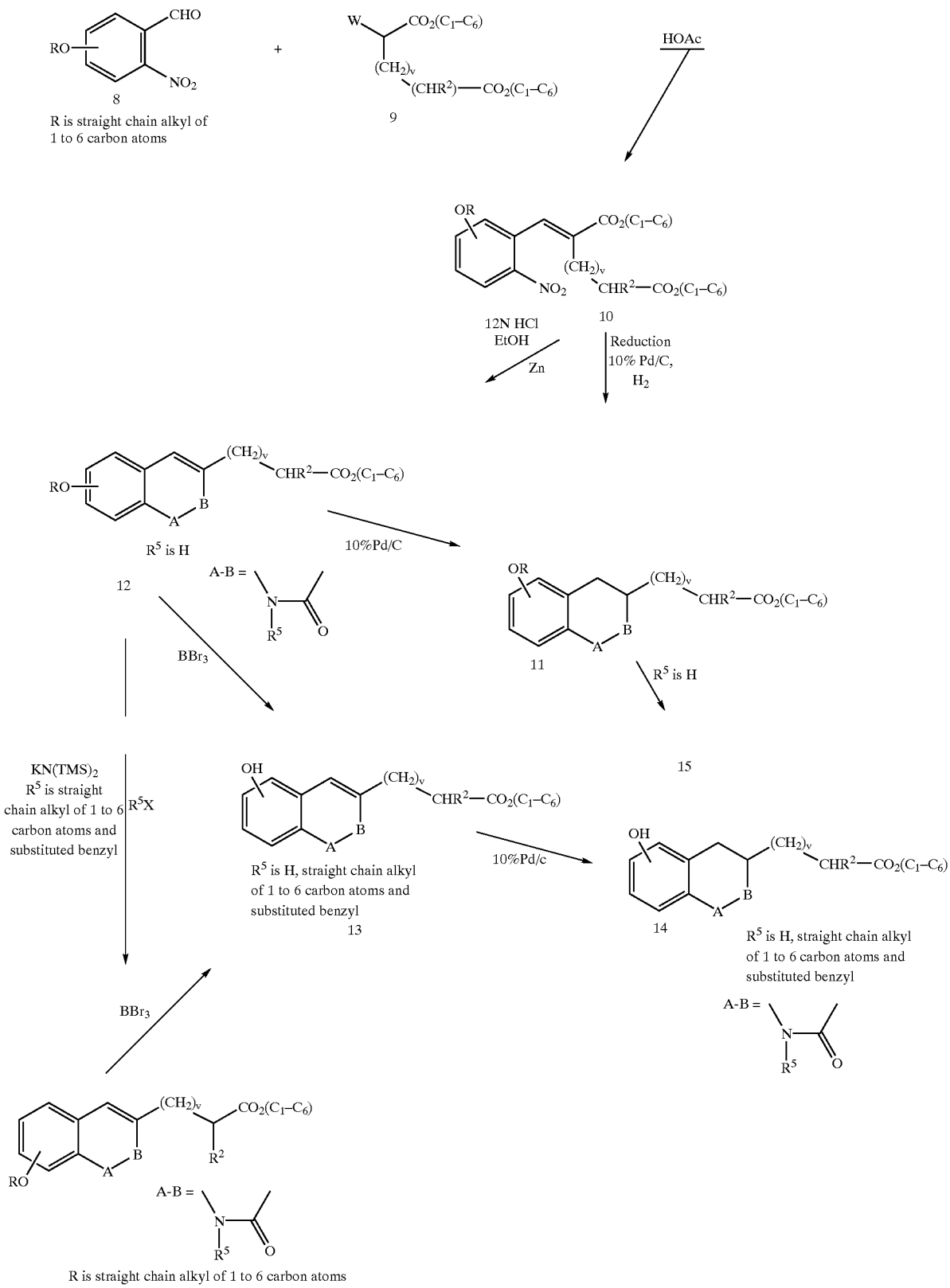

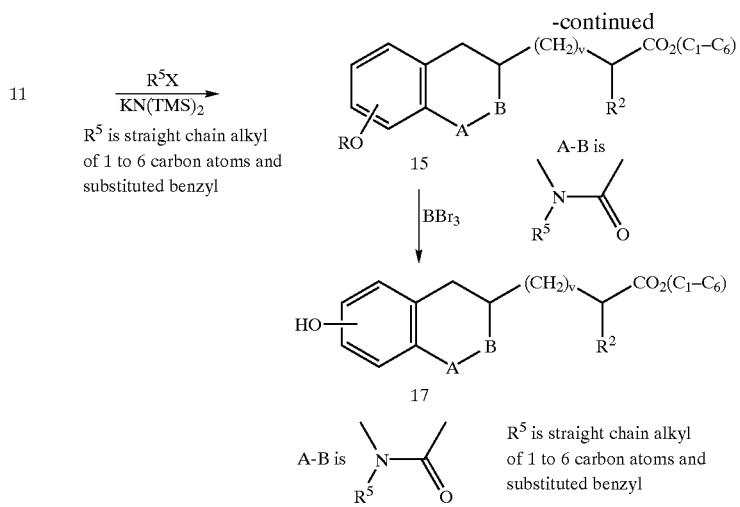

Again referring to Scheme II, tetrahydroquinolinone 11 where R and $R^2$ are hereinbefore defined and $R^5$ is H is alkylated with $R^5X$ where $R^5$ is hereinbefore defined excluding hydrogen and X is a leaving group which includes but is not limited to —Cl, —Br, —I and methanesulfonyl in the presence of potassium bis(trimethylsilyl)amide (KN(TMS) 2) to give ester 15. Treating ester 15 with boron tribromide can afford phenol 17.

reaction with thionyl chloride or oxalyl chloride. Further reaction of amide 20 where v and $R^2$ are hereinbefore defined with phosphorous oxychloride in N,N-dimethylformamide affords 2-chloro-substituted quinoline 21. Hydrolysis of 2-chloro-substituted quinoline 21 with aqueous HCl in methanol affords substituted (1,2-dihydro-3-yl)alkanoate ester 12 (R is $CH_3$), where v and $R^2$ are hereinbefore defined.

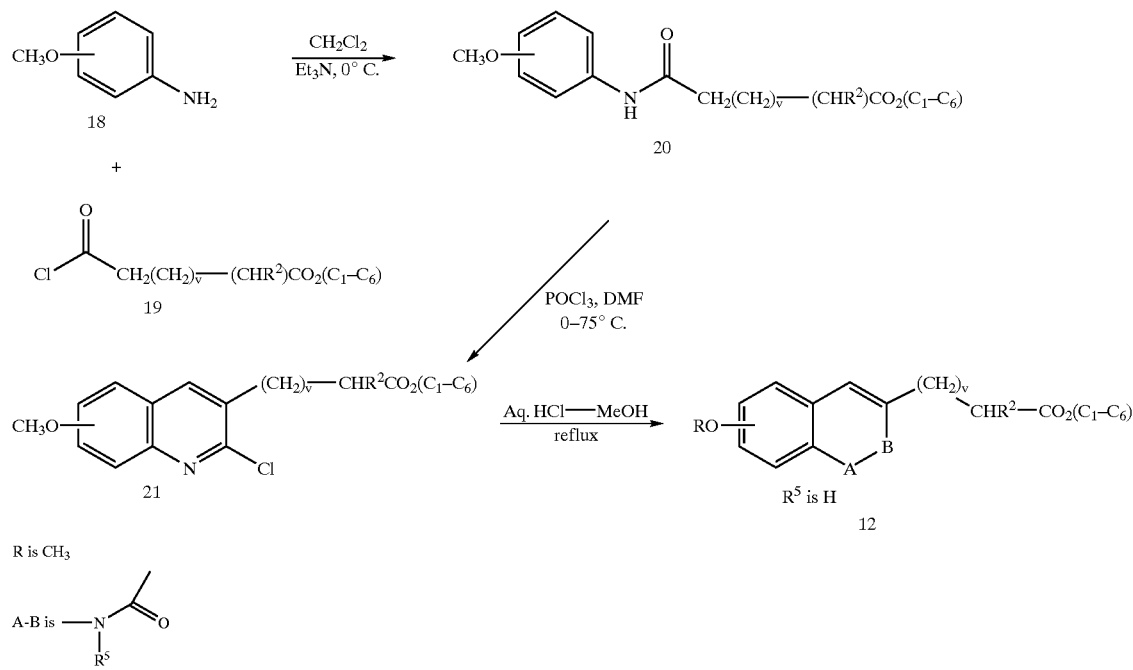

Additionally, a method of preparing substituted (1,2-dihydro-3-yl)alkanoate ester 12 is shown in Scheme III using the method as described by O. Meth-Cohn et al, J. Chem. Soc. Perkin I, 1537–1543 (1981). Methoxy substituted aniline 18 is reacted with acid chloride 19 where v and $R^2$ are hereinbefore defined to give amide 20. Acid chloride 19 is prepared from the corresponding half acid-ester by As described in Scheme IV, aldehyde 22 is reacted with tri($C_1$–$C_6$)alkyl phosphonoacetate 2 where v is 0 and $R^2$ is H in the presence of sodium hydride in tetrahydrofuran to give ester 23 which is hydrolyzed with 12N HCl to afford (1,2-dihydro-3-yl)alkanoate ester 24. reduction of (1,2-dihydro-3-yl)alkanoate ester 24 with hydrogen in the presence of 10% Pd/C in acetic acid affords tetrahydroquinolinone 25 which is further reacted with BBr₃ in methylene chloride to give phenol 14a where V is 1, R² is H and R⁵ is H.

SCHEME IV

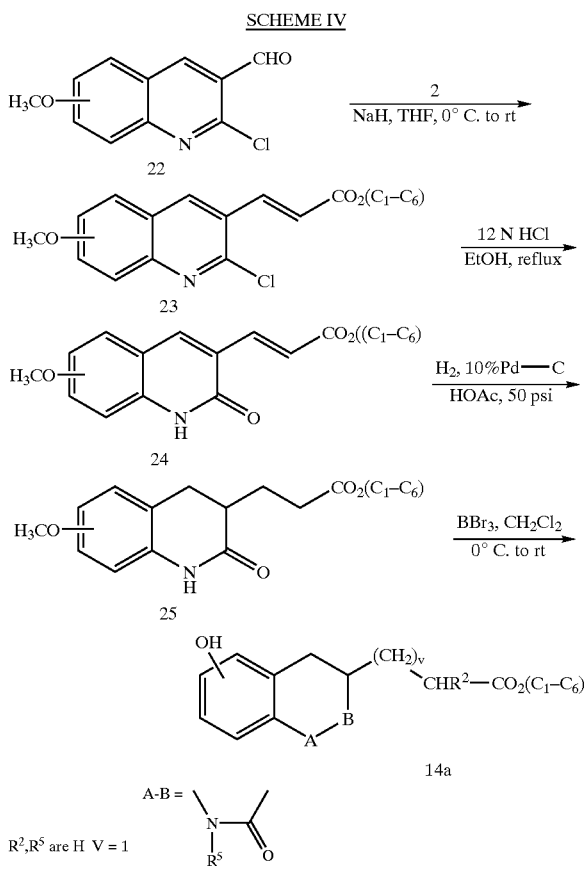

As shown in Scheme V, substituted amino alcohol 26 where R¹ and n are hereinbefore defined is converted to tert-butyl carbamate 27 by reaction with di-tert-butyl dicarbonate in the presence of potassium carbonate and which is further reacted with carbon tetrabromide in the presence of triphenylphosphine to give (bromoalkyl)carbamic acid tert-butyl ester 28 where R¹ and n are hereinbefore defined.

SCHEME V

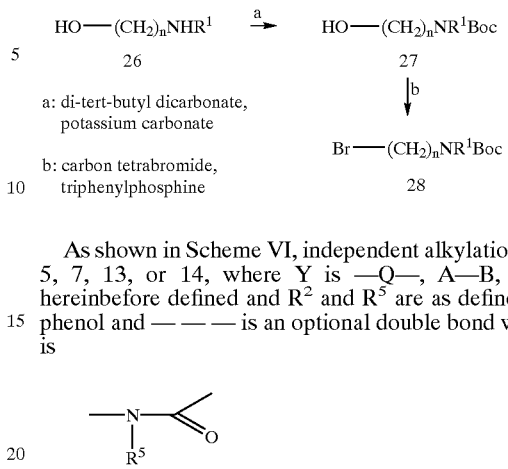

As shown in Scheme VI, independent alkylation of phenol 5, 7, 13, or 14, where Y is —Q—, A—B, m, V, are hereinbefore defined and R² and R⁵ are as defined for each phenol and — — — is an optional double bond when A—B is $$-\underset{R^5}{N}-\overset{O}{\underset{}{\diagdown}}$$

with (bromoalkyl) carbamic acid tert-butyl ester 28 where R¹ and n are hereinbefore defined using sodium ethoxide in N,N-dimethylformamide gives ether 29 where R¹, R², R⁵, n, v, A—B and m are hereinbefore defined and Y is —O—. Removal of the tert-butyl ester of ether 29 with trifluoroacetic acid (TFA) gives amine 30.

SCHEME VI

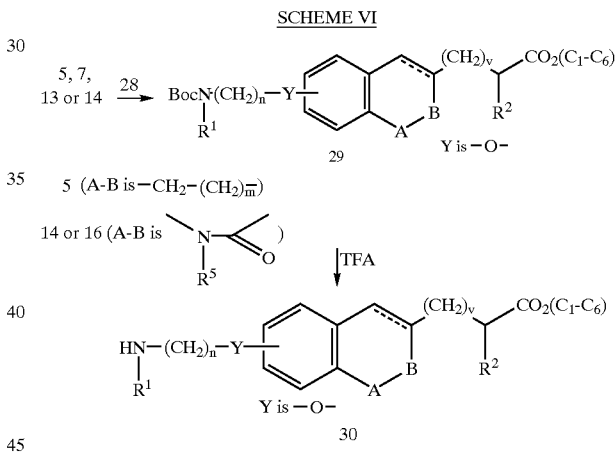

Scheme VII

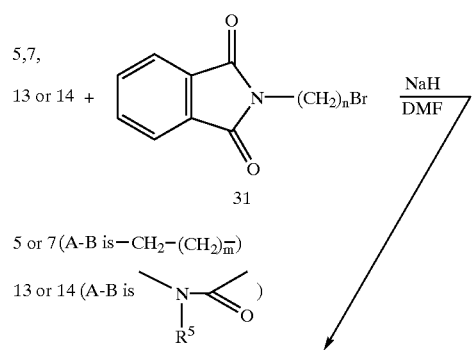

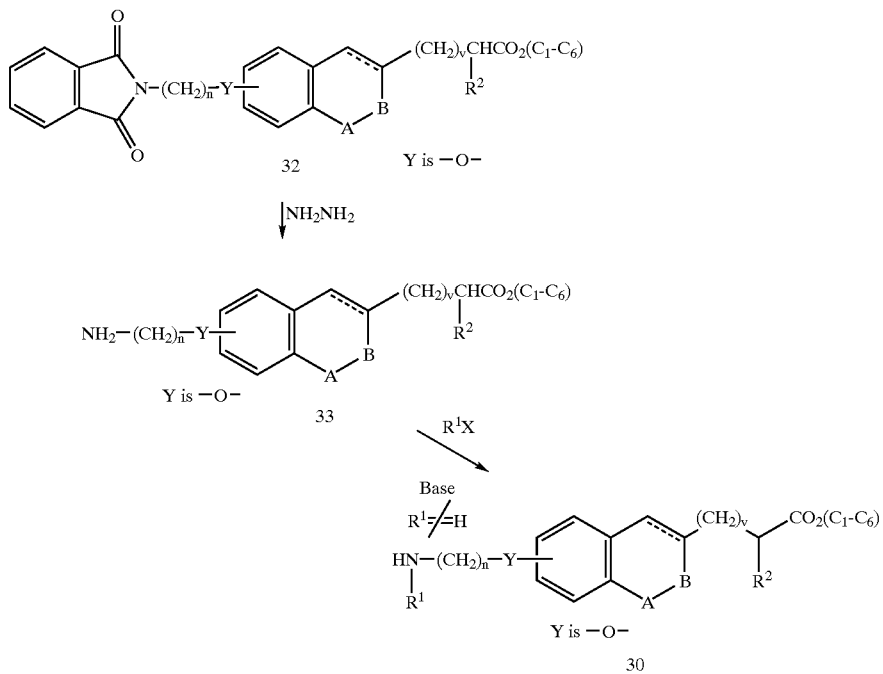

An alternative to using bromoalkylcarbamic acid t-butylester 28 is shown in Scheme VII where independent alkylation of phenol 5, 7, 13, or 14 with N-(brormoalkyl)-phthalimide 31 where n is hereinbefore defined, in the presence of sodium hydride in N,N-dimethylformamide affords ester 32 where Y is —O— and v, n, m, A—B, $R^2$ and $R^5$ are hereinbefore defined and — — — is an optional double bond when A—B is

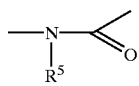

The phthalimide blocking group of ester 32 is removed by reaction with hydrazine in isopropyl alcohol to give amine 33 where Y is —O—, and $R^5$, $R^2$, v, n, m and A—B are hereinbefore defined. Ester 33 may be alkylated with $R^1X$ where $R^1$ is not H in the presence of base to give amine 30.

SCHEME VIII

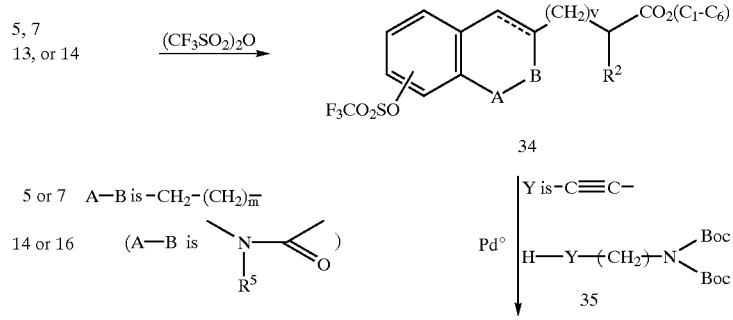

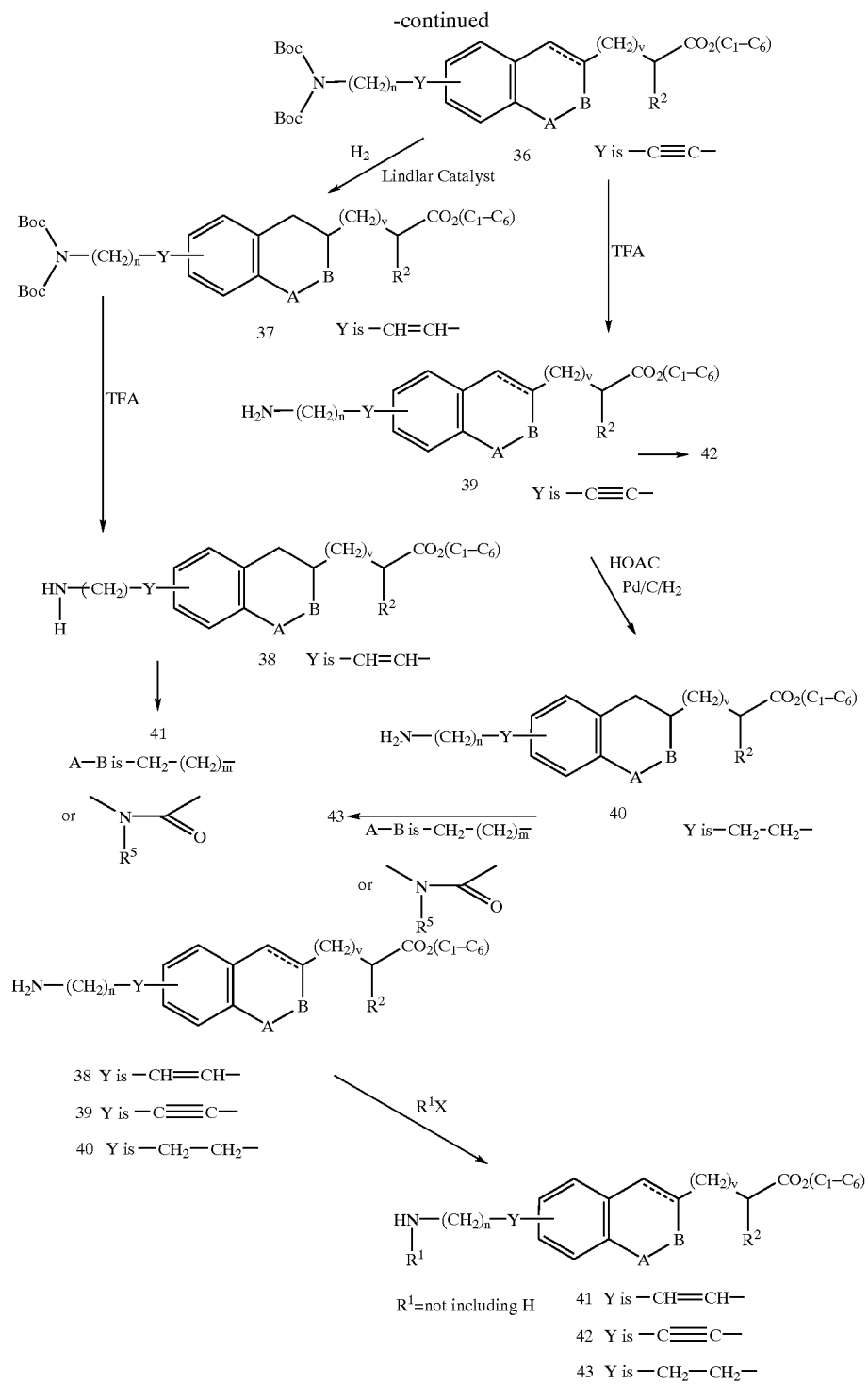

As outlined in Scheme VIII, phenol 5, 7, 13, or 14, where Y is —O— and A—B, m, and v are hereinbefore defined and $R^2$ and $R^5$ are as defined for each phenol which can be independently reacted with trifluoro-methane sulfonic anhydride ($Tf_2O$) to give triflate 34. Palladium mediated coupling of triflate 34 with tert-butyloxycarbonyl (Boc) protected acetylene 35 where n is hereinbefore defined and Y is:

—C≡C— gives acetylene 36 where Y is:

—C≡C—, and A—B, $R^2$, $R^5$, n, m and v are hereinbefore defined. Reduction of acetylene 36 with hydrogen in the presence of Lindlar catalyst gives olefin 37 where Y is —CH═CH— and A—B, $R^5$ $R^2{}_1$, v, n, m are hereinbefore defined and ———— is a single bond. Olefin 37 can be reacted with trifluoroacetic acid to give amine 38 where Y is —CH=CH— and A—B, $R^2$, $R^5$, n, m and v are hereinbefore defined and — — — is a single bond. Acetylene 36 can be reacted with trifluoroacetic acid to give amine 39 where Y is

—C≡C— and A—B, $R^2$, $R^5$, n, m and v are hereinbefore defined. Reduction of amine 39 in the presence of palladium-on-carbon and hydrogen in acetic acid gives amine 40 where Y is —CH$_2$—CH$_2$— and A—B, $R^2$, $R^5$, n, m and v are hereinbefore defined. Independent alkylation of amines 38, 39, and 40 with $R^1X$ where $R^1$ is hereinbefore defined, provided that $R^1$ is not H, in the presence of base such as sodium methoxide and X is a leaving group gives amines 41, 42, and 43 respectively.

Compounds of Formulae (I) or (II) wherein Y is

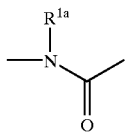

where $R^{1a}$ is hereinbefore defined; A—B is the diradical

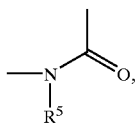

$R^5$ is H straight chain alkyl of 1 to 6 carbon atoms and substituted benzyl, n is an integer from 2 to 4 and v is an integer of 0 or 1 may be prepared as shown in Scheme IX, where tert-butyl-3-nitro-4-bromomethyl-benzoate 44 (Y. Kashman and J. A. Edwards, J. org. Chem. 43, 1538–1540 (1978)) is first reacted with pyridine in ethanol followed by further reaction with p-nitrosodimethylamine in the presence of aqueous 2.0 N sodium hydroxide followed by further treatment with aqueous 6 N sulfuric acid affords aldehyde 45 using the conditions described in organic Synthesis, Collective Volume V, page 825. Reaction of aldehyde 45 with diester 9 where v and $R^2$ are hereinbefore defined gives tert-butyl ester 46. Catalytic hydrogenation of tert-butyl ester 46 in the presence of 10% Pd/C and spontaneous cyclization gives lactam 47 where A—B is the diradical

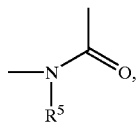

where R and v are hereinbefore defined and $R^5$ is H. Alkylation of lactam 47 with $R^5X$ where $R^5$ is hereinbefore defined excluding H and X is a leaving group hereinbefore defined in the presence of base can form ester 48. Hydrolysis of lactam 47 and ester 48 with aqueous 4 N hydrochloric acid in dioxane gives carboxylic acid 49 where $R^2$, v and $R^5$ are hereinbefore defined. Reaction of carboxylic acid 49 with 1-hydroxybenzotriazole hydrate (HOBT) and carbodiimide 50 where n is hereinbefore defined gives ester 51 where A—B is the diradical Y is

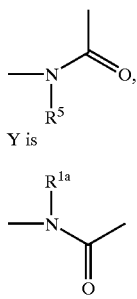

and $R^{1a}$, $R^2$, $R^5$, n and v are hereinbefore defined. The N-tertbutoxycarbonyl blocking group on ester 51 is removed by stirring with trifluoroacetic acid in methylene chloride to give amine 52. Alkylation of amine 52 with $R^1X$ where $R^1$ is hereinbefore defined excluding H can afford amine 53.

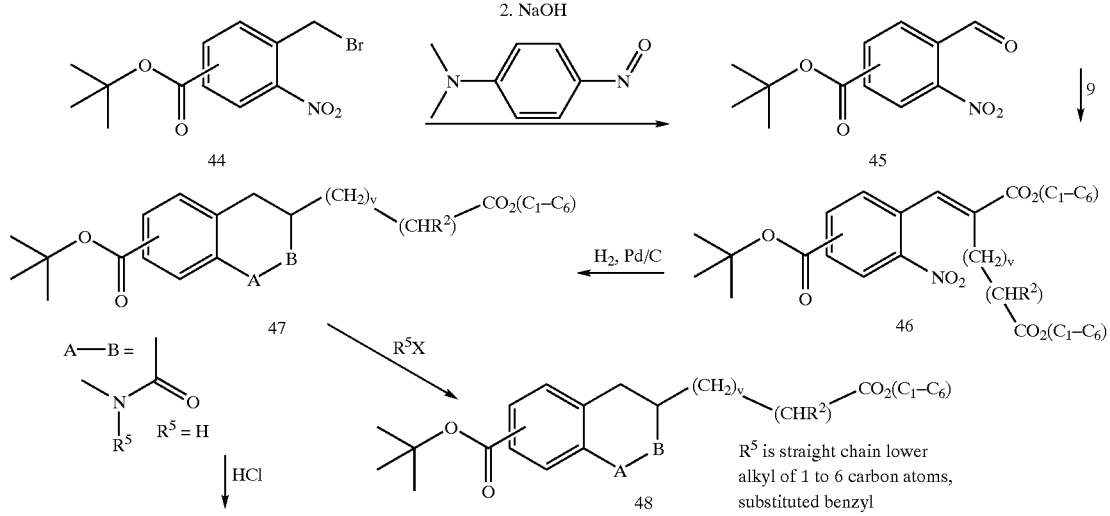

Scheme IX

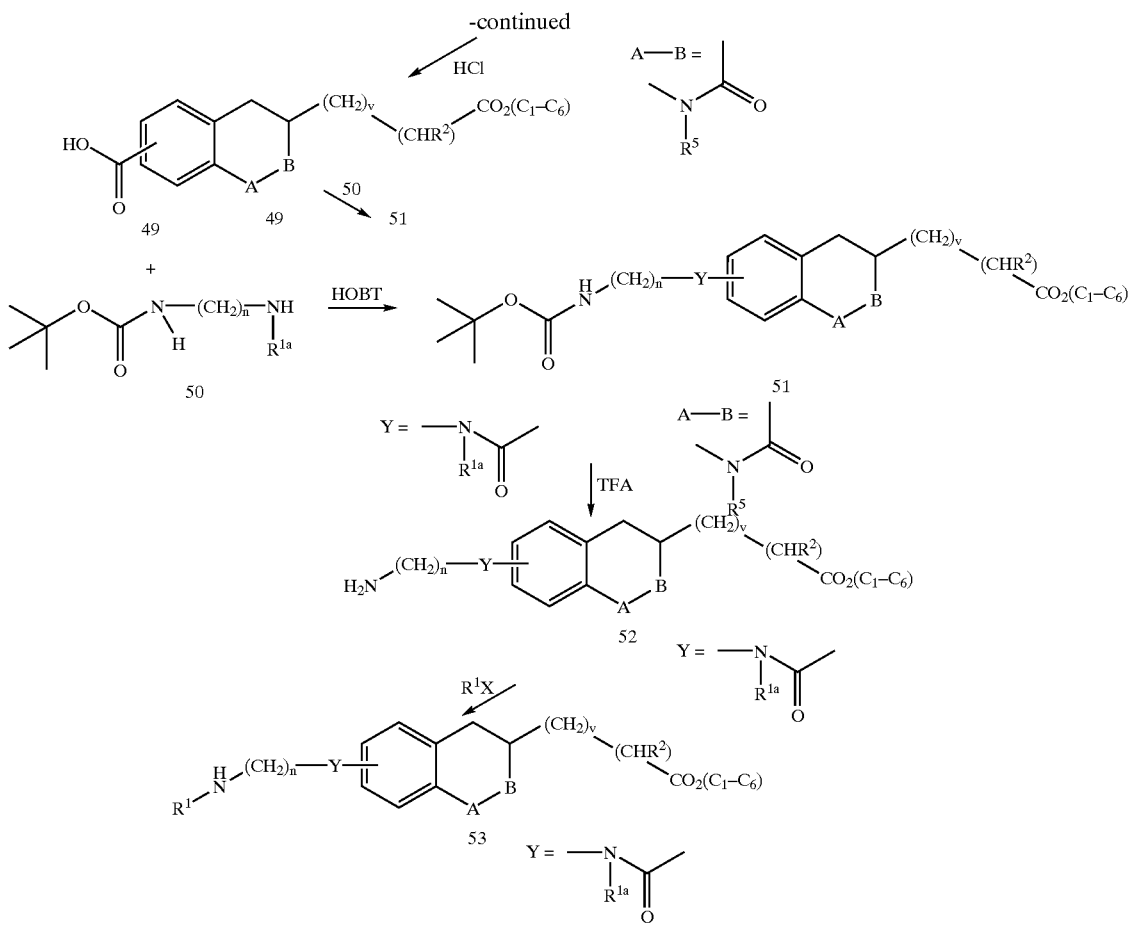

Compounds of Formulae (I) or (II) wherein Y is

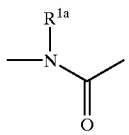

A—B is the diradical —$CH_2$—$(CH_2)_m$—, $R^{1a}$ and m are hereinbefore defined may be prepared as shown in Scheme X, where phenol 5 can be reacted with trifluoromethane sulfonic anhydride ($Tf_2O$) to give triflate 54 which can be further reacted with CO in the presence of $Pd^\circ$ followed by treatment with aqueous base to give carboxylic acid 55 where A—B is the diradical —$CH_2$—$(CH_2)_m$, and m, v and $R^2$ are hereinbefore defined. Reaction of carboxylic acid 55 with 1-hydroxybenzo-triazole hydrate (HOBT) and carbo-diimide 50 where n and $R^{1a}$ are hereinbefore defined can give ester 56. The N-tertbutoxy-carbonyl blocking group on ester 56 may be removed by stirring with trifluoroacetic acid in methylene chloride to form amine 57 where n, v, $R^{1a}$ and $R^2$ are hereinbefore defined, Y is

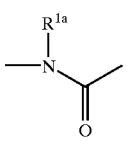

and A—B is the diradical —$CH_2$—$(CH_2)_m$—. Alkylation of amine 57 with $R^1X$ where $R^1$ is hereinbefore defined excluding H can afford amine 58.

SCHEME X

A—B = —$CH_2$—$(CH_2)m$—

Base | $Tf_2O$

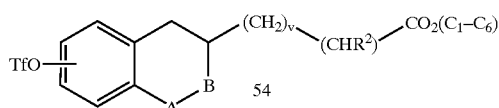

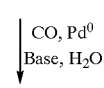
CO, $Pd^0$
Base, $H_2O$

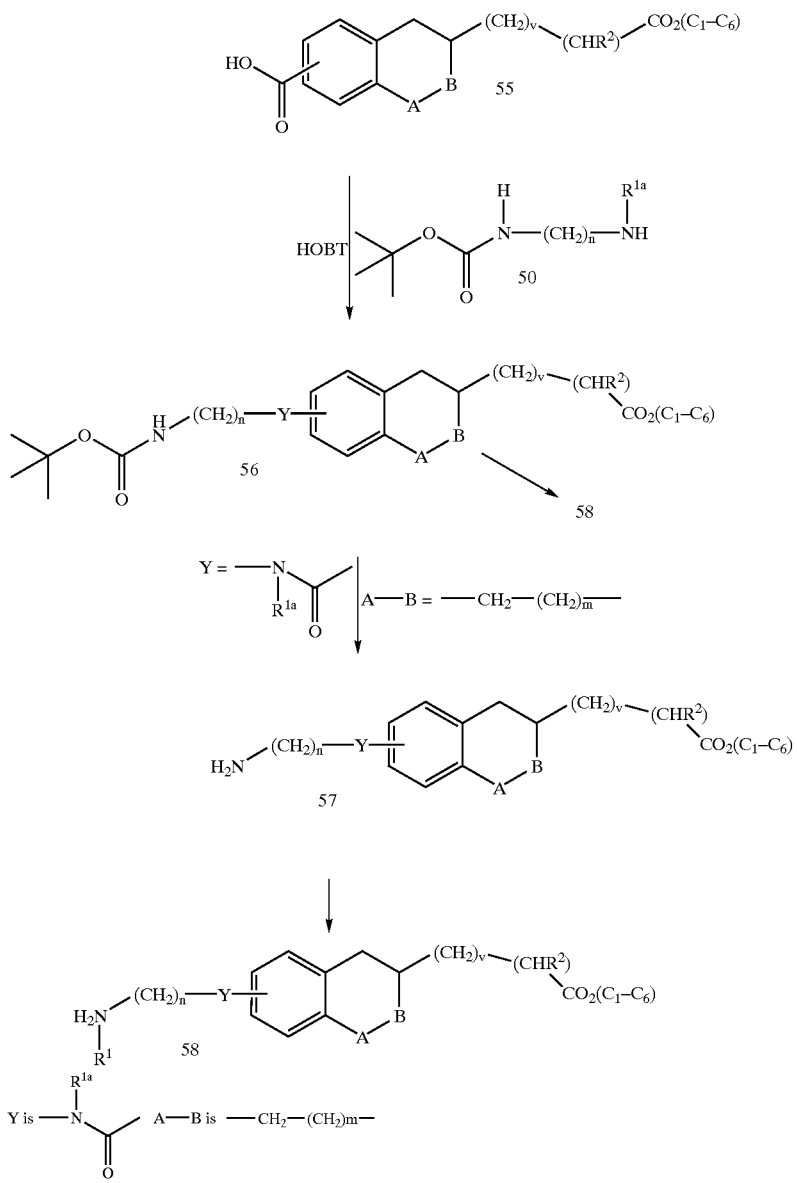

As shown in Scheme XI, amines 30, 38, 39, 40, 41, 42, 43, 52, 53, 57, and 58 are independently reacted with a G-reagent 59 where G is hereinbefore defined using the conditions and methods as described in WO0 97/36862, WO 97/33887, WO 97/37655 and CA2199923 with the exception where G is pyrimidine, the preferred method is to in situ activate amines 30, 38, 39, 40, 41, 42, 43, 52, 53, 57, and 58 with trimethylsilyl chloride in the presence of 2-bromopyrimidine in refluxing anhydrous 1,4-dioxane to give ester 60. G-reagent 59 includes but is not limited to those in Table A. In particular, alkylation of amines 30, 38, 39, 40, 41, 42, 43, 52, 53, 57, and 58 with 2-methylthio-3,4,5,6-tetrahydropyrimidine hydroiodide, a G-reagent 59, using the conditions as described (WO 96/37492 Example 83) can give ester 60 where G is

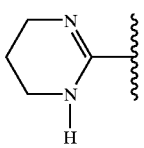

Alternatively, condensation of amines 30, 38, 39, 40, 41, 42, 43, 52, 53, 57, and 58 with N,N'-bis(tert-butoxycarbonyl)-2-(1H)-tetrahydropyrimidine-thione followed by deprotection with hydrochloric acid can give ester 60 where G is

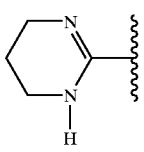

Independent base hydrolysis of ester 60 with aqueous base gives carboxylic acid 61. Suitable bases include sodium hydroxide, potassium hydroxide, lithium hydroxide, sodium carbonate and potassium carbonate.

Again referring to Scheme XI, carboxylic acid 61 was reacted with substitutedbenzenesulfonamide 62

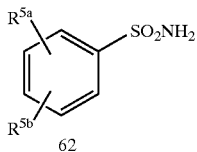

where $R^{5a}$ and $R^{5b}$ are hereinbefore defined in the presence of 1-[3-(dimethylamino)propyl]-3-ethyl-carbodiimide hydrochloride, dimethylaminopyridine and N,N-dimethylformamide (DMF) to give substitutedbenzenesulfonamide 63 and v, n, m, G, A—B, $R^1$, $R^{1a}$, $R^2$, $R^5$, $R^{5a}$ and $R^{5b}$ are hereinbefore defined.

Reduction of carboxylic acid 61 where G is the selected moiety

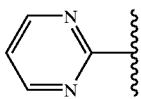

and where Y is —CH=CH—, or

in the presence of hydrochloric acid, acetic acid and an alcohol $(C_1-C_6)OH$ followed by reaction with an alcohol $(C_1-C_6)OH$ in the presence of hydrochloric acid gives an ester where G is reduced to the tetrahydropyrimidine moiety

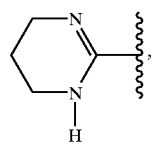

Y is reduced to —CH$_2$—CH$_2$— and the optional double bond — — — — is also reduced to a single bond and v, n, m, A—B, $R^1$, $R^{1a}$, $R^2$, and $R^5$ are hereinbefore defined.

SCHEME XI 30, 38, 39, 40, 41, 42, 43, 52, 53, 57 and 58

A—B is —CH$_2$—(CH$_2$)$_{\overline{m}}$— where - - - - is a single bond or

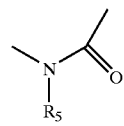

where - - - - is an optional double bond

| G-reagent
↓
59

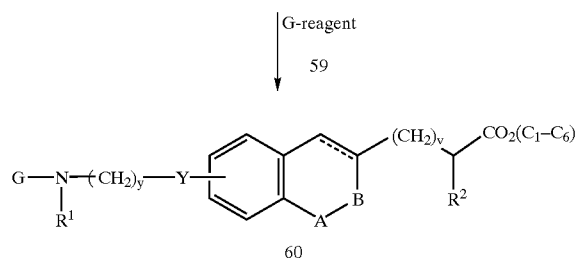

60

| Base
| Hydrolysis
↓

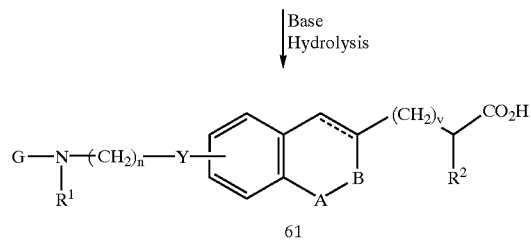

61

(1)   | (1) is substitutedbenzenesulfonamide 62,
      | 1-[3-(dimethylamino)-propyl]-3-
      | ethylcarbodiimide hydrochloride,
      | dimethylaminopyridine, DMF
      ↓

-continued

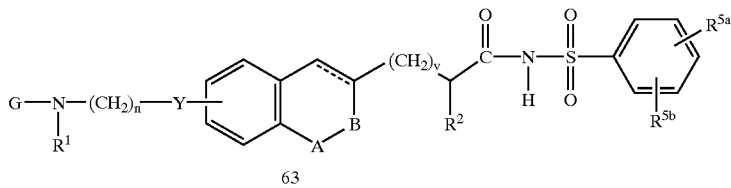

63

A—B is —CH$_2$—(CH$_2$)$_{\overline{m}}$— where ----- is a single bond or 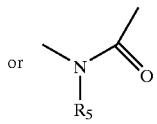 where ----- is an optional double bond

TABLE A

| G-Reagent 59 | Ester Product 60 G-Moiety |
|---|---|
| 3,5-dimethylpyrazole-1-carboxamidine | amidine |
| 2-(methylthio)imidazoline (m = 1 or 2) | imidazoline-2-yl (m = 1 or 2) |
| 2-(methylthio)-4-oxo-imidazoline (m = 1 or 2) | 4-oxo-imidazolin-2-yl (m = 1 or 2) |
| benzyl isocyanate / (C$_1$–C$_6$)NCO | benzyl-NH-C(O)- |
| 2-methoxy-tetrahydropyrimidine (m = 1 or 2) | (C$_1$–C$_6$)—NH—C(O)- |
| 2-bromopyrimidine | tetrahydropyrimidin-2-yl (m = 1 or 2) |

TABLE A-continued

| G-Reagent 59 | Ester Product 60 G-Moiety |
|---|---|
| 2-amino-6-bromopyridine | pyrimidin-2-yl |
| 2-(methylthio)-tetrahydropyrimidine·HI | 6-amino-pyridin-2-yl |
| | tetrahydropyrimidin-2-yl |

The compounds of the present invention can be prepared readily according to hereinbefore described reaction schemes and hereinafter described examples or modifications thereof using readily available starting materials, reagents and conventional synthesis procedures. In these reactions, it is also possible to make use of variants which are themselves known to those of ordinary skill in this art, but are not mentioned in greater detail.

The most particularly preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention.

Representative compounds of the present invention were evaluated in the following pharmacological test procedures which measured Vitronectin Receptor ($\alpha_v\beta_3$) Binding, Osteopontin ($\alpha_v\beta_3$)Cell Attachment, Osteoclast Bone Pitting, PTH-induced hypercalcemia and ADP—Induced Platelet Aggregation and which further show that the compounds of the present invention selectively antagonize the ($\alpha_v\beta_3$) integrin while not displaying ADP-induced platelet aggregation mediated by a fibrinogen ($\alpha_{IIb}\beta_3$) integrin.

Vitronectin Receptor ($\alpha_v\beta_3$) Binding Test Procedure

Measuring the effect of compounds on the $\alpha_v\beta_3$-ligand interaction.

Reagents

Plasma Membrane Isolation: 15 confluent $T_{150}$ flasks of 512P5 cells ($\alpha_v\beta_3$—overexpressing cell line) were washed 2x with Dulbecco's phosphate buffered saline (D-PBS) without calcium or magnesium, pH 7.1. Cells were harvested with 10 mL of trypsin/EDTA and collected by centrifugation. The cell pellet was washed 2x with 0.5 mg/mL of soybean trypsin inhibitor, and resuspended at 10% weight/volume in homogenization buffer (25 mM Tris-HCl, pH=7.4; 250 mM sucrose). The cell suspension was homogenized with 2×30 seconds bursts of a Polytron homogenizer. The homogenate was centrifuged at 3000 g for 10 minutes at 4° C. The supernatant was collected, measured, and made 100 mM in NaCl and 0.2 mM in $MgSO_4$. The supernatant was centrifuged at 22,000 g for 20 minutes at 4° C., the pellet was resuspended in 7 mL of membrane buffer (25 mM Tris-HCl, pH=7.4; 100 mM NaCl; 2 mM $MgCl_2$) by 5 strokes of a Dounce homogenizer (tight pestle) and recentrifuged at 22,000 g for 20 minutes at 4° C. The pellet was resuspended in 0.5 mL/flask of membrane buffer (stock membranes) and frozen at −80° C. Prior to use, stock membranes were Dounce homogenized and diluted 2 µL to 1000 µL in membrane buffer.

Compound Dilution: The stock compounds were dissolved in an appropriate vehicle (typically DMSO) and subsequently diluted in assay buffer composed as follows: 25 mM Tris-HCl (pH=7.4), 100 mM NaCl, 2 mM $MgCl_2$, 0.1% BSA.

Plate Preparation

Wells of Multiscreen-FB assay plates (Millipore MAFB NOB 50) were blocked with 150 µL of 0.1% polyethylenimine for 2 hours at 4° C. Following incubation the wells were aspirated and washed with isotonic saline solution.

Binding Assay

125 µL of assay buffer was added to each well. Next, 25 µL of labeled ligand was added to each well. 25 µL of unlabeled ligand was added to non-specific binding wells (NSB). 25 µL of assay buffer was added to all other wells. 2 µL of compound was added to appropriate sample wells, and 2 µL of DMSO was added to NSB and total binding (TB) wells. Finally, 25 µL of membrane was added to each well.

The plates were covered and incubated at 37° C. for 2 hours in a humidified incubator. Wells were aspirated on a Millipore vacuum manifold, and the wells were washed with 150 µL isotonic saline solution. Wells were again aspirated. The plates were then dried for 1 hour in an 80° C. vacuum drying oven. Plates were placed on a Millipore filter punch apparatus, and filters are placed in 12×75 mm polypropylene culture tubes. The samples were counted on a Packard gamma counter.

EXAMPLE

Using $^{125}$I- Echistatin (specific activity=2000 Ci/mmol) supplied by Amersham at a final concentration of 50 pM, the following parameters were routinely observed;

Input 80000 cpm

Total Counts 8000 cpm

Non-specific binding 200 cpm

Analysis of Results

The individual well activity was expressed as a percentage of the specific binding; % Max, and reported as the mean±standard deviation. Dose-inhibition relationships were generated for dose (X-axis) vs. % Max (Y-axis) for active compounds using a non-linear regression computer program (PS-NONLIN), and $IC_{50}$ values with corresponding 95% confidence intervals were estimated from 50% of maximal attachment.

Reference Compounds:

Various Arginine-Glycine-Aspartic Acid (RGD)-containing peptides were assessed for the ability to inhibit $\alpha_v\beta_3$ binding and the corresponding $IC_{50}$ values with 95% confidence intervals were generated; peptide structures are given by the standard single letter designation for amino acids. Values obtained compared favorably with adhesion assay results.

| Peptide | $IC_{50}$ (µM) | 95% Confidence Interval |
|---|---|---|
| GPenGRGDSPCA | 0.064 | 0.038 to 0.102 |
| GRGDSP | 1.493 | 1.058 to 2.025 |
| GRGDTP | 0.490 | 0.432 to 0.556 |
| GRGDS | 0.751 | 0.690 to 0.817 |
| RGDS | 1.840 | 1.465 to 2.262 |
| GRGDNP | 0.237 | 0.144 to 0.353 |
| GdRGDSP | 0.692 | 0.507 to 0.942 |
| GRGESP | inactive at 100 µM | |

REFERENCES

1. Nesbitt, S. A. And M. A. Horton, (1992), A nonradioactive biochemical characterization of membrane proteins using enhanced chemiluminescence, Anal. Biochem., 206 (2), 267–72.

Osteopontin-$\alpha_v\beta_3$ Cell Attachment Test Procedure

Measuring the effect of compounds on the RGD-dependent attachment of cells to osteopontin mediated by the $\alpha_v\beta_3$ integrin.

Reagents

Cell Suspension Media: The cells were suspended for assay in the tissue culture media used for normal culture maintenance buffered with 25 mM HEPES (pH 7.4) without serum supplementation.

Compound Dilution Media: The stock compounds were dissolved in an appropriate vehicle (typically DMSO) and subsequently diluted in the tissue culture media used for normal culture maintenance buffered with 25 mM HEPES (pH 7.4) supplemented with 0.2% BSA (no serum); final vehicle concentration is $\leq 0.5\%$.

Plate Preparation

Human recombinant osteopontin (prepared as described in Stubbs, J. III, Connective Tissue Research, (1996) 35, (1–4), 393–399) was diluted to an appropriate concentration in Dulbecco's phosphate buffered saline (D-PBS) without calcium or magnesium, pH 7.1. 100 µL of this solution was incubated in the wells of PRO-BIND assay plates (Falcon 3915) for 2 hours at 37° C. Following incubation the wells were aspirated and washed once with D-PBS; plates can either be used immediately or stored for up to 1 week at 4° C. Prior to assay, the wells were blocked with 1% bovine serum albumin (BSA) in cell suspension media for 1 hour at 37° C. Following the blocking period, wells were aspirated and washed once with D-PBS.

Cell Suspension $\alpha_v\beta_3$-expressing cell lines are maintained by standard tissue culture techniques. For assay, the cell monolayer was washed three times with D-PBS, and the cells were harvested with 0.05% trypsin/0.53 mM EDTA (GIBCO). The cells were pelleted by low-speed centrifugation and washed three times with 0.5 mg/mL trypsin inhibitor in D-PBS (Sigma). The final cell pellet was resuspended in cell suspension media at a concentration of $10^6$ cells/mL.

Attachment Assay

Incubation: 100 μL of diluted test compound was added to osteopontin-coated wells (in triplicate) followed by 100 μL of cell suspension; background cell attachment was determined in uncoated wells. The plate was incubated at 25° C. in a humidified air atmosphere for 1.5 hours. Following the incubation period, the wells were gently aspirated and washed once with D-PBS.

Cell Number Detection: The number of cells attached was determined by an MFT dye conversion assay (Promega) according to the manufacturer's instructions. Briefly, MTT dye was diluted in cell suspension media (15:85) and 100 μL was added to each well. The assay plates were incubated for 4 hours at 37° C. in a humidified 5% $CO_2$/95% air atmosphere, followed by the addition of 100 μL stopping/solubilization solution. The assay plates were covered and incubated at 37° C. in a humidified air atmosphere overnight. After the solubilization period, the optical density of the wells was measured at a test wavelength of 570 nM with a reference measurement taken simultaneously at 630 nM.

Analysis of Results

The individual well optical density was expressed as a percentage of the maximal attachment (% Max) wells minus background attachment, and reported as the mean±standard deviation. Dose-inhibition relationships were generated for dose (X-axis) vs. % Max (Y-axis) for active compounds using a non-linear regression computer program (PS-NONLIN), and $IC_{50}$ values with corresponding 95% confidence intervals were estimated from 50% of maximal attachment. Reference Compounds Various Arginine-Glycine-Aspartic Acid (RGD)-containing peptides, and monoclonal antibodies were assessed for the ability to inhibit osteopontin-$\alpha_v\beta_3$ attachment and the corresponding $IC_{50}$ values with 95% confidence intervals were generated in the SK-MEL-24 human malignant melanoma cell line; peptide structures are given by the standard single letter designation for amino acids:

| Peptide | $IC_{50}$ (95% Confidence Interval) |
|---|---|
| GPenGRGDSPCA | 0.58 μM (0.51 TO 0.67) |
| n-Me-GRGDSP | 4.0 μM (3.4 TO 4.7) |
| GRGDSP | 4.1 μM (3.4 TO 4.9) |
| GRGDTP | 5.2 μM (3.4 TO 4.9) |

| Antibody | Dilution | % Maximal Attachment (mean ± SD) |
|---|---|---|
| $\alpha_v\beta_5$ (P1F6) | 1:1000 | 111 ± 3.3 |
|  | 1:100 | 112 ± 2.6 |
|  | 1.10 | 111 ± 3.3 |
| $\alpha_v\beta_3$ (LM609) | 1:1000 | 0 |
|  | 1:100 | 5.1 ± 1.7 |

LITERATURE REFERENCES

Ruoslahti, R. Fibronectin and its receptors. Ann. Rev. Biochem. 57:375–413, 1988.

Hynes, R. O. Integrins: Versatility, modulation, and signaling in cell adhesion. Cell. 69:11–25,1992.

The results of this test procedure on representative compounds of this invention are shown in Table I.

TABLE I

Vitronectin Receptor ($\alpha_v\beta_3$) Binding And Measurement Of The Effect Of Compounds On Integrin ($\alpha_v\beta_3$)-Mediated Attachment Of Cells To Osteopontin

| EXAMPLE NO. | ($\alpha_v\beta_3$)—($IC_{50}$) RECEPTOR BINDING | ($\alpha_v\beta_3$)—($IC_{50}$) CELL ATTACHMENT |
|---|---|---|
| 31 | 88% @ 30 μM | 100% @ 100 μM |
| 37 | 2.9 μM | 8.9 μM |
| 40 | 130% @ 30 μM | 47 μM |
| 61 | 1.7 μM | 62.2 μM |
| 62 | 1.4 μM | 14 μM |
| 63 | 3.9 μM | 32.8 μM |
| 84 | 11.4 μM | 24.5 μM |
| 85 | 15.7 μM | 111.4 μM |
| 86 | 7.3 μM | 21.1 μM |
| 100 | 30.9% @ 100 μM | 79 μM |
| 101 | 8.9 μM | 11.5 μM |
| 112 | 7.0 μM | 19.7 μM |
| 113 | 4.0 μM | 17.8 μM |
| 121 | 2.6 μM | 15.1 μM |
| 122 | 3.6 μM | 8.3 μM |
| 149 |  | 71.5% @ 100 μM |
|  |  | 96.3% @ 20 μM |
| 172 | 2.7 μM | 27.3 μM |
| 184 | 67.5% @ 30 μM | 85% @ 100 μM |
|  |  | 108% @ 20 μM |
| 185 |  | 96.8% @ 100 μM |
|  |  | 102% @ 20 μM |
| 186 |  | 68.9% @ 100 μM |
|  |  | 113% @ 20 μM |
| 200 | 31.4% @ 100 μM | 145 μM |
| 201 | 5.8 μM | 25.4 μM |
| 202 | 50% @ 30 μM | 86 μM |
| 212 | 98.7% @ 3 μM |  |
|  | 98.3% @ 10 μM |  |
|  | 101.6% @ 30 μM |  |
|  | 99.3% @ 100 μM |  |
| 213 | 54% @ 100 μM |  |
| 214 | 0.42 μM | 0.479 μM |
| 215 | 2[a] μM | 37.4 μM |
| 216 | 60 μM |  |
| 217 | 14.651[b] μM |  |
| 222 |  | 100% @ 100 μM |
| 223 | 100% @ 30 μM | 104% @ 20 μM |
|  |  | 108% @ 100 μM |
| 224 | 100% @ 30 μM | 100% @ 20 μM |
| 228 | 57% @ 30 μM | 88% @ 100 μM |
| 229 | 100% @ 30 μM | 82% @ 100 μM |
| 230 |  | 100% @ 100 μM |
| 231 | 55.9% @ 30 μM | 93% @ 100 μM |
| 232 | 75.3% @ 30 μM | 97% @ 100 μM |
| 234 | 100% @ 30 μM | 85% @ 100 μM |
| 235 | 100% @ 30 μM | 91% @ 100 μM |
| 237 | 100% @ 30 μM | 114% @ 100 μM |
|  |  | 86.2% @ 20 μM |
| 238 | 100% @ 30 μM | 97.9% @ 100 μM |
|  |  | 102% @ 20 μM |
| 239 | 70% @ 30 μM | 67.5% @ 100 μM |
|  |  | 99.7% @ 20 μM |
| 246 |  | 84.2% @ 100 μM |
|  |  | 102% @ 20 μM |
| 248 | 1.53 mM |  |
| 250 | 102% @ 30 μM | 89% @ 100 μM |
|  |  | 90% @ 10 82 M |

[a]Average of two determinations.
[b]Trifluoroacetic acid salt.

Osteoclast Bone Pitting

The test procedure was conducted as described by R. J. Murrills and D. W. Dempster, Bone, 11, 333–344(1990). Briefly, 4×4×0.2 mm slices of devitalized bovine cortical bone were numbered, placed in the wells of 96-well culture plates and wetted with 100 ul of Medium 199 containing Hanks salts, 10 mM HEPES, pH 7.0 (Medium 199/Hanks). Bone cell suspensions containing osteoclasts were prepared by mincing the long bones of neonatal rats (Sprague- Dawley, 4–6 days old) in Medium 199/Hanks. 100 uL of the suspension were then plated onto each slice and incubated 30 minutes to allow osteoclasts to adhere. The slices were rinsed to remove non-adherent cells and incubated 24 h in Medium 199 containing Earle's salts, 10 mM HEPES and 0.7 g/L NaHCO3, which equilibrates at pH 6.9 in a 5% CO2 atmosphere. At this pH the adherent osteoclasts excavate an adequate number of resorption pits for assay purposes. Slices were fixed in 2.5% glutaraldehyde and osteoclasts counted following tartrate-resistant acid phosphatase staining. In experiments in which osteoclast numbers were significantly reduced in a particular treatment, a check is made for non-specific cytotoxicity by counting the number of contaminant fibroblast-like cells following toluidine staining. All cells were stripped from the slice by sonication on 0.25M NH4OH and the resorption pits formed by the osteoclasts during the experiment stained with toluidine blue. Resorption pits were quantified by manually counting.

Statistics

The experiments were conducted according to a block design with osteoclasts from each animal exposed to each treatment. Three replicate slices were used per treatment per animal, such that a total of 96 slices were examined for an experiment involving four animals and eight treatments (including control). Several parameters were recorded on a "per slice" basis: number of pits, number of osteoclasts, number of pits per osteoclast, number of fibroblast-like bone cells. SAS or JMP statistical software were used for statistical analysis. If analysis of variance reveals significant effects in the experiment, those treatments differing significantly from control were identified using Dunnett's test. IC50s were calculated using dose-response curves.

Reference Compound: Rat Calcitonin

Clinical Relevance

Osteoclasts are responsible for the bone loss that occurs at the onset of osteoporosis and anti-resorptive drugs directed against the osteoclast are a requirement for patients losing bone. Calcitonin and bisphosphonates, both used as anti-resorptives in the clinic, show significant osteoclast inhibitory activity in this test procedure. Hence it is a reasonable test procedure in which to identify novel anti-resorptives.

The results of this test procedure on representative compounds of this invention is shown in Table II.

TABLE II

OSTEOCLAST BONE PITTING TEST PROCEDURE

| EXAMPLE NO. | BONE PITTING INHIBITION |
|---|---|
| 37 | 30% @ 238 $\mu$M |
| 40 | 39% @ 238 $\mu$M |
| 61 | 32% @ 271 $\mu$M |
| 84 | 57% @ 223 $\mu$M |
| 85 | 33% @ 273 $\mu$M |
| 86 | 70% @ 280 $\mu$M |
| 100 | 38% @ 264 $\mu$M |
| 101 | 51% @ 221 $\mu$M |
| 121 | 30% @ 228 $\mu$M |
| 122 | IC$_{50}$ = 159 $\mu$M |
| 158 | 13% @ 216 $\mu$M |
| 172 | 15% @ 190 $\mu$M |
| 184 | 37% @ 271 $\mu$M |
| 185 | 58% @ 239 $\mu$M |
| 186 | 2% @ 228 $\mu$M |
|  | 6% @ 228 $\mu$M |
|  | 23% @ 228 $\mu$M |
| 200 | 20% @ 254 $\mu$M |
| 201 | 45% @ 256 $\mu$M |
| 202 | 37% @ 240 $\mu$M |
| 214 | 19% @ 19 $\mu$M |

TABLE II-continued

OSTEOCLAST BONE PITTING TEST PROCEDURE

| EXAMPLE NO. | BONE PITTING INHIBITION |
|---|---|
| 215 | 90% @ 200 $\mu$M |
| 216 | 95% @ 200 $\mu$M |
| 217 | 51% @ 1 $\mu$M |
| 222 | -58% @ 22 $\mu$M |
| 223 | -72% @ 226 $\mu$M |
| 224 | -62% @ 216 $\mu$M |
| 228 | 7% @ 230 $\mu$M |
| 229 | 2% @ 214 $\mu$M |
| 230 | 15% @ 230 $\mu$M |
| 231 | -34% and -51% @ 230 $\mu$M |
| 232 | -70% @ 216 $\mu$M |
| 234 | 8% @ 230 $\mu$M |
| 235 | -50% @ 221 $\mu$M |
| 237 | -21% @ 222 $\mu$M |
|  | -71% @ 222 $\mu$M |
| 238 | -20% @ 215 $\mu$M |
| 239 | 33% @ 19.1 $\mu$M |
| 246 | 52% @ 26.2 $\mu$M |
| 250 | -5% @ 215 $\mu$M |

Effects of Test Compounds on PTH-induced Hypercalcemia of Thyro-parahyroidectomized Male Rats.

Male thyro-parathyroidectomized (TPTX) rats (Charles River) were randomly assigned to groups of 7 rats/group. Following a baseline serum calcium determination an Alzet 1003D minipump (Alza Corporation, Palo Alto, Calif.) loaded with 0.3 mg/ml PTH (Bachem, Philadelphia, Pa.) was implanted subcutaneously in each rat. For evaluation of prophylactic effects of a test drug, another minipump with appropriate concentration of the test drug solution was implanted subcutaneously at a site away from PTH minipump or implanted as a pellet of the test compound away from the PTH minipump. Alternatively, test drugs were administered by oral gavage as a solution or uniform suspension in an appropriate medium depending on the physical properties of the test compound. A group of 7 unimplanted TPTX rats was set aside as a normal control group. Twenty hours after minipump implantation blood was collected from each rat to confirm the presence of hypercalcemia (udged by elevation of serum calcium levels, 2 SD>normal non-implanted level). At various intervals between 0.5 and 24 hours after dosing (usually one to three time points), blood was collected from each rat and the serum evaluated for total calcium. Serum calcium levels were measured using the Nova 7+7 calcium auto analyzer spectrophotometrically using the Sigma test kit (#587A). Test results were determined by the difference in serum calcium between vehicle and treatment group following PTH administration, using a oneway analysis of variance with Dunnett's test or other multiple comparison methods and are displayed in Tables III–V.

REFERENCES

1. Takeuchi M, Sakamoto S, Kawamuki K, Kudo M, Abe T, Fujita S, Murase K, and Isomura Y, (1990). Synthesis and structure activity relationship of new bisphosphonate derivative. Abstract #53, 199th American Chemical Society Meeting, Boston, Mass.
2. Fisher J, Caulfield M, Sato M, Quartuccio H, Gould R, Garsky V, Rodan G, Rosenblatt M, (1993). Inhibition of osteoclastic bone resorption in vivo by echistatin, an "arginyl-glycyl-aspartyl" (RGD)-containing protein. Endocrinology, Vol. 132 (3) 1411–1413.

TABLE III

Representative In Vivo Biological Data (TPTX rat)

| Ex. No. | Dose | Change in Serum Calcium (mg/dL) |
|---|---|---|
| Vehicle | | 2.20 ± 0.26* |
| Cyclo(-Arg-Gly-Asp-D-Phe-Val)[a] | 100 mg/kg · sc | −0.90 + 0.28 |
| 216 | 100 mg/kg, po | 0.64 _ 0.27* |

[a] p < 0.01 when compared to vehicle control
[a] M. Gurrath et al., Eur. J. Biochem. 210, 911–921 (1992)

TABLE IV

Effects of Echistatin on Serum Calcium in TPTX Male Rats

| Treatment[a] | N | Change in Serum Calcium[b] |
|---|---|---|
| Normal Controls | 6 | 0.58 + 0.11 |
| TPTX | | |
| TPTX Controls | 7 | −0.19 + 0.17 |
| with rat PTH (1–34) 0.15 (g/kg/hr, s.c. | | |
| Example 37 100 mg/kg, s.c. pellet | 6 | 1.57* + 0.06 |
| Cyclo(-Arg-Gly-Asp-D-Phe-Val)[c] 100 mg/kg s.c. pellet | 8 | 1.63* + 0.33 |
| Salmon Calcitonin 5 IU/rat, s.c. | 7 | 0.37** + 0.20 |
| Placebo | 8 | 2.58 + 0.26 |

[a] TPTX surgery was perfomed on male rats who were placed on deionized water and a low calcium diet. Baseline blood samples were collected and Alzet 2001 osmotic micropumps delivering PTH (1–34) at a rate of 0.15 (g/kg/hr were implanted. Sustained release pellets delivering compounds at 100 mg/kg/day were simultaneously implanted into the respective treatment group. Salmon calcitonin was dosed and the salmon calcitonin group bled exactly 1.5 hours after dosing.
[b] Mean (9 mg/dl) + SEM
*p < 0.05 vs TPTX + PTH + placebo
**p < 0.01 vs TPTX + PTH + placebo
[c] M. Gurrath et al., Eur. J. Biochem. 210, 911–921 (1992)

TABLE V

Effects of Compounds on Serum Calcium in TPTX Male Rats Treated with rPTH (1–34)

| Treatment[c] | N | Change in Serum Calcium after 3 hours[d] | N | Change in Serum Calcium after 6 hours[d] |
|---|---|---|---|---|
| Example 37 100 mg/kg, s.c. | 6 | 1.72 ± 0.38 | 6 | 2.22 ± 0.31 |
| Cyclo(-Arg-Gly-Asp-D-Phe-Val)[e] | 7 | 0.69 ± 0.28 | 7 | 1.20* ± 0.26 |
| Vehicle corn oil, s.c. | 7 | 1.26 ± 0.18 | 7 | 2.13 ± 0.21 |
| Example 37 100 mg/kg, s.c. | 9 | 0.97 ± 0.20 | 8 | 2.21 ± 0.18 |
| Cyclo(-Arg-Gly-Asp-D-Phe-Val)[e] | 10 | 0.58** ± 0.28 | 10 | 1.44* ± 0.35 |
| Vehicle corn oil, s.c. | 9 | 1.70 ± 0.25 | 10 | 2.33 ± 0.39 |
| Example 37 100 mg/kg, s.c. | 8 | 0.95 ± | 8 | 1.80 ± |
| Cyclo(-Arg-Gly-Asp-D-Phe-Val)[e] | 8 | 0.01** ± 0.28 | 8 | 0.63 ± 0.33 |
| Vehicle corn oil, s.c. | 6 | 1.17 ± 0.19 | 7 | 1.47 ± 0.23 |
| Example 37 100 mg/kg, s.c. | 7 | 1.31 ± 0.10 | 7 | 1.63 ± 0.13 |
| Cyclo(-Arg-Gly-Asp-D-Phe-Val)[e] | 7 | 0.51** ± 0.16 | 7 | 1.07 ± 0.28 |
| Vehicle corn oil, s.c. | 6 | 1.37 ± 0.11 | 6 | 1.67 ± 0.17 |

Also in this table, just before the second "Cyclo(-Arg-...)" block:
"100 mg/kg, s.c. 0.20 0.44" (for the 100 mg/kg, s.c. row following Example 37)

[c] All animals were treated with rPTH (1–34), 0.45 μg/kg/hr, by Alzet 1003D osmotic micropumps
[d] Mean (mg/dl) ± SEM
*p < 0.05 vs corresponding Vehicle value
**p < 0.01 vs corresponding Vehicle value
[e] M. Gurrath et al. Eur. J. Biochem. 210, 911–921 (1992)

Measurement of the Effect of Compounds on ADP-Induced Platelet Aggregation

Measuring the effect of compounds on ADP-induced platelet aggregation mediated by a fibrinogen-$\alpha_{IIb}\beta_3$ integrin interaction.

Test Procedure

Human Platelets: Platelet-enriched plasma was obtained commercially from a donor pool. The plasma was tested prior to shipment and found to be negative for HIV, HCV and Hepatitis B. Platelet-rich plasma (PRP) was obtained by diluting plasma to an approximate final concentration of 3×10(6) platelets per mL in platelet poor plasma (PPP). PPP was the supernatant of a lowspeed centrifugation of plasma.

Adenosine diphosphate (ADP): ADP was obtained commercially and diluted to 1 mM (stock solution) in distilled, deionized water ($ddH_2O$).

Platelet Aggregation

Incubation: PRP and PPP were prewarmed in a water bath at 37° C. The sample compounds were dissolved in an appropriate vehicle (typically DMSO) and diluted in vehicle to 100× of the testing concentration. PRP plus sample compound in a final volume of 500 uL was added to a pre-warmed cuvette in a ChronoLog aggregometer. A control containing PRP and 5 uL of vehicle was treated similarly to the test cuvette; final vehicle concentration was 1%. The two cuvettes were incubated with stirring (1000 rpm) at 37° C. for 5 minutes. Five hundred microliters of PPP was used as a reference (100% aggregation).

Aggregation: To begin the test, ADP was added yielding a final concentration of 20 uM to both samples (plus and minus sample compound). Light transmittance was monitored continuously and compared to the reference cuvette. After five minutes, the test was terminated and the slope and maximal amplitude of the resulting aggregation plot was calculated by the aggregometer.

Analysis of Results

The percent of maximal aggregation is the ratio of the maximal aggregations of the sample cuvette to the control multiplied by 100 (% Max) and reported as the mean+−standard deviation. Dose-inhibition relationships were generated for dose (X-axis) vs. % Max (Y-axis) for active compounds using a non-linear regression computer program (PS-NONLIN) and IC50 values with corresponding 95% confidence intervals were estimated from 50% of maximal aggregation.

Reference Compounds

Known Arginine-Glycine-Aspartic Acid (RGD)-containing peptides, and snake venoms were tested for their ability to inhibit ADP induced platelet aggregation; peptide structures are given by the standard single letter designation for amino acids. Results are shown in Table VI.

TABLE VI

| Peptide | $IC_{50}$ (95% Confidence Interval) |
|---|---|
| Echistatin (Snake venom distegrin) | 15.6 nM |
| SC-47, 643 | 33 $\mu$M (18 to 51) |
| GPenGRGDSPCA | 46.3 $\mu$M (3.7 to 98.5) |
| GRGDF | 53.2 $\mu$M (31 to 78) |
| RGDF | 97.6 $\mu$M (88 to 106) |
| cyclic RGDFV | 115 $\mu$M (114 to 116) |
| n-Me-GRGDSP | 208 $\mu$M |
| GRGDSP | Inactive at 200 $\mu$M |
| GRGDTP | Inactive at 200 $\mu$M |
| GRGDNP | Inactive at 200 $\mu$M |
| GRGESP | Inactive at 200 $\mu$M |

REFERENCES

Foster M., Hornby E., Brown S., Kitchin J., Hann M. and P. Ward. Improved Potency and Specificity of ARG-GLYASP (RGD) Containing Peptides as Fibrinogen Receptor Blocking Drugs. Thromb Res 1993; 72:231–245.

Ramjit D., Lynch J., Sitko G., Mellott J., Holahan M., Stabilito I., Stranierie M., Zhang G., Lynch R., Manno P., Chang C., Nutt R., Brady S., Veber D., Anderson P., Shebuski R., Friedman P. and R. Gould. Antithrombotic Effects of MK-0852, a Platelet Fibrinogen Receptor Antagonist, in Canine Models of Thrombosis. J. Pharmacol Exp.Ther 1993; 266(3):1501–1511.

Platelet aggregation Test Results for sample compounds are displayed in Table VII.

TABLE VII

Platelet Aggregation Test Results $\alpha_{IIb}\beta_3$

| Example Number | Percent of Maximal |
|---|---|
| 31 | $IC_{50}$ = 160.15 $\mu$M |
| 37 | $IC_{50}$ = 82.4 $\mu$M |
| 40 | $IC_{50}$ = 148 $\mu$M |
| 61 | 85.33@200 $\mu$M |
| 62 | $IC_{50}$ = 169 $\mu$M |
| 63 | 51.5@200 $\mu$M |
| 84 | 62@200 $\mu$M |
| 85 | 93.3@200 $\mu$M |
| 86 | 80.9@200 $\mu$M |
| 100 | $IC_{50}$ = 216 $\mu$M |
| 101 | $IC_{50}$ = 107 $\mu$M |
| 112 | 80.4@200 $\mu$M |
| 113 | 77.1@200 $\mu$M |
| 121 | 62@200 $\mu$M |
| 122 | $IC_{50}$ = 57 $\mu$M |
| 149 | 90.2@200 $\mu$M |
| 155 | 83.7@200 $\mu$M |
| 172 | 71.5@200 $\mu$M |
| 184 | 85.5@200 $\mu$M |
| 185 | 94.8@200 $\mu$M |
| 200 | 94@200 $\mu$M |

TABLE VII-continued

Platelet Aggregation Test Results $\alpha_{IIb}\beta_3$

| Example Number | Percent of Maximal |
|---|---|
| 201 | 85@200 $\mu$M |
| 202 | $IC_{50}$ = 87 $\mu$M |
| 214 | 58@200 $\mu$M |
| 215 | $IC_{50}$ = 151 $\mu$M |
| 217 | 98@200 $\mu$M |
| 222 | 90.3@200 $\mu$M |
| 223 | $IC_{50}$ = 54 $\mu$M |
| 224 | $IC_{50}$ = 53 $\mu$M |
| 228 | 83.7@200 $\mu$M |
| 229 | $IC_{50}$ = 146 $\mu$M |
| 230 | 95.2@200 $\mu$M |
| 231 | 78.3@200 $\mu$M |
| 232 | $IC_{50}$ = 155 $\mu$M |
| 234 | 74.3@200 $\mu$M |
| 235 | 81.1@200 $\mu$M |
| 237 | 96.5@200 $\mu$M |
| 238 | 94@200 $\mu$M |
| 239 | 83.7@200 $\mu$M |
| 247 | 100%@200 $\mu$M |
| 250 | 69@200 $\mu$M |

When the compounds are employed for the above utilities, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It must be stable under conditions of manufacture and storage and must be preserved against the contaminating action of microorganisms such as bacteria and fungi. The carrier can be a solvent or dispersion medium containing, for example, water, ethanol (e.g., glycerol, propylene glycol and liquid polyethylene glycol), suitable mixtures thereof, and vegetable oil.

The compounds of Formulae (I) and (II) of this invention are useful in treating conditions in mammals characterized by bone resorption of mineralized tissue such as in osteoporosis, hypercalcemia of malignancy, osteopenia due to bone metastases, periodontal disease, hyperparathyroidism, periarticular erosions in rheumatoid arthritis, Paget's disease, immobilization-induced osteopenia or glucocorticoid treatment.

In particular, compounds of Formulae (I) and (II) of this invention are therapeutically useful in the treatment and/or prevention of osteoporosis in mammals.

The compounds of this invention and their preparation can be understood further by the following examples, but should not constitute a limitation thereof.

EXAMPLE 1

(6-Methoxy-3,4-dihydro-1H-napthalen-2-ylidene)-acetic acid ethyl ester

A solution of triethyl phosphonoacetate (14.1 g, 63.0 mmol) in tetrahydrofuran (60 mL) was treated with potassium tert-butoxide (7.1 g, 63 mmol) at room temperature. After 10 min, a solution of 6-methoxy-2-tetralone (7.4 g, 42 mmol) in tetrahydrofuran (200 mL) was added via cannula. After 2.5 h, additional potassium tert-butoxide (0.9 g, 8 mmol) was added. After 4 h, the reaction mixture was poured into water (1 L) and extracted with ethyl acetate (3×500 mL). The combined extracts were dried (MgSO$_4$) and concentrated to give a brown oil (8.6 g). Flash chromatography (330 g silica; 1%, then 2% EtOAc-hexane) gave the title compound (4.4 g, 43% yield) as a pale yellow oil.

$^1$H NMR (CDCl$_3$, 300 MHz): δ1.27 (t, J=7 Hz, 3H, CH$_2$CH$_3$), 2.32 (t, J=8 Hz, 2H, CH$_2$CH$_2$C═), 2.82 (t, J=8 Hz, 2H, CH$_2$CH$_2$C═), 3.18 (s, 2H, ArCH$_2$C═), 3.78 (s, 3H, OCH$_3$), 4.16 (q, J=7 Hz, 2H, CO$_2$CH$_2$), 6.29 (s, 1H, CH═), 6.66 (overlapping s, d, J=9 Hz, 2H, ArH), 6.93 (d, J=9 Hz, 1H, ArH).

EXAMPLE 2

(7-Methoxy-3,4-dihydro-1H-nathalen-2-ylidene)-acetic acid ethyl ester

The title compound is prepared according to the procedure of Example 1 except that 7-methoxy-2-tetralone is used in place of 6-methoxy-2-tetralone. The product is obtained as a clear colorless oil.

EXAMPLE 3

E- and Z-(2-Methoxy-5,7,8,9-tetrahydro-benzocyclohepten-6-ylidene)-acetic acid ethyl ester and (2-Methoxy-8,9-dihydro-7H-benzocycloheten-6-yl)-acetic acid ethyl ester The title compound was prepared according to the procedure of Example 1 except that 2-methoxy-5,7,8,9-tetrahydrobenzocyclohepten-6-one (S. Uemura, K. Ohe and N. Sugita, J. Chem. Soc. Perkin Trans. I, 1697, (1990) was used in place of 6-methoxy-2-tetralone.

$^1$H NMR (CDCl$_3$, 300 MHz): δ1.20–1.25 (overlapping m, 3H, total, CH$_2$CH$_3$), 1.82 and 2.02 (m, 2H total, ArCH$_2$CH$_2$), 2.36, 2.44 and 3.07 (t, J=6.5 Hz, 3H total, CH$_2$CH$_2$C═), 2.75–2.85 (overlapping m, 2H total, ArCH$_2$CH$_2$), 3.14, 3.46 and 4.02 (s, 2H total, ArCH$_2$C═, ═CCH$_2$CO$_2$), 3.76 and 3.78 (s, 3H total, OCH$_3$), 4.06–4.20 (overlapping m, 2H total, CO$_2$CH$_2$), 5.63, 5.71, and 6.33 (s, 1H total, CH═), 6.65–6.71 (overlapping m, 2H total, ArH), 7.00–7.08, and 7.34 (overlapping m, d, 1H total, ArH).

EXAMPLE 4

E- and Z-(3-Methoxy-5,7,8,9-tetrahydro-benzocyclohepten-6-ylidene)-acetic acid ethyl ester and (3-Methoxy-8,9-dihydro-7H-benzocyclohepten-6-yl)-acetic acid ethyl ester The title compound is prepared according to the procedure of Example 1 except that 3-methoxy-5,7,8,9-tetrahydrobenzocyclohepten-6-one (G. Pandey, K. K. Girija and M. Karthikeyan, Tet. Letters 34 (41) 6631 (1993)) is used in place of 6-methoxy-2-tetralone.

EXAMPLE 5

(6-Methoxy-1,2,3,4-tetrahydro-napthalen-2-yl)-acetic acid ethyl ester

A solution of (6-methoxy-3,4-dihydro-1H-napthalen-2-ylidene)-acetic acid ethyl ester (4.4 g, 18 mmol) in ethyl acetate (35 mL) was hydrogenated over 10% Pd—C (0.9 g) at 50 psi and left overnight. The reaction mixture was filtered through diatomaceous earth and washed with ethyl acetate (200 mL). The filtrate was concentrated to give the title compound (4.0 g, 91% yield) as a clear, colorless oil.

$^1$H NMR (CDCl$_3$, 300 MHz): δ1.27 (t, J=7 Hz, 3H, CH$_2$CH$_3$), 1.46 (m, 1H, ArCHHCHH), 1.95 (m, 1H, ArCHHCH H), 2.25 (m, 1H, CH), 2.34–2.47 (overlapping m, d, J=7 Hz, 3H, ArCHHCH, CHHCO$_2$), 2.79–2.87 (overlapping m, 3H, ArCHHCHH, ArCHHCH), 3.77 (s, 3H, OCH$_3$), 4.16 (q, J=7 Hz, 2H, CO$_2$CH$_2$), 6.62 (d, J=2.5 Hz, 1H, ArH), 6.68 (dd, J=2.5 Hz, 8.5 Hz, 1H, ArH), 6.96 (d, J=8.5 Hz, 1H, ArH).

EXAMPLE 6

(7-Methoxy-1,2,3,4-tetrahydro-napthalen-2-yl)-acetic acid ethyl ester

The title compound is prepared according to the procedure of Example 5 except that (7-methoxy-3,4-dihydro-napthalen-2-ylidene)-acetic acid ethyl ester is used in place of (6-methoxy-3,4-dihydro-napthalen-2-ylidene)-acetic acid ethyl ester. The product is obtained as a clear colorless oil.

EXAMPLE 7

(2-Methoxy-6,7,8,9-tetrahydro-5H-benzocycloheten-6-yl)-acetic acid ethyl ester

The title compound was prepared according to the procedure of Example 5 except that E- and Z-(2-methoxy-5,7, 8,9-tetrahydro-benzocyclohepten-6-ylidene)-acetic acid ethyl ester and (2-methoxy-8,9-dihydro-7H-benzocyclohepten-6-yl)-acetic acid ethyl ester is used in place of (6-methoxy-3,4-dihydro-1H-napthalen-2-ylidene)-acetic acid ethyl ester. $^1$H NMR (CDCl$_3$, 300 MHz): δ1.26 (t, J=7 Hz, 3H, CH$_2$CH$_3$), 1.45–1.63 (m, 2H, CHCHHCHH), 1.74–1.95 (overlapping m, 2H, CHCHHCHH), 2.00–2.27 (overlapping m, 3H, CHCHHCO$_2$), 2.73 (m, 4H, ArCHH), 3.77 (s, 3H, OCH$_3$), 4.14 (q, J=7 Hz, 2H, CO$_2$CH$_2$), 6.61 (dd, J=2.5 Hz, 8 Hz, 1H, ArH), 6.66 (d, J=2.5 Hz, 1H, ArH), 6.97 (d, J=8 Hz, 1H, ArH).

EXAMPLE 8

(3-Methoxy-6,7,8,9-tetrahydro-5H-benzocyclohepten-6-yl)-acetic acid ethyl ester

The title compound is prepared according to the procedure of Example 5 except that E- and Z-(3-methoxy-5,7,8,9-tetrahydro-benzocyclohepten-6-ylidene)-acetic acid ethyl ester and (3-methoxy-8,9-dihydro-7H-benzocyclo-hepten-6-yl)-acetic acid ethyl ester is used in place of (6-methoxy-3,4-dihydro-1H-napthalen-2-ylidene)-acetic acid ethyl ester.

EXAMPLE 9

(6-Hydroxy-1,2,3,4-tetrahydro-napthalen-2-yl)-acetic acid ethyl ester

A solution of (6-methoxy-1,2,3,4-tetrahydro-napthalen-2-yl)-acetic acid ethyl ester (2.0 g, 8.1 mmol) in methylene chloride (8 mL) was treated with 1.0 M BBr3—CH$_2$Cl$_2$ solution (40 mL, 40 mmol) at 0° C. in an oven-dried flask. After 1 h, the resulting mixture was concentrated in vacuo and the residue treated with ice-cold ethanol and concentrated. Ethanol treatment and concentration was repeated twice more to give a syrup which was partitioned between saturated sodium bicarbonate and methylene chloride. The organic layer was separated and dried(MgSO$_4$) and concentrated in vacuo to give 1.7 g of a brown syrup. Chromatography (60 g silica; 5–20% ethyl acetate-hexane afforded the title compound (1.1 g) as a pale yellow oil which slowly crystallized.

$^1$H NMR (CDCl$_3$, 300 MHz): δ1.28 (t, J=7 Hz, 3H, CH$_3$), 1.44 (m, 1H, ArCHHCHH), 1.92 (m, 1H, ArCHHCHH), 2.23 (m, 1H, CH), 2.35–2.44 (overlapping m, d, J=7 Hz, 3H, ArCHHCH, CHHCO$_2$), 2.74–2.84 (overlapping m, 3H, ArCHHCHH, ArCHHCH), 4.17 (q, J=7 Hz, 2H, CO$_2$CH$_2$), 4.60–5.40 (broad, 1H, ArOH), 6.55–6.62 (overlapping m, 2H, ArH), 6.90 (d, J=8 Hz, 1H, ArH).

EXAMPLE 10

(7-Hydroxy-1,2,3,4-tetrahydro-napthalen-2-yl)-acetic acid ethyl ester

The title compound was prepared according to the procedure of Example 9 except that (7-methoxy-1,2,3,4-tetrahydro-napthalen-2-yl)-acetic acid ethyl ester was used in place of (6-methoxy-1,2,3,4-tetrahydro-napthalen-2-yl)-acetic acid ethyl ester. The crude brown oil was purified by flash chromatography on silica gel by elution with 0.25% methyl alcohol-ammonia/chloroform affording the title compound (1.9 g) as an amber syrup.

EXAMPLE 11

(2-Hydroxy-6,7,8,9-tetrahydro-5H-benzocyclohepten-6-yl)-acetic acid ethyl ester

The title compound was prepared according to the procedure of Example 9 except that (2-methoxy-6,7,8,9-tetrahydro-5H-benzocyclohepten-6-yl)-acetic acid ethyl ester is used in place of (6-methoxy-3,4-dihydro-1H-napthalen-2-yl)-acetic acid ethyl ester.

$^1$H NMR (CDCl$_3$, 300 MHz): δ1.26 (t, J=7 Hz, 3H, CH$_3$), 1.47–1.62 (m, 2H, CHCHHCHH), 1.75–1.95 (overlapping m, 2H, CHCHHCHH), 2.00–2.30 (overlapping m, 3H, CH, CHHCO$_2$), 2.69 (m, 4H, ArCHH), 4.15 (q, J=7 Hz, 2H, CO$_2$CH$_2$), 4.88 (s, 1H, ArOH), 6.54 (dd, J=2.5 Hz, 8 Hz, 1H, ArH), 6.59 (d, J=2.5 Hz, 1H, ArH), 6.89 (d, J=8 Hz, 1H, ArH).

EXAMPLE 12

(3-Hydroxy-6,7,8,9-tetrahydro-5H-benzocycloheten-6-yl)-acetic acid ethyl ester

The title compound is prepared according to the procedure of Example 9 except that (3-methoxy-6,7,8,9-tetrahydro-5H-benzocyclohepten-6-yl)-acetic acid ethyl ester is used in place of (6-methoxy-3,4-dihydro-1H-napthalene-2-yl)-acetic acid ethyl ester.

EXAMPLE 13

(2-Hydroxy-ethyl)-carbamic acid tert-butyl ester

A solution of 2-amino-ethan-1-ol (11.8 mL, 195 mmol) in 2:1 tert-butanol-water (330 mL) was treated with di-tert-butyl dicarbonate (40.8 g, 187 mmol) and potassium carbonate (51.5 g, 373 mmol) at 0° C. After 5–10 min when vigorous bubbling had subsided, the reaction slurry was warmed to room temperature. After 1.5 h, the mixture was concentrated to a wet paste and diluted with water (50 mL). The aqueous phase was extracted with ethyl acetate (3×150 mL), dried (K$_2$CO$_3$) and concentrated to give the title compound (29.4 g, 98% yield) as a pale yellow oil.

1H NMR (DMSO-d$_6$, 300 MHz): δ1.35 (s, 9H, CH$_3$), 2.96 (m, 2H, NCH$_2$), 3.34 (m, 2H, OCH$_2$), 4.55 (m, 1H, OH), 6.66 (m, 1H, NH).

EXAMPLE 14

(3-Hydroxy-propyl)-carbamic acid tert-butyl ester

The title compound is prepared according to the procedure of Example 13 except that 3-amino-1-propanol is used in place of 2-amino-ethan-1-ol.

EXAMPLE 15

(4-Hydroxy-butyl)-carbamic acid tert-butyl ester

The title compound is prepared according to the procedure of Example 13 except that 4-amino-1-butanol is used in place of 2-amino-ethan-1-ol.

EXAMPLE 16

(2-Bromo-ethyl)-carbamic acid tert-butyl ester

A solution of triphenylphosphine (38.1 g, 145 mol) in 3:2 ether-methylene chloride (300 mL) was treated portionwise with carbon tetrabromide (48.2 g, 145 mmol). After 10 min, (2-hydroxy-ethyl)-carbamic acid tert-butyl ester (15.6 g, 96.8 mmol) was added via pipet and the mixture stirred under nitrogen. After 24 h, the reaction mixture was vacuum filtered, washed with ether and the filtrate concentrated to give an orange oil (39.6 g). Flash chromatography (600 g silica; CH$_2$Cl$_2$, then 1%, 2% and 4% MeOH—CH$_2$Cl$_2$) gave the title compound (5.1 g, 40% yield based on recovered (2-hydroxy-ethyl)-carbamic acid tert-butyl ester, 6.3 g) as a clear, colorless oil.

$^1$H NMR (DMSO-d$_6$, 300 MHz): δ1.37 (s, 9H, CH$_3$), 3.28 (m, 2H, NCH$_2$), 3.41 (t, J=6.5 Hz, 2H, CH$_2$Br), 7.09 (broad m, 1H, NH).

EXAMPLE 17

(3-Bromo-propyl)-carbamic acid tert-butyl ester

The title compound is prepared according to the procedure of Example 16 except that 3-amino-1-propanol is used in place of 2-amino-ethan-1-ol.

EXAMPLE 18

(4-Bromo-butyl)-carbamic acid tert-butyl ester

The title compound is prepared according to the procedure of Example 16 except that 4-amino-1-butanol is used in place of 2-amino-ethan-1-ol.

EXAMPLE 19

[7-(3-tertbutoxycarbonylamino-propoxy)-1,2,3,4-tetrahydro-napthalen-2-yl]-acetic acid ethyl ester A solution of (7-hydroxy-1,2,3,4-tetrahydro-napthalen-2-yl)-acetic acid ethyl ester (2.5 g, 10.7 mmol) in N,N-dimethylformamide (16 mL) was treated with a solution of sodium ethoxide (21 wt %) in ethanol (4.0 mL, 10.7 mmol) at 25° C. and after 10 min, (3-bromo-propyl)-carbamic acid tert-butyl ester (2.5 g, 10.5 mmol) was added. After 4 days, the solution was treated with 0.1N ammonium chloride (200 mL) and extracted with ether(3×200 ml). The combined extracts were washed with 5% sodium bicarbonate (200 ml) followed by water(5×200 ml). The organic layer was dried (MgSO$_4$) and evaporated in vacuo to give 4.0 g of a clear amber oil. Flash chromatography (200 g silica; CH$_2$Cl$_2$, then 0.5% MeOH (saturated with NH$_3$)—CH$_2$Cl$_2$) afforded the title compound (2.6 g, 63% yield) as a clear colorless oil.

EXAMPLE 20

[7-(2-tertbutoxycarbonylamino-ethoxy)-1,2,3,4-tetrahydro-napthalen-2-yl]-acetic acid ethyl ester The title compound is prepared according to the procedure of Example 19 except that (2-bromo-ethyl)-carbamic acid tert-butyl ester is used in place of (3-bromo-propyl)-carbamic acid tert-butyl ester.

EXAMPLE 21

[7-(4-tertbutoxycarbonylamino-butoxy)-1,2,3,4-tetrahydro-napthalen-2-yl]-acetic acid ethyl ester The title compound is prepared according to the procedure of Example 19 except that (4-bromo-butyl)-carbamic acid tert-butyl ester is used in place of (3-bromo-propyl)-carbamic acid tert-butyl ester.

EXAMPLE 22

[6-(3-tertbutoxycarbonylamino-propoxy)-1,2,3,4-tetrahydro-napthalen-2-yl]-acetic acid ethyl ester The title compound is prepared according to the procedure of Example 19 except that and (6-hydroxy-1,2,3,4-tetrahydro-napthalen-2-yl)-acetic acid ethyl ester is used in place of (7-hydroxy-1,2,3,4-tetrahydro-napthalen-2-yl)-acetic acid ethyl ester. The product is a clear oil.

EXAMPLE 23

[6-(2-tertbutoxycarbonylamino-ethoxy)-1,2,3,4-tetrahydro-napthalen-2-yl]-acetic acid ethyl ester The title compound is prepared according to the procedure of Example 19 except that (2-bromo-ethyl)-carbamic acid tert-butyl ester is used in place of (3-bromo-propyl)-carbamic acid tert-butyl ester and (6-hydroxy-1,2,3,4-tetrahydro-napthalen-2-yl)-acetic acid ethyl ester is used in place of (7-hydroxy-1,2,3,4-tetrahydro-napthalen-2-yl)-acetic acid ethyl ester.

EXAMPLE 24

[6-(4-tertbutoxycarbonylamino-butoxy)-1,2,3,4-tetrahydro-nanthalen-2-yl]-acetic acid ethyl ester The title compound is prepared according to the procedure of Example 19 except that (4-bromo-butyl)-carbamic acid tert-butyl ester is used in place of (3-bromo-propyl)-carbamic acid tert-butyl ester and (6-hydroxy-1,2,3,4-tetrahydro-napthalen-2-yl)-acetic acid ethyl ester is used in place of (7-hydroxy-1,2,3,4-tetrahydro-napthalen-2-yl)-acetic acid ethyl ester.

EXAMPLE 25

[6-(3-Amino-propoxy)-1,2,3,4-tetrahydro-napthalen-2-yl]-acetic acid ethyl ester trifluoroacetate

[6-(3-tertbutoxycarbonylamino-propoxy)-1,2,3,4-tetrahydro-napthalen-2-yl]-acetic acid ethyl ester (1.3 g, 3.3 mmol) and trifluoroacetic acid (2.6 mL) were combined in methylene chloride (25 mL) at 25° C. After 18 h, the solution was concentrated in vacuo to give a sticky solid which is triturated with ether (100 mL) for 45 minutes to give the trifluoroacetate salt of the title compound (1.2 g) as a white powder.

EXAMPLE 26

[6-(3-Amino-ethoxy)-1,2,3,4-tetrahydro-napthalen-2-yl]-acetic acid ethyl ester trifluoroacetate The title compound is prepared according to the procedure of Example 25 except that [6-(2-tertbutoxycarbonylamino-ethoxy)-1,2,3,4-tetrahydro-napthalen-2-yl]-acetic acid ethyl ester is used in place of [6-(3-tertbutoxycarbonylamino-propoxy)-1,2,3,4-tetrahydro-napthalen-2-yl]-acetic acid ethyl ester.

EXAMPLE 27

[6-(4-Amino-butoxy)-1,2,3,4-tetrahydro-napthalen-2-yl]-acetic acid ethyl ester trifluoroacetate The title compound is prepared according to the procedure of Example 25 except that [6-(4-tertbutoxycarbonylamino-butoxy)-1,2,3,4-tetrahydro-napthalen-2-yl]-acetic acid ethyl ester is used in place of [6-(3-tertbutoxycarbonylamino-propoxy)-1,2,3,4-tetrahydro-napthalen-2-yl]-acetic acid ethyl ester.

EXAMPLE 28

[7-(3-Amino-propoxy)-1,2,3,4-tetrahydro-napthalen-2-yl]-acetic acid ethyl ester trifluoroacetate The title compound is prepared according to the procedure of Example 25 except that [7-(3- tertbutoxycarbonylamino-propoxy)-1,2,3,4-tetrahydro-napthalen-2-yl]-acetic acid ethyl ester is used in place of [6-(3-tertbutoxycarbonylamino-propoxy)-1,2,3,4-tetrahydro-napthalen-2-yl]-acetic acid ethyl ester.

EXAMPLE 29

[7-(2-Amino-ethoxy)-1,2,3,4-tetrahydro-napthalen-2-yl]-acetic acid ethyl ester trifluoroacetate The title compound is prepared according to the procedure of Example 25 except that [7-(2-tertbutoxycarbonylamino-ethoxy)-1,2,3,4-tetrahydro-napthalen-2-yl]-acetic acid ethyl ester is used in place of [6-(3-tertbutoxycarbonylamino-propoxy)-1,2,3,4-tetrahydro-napthalen-2-yl]-acetic acid ethyl ester.

EXAMPLE 30

[7-(4-Amino-butoxy)-1,2,3,4-tetrahydro-napthalen-2-yl]-acetic acid ethyl ester trifluoroacetate The title compound is prepared according to the procedure of Example 25 except that [7-(4-tertbutoxycarbonylamino-butoxy)-1,2,3,4-tetrahydro-napthalen-2-yl]-acetic acid ethyl ester is used in place of [6-(3-tertbutoxycarbonylamino-propoxy)-1,2,3,4-tetrahydro-napthalen-2-yl]-acetic acid ethyl ester.

EXAMPLE 31

[6-(3-Guanidinopropoxy)-1,2,3,4-tetrahydro-napthalen-2-yl]-acetic acid ethyl ester A suspension of [6-(3-amino-propoxy)-1,2,3,4-tetrahydro-napthalen-2-yl]-acetic acid ethyl ester trifluoroacetate salt(1.21 g, 2.98 mmol), 3,5-dimethylpyrazole carboxamidine nitrate (0.66 g, 3.28 mmol) and diisopropylethylamine (1.1 mL,6.31 mmol) in 3:1 dioxane-water (8.5 mL) was heated at reflux for 24 h. The cooled solution was concentrated in vacuo to yield 2.21 g of a viscous oil. Purification by reverse phase HPLC by elution with 5–50%-acetonitrile:0.1% trifluoroacetic acid in water afforded the title compound (0.91 g, 68%) as a clear, colorless oil.

EXAMPLE 32

[6-(2-Guanidino-ethoxy)-1,2,3,4-tetrahydro-napthalen-2-yl]-acetic acid ethyl ester The title compound is prepared according to the procedure of Example 31 except that [6-(2-amino-ethoxy)-1,2,3,4-tetrahydro-napthalen-2-yl]-acetic acid ethyl ester trifluoroacetate salt is used in place of [6-(3-amino-propoxy)-1,2,3,4-tetrahydro-napthalen-2-yl]-acetic acid ethyl ester trifluoroacetate salt.

EXAMPLE 33

[6-(4-Guanidino-butoxy)-1,2,3,4-tetrahydro-napthalen-2-yl]-acetic acid ethyl ester The title compound is prepared according to the procedure of Example 31 except that [6-(4-amino-butoxy)-1,2,3,4-tetrahydro-napthalen-2-yl]-acetic acid ethyl ester trifluoroacetate salt is used in place of [6-(3-amino-propoxy)-1,2,3,4-tetrahydro-napthalen-2-yl]-acetic acid ethyl ester trifluoroacetate salt.

EXAMPLE 34

[7-(3-Guanidinopropoxy)-1,2,3,4-tetrahydro-napthalen-2-yl]-acetic acid ethyl ester The title compound is prepared according to the procedure of Example 31 except that [7-(3-amino-propoxy)-1,2, 3,4-tetrahydro-napthalen-2-yl]-acetic acid ethyl ester trifluoroacetate salt is used in place of [6-(3-amino-propoxyy)-1,2,3,4-tetrahydro-napthalen-2-yl]-acetic acid ethyl ester trifluoroacetate salt.

EXAMPLE 35

[7-(2-Guanidino-ethoxy)-1,2,3,4-tetrahydro-napthalen-2-yl]-acetic acid ethyl ester The title compound is prepared according to the procedure of Example 31 except that [7-(2-amino-ethoxy)-1,2,3, 4-tetrahydro-napthalen-2-yl]-acetic acid ethyl ester trifluoroacetate salt is used in place of [6-(3 -amino-propoxy)-1,2,3,4-tetrahydro-napthalen-2-yl]-acetic acid ethyl ester trifluoroacetate salt.

EXAMPLE 36

[7-(4-Guanidino-butoxy)-1,2,3,4-tetrahydro-napthalen-2-yl]-acetic acid ethyl ester The title compound is prepared according to the procedure of Example 31 except that [7-(4-amino-butoxy)-1,2,3, 4-tetrahydro-napthalen-2-yl]-acetic acid ethyl ester trifluoroacetate salt is used in place of [6-(3-amino-propoxy)-1,2, 3,4-tetrahydro-napthalen-2-yl]-acetic acid ethyl ester trifluoroacetate salt.

EXAMPLE 37

[6-(3-Guanidino-propoxy)-1,2,3,4-tetrahydro-napthalen-2-yl]-acetic acid trifluoroacetate A solution of [6-(3-guanidino-propoxy)-1,2,3,4-tetrahydro-napthalen-2-yl]-acetic acid ethyl ester(0.88 g, 1.97 mmol) in 8 ml of ethyl alcohol was treated with 8.0 ml (4.0 mmol) of 0.5 N sodium hydroxide and refluxed for 30 minutes. The cooled solution was treated with 1.5 ml of trifluoroacetic acid and evaporated in vacuo. The resulting oil was dissolved in 100 ml of ethyl alcohol and concentrated in vacuo to give 1.49 g of a colorless glass which was dissolved in 5 ml of 1:1 N,N-dimethylformamide:water and chromatographed on a $C_{18}$ reverse phase column to give 0.68 g of the title compound as the trifluoroacetate salt as a white powder.

Mp. 134–36° C.

IR (KBr): 3440 (s), 3230 (m), 1708 (s), 1665 (s), 1640 (s), 1440 (m), 1190 (s), 1143 (s), 848 (m), 800 (m), 730 (m) $cm^{-1}$.

$^1$H NMR (DMSO-$d_6$, 400 MHz): δ1.36 (m, 1H, ArCHHC$\underline{H}$H), 1.84–1.92 (overlapping m, 3H, ArCHHCH$\underline{H}$, NCH$_2$C$\underline{H}_2$), 2.04 (m, 1H, C$\underline{H}$), 2.25 (d, J=7 Hz, 2H, C$\underline{HH}$CO$_2$), 2.32 (dd, J=10 Hz, 16 Hz, 1H, ArC$\underline{H}$HCH), 2.71–2.78 (overlapping m, 3H, ArC$\underline{HH}$CHH, ArCH$\underline{H}$CH), 3.25 (m, 2H, NC$\underline{H}_2$), 3.94 (t, J=6 Hz, 2H, OC$\underline{H}_2$), 6.63 (d, J=2 Hz, 1H, Ar$\underline{H}$), 6.66 (dd, J=2 Hz, 8.5 Hz, 1H, Ar$\underline{H}$), 6.70–7.50 (broad, 4H, [C(N$\underline{H}_2$)$_2$]$^+$), 6.94 (d, J=8.5 Hz, 1H, Ar$\underline{H}$), 7.57 (t, J=6 Hz, 1H, N$\underline{H}$CH$_2$), 12.1 (s, 1H, CO$_2\underline{H}$).

MS (–FAB) m/e (rel. intensity): 304 (M–H, 17).

Analysis calc. for $C_{16}H_{23}N_3O_3 \cdot CF_3COOH$: C, 51.55; H, 5.77; N, 10.03; Found: C, 51.60; H, 5.75; N, 9.98.

EXAMPLE 38

[6-(2-Guanidino-ethoxy)-1,2,3,4-tetrahydro-napthalen-2-yl]-acetic acid trifluoroacetate The title compound is prepared according to the procedure of Example 37 except that [6-(2-guanidino-ethoxy)-1, 2,3,4-tetrahydro-napthalen-2-yl]-acetic acid ethyl ester is used in place of [6-(3-guanidino-propoxy)-1,2,3,4-tetrahydro-napthalen-2-yl]-acetic acid ethyl ester.

EXAMPLE 39

[6-(4-Guanidino-butoxy)-1,2,3,4-tetrahydro-napthalen-2-yl]-acetic acid trifluoroacetate The title compound is prepared according to the procedure of Example 37 except that [6-(4-guanidino-butoxy)-1,2,3,4-tetrahydro-napthalen-2-yl]-acetic acid ethyl ester is used in place of [6-(3-guanidino-propoxy)-1,2,3,4-tetrahydro-napthalen-2-yl]-acetic acid ethyl ester.

EXAMPLE 40

[7-(3-Guanidino-propoxy)-1,2,3,4-tetrahydro-napthalen-2-yl]-acetic acid trifluoroacetate The title compound was prepared according to the procedure of Example 37 except that [7-(3-guanidino-propoxy)-1,2,3,4-tetrahydro-napthalen-2-yl]-acetic acid ethyl ester was used in place of [6-(3-guanidino-propoxy)-1,2,3,4-tetrahydro-napthalen-2-yl]-acetic acid ethyl ester.

Mp. 148–50° C.

IR (KBr): 3410 (s), 3210 (s), 1695 (s), 1660 (s), 1630 (s), 1426 (m), 1248 (s), 1180 (s), 1135 (s), 838 (m), 815 (m), 795 (m), 720 (m) cm$^{-1}$.

$^1$H NMR (DMSO-d$_6$, 400 MHz): δ1.36 (m, 1H, ArCHHC$\underline{H}$H), 1.84–1.92 (overlapping m, 3H, ArCHHC$\underline{HH}$, NCH$_2$C$\underline{H}_2$), 2.05 (m, 1H, C$\underline{H}$), 2.26 (d, J=7 Hz, 2H, C$\underline{HH}$CO$_2$), 2.39 (dd, J=10 Hz, 16.5 Hz, 1H, ArC$\underline{HH}$CH), 2.68 (m, 2H, ArC$\underline{HH}$CHH), 2.79 (dd, J=5 Hz, 16.5 Hz, 1H, ArCH$\underline{H}$CH), 3.25 (m, 2H, NC$\underline{H}_2$), 3.94 (t, J=6 Hz, 2H, OC$\underline{H}_2$), 6.61 (d, J=2.5 Hz, 1H, Ar$\underline{H}$). 6.67 (dd, J=2.5 Hz, 8 Hz, 1H, Ar$\underline{H}$), 6.70–7.50 (broad, 4H, [C(N$\underline{H}_2$)$_2$]$^+$), 6.96 (d, J=8 Hz, 1H, Ar$\underline{H}$), 7.58 (t, J=5 Hz, 1H, N$\underline{H}$CH$_2$), 12.1 (s, 1H, CO$_2\underline{H}$).

MS (+FAB) m/e (rel. intensity): 306 (M+H, 40).

Analysis calc. for C$_{16}$H$_{23}$N$_3$O$_3$·CF$_3$COOH: C, 51.55; H, 5.77; N, 10.02; Found: C, 51.57; H, 5.72; N, 10.03.

EXAMPLE 41

[7-(2-Guanidino-ethoxy)-1,2,3,4-tetrahydro-napthalen-2-yl]-acetic acid trifluoroacetate The title compound is prepared according to the procedure of Example 37 except that [7-(2-guanidino-ethoxy)-1,2,3,4-tetrahydro-napthalen-2-yl]-acetic acid ethyl ester is used in place of [6-(3-guanidino-propoxy)-1,2,3,4-tetrahydro-napthalen-2-yl]-acetic acid ethyl ester.

EXAMPLE 42

[7-(4-Guanidino-butoxy)-1,2,3,4-tetrahydro-napthalen-2-yl]-acetic acid trifluoroacetate The title compound is prepared according to the procedure of Example 37 except that [7-(4-guanidino-butoxy)-1,2,3,4-tetrahydro-napthalen-2-yl]-acetic acid ethyl ester is used in place of [6-(3-guanidino-propoxy)-1,2,3,4-tetrahydro-napthalen-2-yl]-acetic acid ethyl ester.

EXAMPLE 43

[2-(2-tert-Butoxycarbonylamino-ethoxy)-6,7,8,9-tetrahydro-5H-benzocyclohepten-6-yl]-acetic acid ethyl ester The title compound was prepared according to the procedure of Example 19 except that (2-bromo-ethyl)-carbamic acid tert-butyl ester was used in place of (3-bromo-propyl)-carbamic acid tert-butyl ester and (2-hydroxy-6,7,8,9-tetrahydro-5H-benzocyclohepten-6-yl)-acetic acid ethyl ester was used in place of (7-hydroxy-1,2,3,4-tetrahydro-napthalen-2-yl)-acetic acid ethyl ester and the title compound was isolated as a pale yellow oil.

EXAMPLE 44

[2-(3-tert-Butoxycarbonylamino-propoxy)-6,7,8,9-tetrahydro-5H-benzocyclohepten-6-yl]-acetic acid ethyl ester The title compound was prepared according to the procedure of Example 19 except that (2-hydroxy-6,7,8,9-tetrahydro-5H-benzocyclohepten-6-yl)-acetic acid ethyl ester is used in place of (7-hydroxy-1,2,3,4-tetrahydro-1H-napthalen-2-yl)-acetic acid ethyl ester and the title compound was isolated as a clear yellow oil.

EXAMPLE 45

[2-(4-tert-Butoxycarbonylamino-butoxy)-6,7,8,9-tetrahydro-5H-benzocyclohepten-6-yl]-acetic acid ethyl ester The title compound was prepared according to the procedure of Example 19 except that (4-bromo-butyl)-carbamic acid tert-butyl ester was used in place of (3-bromo-propyl)-carbamic acid tert-butyl ester and (2-hydroxy-6,7,8,9-tetrahydro-5H-benzo-cyclohepten-6-yl)-acetic acid ethyl ester was used in place of (7-hydroxy-1,2,3,4-tetrahydro-napthalen-2-yl)-acetic acid ethyl ester.

The title compound was isolated as a clear yellow oil.

EXAMPLE 46

[3-(2-tert-Butoxycarbonylamino-ethoxy)-6,7,8.9-tetrahydro-5H-benzocyclohepten-6-yl]-acetic acid ethyl ester The title compound is prepared according to the procedure of Example 19 except that (2-bromo-ethyl)-carbamic acid tert-butyl ester is used in place of (3-bromo-propyl)-carbamic acid tert-butyl ester and (3-hydroxy-6,7,8,9-tetrahydro-5H-benzocyclohepten-6-yl)-acetic acid ethyl ester is used in place of (7-hydroxy-1,2,3,4-tetrahydro-napthalene-2-yl)-acetic acid ethyl ester.

EXAMPLE 47

[3-(3-tert-Butoxycarbonylamino-propoxy)-6,7,8,9-tetrahydro-5H-benzocyclohepten-6-yl]-acetic acid ethyl ester The title compound is prepared according to the procedure of Example 19 except that (3-hydroxy-6,7,8,9-tetrahydro-5H-benzocyclohepten-6-yl)-acetic acid ethyl ester is used in place of (7-hydroxy-1,2,3,4-tetrahydro-napthalene-2-yl)-acetic acid ethyl ester.

EXAMPLE 48

[3-(4-tert-Butoxycarbonylamino-butoxy)-6,7,8,9-tetrahydro-5H-benzocyclohepten-6-yl]-acetic acid ethyl ester The title compound is prepared according to the procedure of Example 19 except that (4-bromo-butyl)-carbamic acid tert-butyl ester is used in place of (3-bromo-propyl)- carbamic acid tert-butyl ester and (3-hydroxy-6,7,8,9-tetrahydro-5H-benzo-cyclohepten-6-yl)-acetic acid ethyl ester is used in place of (7-hydroxy-1,2,3,4-tetrahydro-napthalen-2-yl)-acetic acid ethyl ester.

EXAMPLE 49

[2-(2-Amino-ethoxy)-6,7,8,9-tetrahydro-5H-benzocyclohepten-6-yl]-acetic acid ethyl ester trifluoroacetate The title compound is prepared according to the procedure of Example 25 except that [2-(2-tert-butoxycarbonylamino-ethoxy)-6,7,8,9-tetrahydro-5H-benzocyclohepten-6-yl]-acetic acid ethyl ester is used in place of [6-(3-tertbutoxycarbonylamino-propoxy)-1,2,3,4-tetrahydro-napthalen-2-yl]-acetic acid ethyl ester and the title compound is isolated as the trifluoroacetate salt.

EXAMPLE 50

[2-(3-Amino-propoxy)-6,7,8,9-tetrahydro-5H-benzocyclohepten-6-yl]-acetic acid ethyl ester trifluoroacetate The title compound is prepared according to the procedure of Example 25 except that [2-(3-tert-butoxycarbonylamino-propoxy)-6,7,8,9-tetrahydro-5H-benzocyclohepten-6-yl]-acetic acid ethyl ester is used in place of [6-(3-tertbutoxycarbonylamino-propoxy)-1,2,3,4-tetrahydro-napthalen-2-yl]-acetic acid ethyl ester and the title compound is isolated as the trifluoroacetate salt.

EXAMPLE 51

[2-(4-Amino-butoxy)-6,7,8,9-tetrahydro-5H-benzocyclohepten-6-yl]-acetic acid ethyl ester trifluoroacetate The title compound is prepared according to the procedure of Example 25 except that [2-(4-tert-butoxycarbonylamino-butoxy)-6,7,8,9-tetrahydro-5H-benzocyclohepten-6-yl]-acetic acid ethyl ester is used in place of [6-(3-tertbutoxycarbonylamino-propoxy)-1,2,3,4-tetrahydro-napthalen-2-yl]-acetic acid ethyl ester and the title compound is isolated as the trifluoroacetate salt.

EXAMPLE 52

[3-(2-Amino-ethoxy)-6,7,8,9-tetrahydro-5H-benzocyclohepten-6-yl]-acetic acid ethyl ester trifluoroacetate The title compound is prepared according to the procedure of Example 25 except that [3-(2-tert-butoxycarbonylamino-ethoxy)-6,7,8,9-tetrahydro-5H-benzocyclohepten-6-yl]-acetic acid ethyl ester is used in place of [6-(3-tertbutoxycarbonylamino-propoxy)-1,2,3,4-tetrahydro-napthalen-2-yl]-acetic acid ethyl ester and the title compound is isolated as the trifluoroacetate salt.

EXAMPLE 53

[3-(3-Amino-propoxy)-6,7,8,9-tetrahydro-5H-benzocyclohepten-6-yl]-acetic acid ethyl ester trifluoroacetate The title compound is prepared according to the procedure of Example 25 except that [3-(3-tert-butoxycarbonylamino-propoxy)-6,7,8,9-tetrahydro-5H-benzocyclohepten-6-yl]-acetic acid ethyl ester is used in place of [6-(3-tertbutoxycarbonylamino-propoxy)-1,2,3,4-tetrahydro-napthalen-2-yl]-acetic acid ethyl ester and the title compound is isolated as the trifluoroacetate salt.

EXAMPLE 54

[3-(4-Amino-butoxy)-6,7,8,9-tetrahydro-5H-benzocyclohepten-6-yl]-acetic acid ethyl ester trifluoroacetate The title compound is prepared according to the procedure of Example 25 except that [3-(4-tert-butoxycarbonylamino-butoxy)-6,7,8,9-tetrahydro-5H-benzocyclohepten-6-yl]-acetic acid ethyl ester is used in place of [6-(3-tertbutoxycarbonylamino-propoxy)-1,2,3,4-tetrahydro-napthalen-2-yl]-acetic acid ethyl ester and the title compound is isolated as the trifluoroacetate salt.

EXAMPLE 55

[2-(2-Guanidino-ethoxy)-6,7,8,9-tetrahydro-5H-benzocyclohepten-6-yl]-acetic acid ethyl ester trifluoroacetate The title compound is prepared according to the procedure of Example 31 except that [2-(2-Amino-ethoxy)-6,7,8,9-tetrahydro-5H-benzocyclohepten-6-yl]-acetic acid ethyl ester trifluoroacetate is used in place of [6-(3-amino-propoxy)-1,2,3,4-tetrahydro-napthalen-2-yl]-acetic acid ethyl ester trifluoroacetate.

EXAMPLE 56

[2-(3-Guanidino-propoxy)-6,7,8,9-tetrahydro-5H-benzocyclohepten-6-yl]-acetic acid ethyl ester trifluoroacetate The title compound is prepared according to the procedure of Example 31 except that [2-(3-amino-propoxy)-6,7,8,9-tetrahydro-5H-benzocyclohepten-6-yl]-acetic acid ethyl ester trifluoroacetate is used in place of [6-(3-amino-propoxy)-1,2,3,4-tetrahydro-napthalen-2-yl]-acetic acid ethyl ester trifluoroacetate.

EXAMPLE 57

[2-(4-Guanidino-butoxy)-6,7,8,9-tetrahydro-5H-benzocyclohepten-6-yl]-acetic acid ethyl ester trifluoroacetate The title compound is prepared according to the procedure of Example 31 except that [2-(4-amino-butoxy)-6,7,8,9-tetrahydro-5H-benzocyclohepten-6-yl]-acetic acid ethyl ester trifluoroacetate is used in place of [6-(3-amino-propoxy)-1,2,3,4-tetrahydro-napthalen-2-yl]-acetic acid ethyl ester trifluoroacetate.

EXAMPLE 58

[3-(2-Guanidino-ethoxy)-6,7,8,9-tetrahydro-5H-benzocyclohepten-6-yl]-acetic acid ethyl ester trifluoroacetate The title compound is prepared according to the procedure of Example 31 except that [3-(2-amino-ethoxy)-6,7,8,9-tetrahydro-5H-benzocyclohepten-6-yl]-acetic acid ethyl ester trifluoroacetate is used in place of [6-(3-amino-propoxy)-1,2,3,4-tetrahydro-napthalen-2-yl]-acetic acid ethyl ester trifluoroacetate.

EXAMPLE 59

[3-(3-Guanidino-propoxy)-6,7,8,9-tetrahydro-5H-benzocyclohepten-6-yl]-acetic acid ethyl ester trifluoroacetate The title compound is prepared according to the procedure of Example 31 except that [3-(3-amino-propoxy)-6,7,8,9-tetrahydro-5H-benzocyclohepten-6-yl]-acetic acid ethyl ester trifluoroacetate is used in place of [6-(3-amino-propoxy)-1,2,3,4-tetrahydro-napthalen-2-yl]-acetic acid ethyl ester trifluoroacetate.

EXAMPLE 60

[3-(4-Guanidino-butoxy)-6,7,8,9-tetrahydro-5H-benzocyclohepten-6-yl]-acetic acid ethyl ester trifluoroacetate The title compound is prepared according to the procedure of Example 31 except that [3-(4-amino-butoxy)-6,7,8,9-tetrahydro-5H-benzocyclohepten-6-yl]-acetic acid ethyl ester trifluoroacetate is used in place of [6-(3-amino-propoxy)-1,2,3,4-tetrahydro-napthalen-2-yl]-acetic acid ethyl ester trifluoroacetate.

EXAMPLE 61

[2-(2-Guanidino-ethoxy)-6,7,8,9-tetrahydro-5H-benzocyclohepten-6-yl]-acetic acid hydrochloride The title compound was prepared according to the procedure of Example 37 except that [2-(2-guanidino-ethoxy)-6,7,8,9-tetrahydro-5H-benzocyclohepten-6-yl]-acetic acid ethyl ester trifluoroacetate was used in place of [6-(3-guanidino-propoxy)-1,2,3,4-tetrahydro-napthalen-2-yl]-acetic acid ethyl ester trifluoroacetate. The title compound was isolated as the hydrochloride salt.

IR (KBr): 3400 (s), 3150 (s), 1695 (s), 1650 (s), 1265 (m), 1251 (m), 1175 (m), 800 (w), 720 (w) cm$^{-1}$.

$^1$H NMR (DMSO-d$_6$, 400 MHz): δ1.37 (m, 1H, CHC HHCHH), 1.51 (m, 1H, CHCHHCHH), 1.72 (m, 1H, CH), 1.85 (m, 2H, CHCHHCHH), 2.04 (dd, J=7 Hz, 15.5 Hz, 1H, CHHCO$_2$), 2.13 (dd, J=7 Hz, 15.5 Hz, 1H, CHHCO$_2$), 2.61–2.72 (overlapping m, 4H, ArCHH), 3.49 (m, 2H, NCH$_2$), 4.00 (t, J=5 Hz, 2H, OCH$_2$), 6.63 (dd, J=2.5 Hz, 8 Hz, 1H, ArH), 6.70 (d, J=2.5 Hz, 1H, ArH), 6.94 (d, J=8 Hz, 1H, ArH), 6.97–7.66 (broad, 4H, [C(NH$_2$)$_2$$^+$]), 7.75 (t, J=5.5 Hz, 1H, NHCH$_2$), 11.8–12.4 (broad, 1H, CO$_2$H).

MS (−FAB) m/e (rel. intensity): 306 (M−H, 100).

Analysis calc. for C$_{16}$H$_{23}$N$_3$O$_3$.HCl.H$_2$O: C, 53.40; H, 7.28; N, 11.68; Found: C, 53.38; H, 6.84; N, 11.32.

EXAMPLE 62

[2-(3-Guanidino-propoxy)-6,7,8,9-tetrahydro-5H-benzocyclohepten-6-yl]-acetic acid trifluoroacetate The title compound was prepared according to the procedure of Example 37 except that [2-(3-guanidino-propoxy)-6,7,8,9-tetrahydro-5H-benzocyclohepten-6-yl]-acetic acid ethyl ester trifluoroacetate was used in place of [6-(3-guanidino-propoxy)-1,2,3,4-tetrahydro-napthalen-2-yl]-acetic acid ethyl ester trifluoroacetate. The title compound was isolated as the trifluoroacetate.

Mp. 109–14° C.

IR (KBr): 3465 (s), 3370 (s), 3200 (m), 1715 (s), 1680 (s), 1615 (s), 1249 (m), 1195 (m), 1130 (s), 820 (w), 720 (m) cm$^{-1}$.

$^1$H NMR (DMSO-d$_6$, 400 MHz): δ1.37 (m, 1H, CHC HHCHH), 1.51 (m, 1H, CHCHHCHH), 1.72 (m, 1H, CH), 1.83–1.92 (overlapping m, 4H, CHCHHCHH, NCH$_2$CH$_2$), 2.04 (dd, J=7 Hz, 15.5 Hz, 1H, CHHCO$_2$), 2.13 (dd, J=7 Hz, 15.5 Hz, 1H, CHHCO$_2$), 2.60–2.72 (overlapping m, 4H, ArC HH), 3.25 (m, 2H, NCH$_2$), 3.94 (t, J=6 Hz, 2H, OCH$^2$), 6.62 (dd, J=2.5 Hz, 8 Hz, 1H, ArH), 6.68 (d, J=2.5 Hz, 1H, ArH), 6.75–7.55 (broad, 4H, [C(NH$_2$)$_2$$^+$]), 6.92 (d, J=8 Hz, 1H, Ar H), 7.65 (t, J=5 Hz, 1H, NHCH$_2$), 12.0 (s, 1H, CO$_2$H).

MS (+FAB) m/e (rel. intensity): 320 (M+H, 100).

Analysis calc. for C$_{17}$H$_{25}$N$_3$O$_3$.CF$_3$COOH: C, 52.65; H, 6.05; N, 9.70; Found: C, 52.59; H, 6.05; N, 9.61.

EXAMPLE 63

[2-(4-Guanidino-butoxy)-6,7,8,9-tetrahydro-5H-benzocyclohepten-6-yl]-acetic acid trifluoroacetate The title compound was prepared according to the procedure of Example 37 except that [2-(4-guanidino-butoxy)-6,7,8,9-tetrahydro-5H-benzocyclohepten-6-yl]-acetic acid ethyl ester trifluoroacetate was used in place of [6-(3-guanidino-propoxy)-1,2,3,4-tetrahydro-napthalen-2-yl]-acetic acid ethyl ester trifluoroacetate. The title compound was isolated as the trifluoroacetate salt as a white solid.

Mp. Shrinks from 72–89° C., then melts from 89–96° C.

IR (KBr): 3400 (s), 3180 (s), 1699 (s), 1630 (s), 1251 (m), 1201 (s), 1130 (s), 840 (m), 799 (m), 725 (m) cm$^{-1}$.

$^1$H NMR (DMSO-d$_6$, 400 MHz): δ1.37 (m, 1H, CHC HHCHH), 1.47–1.76 (overlapping m, 6H, NCH$_2$CH$_2$CH$_2$, C HCHHCHH), 1.84 (m, 2H, CHCHHCHH), 2.04 (dd, J=7 Hz, 15.5 Hz, 1H, CHHCO$_2$), 2.13 (dd, J=7 Hz, 15.5 Hz, 1H, CHHCO$_2$), 2.59–2.71 (overlapping m, 4H, ArCHHCH, ArC HHCHH), 3.25 (m, 2H, NCH$_2$), 3.92 (t, J=6 Hz, 2H, OCH$_2$), 6.60 (dd, J=2.5 Hz, 8 Hz, 1H, ArH), 6.66 (d, J=2.5 Hz, 1H, ArH), 6.70–7.50 (broad, 4H, [C(NH$_2$)$_2$$^+$]), 6.91 (d, J=8 Hz, 1H, ArH), 7.59 (t, J=5 Hz, 1H, NHCH$_2$), 12.0 (s, 1H, CO$_2$H).

MS (+FAB) m/e (rel. intensity): 334 (M+H, 100).

Analysis calc. for C$_{18}$H$_{27}$N$_3$O$_3$.CF$_3$COOH: C, 53.69; H, 6.31; N, 9.39; Found: C, 53.54; H, 6.31; N, 9.89; 10.03.

EXAMPLE 64

[3-(2-Guanidino-ethoxy)-6,7,8,9-tetrahydro-5H-benzocyclohepten-6-yl]-acetic acid hydrochloride The title compound is prepared according to the procedure of Example 37 except that [3-(2-guanidino-ethoxy)-6,7,8,9-tetrahydro-5H-benzocyclohepten-6-yl]-acetic acid ethyl ester trifluoroacetate is used in place of [6-(3-guanidino-propoxy)-1,2,3,4-tetrahydronapthalen-2-yl]-acetic acid ethyl ester trifluoroacetate. The title compound is isolated as the hydrochloride salt.

EXAMPLE 65

[3-(3-Guanidino-propoxy)-6,7,8 9-tetrahydro-5H-benzocyclohepten-6-yl]-acetic acid trifluoroacetate The title compound is prepared according to the procedure of Example 37 except that [3-(3-guanidino-propoxy)-6,7,8,9-tetrahydro-5H-benzocyclohepten-6-yl]-acetic acid ethyl ester trifluoroacetate is used in place of [6-(3-guanidino-propoxy)-1,2,3,4-tetrahydro-napthalen-2-yl]-acetic acid ethyl ester trifluoroacetate. The title compound is isolated as the trifluoroacetate salt.

EXAMPLE 66

[3-(4-Guanidino-butoxy)-6,7,8 9-tetrahydro-5H-benzocyclohepten-6-yl]-acetic acid trifluoroacetate The title compound is prepared according to the procedure of Example 37 except that [3-(4-guanidino-butoxy)-6, 7,8,9-tetrahydro-5H-benzocyclohepten-6-yl]-acetic acid ethyl ester trifluoroacetate is used in place of [6-(3-guanidino-propoxy)-1,2,3,4-tetrahydro-napthalen-2-yl]-acetic acid ethyl ester trifluoroacetate. The title compound is isolated as the trifluoroacetate salt as a white solid.

EXAMPLE 67

2-(5-Hydroxy-2-nitro-benzylidene)-succinic acid diethyl ester

Triphenylphosphine (12.2 g, 46.5 mmol) and diethyl maleate (8.0 g, 46.5 mmol) were combined in glacial acetic acid (7 mL) at 25° C. and the slurry was stirred for 6.5 h and the resulting solution was treated with 5-hydroxy-2-nitrobenzaldehyde (5.2 g, 31.1 mmol). Benzene (250 mL) was added and the solution heated to reflux. After 18 h, the solution was concentrated in vacuo to give a clear orange oil (27.6 g). Flash chromatography (700 g silica; 5%, then 10%, then 20%, then 40% EtOAc-hexane) gives the title compound (6.9 g; 69% yield) as a pale yellow solid.

$^1$H NMR: (DMSO-d$_6$, 300 MHz): δ1.15 (t, J=7.5 Hz, 3H, CH$_3$), 1.22 (t, J=7.5 Hz, 3H, CH$_3$), 3.25 (s, 2H, CH$_2$CO$_2$), 4.05 (q, J=7.5 Hz, 2H, CO$_2$CH$_2$), 4.20 (q, J=7.5 Hz, 2H, CO$_2$CH$_2$), 6.70 (s, 1H, ArH), 6.95 (d, J=9 Hz, 1H, ArH), 7.99 (s, 1H, CH=), 8.13 (d, J=9 Hz, 1H, ArH), 11.2 (s, 1H, ArOH).

EXAMPLE 68

2-(4-Hydroxy-2-nitro-benzylidene)-succinic acid diethyl ester

The title compound is prepared according to the procedure of Example 67 except that 4-hydroxy-2-nitrobenzaldehyde is used in place of 5-hydroxy-2-nitrobenzaldehyde.

EXAMPLE 69

(6-Hydroxy-2-oxo-1,2,3,4-tetrahydro-quinolin-3-yl)-acetic acid ethyl ester

A solution of 2-(5-hydroxy-2-nitro-benzylidene)-succinic acid diethyl ester (3.8 g, 12 mmol) in ethanol (35 mL) was hydrogenated over 10% Pd—C (0.8 g) at 25° C. and 1 atm. After 20 h, the catalyst was filtered through diatomaceous earth and washed with ethanol (3×35 mL). The filtrate was concentrated giving a mixture of solid and foam (2.8 g). Flash chromatography (190 g silica; 20%, then 40% EtOAc-hexane) gives the title compound (1.3 g, 45% yield) as a pale yellow solid.

$^1$H NMR: (DMSO-d$_6$, 300 MHz): δ1.18 (t, J=7.5 Hz, 3H, CH$_3$), 2.15–2.80 (overlapping m, 5H, ArCHH,CHCHH), 4.05 (q, J=7.5 Hz, 2H, CO$_2$CH$_2$), 6.53 (overlapping a, d, 2H, ArH), 6.66 (d, J=9 Hz, 1H, ArH), 9.03 (s, 1H, ArOH), 9.95 (s, 1H, ArNH).

EXAMPLE 70

(7-Hydroxy-2-oxo-1,2,3,4-tetrahydro-quinolin-3-yl)-acetic acid ethyl ester

The title compound is prepared according to the procedure of Example 69 except that 2-(4-hydroxy-2-nitro-benzylidene)-succinic acid diethyl ester is used in place of 2-(5-hydroxy-2-nitro-benzylidene)-succinic acid diethyl ester.

EXAMPLE 71

(7-Methoxy-2-oxo-1,2-dihydro-quinolin-3-yl)-acetic acid methyl ester

A suspension of 3-(2-chloro-7-methoxy-quinolin-3-yl)-acetic acid methyl ester prepared from the 7-methoxy-2-chloro-3-formylquinoline (O. Meth-Cohn et al, Tetrahedron Letters, 33, 3111–3114(1979) and O. Meth-Cohn et al, J.Chem.Soc. Perkin I, 1520–1530(1981)) 30.4 g (114 mmol) was refluxed with 12N aqueous hydrochloric acid for 12 hours forming a solution. The mixture was cooled to 0–5° C. for 2 hours and filtered. The filter cake was washed with cold methyl alcohol and air dried to give the title compound (25.6 g, 90% yield).

Mp. 195.0–96.5° C.

$^1$H NMR (DMSO-d$_6$, 300 MHz): δ3.49 (s, 2H, CH$_2$), 3.59 (s, 3H, CO$_2$CH$_3$), 3.79 (s, 3H, OCH$_3$), 6.77–6.81 (overlapping m, 2H, ArH), 7.53 (d, J=9 Hz, 1H, ArH), 7.76 (s, 1H, ArCH=), 11.7 (s, 1H, ArNH).

EXAMPLE 72

(7-Methoxy-2-oxo-1,2 3,4-tetrahydro-quinolin-3-yl)-acetic acid methyl ester

A solution of (7-methoxy-2-oxo-1,2-dihydro-quinolin-3-yl)-acetic acid methyl ester (8.2 g, 33.2 mmol) in 450 ml of acetic acid in the presence of 8.2 g of 10% Pd/C was hydrogenated at 50 psi of hydrogen for 2.5 days. The mixture was filtered through diatomaceous earth and the filter cake washed with hot acetic acid (2×200 ml). The filtrate was evaporated in vacuo to give 8.4 g of a tan solid which was crystallized from methyl alcohol (250 ml) to afford 5.4 g of the title compound as off-white crystals after washing with ice-cold methyl alcohol, ether and hexane, mp 152–155° C.

$^1$H NMR (DMSO-d$_6$, 300 MHz): δ2.44 (m, 1H, ArCHH), 2.68–2.87 (overlapping m, 4H, ArCHH, CH, CHHCO$_2$), 3.59 (s, 3H, CO$_2$CH$_3$), 3.68 (s, 3H, OCH$_3$), 6.44 (d, J=2.5 Hz, 1H, ArH), 6.49 (dd, J=2.5 Hz, 8 Hz, 1H, ArH), 7.05 (d, J=8 Hz, 1H, ArH), 10.1 (s, 1H, ArNH).

EXAMPLE 73

(7-Hydroxy-2-oxo-1,2,3,4-tetrahydro-quinolin-3-yl)-acetic acid methyl ester

A suspension of (7-methoxy-2-oxo-1,2,3,4-tetrahydro-quinolin-3-yl)-acetic acid methyl ester (5.4 g, 21.7 mmol) in 50 ml of methylene chloride at 0° C. was treated with 1.0 M BBr$_3$—CH$_2$Cl$_2$ (200 ml, 200 mmol) under inert gas for 1 hour. The reaction mixture was allowed to warm to room temperature over an additional 2 hours. The volatiles were evaporated in vacuo to a brown oil which was treated with ice-cold methyl alcohol (400 ml×2) and evaporated after each treatment to a residue. The residue was refluxed with 5 ml of 12 N HCl and 100 ml of methyl alcohol for 2 hours and evaporated to a residue which was crystallized from methyl alcohol (25 ml) to give the title compound, (3.9 g) as fluffy tan needles, mp 178–179.5° C.

$^1$H NMR (DMSO-d$_6$, 300 MHz): δ2.43 (m, 1H, ArCHH), 2.59–2.81 (overlapping m, 4H, ArCHH, CH, CHHCO$_2$), 3.59 (s, 3H, CH$_3$), 6.28–6.33 (overlapping m, 2H, ArH), 6.90 (d, J=8 Hz, 1H, ArH), 9.27 (s, 1H, ArOH), 10.0 (s, 1H, ArNH).

EXAMPLE 74

(7-Hydroxy-2-oxo-1,2-dihydro-quinolin-3-yl)-acetic acid methyl ester

Treatment of (7-methoxy-2-oxo-1,2-dihydro-quinolin-3-yl)-acetic acid methyl ester with boron tribromide in dichloromethane using the conditions of Example 73 gives the title compound (3.5 g, 58% yield).

Mp. 221–23° C. (dec).

$^1$H NMR (DMSO-d$_6$, 300 MHz): δ3.46 (s, 2H, CH$_2$), 3.58 (s 3H, CH$_3$), 6.62 (dd, J=2 Hz, 8.5 Hz, 1H, ArH), 6.69 (d, J=2 Hz, 1H, ArH), 7.42 (d, J=8.5 Hz, 1H, ArH), 7.70 (s, 1H, ArCH=), 10.1 (broad s, 1H, ArOH), 11.6 (s, 1H, ArNH).

EXAMPLE 75

[7-(2-tert-Butoxycarbonylamino-ethoxy)-2-oxo-1,2,3 4-tetrahydro-quinolin-3-yl]-acetic acid methyl ester A solution of 7-hydroxy-2-oxo-1,2,3,4-tetrahydro-quinolin-3-yl)-acetic acid methyl ester (2.6 g, 11.1 mmol) in N,N-dimethylformamide (20 mL) was treated with a solution of sodium ethoxide (25 wt %) in methanol (2.5 mL, 10.9 mmol) at 25° C. and after 10 min, (2-bromoethyl)-carbamic acid tert-butyl ester (2.5 g, 11.2 mmol) was added. After 3 days, the solution was treated with water (100 mL) and the resulting gum was briskly stirred at 0° C. The precipitated solid was filtered and dried to give crude product (2.9 g). Flash chromatography (90 g silica; CHCl$_3$, then 1% MeOH (saturated with NH$_3$)—CHCl$_3$) gives the title compound (2.0 g) as a white solid.

EXAMPLE 76

[7-(4-tert-Butoxycarbonylamino-butoxy)-2-oxo-1,2, 3,4-tetrahydro-quinolin-3-yl]-acetic acid methyl ester The title compound is prepared according to the procedure of Example 75 except that (4-bromobutyl)-carbamic acid tert-butyl ester is used in place of (2-bromoethyl)-carbamic acid tert-butyl ester.

EXAMPLE 77

[7-(3-tert-Butoxycarbonylamino-propoxy)-2-oxo-1, 2,3,4-tetrahydro-quinolin-3-yl]-acetic acid methyl ester The title compound is prepared according to the procedure of Example 75 except that (3-bromopropyl)-carbamic acid tert-butyl ester is used in place of (2-bromoethyl)-carbamic acid tert-butyl ester.

EXAMPLE 78

[7-(2-Amino-ethoxy)-2-oxo-1,2,3,4-tetrahydro-quinolin-3-yl]-acetic acid methyl ester Trifluoroacetate

[7-(2-tert-Butoxycarbonylamino-ethoxy)-2-oxo-1,2,3,4-tetrahydro-quinolin-3-yl]-acetic acid methyl ester (2.5 g, 6.6 mmol) and trifluoroacetic acid (5.1 mL, 66 mmol) were combined in methylene chloride (25 mL) at 25° C. After 18 h, the solution was concentrated in vacuo to give the title compound as a tan solid (2.6 g).

EXAMPLE 79

[7-(4-amino-butoxy)-2-oxo-1,2,3,4-tetrahydro-quinolin-3-yl]-acetic acid methyl ester Trifluoroacetate The title compound is prepared according to the procedure of Example 78 except that [7-(4-tert-butoxycarbonylamino-butoxy)-2-oxo-1,2,3,4-tetrahydro-quinolin-3-yl]-acetic acid methyl ester is used in place of [7-(2-tert-butoxycarbonylamino-ethoxy)-2-oxo-1,2,3,4-tetrahydro-quinolin-3-yl]-acetic acid methyl ester.

EXAMPLE 80

[7-(3-amino-propoxy)-2-oxo-1,2,3,4-tetrahydro-quinolin-3-yl]-acetic acid methyl ester Trifluoroacetate The title compound is prepared according to the procedure of Example 78 except that [7-(3-tert-butoxycarbonylamino-propoxy)-2-oxo-1,2,3,4-tetrahydro-quinolin-3-yl]-acetic acid methyl ester is used in place of [7-(2-tert-butoxycarbonylamino-ethoxy)-2-oxo-1,2,3,4-tetrahydro-quinolin-3-yl]-acetic acid methyl ester.

EXAMPLE 81

[7-(2-Guanidino-ethoxy)-2-oxo1,2,3,4-tetrahydro-quinolin-3-yl]-acetic acid methyl ester A suspension of [7-(2-amino-ethoxy)-2-oxo-1,2,3,4-tetrahydro-quinolin-3-yl]-acetic acid methyl ester trifluoroacetate (1.49 g, 3.8 mmol), 3,5-dimethylpyrazole carboxamidine nitrate (0.84 g, 4.18 mmol) and diisopropylethylamine (1.45 mL, 8.32 mmol) in 3:1 dioxane-water (11 mL) were heated at reflux for 22 h. The cooled solution was concentrated in vacuo to yield a viscous yellow syrup. Washing the syrup with ice-cold water (3×5 ml) gives the title compound as a dried white solid (1.04 g).

EXAMPLE 82

[7-(4-Guanidino-butoxy)-2-oxo-1,2,3,4-tetrahydro-quinolin-3-yl]-acetic acid methyl ester trifluoroacetate The title compound is prepared according to the procedure of Example 81 except that [7-(2-amino-ethoxy)-2-oxo-1,2,3,4-tetrahydro-quinolin-3-yl]-acetic acid methyl ester trifluoroacetate is replaced with [7-(4-amino-butoxy)-2-oxo-1,2,3,4-tetrahydro-quinolin-3-yl]-acetic acid methyl ester trifluoroacetate.

EXAMPLE 83

[7-(3-Guanidino-propoxy)-2-oxo-1,2,3,4-tetrahydro-quinolin-3-yl]-acetic acid methyl ester trifluoroacetate The title compound is prepared according to the procedure of Example 81 except that [7-(2-amino-ethoxy)-2-oxo-1,2,3,4-tetrahydro-quinolin-3-yl]-acetic acid methyl ester trifluoroacetate is replaced with [7-(3-amino-propoxy)-2-oxo-1,2,3,4-tetrahydro-quinolin-3-yl]-acetic acid methyl ester trifluoroacetate.

EXAMPLE 84

[7-(4-Guanidino-butoxy)-2-oxo-1,2,3,4-tetrahydro-quinolin-3-yl]-acetic acid Trifluoroacetate A solution of [7-(4-guanidino-butoxy)-2-oxo-1,2,3,4-tetrahydro-quinolin-3-yl]-acetic acid methyl ester trifluoroacetate(0.75 g, 1.6 mmol) in methanol (7 mL) was treated with 0.5 N aqueous NaOH (7.1 ml, 3.6 mmol) and heated at reflux for 1.5 h. The cooled solution was treated with trifluoroacetic acid (2.0 mL×5) and the solution thus formed concentrated in vacuo to give 1.5 g of a clear colorless oil. The oil was dissolved in 1:1 water:N,N-dimethylformamide and purified by reverse phase HPLC giving the title compound (0.57 g) as a white fluffy solid.

Mp. 189–91° C.

IR (KBr): 3435 (m), 3350 (m), 3170 (m), 1695 (s), 1660 (s), 1197 (s), 1180 (s), 1122 (m), 832 (m), 788 (m), 712 (m) cm$^{-1}$.

$^1$H NMR (DMSO-d$_6$, 400 MHz): δ1.60 (m, 2H, NCH$_2$CH$_2$), 1.71 (m, 2H, OCH$_2$CH$_2$), 2.34 (m, 1H, ArCHH), 2.65–2.87 (overlapping m, 4H, ArCHH, CH, CHHCO$_2$), 3.15 (m, 2H, NCH$_2$), 3.91 (t, J=6 Hz, 2H, OCH$_2$), 6.42 (d, J=2.5 Hz, 1H, ArH), 6.49 (dd, J=2.5 Hz, 8 Hz, 1H, ArH), 6.60–7.50 (broad, 4H [C(NHH$_2$)$_2$]$^+$), 7.05 (d, J=8 Hz, 1H, ArH), 7.59 (t, J=5.5 Hz, 1H, NHCH$_2$), 10.1 (s, 1H, ArNH), 12.2 (s, 1H, CO$_2$H).

MS (+DCI) m/e (rel. intensity): 335 (M+H, 21).

Analysis calc. for C$_{16}$H$_{22}$N$_4$O$_4$.CF$_3$COOH C, 48.21; H, 5.17; N, 12.50. Found C, 48.17; H, 4.97; N, 12.47.

EXAMPLE 85

[7-(2-Guanidino-ethoxy)-2-oxo-1,2,3,4-tetrahydro-quinolin-3-yl]-acetic acid Hydrochloride The product of the example was obtained using the conditions of Example 84 and [7-(2-guanidino-ethoxy)-2-oxo-1,2,3,4-tetrahydro-quinolin-3-yl]-acetic acid methyl ester trifluoroacetate. Following reverse phase chromatography the crude mixture was dissolved in 5 ml of 0.5 N sodium hydroxide, warmed slightly to effect solution and cooled at 0° C. The resulting solid was collected by filtration, dissolved in 4 ml of water and treated with 12 N hydrochloric acid, warmed to effect a solution, cooled to 0° C. and the resulting solid collected and dried giving a white solid, as the hydrochloride salt.

IR (KBr): 3430 (s), 3350 (s), 3162 (s), 1730 (s), 1665 (s), 1615 (s), 1445 (m), 1400 (m), 1278 (s), 1228 (m), 1160 (s), 1132 (s), 850 (m), 815 (m), 805 (m) cm$^{-1}$.

$^1$H NMR (DMSO-d$_6$, 400 MHz): δ2.34 (m, 1H, ArCHH), 2.66–2.87 (overlapping m, 4H, ArCHH, CH, CHHCO$_2$), 3.55 (m, 2H, NCH$^2$), 3.97 (t, J=5 Hz, 2H, OCH$_2$), 6.46 (d, J=2.5 Hz, 1H, ArH), 6.51 (dd, J=2.5 Hz, 8 Hz, 1H, ArH), 6.80–7.50 (broad, 4H, [C(NH$_2$)$_2$]$^+$), 7.07 (d, J=8 Hz, 1H, ArH), 7.80 (t, J=5.5 Hz, 1H, NHCH$_2$), 10.1 (s, 1H, ArNH), 12.2 (broad s, 1H, CO$_2$H).

MS (+FAB) m/e (rel. intensity): 307 (M+H, 11).

Analysis calc. for C$_{14}$H$_{18}$N$_4$O$_4$.HCl.H$_2$O C, 46.61; H, 5.86; N, 15.53. Found C, 46.80; H, 5.70; N, 15.53.

EXAMPLE 86

[7-(3-Guanidino-propoxy)-2-oxo-1,2,3,4-tetrahydro-quinolin-3-yl]-acetic acid Hydrochloride Using the conditions of Example 85 and [7-(3-guanidino-propoxy)-2-oxo-1,2,3,4-tetrahydro-quinolin-3-yl]-acetic acid methyl ester trifluoroacetate the product of the example was obtained and isolated as the hydrochloride salt.

Mp. 227–29° C.

IR (KBr): 3438 (s), 3360 (s), 3190 (m), 1715 (s), 1673 (s), 1662 (s), 1618 (s), 1470 (m), 1404 (m), 1262 (m), 1232 (s), 1188 (s), 1156 (s), 834 (m), 810 (w), 798 (w) cm$^{-1}$.

$^1$H NMR (DMSO-d$_6$, 400 MHz): δ1.90 (m, 2H, NCH$_2$CH$_2$), 2.34 (m, 1H, ArCHH), 2.66–2.87 (overlapping m, 4H, ArCHH, CH, CHHCO$_2$), 3.25 (m, 2H, NCH$_2$), 3.95 (t, J=6 Hz,,2H, OCH$_2$), 6.45 (d, J=2.5 Hz, 1H, ArH), 6.50 (dd, J=2.5 Hz, 8 Hz, 1H, ArH), 6.70–7.50 (broad, 4H, [C(NH$_2$)$_2$]$^+$), 7.06 (d, J=8Hz, 1H, ArH), 7.79 (t, J=5.5 Hz, 1H, NHCH$_2$), 10.1 (s, 1H, ArNH), 12.2 (broad s, 1H, CO$_2$H).

MS (+FAB) m/e (rel. intensity): 321 (M+H, 100).

Analysis calc. for C$_{15}$H$_{20}$N$_4$O$_4$.HCl C, 50.49; H, 5.93; N, 15.70. Found C, 50.35; H, 5.85; N, 15.96.

EXAMPLE 87

[2-Oxo-7-(trifluoro-methanesulfonyloxy)-1,2,3,4-tetrahydroquinolin-3-yl]-acetic acid methyl ester A solution of (7-hydroxy-2-oxo-1,2,3,4-tetrahydroquinolin-3-yl)-acetic acid methyl ester (5.5 g, 23 mmol) and triethylamine (16.3 mL, 117 mmol) in 1,4-dioxane (200 mL) was cooled to 0° C. and the resulting slurry treated dropwise with trifluoromethanesulfonic anhydride (7.9 mL, 47 mmol). The reaction mixture was warmed to 25° C. and after 1.5 h was concentrated in vacuo to an oily residue. The oily residue was taken up in methylene chloride (600 mL) and washed successively with water, 5% aqueous NaHCO$_3$ and brine (300 mL each). The organic phase was dried (MgSO$_4$) and concentrated to give a dark brown solid. Flash chromatography (220 g silica; 20%, then 40% EtOAc-hexane) gives the title compound (6.7 g, 78% yield) as a fluffy, pale yellow solid.

$^1$H NMR (CDCL$_3$, 300 MHz): δ2.54 (dd, J=7 Hz, 17 Hz, 1H, ArCHH), 2.87–3.15 (overlapping m, 4H, ArCHH, CH, CHHCO$_2$), 3.74 (s, 3H, CH$_3$), 6.74 (d, J=2.5 Hz, 1H, ArH), 6.91 (dd, J=2.5 Hz, 8 Hz, 1H, ArH), 7.23 (d, J=8 Hz, 1H, ArH), 8.78 (s, 1H, ArNH).

EXAMPLE 88

N-But-3-ynyl-imidodicarbonic acid di-tert-butyl ester

A solution of di-tert-butyliminodicarboxylate (17.4 g, 80.1 mmol) and triphenylphosphine (21.0 g, 80.1 mmol) in tetrahydrofuran (100 mL) was treated dropwise simultaneously with 3-butyn-1-ol (6.0 mL, 79 mmol) and diethylazodicarboxylate (12.6 mL, 80.0 mmol) during 5–10 min. The solution was heated to reflux for 24 h, cooled to room temperature and concentrated in vacuo to give a yellow oil (57.4 g, incomplete reaction). Flash chromatography (500 g silica; 0.5%, then 1%, then 2%, then 4% EtOAc-hexane) gave the title compound (5.3 g, 25% yield based on starting 3-butyn-1-ol) as a white solid.

$^1$H NMR (CDCl$_3$, 300 MHz): δ1.49 (s, 18H, CH$_3$), 1.93 (t, J=3 Hz, 1H, ≡CH), 2.46 (td, J=3 Hz, 7 Hz, 2H, NCH$_2$CH$_2$), 3.75 (t, J=7 Hz, 2H, NCH$_2$).

EXAMPLE 89

N-Pent-4-ynylimidodicarbonic acid di-tert-butyl ester

Using the conditions of Example 88 and replacing 3-butyn-1-ol with 4-pentyn-1-ol the product of the example was obtained.

$^1$H NMR (CDCl$_3$, 300 MHz): δ1.49 (s, 18H, CH$_3$),1.79 (m, 2H, NCH$_2$CH$_2$), 1.94 (t, J=3 Hz, 1H, ≡CH), 2.20 (td, J=3 Hz, 7 Hz, 2H, ≡CCH$_2$), 3.65 (t, J=7 Hz, 2H, NCH$_2$).

EXAMPLE 90

N-Hex-5-ynylimidodicarbonic acid di-tert-butyl ester

Using the conditions of Example 88 and replacing 3-butyn-1-ol with 5-hexyn-1-ol the product of the example is obtained.

EXAMPLE 91

(7-{4-[Bis-(tert-butoxycarbonyl)-amino]-but-1-ynyl}-2-oxo-1,2,3,4-tetrahydro-quinolin-3-yl)-acetic acid methyl ester A suspension of N-but-3-ynyl-imidodicarbonic acid di-tert-butyl ester (4.65 g, 17.3 mmol), [2-oxo-7-(trifluoro-methanesulfonyloxy)-1,2,3,4-tetrahydro-quinolin-3-yl]-acetic acid methyl ester (6.36 g, 17.3 mmol), tetrakis(triphenylphosphine)palladium (2.0 g, 1.7 mmol) and copper (I) iodide (0.49 g, 2.6 mmol) in N-methylpyrrolidine (50 mL; purged with $N_2$) was heated to 60° C. The resulting solution was treated with the original amounts of both catalysts, two additional times, at 1.5 h intervals. After 22 h, the reaction mixture was filtered and concentrated. The resulting dark oil was treated with saturated aqueous $NH_4Cl$ (250 mL), extracted with chloroform (3×250 mL), dried ($MgSO_4$) and concentrated to give a dark mixture of oil and foam (16.2 g). Flash chromatography (260 g silica; 5%, then 10%, then 20%, then 40% EtOAc-hexane) gave the title compound (5.2 g, 62% yield) as an impure yellow foam.

$^1$H NMR ($CDCl_3$, 300 MHz): δ1.51 (s, 18H, C(C$\underline{H}_3$)$_3$), 2.50 (dd, J=7 Hz, 16 Hz, 1H, ArC$\underline{H}$H), 2.69 (t, J=7 Hz, 2H, NCH$_2$C$\underline{H}_2$), 2.81–3.13 (overlapping m, 4H, ArCH$\underline{H}$, C$\underline{H}$, C H$\underline{H}$CO$_2$), 3.74 (s, 3H, CO$_2$C$\underline{H}_3$), 3.83 (t, J=7 Hz, 2H, NC $\underline{H}_2$), 6.80 (d, J=1 Hz, 1H, Ar$\underline{H}$), 7.02 (dd, J=1 Hz, 8 Hz, 1H, Ar$\underline{H}$), 7.06 (d, J=8 Hz, 1H, Ar$\underline{H}$), 8.25 (s, 1H, ArN$\underline{H}$).

EXAMPLE 92

{7-[5-Bis(tert-butylcarbonyloxy)amino-pent-1-ynyl]-2-oxo-1,2,3.4-tetrahydro-quinolin-3-yl}-acetic acid methyl ester Using the conditions of Example 91 and replacing N-but-3-ynyl-imidodicarbonic acid di-tert-butyl ester with N-pent-4-ynyl imidodicarbonic acid di-tert-butyl ester, the product of the example is obtained.

EXAMPLE 93

{7-[6-Bis(tert-butylcarbonyloxy)amino-hex-1-ynyl]-2-oxo-1,2,3,4-tetrahydro-quinolin-3-yl}-acetic acid methyl ester Using the conditions of Example 91 and replacing N-but-3-ynyl-imidodicarbonic acid di-tert-butyl ester with N-hex-5-ynylimidodicarbonic acid di-tert-butyl ester, the product of the example is obtained.

EXAMPLE 94

[7-(4-Amino-but-1-enyl)-2-oxo-1,2,3,4-tetrahydro-quinolin-3-yl]-acetic acid methyl ester A solution of (7-{4-[bis-(tert-butoxycarbonyl)-amino]-but-1-ynyl}-2-oxo-1,2,3,4-tetrahydro-quinolin-3-yl)-acetic acid methyl ester (5.2 g, 10.7 mmol) and trifluoroacetic acid (8.2 mL, 106 mmol) were combined in methylene chloride (40 mL) at 25° C. under nitrogen and stirred for 2 h. The solution was concentrated in vacuo to give a cloudy orange oil (6.8 g) which was stirred vigorously with saturated sodium bicarbonate (100 ml). The aqueous phase was extracted with chloroform (3×100 ml), dried ($K_2CO_3$) and evaporated in vacuo to give 3.2 g of a residue. The residue was purified by flash chromatography (90 g silica; $CHCl_3$, then 1% MeOH (saturated with $NH_3$)-$CHCl_3$) to give the title compound as a yellow solid (2.1 g).

EXAMPLE 95

[7-(5-Amino-pent-1-ynyl)-2-oxo-1,2,3,4-tetrahydro-quinolin-3-yl]-acetic acid methyl ester Using the conditions of Example 94 and replacing (7-{4-[bis-(tert-butoxycarbonyl)-amino]-but-1-ynyl}-2-oxo-1,2,3,4-tetrahydro-quinolin-3-yl)-acetic acid methyl ester with {7-[5-bis(tert-butylcarbonyloxy)amino-pent-1-ynyl]-2-oxo-1,2,3,4-tetrahydro-quinolin-3-yl}-acetic acid methyl ester, the product of the example is obtained.

EXAMPLE 96

[7-(6-Amino-hex-1-ynyl)-2-oxo-1,2,3,4-tetrahydro-quinolin-3-yl]-acetic acid methyl ester Using the conditions of Example 94 and replacing (7-{4-[bis-(tert-butoxycarbonyl)-amino]-but-1-ynyl}-2-oxo-1,2,3,4-tetrahydro-quinolin-3-yl)-acetic acid methyl ester with {7-[6-bis(tert-butylcarbonyloxy)amino-hex-1-ynyl]-2-oxo-1,2,3,4-tetrahydro-quinolin-3-yl}-acetic acid methyl ester, the product of the example is obtained.

EXAMPLE 97

[7-(4-Guanidino-but-1-ynyl)-2-oxo-1.2,3,4-tetrahydro-quinolin-3-yl]-acetic acid Methyl Ester Using the conditions of Example 81 and [7-(4-amino-but-1-enyl)-2-oxo-1,2,3,4-tetrahydro-quinolin-3-yl]-acetic acid methyl ester trifluoroacetate in place of [7-(2-amino-ethoxy)-2-oxo-1,2,3,4-tetrahydro-quinolin-3-yl]-acetic acid methyl ester trifluoroacetate the product of the example is obtained.

EXAMPLE 98

[7-(5-Guanidino-pent-1-ynyl)-2-oxo-1,2,3,4-tetrahydro-quinolin-3-yl]-acetic acid methyl ester Using the conditions of Example 81 and [7-(5-amino-pent-1-ynyl)-2-oxo-1,2,3,4-tetrahydro-quinolin-3-yl]-acetic acid methyl ester in place of [7-(2-amino-ethoxy)-2-oxo-1,2,3,4-tetrahydro-quinolin-3-yl]-acetic acid methyl ester trifluoroacetate the product of the example is obtained.

EXAMPLE 99

[7-(6-Guanidino-hex-1-ynyl)-2-oxo-1.2,3.4-tetrahydro-quinolin-3-yl]-acetic acid methyl ester Using the conditions of Example 81 and [7-(6-amino-hex-1-ynyl)-2-oxo-1,2,3,4-tetrahydro-quinolin-3-yl]-acetic acid methyl ester in place of [7-(2-amino-ethoxy)-2-oxo-1,2,3,4-tetrahydro-quinolin-3-yl]-acetic acid methyl ester trifluoroacetate the product of the example is obtained.

EXAMPLE 100

[7-(4-Guanidino-but-1-ynyl)-2-oxo-1,2,3,4-tetrahydro-quinolin-3-yl]-acetic acid Hydrochloride

[7-(4-Guanidino-but-1-ynyl)-2-oxo-1,2,3,4-tetrahydro-quinolin-3-yl]-acetic acid methyl ester was converted to the title compound in a manner analogous to that described for compound 84 and converted to the hydrochloride using the method described in Example 85.

Mp. 130–80 ° .C (slowly degasses).

IR (KBr): 3375 (s), 3250 (s), 3190 (s), 1710 (s), 1670 (s), 1620 (s), 1480 (m), 1230 (m), 1155 (m), 840 (w), 775 (m), 740 (m) cm$^{-1}$.

$^1$H NMR (DMSO-d$_6$, 400 MHz): δ2.36 (m, 1H, ArC$\underline{H}$H), 2.63 (t, J=7 Hz, 2H, NCH$_2$C$\underline{H}_2$), 2.68–2.94 (overlapping m, 4H, ArCH$\underline{H}$, C$\underline{H}$, C$\underline{H}$HCO$_2$), 3.35 (m, 2H, NC$\underline{H}_2$), 6.75–7.64 (broad, 4H, [C(N$\underline{H}_2$)$_2$]$^+$), 6.88 (d, J=1.5 Hz, 1H, Ar$\underline{H}$), 6.95 (dd, J=1.5 Hz, 8 Hz, 1H, Ar$\underline{H}$), 7.14 (d, J=8 Hz, 1H, Ar$\underline{H}$), 7.73 (t, >J=6 Hz, 1H, N$\underline{H}$CH$_2$), 10.2 (s, 1H, ArN $\underline{H}$), 12.2 (s, 1H, CO$_2$H).

MS (−FAB) m/e (rel. intensity): 313 (M−H, 31).

Analysis calc. for $C_{16}H_{18}N_4O_3 \cdot HCl \cdot 1.5\ H_2O$ C, 50.86; H, 5.87; N, 14.83. Found C, 50.77; H, 5.86; N, 14.56.

EXAMPLE 101

[7-(5-Guanidino-pent-1-ynyl)-2-oxo-1,2,3,4-tetrahydro-quinolin-3-yl]-acetic acid Trifluoroacetate Using the conditions of Examples 84 and 85 and [7-(5-guanidino-pent-1-ynyl)-2-oxo-1,2,3,4-tetrahydro-quinolin-3-yl]-acetic acid methyl ester in place of [7-(4-guanidino-but-1-ynyl)-2-oxo-1,2,3,4-tetrahydro-quinolin-3-yl]-acetic acid methyl ester, the product of the example was obtained.

Mp. Shrinks noticeably from 98–99 °C., then melts with degassing from 103–11° C.

IR (KBr): 3410 (s), 3350 (s), 3170 (s), 1670 (s), 1660 (s), 1200 (s), 1140 (s), 840 (m), 800 (m), 720 (m) cm$^{-1}$.

$^1$H NMR (DMSO-d$_6$, 400 MHz): δ1.74 (m, 2H, NCH$_2$CH$_2$), 2.36 (m, 1H, ArCHH), 2.45 (t, J=7 Hz, 2H, ≡CCH$_2$), 2.66–2.94 (overlapping m, 4H, ArCHH, CH, CHHCO$_2$), 3.20 (m, 2H, NCH$_2$), 6.60–7.58 (broad, 4H,[C(NH$_2$)$_2$]$^+$), 6.83 (d J=1.5 Hz, 1H, ArH), 6.93 (dd, J=1.5 Hz, 8 Hz, 1H, ArH, 7.13 (d, J=8 Hz, 1H, ArH), 7.62 (t, J=5.5 Hz, 1H, NHCH$_2$), 10.2 (s, 1H, ArNH), 12.2 (s, 1H, CO$_2$H).

MS (−FAB) m/e (rel. intensity): 327 (M − H, 27).

| Analysis calc. for $C_{17}H_{20}N_4O_3 \cdot CF_3COOH \cdot 0.6\ H_2O$ | C, 50.35; H, 4.94; N, 12.36 |
|---|---|
| Found | C, 50.04; H, 4.67; N, 12.25 |

EXAMPLE 102

[7-(6-Guanidino-hex-1-ynyl)-2-oxo-1,2,3,4-tetrahydro-quinolin-3-yl]-acetic acid hydrochloride Using the conditions of Examples 84 and 85 and [7-(6-guanidino-hex-1-ynyl)-2-oxo-1,2,3,4-tetrahydro-quinolin-3-yl]-acetic acid methyl ester in place of [7-(4-guanidino-but-1-ynyl)-2-oxo-1,2,3,4-tetrahydro-quinolin-3-yl]-acetic acid methyl ester, the product of the example is obtained.

EXAMPLE 103

[7-(4-tert-Butoxycarbonylamino-but-1-ynyl)-2-oxo-1,2,3,4-tetrahydro-quinolin-3-yl]-acetic acid methyl ester A suspension of [7-(4-amino-but-1-ynyl)-2-oxo-1,2,3,4-tetrahydro-quinolin-3-yl]-acetic acid methyl ester (0.48 g, 1.7 mmol), di-tert-butyl dicarbonate (0.37 g, 1.7 mmol) and potassium carbonate (0.47 g, 3.4 mmol) in 1:1 MeOH: (3:1) dioxane-water (17 mL) was stirred at 25° C. After 2 h, the mixture was concentrated and the resulting solid partitioned between water and chloroform (25 mL each). The layers were separated and the aqueous phase re-extracted with chloroform (2×25 mL). The combined extracts were dried (MgSO$_4$) and concentrated to give the title compound (0.61 g, 94% yield) as a white foam.

$^1$H NMR (CDCl$_3$, 300 MHz): δ1.46 (s, 18H, C(CH$_3$)$_3$), 2.46–2.62 (overlapping m, 3H, ArCHH, CCH2), 2.82–3.13 (overlapping m, 4H, ArCHH, CH, CHHCO$_2$), 3.36 (m, 2H, NCH$_2$), 3.84 (s, 3H, CO$_2$CH$_3$), 4.87 (broad s, 1H, NHCH$_2$), 6.80 (s, 1H, ArH), 7.02–7.10 (overlapping m, 2H, ArH), 7.94 (s, 1H, ArNH).

EXAMPLE 104

[7-(5-tert-Butoxycarbonylamino-pent-1-ynyl)-2-oxo-1 2,3,4-tetrahydro-quinolin-3-yl]-acetic acid methyl ester Using the conditions of Example 103 and [7-(5-amino-pent-1-ynyl)-2-oxo-1,2,3,4-tetrahydro-quinolin-3-yl]-acetic acid methyl ester in place of [7-(4-amino-but-1-ynyl)-2-oxo-1,2,3,4-tetrahydro-quinolin-3-yl]-acetic acid methyl ester the product of the example is obtained.

EXAMPLE 105

[7-(6-tert-Butoxycarbonylamino-hex-1-ynyl)-2-oxo-1,2,3,4-tetrahydro-quinolin-3-yl]-acetic acid methyl ester Using the conditions of Example 103 and [7-(6-amino-hex-1-ynyl)-2-oxo-1,2,3,4-tetrahydro-quinolin-3-yl]-acetic acid methyl ester in place of [7-(4-amino-but-1-ynyl)-2-oxo-1,2,3,4-tetrahydro-quinolin-3-yl]-acetic acid methyl ester the product of the example is obtained.

EXAMPLE 106

[7-(4-Amino-but-1-enyl)-2-oxo-1,2,3,4-tetrahydro-quinolin-3-yl]-acetic acid methyl ester A solution of [7-(4-tert-butoxycarbonylamino-but-1-ynyl)-2-oxo-1,2,3,4-tetrahydro-quinolin-3-yl]-acetic acid methyl ester (1.10 g, 2.85 mmol) in 2:1 methanol-dioxane (70 mL) containing quinoline (1.1 mL) was hydrogenated over Lindlar's catalyst (5% Pd—CaCO$_3$ poisoned with lead, 0.21 g) at 250° C. and 1 atm. After 2 h, the catalyst was removed by filtration and the filtrate concentrated to give a pale yellow oil (1.50 g) which was treated with trifluoroacetic acid in dichloromethane. The resulting crude trifluoroacetate salt was treated with saturated aqueous NaHCO$_3$ (25 mL) and extracted with chloroform (3×25 mL). The extracts were dried (MgSO$_4$) and concentrated to give a cloudy, yellow oil (0.89 g). Flash chromatography (20 g silica; 0.5%, then 1%, then 2%, then 4%, then 8%, then 10% MeOH (saturated with NH$_3$)—CHCl$_3$) gives the title compound (0.46 g; 56% yield) as a pale yellow oil.

$^1$H NMR (CDCl$_3$, 300 MHz): δ1.24 (broad s, 2H, NH$_2$), 2.44–2.55 (overlapping m, 3H, ArCHH, =CHCH$_2$), 2.82–3.14 (overlapping m, 6H, ArCHH, CH, CHHCO$_2$, NCH$_2$), 3.74 (s, 3H, CO$_2$CH$_3$), 5.67 (dt, J=7 Hz, 12 Hz, 1H, =CHCH$_2$), 6.46 (d, J=12 Hz, 1H, =CHAr), 6.74 (s, 1H, ArH), 6.92 (dd, J=1 Hz, 8 Hz, 1H, ArH), 7.11 (d, J=8 Hz, 1H, Ar H), 8.69 (broad s, 1H, ArNH).

EXAMPLE 107

[7-(5-Amino-pent-1-enyl)-2-oxo-1,2,3,4-tetrahydro-quinolin-3-yl]-acetic acid methyl ester Using the conditions of Example 106 and [7-(5-tert-butoxycarbonylamino-pent-1-ynyl)-2-oxo-1,2,3,4-tetrahydro-quinolin-3-yl]-acetic acid methyl ester in place of [7-(4-amino-but-1-enyl)-2-oxo-1,2,3,4-tetra-hydro-quinolin-3-yl]-acetic acid methyl ester, the product of the example is obtained.

EXAMPLE 108

[7-(6-Amino-hex-1-enyl)-2-oxo-1,2,3,4-tetrahydro-quinolin-3-yl]-acetic acid methyl ester Using the conditions of Example 106 and [7-(6-tert-butoxycarbonylamino-hex-1-ynyl)-2-oxo-1,2,3,4-tetrahydro-quinolin-3-yl]-acetic acid methyl ester in place of [7-(4-tert-butoxy-carbonylamino-but-1-enyl)-2-oxo-1,2,3,4-tetra-hydro-quinolin-3-yl]-acetic acid methyl ester, the product of the example is obtained.

EXAMPLE 109

[7-(4-Guanidino-but-1-enyl)-2-oxo-1,2,3,4-tetrahydro-quinolin-3-yl]-acetic acid Methyl Ester Using the conditions of Example 81 and [7-(4-amino-but-1-enyl)-2-oxo-1,2,3,4-tetrahydro-quinolin-3-yl]-acetic acid methyl ester in place of [7-(2-amino-ethoxy)-2-oxo-1,2,3,4-tetrahydro-quinolin-3-yl]-acetic acid methyl ester trifluoroacetate the product of the example is obtained.

EXAMPLE 110

[7-(5-Guanidino-pent-1-enyl)-2-oxo-1,2,3,4-tetrahydro-quinolin-3-yl]-acetic acid Methyl Ester Using the conditions of Example 81 and [7-(5-amino-pent-1-enyl)-2-oxo-1,2,3,4-tetrahydro-quinolin-3-yl]-acetic acid methyl ester in place of [7-(2-amino-ethoxy)-2-oxo-1,2,3,4-tetrahydro-quinolin-3-yl]-acetic acid methyl ester trifluoroacetate, the product of the example is obtained.

EXAMPLE 111

[7-(6-Guanidino-hex-1-enyl)-2-oxo-1,2,3,4-tetrahydro-quinolin-3-yl]-acetic acid Methyl Ester Using the conditions of Example 81 and [7-(6-amino-hex-1-enyl)-2-oxo-1,2,3,4-tetrahydro-quinolin-3-yl]-acetic acid methyl ester in place of [7-(2-amino-ethoxy)-2-oxo-1,2,3,4-tetrahydro-quinolin-3-yl]-acetic acid methyl ester trifluoroacetate, the product of the example is obtained.

EXAMPLE 112

[7-(4-Guanidino-but-1-enyl)-2-oxo-1,2,3,4-tetrahydro-quinolin-3-yl]-acetic acid Trifluoroacetate

[7-(4-Guanidino-but-1-enyl)-2-oxo-1,2,3,4-tetra-hydro-quinolin-3-yl]-acetic acid methyl ester was converted to the title compound in a manner analogous to that described for Example 84.

Mp. 173–76° C.

IR (KBr): 3430 (s), 3330 (s), 3220 (s), 1680 (s), 1660 (s), 1625 (s), 1490 (m), 1425 (m), 1400 (s), 1250 (s), 1180 (s), 1135 (s), 870 (m), 830 (m), 799 (m) cm$^{-1}$.

$^1$H NMR (DMSO-d$_6$, 400 MHz): δ2.36 (m, 1H, ArCHH), 2.47 (m, 2H, =CHCH$_2$), 2.69–2.97 (overlapping m, 4H, ArCHH, CH, CHHCO$_2$), 3.22 (m, 2H, NCH$_2$), 5.57 (dt, J=7 Hz, 12 Hz, 1H, =CHCH$_2$), 6.45 (d, J=12 Hz, 1H, ArCH=), 6.60–7.45 (broad, 4H, [C(NH$_2$)$_2$]$^+$), 6.79 (d, J=1Hz, 1H, ArH), 6.84 (dd, J=1 Hz, 8 Hz, 1H, ArH), 7.15 (d, J=8 Hz, 1H, ArH), 7.52 (t, J=6 Hz, 1H, NHCH$_2$), 10.1 (s, 1H, ArNH), 12.2 (s, 1H, CO$_2$H).

MS (+ESI) m/e (rel. intensity): 317 (M+H, 100).

Analysis calc. for C$_{16}$H$_{20}$N$_4$O$_3$.CF$_3$COOH [3COOH C, 50.23;H, 4.92; N, 13.02. Found C, 49.93;H, 4.87; N, 12.84.

EXAMPLE 113

[7-(5-Guanidino-pent-1-enyl)-2-oxo-1,2,3,4-tetrahydro-quinolin-3-yl]-acetic acid Trifluoroacetate

[7-(5-Guanidino-pent-1-enyl)-2-oxo-1,2,3,4-tetra-hydro-quinolin-3-yl]-acetic acid methyl ester was converted to the title compound in a manner analogous to that described for Example 112.

Mp. 162–65° C.

IR (KBr): 3440 (s), 3350 (s), 3200 (m), 1710 (s), 1675 (s), 1430 (m), 1400 (m), 1250 (m), 1180 (s), 1132 (s), 830 (m), 795 (m), 725 (m) cm$^{-1}$.

$^1$H NMR (DMSO-d$_6$, 400 MHz): δ1.60 (m, 2H, NCH$_2$CH$_2$), 2.26–2.39 (overlapping m, 3H, ArCHH, CH$_2$CH=), 2.69–2.96 (overlapping m, 4H, ArCHH, CH, CHHCO$_2$), 3.11 (m, 2H, NCH$_2$), 5.62(dt, J=7 Hz, 12 Hz, 1H, CH$_2$CH=), 6.35 (d, J=12 Hz, 1H, ArCH=), 6.60–7.45 (broad, 4H, [C(NH$_2$)$_2$]$^+$), 6.79 (d, J=1 Hz, 1H, ArH, 6.83 (dd, J=1 Hz, 8 Hz, 1H, ArH), 7.14 (d, J=8 Hz, 1H, ArH, 7.53 (t, J=6 Hz, 1H, NHCH$_2$), 10.1 (s, 1H ArNH, 12.2 (s, 1H, CO$_2$H).

MS (+ESI) m/e (rel. intensity): 331 (M+H, 34).

Analysis calc. for C$_{17}$H$_{22}$N$_4$O$_3$.CF$_3$COOH C, 51.35; H, 5.22; N, 12.61. Found C, 50.95;H, 5.19; N, 12.32.

EXAMPLE 114

[7-(6-Guanidino-hex-1-enyl)-2-oxo-1,2,3,4-tetrahydro-quinolin-3-yl]-acetic acid Trifluoroacetate

[7-(6-Guanidino-hex-1-enyl)-2-oxo-1,2,3,4-tetra-hydro-quinolin-3-yl]-acetic acid methyl ester is converted to the title compound in a manner analogous to that described for Example 112.

EXAMPLE 115

[7-(4-Amino-butyl)-2-oxo-1,2,3,4-tetrahydro-quinolin-3-yl]-acetic acid methyl ester A solution of [7-(4-amino-but-1-enyl)-2-oxo-1,2,3,4-tetrahydro-quinolin-3-yl]-acetic acid methyl ester (0.41 g, 1.43 mmol) and 86 mg of 10% palladium-on-carbon in 40 ml of acetic acid was hydrogenated under 55 psi of hydrogen for 3 hours. The reaction mixture was filtered through diatomaceous earth and the filter cake washed with acetic acid (2×20 ml). The filtrate was evaporated in vacuo to a residue of oil and crystalline solid (0.57 g) which was partitioned between saturated sodium bicarbonate (20 ml) and chloroform and extracted (3×20 ml). The combined extracts were dried (K$_2$CO$_3$) and evaporated in vacuo to give 0.24 g (free base, 57% crude yield) of a pale yellow solid.

$^1$H NMR (DMSO-d$_6$, 400 MHz): δ1.32 (m, 2H, NCH$_2$CH$_2$), 1.51 (m, 2H, ArCH$_2$CH$_2$), 2.43–2.88 (m, 9H, ArCHHCH, CHHCO$_2$, ArCH$_2$CH$_2$, NCH$_2$), 3.32 (broad, 2H, NH$_2$), 3.60 (s, 3H, CH$_3$), 6.66 (d, J=1.5 Hz, 1H, ArH), 6.73 (dd, J=1.5 Hz, 7.5 Hz, 1H, ArH), 7.03 (d, J=7.5 Hz, 1H, ArH), 10.1 (broad s, 1H, ArNH).

EXAMPLE 116

[7-(5-Amino-pentyl)-2-oxo-1,2,3,4-tetrahydro-quinolin-3-yl]-acetic acid methyl ester Using the conditions of Example 115 and [7-(5-amino-pent-1-enyl)-2-oxo-1,2,3,4-tetrahydro-quinolin-3-yl]-acetic acid methyl ester in place of [7-(4-amino-but-1-enyl)-2-oxo-1,2,3,4-tetrahydro-quinolin-3-yl]-acetic acid methyl ester, the product of the example is obtained.

EXAMPLE 117

[7-(6-Amino-hexyl)-2-oxo-1,2,3,4-tetrahydro-quinolin-3-yl]-acetic acid methyl ester Using the conditions of Example 115 and [7-(6-amino-hex-1-enyl)-2-oxo-1,2,3,4-tetrahydro-quinolin-3-yl]-acetic acid methyl ester in place of [7-(4-amino-but-1-enyl)-2-oxo-1,2,3,4-tetrahydro-quinolin-3-yl]-acetic acid methyl ester, the product of the example is obtained.

EXAMPLE 118

[7-(4-Guanidino-butyl)-2-oxo-1,2,3,4-tetrahydro-quinolin-3-yl]-acetic acid Methyl Ester Using the conditions of Example 81 and [7-(4-amino-butyl)-2-oxo-1,2,3,4-tetrahydro-quinolin-3-yl]-acetic acid methyl ester in place of [7-(2-amino-ethoxy)-2-oxo-1,2,3,4-tetrahydro-quinolin-3-yl]-acetic acid methyl ester trifluoroacetate the product of the example is obtained.

EXAMPLE 119

[7-(5-Guanidino-pentyl)-2-oxo-1,2,3,4-tetrahydro-quinolin-3-yl]-acetic acid Methyl Ester Using the conditions of Example 81 and [7-(5-amino-pentyl)-2-oxo-1,2,3,4-tetrahydro-quinolin-3-yl]-acetic acid methyl ester in place of [7-(2-amino-ethoxy)-2-oxo-1,2,3,4-tetrahydro-quinolin-3-yl]-acetic acid methyl ester trifluoroacetate, the product of the example is obtained.

EXAMPLE 120

[7-(6-Guanidino-hexyl)-2-oxo-1,2,3,4-tetrahydro-quinolin-3-yl]-acetic acid Methyl Ester Using the conditions of Example 81 and [7-(6-amino-hexyl)-2-oxo-1,2,3,4-tetrahydro-quinolin-3-yl]-acetic acid methyl ester in place of [7-(2-amino-ethoxy)-2-oxo-1,2,3,4-tetrahydro-quinolin-3-yl]-acetic acid methyl ester trifluoroacetate, the product of the example is obtained.

EXAMPLE 121

[7-(4-Guanidino-butyl)-2-oxo-1,2,3,4-tetrahydro-quinolin-3-yl]-acetic acid Trifluoroacetate

[7-(4-Guanidino-butyl)-2-oxo-1,2,3,4-tetrahydro-quinolin-3-yl]-acetic acid methyl ester was converted to the title compound in a manner analogous to that described for Example 84.

Mp. 157–60° C.

IR (KBr): 3405 (s), 3180 (s), 1680 (s), 1625 (s), 1480 (m), 1430 (m), 1400 (m), 1295 (m), 1250 (m), 1190 (s), 1140 (s), 840 (m), 800 (m), 725 (m) cm$^{-1}$.

$^1$H NMR. (DMSO-d$_6$, 400 MHz): δ1.42–1.58 (overlapping m, 4H, NCH$_2$C$\underline{H}_2$, ArCH$_2$C$\underline{H}_2$), 2,31–2.92 (overlapping m, 7H, ArC$\underline{H}$HC$\underline{H}$, C$\underline{H}$HCO$_2$, ArC$\underline{H}_2$CH$_2$), 3.09 (m, 2H, NC$\underline{H}_2$). 6.56–7.40 (broad, 4H, [C(N$\underline{H}_2$)$_2$]$^+$), 6.65 (d, J=1.5 Hz, 1H, Ar$\underline{H}$), 6.74 (dd, J=1.5 Hz, 8 Hz, 1H, Ar$\underline{H}$), 7.06 (d, J=8 Hz, 1H, Ar$\underline{H}$), 7.46 (t, J=5 Hz, 1H, N$\underline{H}$CH$_2$), 10.1 (s, 1H, ArN$\underline{H}$), 12.2 (s, 1H, CO$_2\underline{H}$).

MS (-FAB) m/e (rel. intensity): 317 (M–H, 34).

Analysis calc. for C$_{16}$H$_{22}$N$_4$O$_3$.CF$_3$COOH.0.3 H$_2$O C, 49.38; H, 5.43; N, 12.80. Found C, 49.12;H, 5.23; N, 12.72.

EXAMPLE 122

[7-(5-Guanidino-pentyl)-2-oxo-1,2,3,4-tetrahydro-quinolin-3-yl]-acetic acid Trifluoroacetate

[7-(5-Guanidino-pentyl)-2-oxo-1,2,3,4-tetrahydro-quinolin-3-yl]-acetic acid methyl ester was converted to the title compound in a manner analogous to that described for Example 84.

Mp. 148–51° C.

IR (KBr): 3380 (s), 3180 (s), 1700 (s), 1675 (s), 1475 (m), 1435 (m), 1400 (m), 1199 (s doublet), 1135 (s), 840 (m), 795 (m), 725 (m) cm$^{-1}$.

$^1$H NMR (DMSO-d$_6$, 400 MHz): δ1.27 (m, 2H, NCH$_2$CH$_2$C$\underline{H}_2$), 1.43–1.56 (overlapping m, 4H, NCH$_2$C$\underline{H}_2$, ArCH$_2$C$\underline{H}_2$), 2,31–2.91 (overlapping m, 7H, ArC$\underline{H}$HCH, C$\underline{H}$HCO$_2$, ArC$\underline{H}_2$CH$_2$), 3.06 (m, 2H, NC$\underline{H}_2$), 6.56–7.42 (broad, 4H, [C(N$\underline{H}_2$)$_2$]$^+$), 6.65 (d, J=1 Hz, 1H, Ar$\underline{H}$), 6.73 (dd, J=1 Hz, 7.5 Hz, 1H, ArN$\underline{H}$) 7.05 (d, J=7.5 Hz, 1H, Ar $\underline{H}$, 7.49 (t, J=5 Hz, 1H, N$\underline{H}$CH$_2$), 10.1 (s, 1H, ArN$\underline{H}$), 12.2 (s, 1H, CO$_2$H).

MS (–FAB) m/e (rel. intensity): 331 (M – H, 14).

| | |
|---|---|
| Analysis calc. for C$_{17}$H$_{24}$N$_4$O$_3$.CF$_3$COOH | C, 51.12; H, 5.64; N, 12.55 |
| Found | C, 51.33; H, 5.70; N, 12.65 |

EXAMPLE 123

[7-(6-Guanidino-hexyl)-2-oxo-1,2,3,4-tetrahydro-quinolin-3-yl]-acetic acid Trifluoroacetate

[7-(6-Guanidino-hexyl)-2-oxo-1,2,3,4-tetrahydro-quinolin-3-yl]-acetic acid methyl ester is converted to the title compound in a manner analogous to that described for Example 84.

EXAMPLE 124

(1-Ethyl-7-methoxy-2-oxo-1,2-dihydro-quinolin-3-yl)-acetic acid methyl ester

A slurry of (7-methoxy-2-oxo-1,2-dihydro-quinolin-3-yl)-acetic acid methyl ester (5.0 g, 20 mmol) in tetrahydrofuran (40 mL) was treated with potassium bis(trimethylsilyl)amide (0.5 M in toluene, 41 mL, 21 mmol) at 25° C. and the mixture heated to reflux. After 1 h at reflux, ethyl iodide (16 mL, 200 mmol) was added. After an additional 3 h at reflux, the cooled mixture was quenched with 0.1N aqueous HCl (50 mL) and concentrated in vacuo. Water (200 mL) was added and the aqueous phase extracted with chloroform (3×200 mL). The extracts were dried (K$_2$CO$_3$) and concentrated in vacuo to give the crude product (5.3 g). Flash chromatography (225 g silica; 2:1, then 1:1 hexane-ether, then 100% ether) gave the title compound (4.4 g, 79% yield) as a white solid.

$^1$H NMR (DMSO-d$_6$, 300 MHz): δ1.19 (t, J=7 Hz, 3H, CH$_2$C$\underline{H}_3$), 3.53 (s, 2H, C$\underline{H}_2$CO$_2$), 3.60 (s, 3H, CO$_2$C$\underline{H}_3$), 3.89 (s, 3H, OC$\underline{H}_3$ ), 4.25 (q, J=7 Hz, 2H, NC$\underline{H}_2$), 6.90 (d, J=9 Hz, 1H, Ar$\underline{H}$), 6.96 (s, 1H, Ar$\underline{H}$), 7.61 (s, J=9 Hz, 1H, Ar$\underline{H}$), 7.78 (s, 1H, ArCH=).

EXAMPLE 125

(1-Benzyl-7-methoxy-2-oxo-1,2-dihydro-quinolin-3-yl)-acetic acid methyl ester

The title compound (5.2 g, 76% yield) was prepared in essentially the same manner as described for the preparation of Example 124 using benzyl bromide in place of ethyl iodide.

Mp. 118.0–119.5 ° C.

$^1$H NMR (DMSO-d$_6$, 300 MHz): δ3.61 (s, 5H, CO$_2$C$\underline{H}_3$, C$\underline{H}_2$CO$_2$), 3.73 (s, 3H, OC$\underline{H}_3$), 5.52 (s, 2H, C$\underline{H}_2$Ph), 6.82–6.88 (overlapping m, 2H, Ar$\underline{H}$), 7.20 (m, 3H, Ar$\underline{H}$), 7.30 (m, 2H, Ar$\underline{H}$), 7.62 (d, J=8.5 Hz, 1H, Ar$\underline{H}$), 7.87 (s, 1H, ArC$\underline{H}$=).

EXAMPLE 126

(1-Ethyl-7-hydroxy-2-oxo-1,2-dihydro-quinolin-3-yl)-acetic acid

A suspension of (1-ethyl-7-methoxy-2-oxo-1,2-dihydro-quinolin-3-yl)-acetic acid methyl ester (4.0 g, 14.5 mmol) in 1:1 48% aqueous HBr—HOAc (30 mL) was heated at reflux for 48 h. The resulting solution was cooled to 250° C. and the resulting crystalline solid was stored at 0–50° C. for 2 h, then vacuum filtered, washed with water and air-dried to give the title compound (3.2 g, 89% yield) as tan needles.

Mp. 226–29 ° C.

$^1$H NMR (DMSO-d$_6$, 300 MHz): δ1.18 (t, J=7 Hz, 3H, C$\underline{H}_3$), 3.41 (s, 2H, C$\underline{H}_2$CO$_2$), 4.17 (q, J=7 Hz, 2H, NC$\underline{H}_2$), 6.73 (dd, J=2 Hz, 8.5 Hz, 1H, Ar$\underline{H}$), 6.83 (d, J=2Hz, 1H, Ar$\underline{H}$), 7.49 (d, J=8.5 Hz, 1H, Ar$\underline{H}$), 7.70 (s, 1H, ArCH=), 10.2 (s, 1H, ArO$\underline{H}$), 12.2 (broad s, 1H, CO$_2\underline{H}$).

EXAMPLE 127

(1-Ethyl-7-hydroxy-2-oxo-1,2-dihydro-quinolin-3-yl)-acetic acid methyl ester

A suspension of (1-ethyl-7-hydroxy-2-oxo-1,2-dihydro-quinolin-3-yl)-acetic acid (2.9 g, 12 mmol) in methanol (30 mL) was treated with 12 N aqueous HCl (3 mL, 36 mmol) and the mixture heated to reflux. After 5 h, the resulting solution was cooled to room temperature, filtered and left standing overnight. The resulting solid was vacuum filtered, washed with ice-cold methanol and air-dried to give the title compound (1.8 g, 58% yield) as white needles.

Mp. 175.5–78.0° C.

$^1$H NMR (DMSO-d$_6$, 300 MHz): δ1.18 (t, J=7 Hz, 3H, CH$_2$C$\underline{H}_3$), 3.50 (S, 2H, C$\underline{H}_{22}$CO$_2$), 3.59 (s, 3H, CO$_2$CH$_3$), 4.17 (q, J=7 Hz, 2H, NC$\underline{H}_2$), 6.73 (dd, J=2 Hz, 8.5 Hz, 1H, Ar$\underline{H}$), 6.83 (d, J=2 Hz, 1H, Ar$\underline{H}$), 7.50 (d, J=8.5 Hz, 1H, Ar$\underline{H}$), 7.72 (s, 1H, ArC$\underline{H}$=), 10.2 (s, 1H, ArO$\underline{H}$).

EXAMPLE 128

(1-Benzyl-7-hydroxy-2-oxo-1,2-dihydro-quinolin-3-yl)-acetic acid

The title compound (4.1 g, 89% yield) was prepared in essentially the same manner as described for the preparation of Example 126 using (1-benzyl-7-methoxy-2-oxo-1,2-dihydro-quinolin-3-yl)-acetic acid methyl ester in place of (1-ethyl-7-methoxy-2-oxo-1,2-dihydro-quinolin-3-yl)-acetic acid methyl ester.

$^1$H NMR (DMSO-d$_6$, 300 MHz): δ3.49 (s, 2H, CH$_2$CO$_2$), 5.42 (broad s, 2H, C$\underline{H}_2$Ph), 6.67–6.70 (overlapping m, 2H, Ar$\underline{H}$), 7.15–7.33 (overlapping m, 5H, Ar$\underline{H}$), 7.49 (d, J=8 Hz, 1H, Ar$\underline{H}$), 7.78 (s, 1H, ArC$\underline{H}$=), 10.1 (s, 1H, ArO$\underline{H}$), 12.2 (s, 1H, CO$_2\underline{H}$).

EXAMPLE 129

(1-Benzyl-7-hydroxy-2-oxo-1,2-dihydro-quinolin-3-yl)-acetic acid methyl ester

The title compound (2.4 g, 56% yield) was prepared in essentially the same manner as described for the preparation of Example 127 using (1-benzyl-7-hydroxy-2-oxo-1,2-dihydro-quinolin-3-yl)-acetic acid in place of (1-ethyl-7-hydroxy-2-oxo-1,2-dihydro-quinolin-3-yl)-acetic acid.

$^1$H NMR (DMSO-d$_6$, 300 MHz): δ3.58 (s, 2H, C$\underline{H}_2$CO$_2$), 3.60 (s, 3H, C$\underline{H}_3$), 5.42 (broad s, 2H, C$\underline{H}_2$Ph), 6.67–6.70 (overlapping m, 2H, Ar$\underline{H}$), 7.14–7.34 (overlapping m, 5H, Ar$\underline{H}$), 7.51 (d, J=8 Hz, 1H, Ar$\underline{H}$), 7.82 (s, 1H, ArC$\underline{H}$=), 10.1 (S, 1H, ArO$\underline{H}$).

EXAMPLE 130

[7-(3-tert-Butoxycarbonylaminopropoxy)-1-benzyl-2-oxo-1,2-dihydro-quinolin-3-yl]acetic acid methyl ester The title compound was prepared using the procedure of Example 75 and (1-benzyl-7-hydroxy-2-oxo-1,2-dihydro-quinolin-3-yl)-acetic acid methyl ester in place of 7-hydroxy-2-oxo-1,2,3,4-tetrahydro-quinolin-3-yl)acetic acid methyl ester and (3-bromopropyl)carbamic acid tert-butyl ester in place of (2-bromoethyl)carbamic acid tert-butyl ester.

EXAMPLE 131

[7-(2-tert-Butoxycarbonylaminoethoxy)-1-benzyl-2-oxo-1 2-dihydro-quinolin-3-yl]acetic acid methyl ester The title compound is prepared using the procedure of Example 75 and (1-benzyl-7-hydroxy-2-oxo-1,2-dihydro-quinolin-3-yl)-acetic acid methyl ester in place of 7-hydroxy-2-oxo-1,2,3,4-tetrahydro-quinolin-3-yl)acetic acid methyl ester

EXAMPLE 132

[7-(4-tert-Butoxycarbonylaminobutoxy)-1-benzyl-2-oxo-1,2-dihydro-quinolin-3-yl]acetic acid methyl ester The title compound is prepared using the conditions of Example 75 and (1-benzyl-7-hydroxy-2-oxo-1,2-dihydro-quinolin-3-yl)-acetic acid methyl ester in place of 7-hydroxy-2-oxo-1,2,3,4-tetrahydro-quinolin-3-yl)acetic acid methyl ester and (4-bromobutyl)carbamic acid tert-butyl ester in place of (2-bromoethyl) carbamic acid tert-butyl ester.

EXAMPLE 133

[1-Benzyl-7-(3-aminopropoxy)-2-oxo-1,2-dihydro-quinolin-3-yl]acetic acid methyl ester The title compound is prepared according to the procedure of Example 78 except that [7-(2-tert-butoxycarbonylamino-ethoxy)-2-oxo-1,2,3,4-tetrahydro-quinolin-3-yl]-acetic acid methyl ester is replaced with [7-(3-tert-butoxycarbonylaminopropoxy)-1-benzyl-2-oxo-1,2-dihydro-quinolin-3-yl]acetic acid methyl ester.

EXAMPLE 134

[1-Benzyl-7-(2-aminoethoxy)-2-oxo-1,2-dihydro-quinolin-3-yl]acetic acid methyl ester The title compound is prepared according to the procedure of Example 78 except that [7-(2-tert-butoxycarbonylamino-ethoxy)-2-oxo-1,2,3,4-tetrahydro-quinolin-3-yl]-acetic acid methyl ester is replaced with [7-(2-tert-butoxycarbonylaminoethoxy)-1-benzyl-2-oxo-1,2-dihydro-quinolin-3-yl]acetic acid methyl ester.

EXAMPLE 135

[1-Benzyl-7-(4-aminobutoxy)-2-oxo-1,2-dihydro-quinolin-3-yl]acetic acid methyl ester The title compound is prepared according to the procedure of Example 78 except that [7-(2-tertbutoxycarbonylamino-ethoxy)-2-oxo-1,2,3,4-tetrahydro-quinolin-3-yl]-acetic acid methyl ester is replaced with [7-(4-tert-butoxycarbonylaminobutoxy)-1-benzyl-2-oxo-1,2-dihydro-quinolin-3-yl]acetic acid methyl ester.

EXAMPLE 136

[1-Benzyl-7-(3-amino-propoxy)-2-oxo-1,2-dihydro-quinolin-3-yl]-acetic acid

The title compound was prepared according to the procedure of Example 84 except that [7-(3-guanidino-propoxy)-2-oxo-1,2,3,4-tetrahydro-quinolin-3-yl]-acetic acid methyl ester trifluoroacetate was replaced with [1-benzyl-7-(3-aminopropoxy)-2-oxo-1,2-dihydro-quinolin-3-yl]acetic acid methyl ester.

Mp. 126–28° C.

IR (KBr): 3420 (m), 3050 (m), 1673 (s), 1642 (s), 1585 (s), 1240 (m), 1196 (s), 1125 (s), 838 (m), 820 (m), 795 (m), 720 (m), 700 (m) cm$^{-1}$.

$^1$H NMR (DMSO-d$_6$, 400 MHz): δ1.96 (m, 2H, NCH$_2$CH$_2$), 2.92 (m, 2H, NCH$_2$CH$_2$), 3.52 (s, 2H, CH$_2$CO$_2$), 4.06 (t, J=6 Hz, 2H, OCH$_2$), 5.51 (broad s, 2H, CH$_2$Ph), 6.82 (d, J=2 Hz, 1H, ArH), 6.88 (dd, J=2 Hz, 9 Hz, 1H, ArH), 7.19–7.25 (overlapping m, 3H, ArH), 7.31 (m, 2H, ArH), 7.64 (d, J=9 Hz, 1H, ArH), 7.71 (broad s, 3H, NH$_3$$^+$), 7.85 (s, 1H, ArCH=), 12.2 (broad s, 1H, CO$_2$H).

MS (+FAB) m/e (rel. intensity): 367 (M+H, 60).

Analysis calc. for C$_{21}$H$_{22}$N$_2$O$_4$.CF$_3$COOH.1.2 H$_2$O C, 55.02;H, 5.10; N, 5.58. Found C, 54.97; H, 4.95; N, 5.54.

EXAMPLE 137

[1-Benzyl-7-(2-aminoethoxy)-2-oxo-1,2-dihydro-quinolin-3-yl]acetic acid

The title compound is prepared according to the procedure of Example 84 except that [7-(4-guanidino-butoxy)-2-oxo-1,2,3,4-tetrahydro-quinolin-3-yl]-acetic acid methyl ester trifluoroacetate is replaced with [l-benzyl-7-(2-aminoethoxy)-2-oxo-1,2-dihydro-quinolin-3-yl]acetic acid methyl ester.

EXAMPLE 138

[1-Benzyl-7-(4-aminobutoxy)-2-oxo-1,2-dihydro-quinolin-3-yl]acetic acid

The title compound is prepared according to the procedure of Example 84 except that [7-(4-guanidino-butoxy)-2-oxo-1,2,3,4-tetrahydro-quinolin-3-yl]-acetic acid methyl ester trifluoroacetate is replaced with [1-benzyl-7-(2-aminobutoxy)-2-oxo-1,2-dihydro-quinolin-3-yl]acetic acid methyl ester.

EXAMPLE 139

[7-(3-tert-Butoxycarbonylaminopropoxy)-1-ethyl-2-oxo-1,2-dihydro-quinolin-3-yl]acetic acid methyl ester The title compound is prepared using the procedure of Example 75 and (1-ethyl-7-hydroxy-2-oxo-1,2-dihydro-quinolin-3-yl)-acetic acid methyl ester in place of 7-hydroxy-2-oxo-1,2,3,4-tetrahydro-quinolin-3-yl)acetic acid methyl ester and (3-bromo-propyl)carbamic acid tert-butyl ester in place of (2-bromoethyl)carbamic acid tert-butyl ester.

EXAMPLE 140

[7-(2-tert-Butoxycarbonylaminoethoxy)-1-ethyl-2-oxo-1,2-dihydro-quinolin-3-yl]acetic acid methyl ester The title compound is prepared using the procedure of Example 75 and (1-ethyl-7-hydroxy-2-oxo-1,2-dihydro-quinolin-3-yl)-acetic acid methyl ester in place of 7-hydroxy-2-oxo-1,2,3,4-tetrahydro-quinolin-3-yl)acetic acid methyl ester.

EXAMPLE 141

[7-(4-tert-Butoxycarbonylaminobutoxy)-1-ethyl-2-oxo-1,2-dihydro-quinolin-3-yl]acetic acid methyl ester The title compound is prepared using the procedure of Example 75 and (1-ethyl-7-hydroxy-2-oxo-1,2-dihydro-quinolin-3-yl)-acetic acid methyl ester in place of 7-hydroxy-2-oxo-1,2,3,4-tetrahydro-quinolin-3-yl)acetic acid methyl ester and (4-bromobutyl)carbamic acid tert-butyl ester in place of (2-bromoethyl)carbamic acid tert-butyl ester.

EXAMPLE 142

[1-Ethyl-7-(3-amino-propoxy)-2-oxo-1,2-dihydro-quinolin-3-yl]acetic acid Trifluoroacetate The title compound was prepared according to the procedure of Example 84 except that [7-(3-tert-butoxy-carbonylaminopropoxy)-1-ethyl-2-oxo-1,2-dihydro-quinolin-3-yl]acetic acid methyl ester was used in place of [7-(4-guanidino-butoxy)-2-oxo-1,2,3,4-tetrahydro-quinolin-3-yl]acetic acid methyl ester trifluoroacetate.

Mp. 182–84° C.

IR (KBr): 3410 (m), 3130 (m), 3060 (m), 1715 (s), 1648 (s), 1600 (s), 1235 (m), 1202 (s), 1178 (s), 1126 (s), 1105 (m), 852 (m), 792 (m), 788 (m), 720 (m) cm$^{-1}$.

$^1$H NMR (DMSO-d$_6$, 400 MHz): δ1.20 (t, J=7 Hz, 3H, CH$_3$), 2.05 (m, 2H, NCH$_2$CH$_2$), 3.01 (m, 2H, NCH$_2$CH$_2$), 3.45 (s, 2H, CH$_2$CO$_2$), 4.21 (t, J=6 Hz, 2H, OCH$_2$), 4.26 (q, J=7 Hz, 2H, NCH$_2$CH$_3$), 6.91 (dd, J=2 Hz, 9 Hz, 1H, ArH), 6.97 (d, J=2 Hz, 1H, ArH), 7.63 (d, J=9 Hz, 1H, ArH), 7.77 (overlapping s, broad s, 4H, ArCH=, NH$_3$$^+$), 12.2 (broad s, 1H, CO$_2$H).

MS (+FAB) m/e (rel. intensity): 305 (M+H, 100).

Analysis calc. for C$_{16}$H$_{20}$N$_2$O$_4$.CF$_3$COOH. C, 51.67; H, 5.06; N, 6.70. Found C, 51.69; H, 4.96; N, 6.77.

EXAMPLE 143

[1-Ethyl-7-(2-aminoethoxy)-2-oxo-1,2-dihydro-quinolin-3-yl]acetic acid methyl ester The title compound is prepared according to the procedure of Example 78 except that [7-(2-tert-butoxycarbonylamino-ethoxy)-2-oxo-1,2,3,4-tetrahydro-quinolin-3-yl]acetic acid methyl ester is replaced with [7-(2-tert-butoxycarbonylaminoethoxy)-1-ethyl-2-oxo-1,2-dihydro-quinolin-3-yl]acetic acid methyl ester.

EXAMPLE 144

[1-Ethyl-7-(3-aminopropoxy)-2-oxo-1,2-dihydro-quinolin-3-yl]acetic acid methyl ester The title compound is prepared according to the procedure of Example 78 except that [7-(2-tert-butoxy-carbonylamino-ethoxy)-2-oxo-1,2,3,4-tetrahydroquinolin-3-yl]acetic acid methyl ester is replaced with [7-(3-tert-butoxycarbonylaminopropoxy)-1-ethyl-2-oxo-1,2-dihydro-quinolin-3-yl]acetic acid methyl ester.

EXAMPLE 145

[1-Ethyl-7-(4-aminobutoxy)-2-oxo-1,2-dihydro-quinolin-3-yl]acetic acid methyl ester The title compound is prepared according to the procedure of Example 78 except that [7-(2-tertbutoxycarbonylamino-ethoxy)-2-oxo-1,2,3,4-tetrahydro-quinolin-3-yl]acetic acid methyl ester is replaced with [7-(4-tert-butoxycarbonylaminobutoxy)-1-ethyl-2-oxo-1,2-dihydro-quinolin-3-yl]acetic acid methyl ester.

EXAMPLE 146

[1-Ethyl-7-(3-guanidino-propoxy)-2-oxo-1, 2-dihydro-quinolin-3-yl]-acetic acid Methyl Ester The title compound is prepared according to the procedure of Example 81 except that [1-ethyl-7-(3-aminopropoxy)-2-oxo-1,2-dihydro-quinolin-3-yl]acetic acid methyl ester is used in place of [7-(2-amino-ethoxy)-2-oxo-1,2,3,4-tetrahydro-quinolin-3-yl]acetic acid methyl ester trifluoroacetate.

EXAMPLE 147

[1-Ethyl-7-(2-guanidino-ethoxy)-2-oxo-1,2-dihydro-quinolin-3-yl]acetic acid methyl ester The title compound is prepared according to the procedure of Example 81 except that [7-(2-amino-ethoxy)-1-benzyl-2-oxo-1,2-dihydro-quinolin-3-yl]acetic acid methyl ester is used in place of [7-(2-amino-ethoxy)-2-oxo-1,2,3,4-tetrahydro-quinolin-3-yl]acetic acid methyl ester trifluoroacetate.

EXAMPLE 148

[1-Ethyl-7-(4-guanidino-butoxy)-2-oxo-1,2-dihydro-quinolin-3-yl]acetic acid methyl ester The title compound is prepared according to the procedure of Example 81 except that [7-(4-amino-butoxy)-1-ethyl-2-oxo-1,2-dihydro-quinolin-3-yl]acetic acid methyl ester is used in place of [7-(2-amino-ethoxy)-2-oxo-1,2,3,4-tetrahydro-quinolin-3-yl]acetic acid methyl ester trifluoroacetate.

EXAMPLE 149

[1-Ethyl-7-(3-guanidino-propoxy)-2-oxo-1,2-dihydro-quinolin-3-yl]-acetic acid Trifluoroacetate The title compound was prepared using the procedure of Example 84 except that [7-(4-guanidino-butoxy)-2-oxo-1,2,3,4-tetrahydro-quinolin-3-yl]acetic acid methyl ester trifluoroacetate was replaced with [1-ethyl-7-(3-guanidino-propoxy)-2-oxo-1,2-dihydro-quinolin-3-yl]-acetic acid methyl ester.

Mp. 131° C. (degasses).

IR (KBr): 3515 (m), 3460 (m), 3300 (m), 1720 (m), 1645 (s), 1599 (s), 1410 (m), 1222 (s), 1190 (s), 1140 (s), 822 (m), 800 (m), 792 (m), 725 (m) cm$^{-1}$.

$^1$H NMR (DMSO-d$_6$, 400 MHz): δ1.20 (t, J=7 Hz, 3H, CH$_3$), 1.98 (m, 2H, NCH$_2$CH$_2$), 3.31 (m, 2H, NCH$_2$CH$_2$), 3.45 (s, 2H, CH$_2$CO$_2$), 4.17 (t, J=6 Hz, 2H, OCH$_2$), 4.26 (q, J=7 Hz, 2H, NCH$_2$CH$_3$), 6.60–7.50 (broad, 4H, [C(NH$_2$)$_2$]$^+$), 6.91 (dd, J=2 Hz, 8.5 Hz, 1H, ArH), 6.96 (d, J=2 Hz, 1H, ArH), 7.61–7.65 (overlapping m, 2H, ArH, NHCH$_2$), 7.76 (s, 1H, ArCH=), 12.2 (broad s, 1H, CO$_2$H).

MS (+FAB) m/e (rel. intensity): 347 (M+H, 100).

Analysis calc. for C$_{17}$H$_{22}$N$_4$O$_4$·CF$_3$COOH·H$_2$O C, 47.70; H, 5.27; N, 11.71. Found C, 47.73; H, 5.25; N, 11.70.

EXAMPLE 150

[1-Ethyl-7-(2-guanidino-ethoxy)-2-oxo-1,2-dihydro-quinolin-3-yl]acetic acidTrifluoroacetate The title compound is prepared using the procedure of Example 84 except that [7-(4-guanidino-butoxy)-2-oxo-1,2,3,4-tetrahydro-quinolin-3-yl]acetic acid methyl ester trifluoroacetate is replaced with [1-ethyl-7-(2-guanidino-ethoxy)-2-oxo-1,2-dihydro-quinolin-3-yl]acetic acid methyl ester.

EXAMPLE 151

[1-Ethyl-7-(4-guanidino-butoxy)-2-oxo-1,2-dihydro-quinolin-3-yl]acetic acid Trifluoroacetate The title compound is prepared using the procedure of Example 84 except that [7-(4-guanidino-butoxy)-2-oxo-1,2,3,4-tetrahydro-quinolin-3-yl]acetic acid methyl ester trifluoroacetate is replaced with [1-ethyl-7-(4-guanidino-butoxy)-2-oxo-1,2-dihydro-quinolin-3-yl]acetic acid methyl ester.

EXAMPLE 152

[1-Benzyl-7-(3-guanidino-propoxy)-2-oxo-1,2-dihydro-quinolin-3-yl]acetic acid methyl ester The title compound is prepared according to the procedure of Example 81 except that [1-benzyl-7-(3-aminopropoxy)-2-oxo-1,2-dihydro-quinolin-3-yl]acetic acid methyl ester is used in place of [7-(2-amino-ethoxy)-2-oxo-1,2,3,4-tetrahydro-quinolin-3-yl]acetic acid methyl ester trifluoroacetate.

EXAMPLE 153

[1-Benzyl-7-(2-guanidino-ethoxy)-2-oxo-1,2-dihydro-quinolin-3-yl]acetic acid methyl ester The title compound is prepared according to the procedure of Example 81 except that [1-benzyl-7-(2-aminoethoxy)-2-oxo-1,2-dihydro-quinolin-3-yl]acetic acid methyl ester is used in place of [7-(2-amino-ethoxy)-2-oxo-1,2,3,4-tetrahydro-quinolin-3-yl]acetic acid methyl ester trifluoroacetate.

EXAMPLE 154

[1-Benzyl-7-(4-guanidino-butoxy)-2-oxo-1,2-dihydro-quinolin-3-yl]acetic acid methyl ester The title compound is prepared according to the procedure of Example 81 except that [1-benzyl-7-(4-aminobutoxy)-2-oxo-1,2-dihydro-quinolin-3-yl]acetic acid methyl ester is used in place of [7-(2-amino-ethoxy)-2-oxo-1,2,3,4-tetrahydro-quinolin-3-yl]acetic acid methyl ester trifluoroacetate.

EXAMPLE 155

[1-Benzyl-7-(3-guanidino-propoxy)-2-oxo-1,2-dihydro-quinolin-3-yl]-acetic acid

The title compound was prepared according to the procedure of Example 84 except that [7-(4-guanidino-butoxy)-2-oxo-1,2,3,4-tetrahydro-quinolin-3-yl]acetic acid methyl ester trifluoroacetate was replaced with (1-benzyl-7-(3-guanidino-propoxy)-2-oxo-1,2-dihydro-quinolin-3-yl]acetic acid methyl ester.

Mp. 132–34° C.

IR (KBr): 3342 (m), 3190 (m), 1715 (s), 1670 (s), 1645 (s), 1594 (s), 1408 (m), 1199 (s) 1133 (m), 840 (m), 799 (m), 723 (m) cm$^{-1}$.

$^1$H NMR (DMSO-d$_6$, 400 MHz): δ1.88 (m, 2H, NCH$_2$CH$_2$), 3.23 (m, 2H, NCH$_2$CH$_2$), 3.52 (s, 2H, CH$_2$CO$_2$), 4.01 (t, J=6 Hz, 2H, OCH$_2$), 5.52 (broad s, 2H, CH$_2$Ph), 6.60–7.50 (broad, 4H, [C(NH$_2$)$_2$]$^+$), 6.81 (s, 1H, ArH), 6.88

(d, J=9 Hz, 1H, ArH), 7.19–7.35 (overlapping m, 5H, ArH), 7.60 (t, J=5 Hz, 1H, NHCH$_2$), 7.63 (d, J=9 Hz, 1H, ArH), 7.85 (s, 1H, ArCH=), 12.2 (broad s, 1H, CO$_2$H), MS (+FAB) m/e (rel. intensity): 409 (M+H, 100).

Analysis calc. for C$_{22}$H$_{24}$N$_4$O$_4$.CF$_3$COOH C, 55.17; H, 4.82; N, 10.72. Found C, 55.07; H, 4.74; N, 10.80.

EXAMPLE 156

[1-Benzyl-7-(2-guanidino-ethoxy)-2-oxo-1,2-dihydro-quinolin-3-yl]acetic acid

The title compound is prepared according to the procedure of Example 84 except that [7-(4-guanidino-butoxy)-2-oxo-1,2,3,4-tetrahydro-quinolin-3-yl]acetic acid methyl ester trifluoroacetate is replaced with [1-benzyl-7-(2-guanidino-ethoxy)-2-oxo-1,2-dihydro-quinolin-3-yl]acetic acid methyl ester.

EXAMPLE 157

[1-Benzyl-7-(4-guanidino-butoxy)-2-oxo-1,2-dihydro-quinolin-3-yl]acetic acid

The title compound is prepared according to the procedure of Example 84 except that [7-(4-guanidino-butoxy)-2-oxo-1,2,3,4-tetrahydro-quinolin-3-yl]acetic acid methyl ester trifluoroacetate is replaced with [1-benzyl-7-(4-guanidino-butoxy)-2-oxo-1,2-dihydro-quinolin-3-yl]acetic acid methyl ester.

EXAMPLE 158

[1-Ethyl-7-(3-guanidino-propoxy)-2-oxo-1,2,3,4-tetrahydro-quinolin-3-yl]-acetic acid Trifluoroacetate A solution of [1-ethyl-7-(3-guanidino-propoxy)-2-oxo-1,2-dihydro-quinolin-3-yl]-acetic acid trifluoroacetate (400 mg, 0.87 mmol) in 20 ml of methyl alcohol and 0.4 g of 10% Pd/C was hydrogenated under 50 psi of hydrogen for 3 days. The reaction mixture was filtered through diatomaceous earth and the filtrate concentrated in vacuo to a residue which was dissolved in 10 ml of hot acetic acid and hydrogenated over 0.4 g of 10% Pd/C for 3 days. The reaction mixture was filtered through diatomaceous earth and the filter cake washed with hot methyl alcohol. The combined filtrates were evaporated in vacuo to a residue of oil and solid. The residue was purified by chromatography on a reverse phase column to afford 57 mg of the title compound as a pale yellow solid.

Mp. 165–66° C.

$^1$H NMR (DMSO-d$_6$, 400 MHz): δ1.10 (t, J=7 Hz, 3H, CH$_3$), 1.92 (m, 2H, NCH$_2$CH$_2$), 2.33 (dd, J=6 Hz, 16 Hz, 1H, ArCHH), 2.64–2.84 (overlapping m, 4H, CH, ArCHH, CHHCO$_2$), 3.28 (m, 2H, NCH$_2$CH$_2$), 3.88 (overlapping m, 2H, NCHHCH$_3$), 4.02 (t, J=6 Hz, 2H, OCH$_2$), 6.60 (dd, J=2 Hz, 8 Hz, 1H, ArH), 6.65 (d, J=2 Hz, 1H, ArH), 6.70–7.50 (broad, 4H, [C(NH$_2$)$_2$]$^+$), 7.12 (d, J=8 Hz, 1H, ArH), 7.58 (t, J=6 Hz, 1H, NHCH$_2$), 12.1 (broad s, 1H, CO$_2$H).

MS (+FAB) m/e (rel. intensity): 349 (M+H, 20).

Analysis calc. for C$_{17}$H$_{24}$N$_4$O$_4$.CF$_3$COOH C, 49.35; H, 5.45; N, 12.12. Found C, 49.05; H, 5.40; N, 11.89.

EXAMPLE 159

[1-Ethyl-7-(2-guanidino-ethoxy)-2-oxo-1,2,3,4-tetrahydro-quinolin-3-yl]acetic acid Trifluoroacetate The title compound is prepared using the procedure of Example 158 except that [1-ethyl-7-(3-guanidino-propoxy)-2-oxo-1,2-dihydro-quinolin-3-yl]acetic acid trifluoroacetate is replaced with [1-ethyl-7-(2-guanidino-ethoxy)-2-oxo-1,2-dihydro-quinolin-3-yl]acetic acid trifluoroacetate.

EXAMPLE 160

[1-Ethyl-7-(4-guanidino-butoxy)-2-oxo-1,2,3,4-tetrahydro-quinolin-3-yl]acetic acid Trifluoroacetate The title compound is prepared using the procedure of Example 158 except that [1-ethyl-7-(3-guanidino-propoxy)-2-oxo-1,2-dihydro-quinolin-3-yl]acetic acid trifluoroacetate is replaced with [1-ethyl-7-(4-guanidino-butoxy)-2-oxo-1,2-dihydro-quinolin-3-yl]acetic acid trifluoroacetate.

EXAMPLE 161

[1-Benzyl-7-methoxy-2-oxo-1,2,3,4-tetrahydro-quinolin-3-yl]acetic acid methyl ester The title compound (4.3 g, 88% yield) was prepared using the conditions of Example 124 using (7-methoxy-2-oxo-1,2,3,4-tetrahydro-quinolin-3-yl)-acetic acid methyl ester in place of (7-methoxy-2-oxo-1,2-dihydro-quinolin-3-yl)acetic acid methyl ester and benzyl bromide in place of ethyl iodide.

$^1$H NMR (DMSO-d$_6$, 300 MHz): δ2.57 (dd, J=6 Hz, 16 Hz, ArCHH), 2.78–3.06 (overlapping m, 4H, ArCHH, CH, CHHCO$_2$), 3.61 (s, 6H, OCH$_3$, CO$_2$CH$_3$), 5.05 (d, J=17 Hz, 1H, CHHPh), 5.17 (d, J=17 Hz, 1H, CHHPh), 6.44 (s, 1H, ArH), 6.55 (d, J=9 Hz, 1H, ArH), 7.11 (d, J=9 Hz, 1H, ArH), 7.18–7.33 (overlapping m, 5H, ArH).

EXAMPLE 162

(1-Benzyl-7-hydroxy-2-oxo-1,2,3,4-tetrahydro-quinolin-3-yl)-acetic acid methyl ester The title compound (3.9 g, 100% yield) was prepared using the conditions of Example 209 using [1-benzyl-7-methoxy-2-oxo-1,2,3,4-tetrahydro-quinolin-3-yl]acetic acid methyl ester in place of (1-ethyl-7-methoxy-2-oxo-1,2-dihydro-quinolin-3-yl)acetic acid methyl ester.

$^1$H NMR (DMSO-d$_6$, 300 MHz): δ2.54 (dd, J=6 Hz, 16.5 Hz, 1H, ArCHH), 2.77–2.86 (overlapping m, 3H, ArCHH, CHHCO$_2$), 3.00 (m, 1H, CH), 3.61 (s, 3H, CH$_3$), 4.97 (d, J=17 Hz, 1H, CHHPh), 5.13 (d, J=17 Hz, 1H, CHHPh), 6.35–6.39 (overlapping m, 2H, ArH), 6.98 (d, J=8 Hz, 1H, ArH), 7.17–7.34 (overlapping m, 5H, ArH), 9.33 (s, 1H, ArOH).

EXAMPLE 163

[7-(3-tert-Butoxycarbonylaminopropoxy)-1-benzyl-2-oxo-1,2,3,4-tetrahydro-quinolin-3-yl]acetic acid methyl ester The title compound is prepared using the procedure of Example 75 and (1-benzyl-7-hydroxy-2-oxo-1,2,3,4-tetrahydro-quinolin-3-yl)-acetic acid methyl ester in place of 7-hydroxy-2-oxo-1,2,3,4-tetrahydro-quinolin-3-yl)acetic acid and (3-bromopropyl)carbamic acid tert-butyl ester in place of (2-bromoethyl)carbamic acid tert-butyl ester.

EXAMPLE 164

[7-(2-tert-Butoxycarbonylaminoethoxy)-1-benzyl-2-oxo-1,2,3,4-tetrahydro-quinolin-3-yl]acetic acid methyl ester The title compound is prepared using the procedure of Example 75 and (1-benzyl-7-hydroxy-2-oxo-1,2,3,4

-tetrahydro-quinolin-3-yl)-acetic acid methyl ester in place of [7-(3-tert-butoxycarbonylaminopropoxy)-1-benzyl-2-oxo-1,2-dihydro-quinolin-3-yl]acetic acid methyl ester.

EXAMPLE 165

[7-(4-tert-Butoxycarbonylaminobutoxy)-1-benzyl-2-oxo-1,2,3,4-tetrahydro-quinolin-3-yl]acetic acid methyl ester The title compound is prepared using the conditions of Example 75 and (1-benzyl-7-hydroxy-2-oxo-1,2,3,4-tetrahydro-quinolin-3-yl)-acetic acid methyl ester in place of [7-(3-tert-butoxycarbonylaminopropoxy)-1-benzyl-2-oxo-1,2-dihydro-quinolin-3-yl]acetic acid methyl ester and (4-bromobutyl)carbamic acid tert-butyl ester in place of (2-bromoethyl)carbamic acid tert-butyl ester.

EXAMPLE 166

[1-Benzyl-7-(3-aminopropoxy)-2-oxo-1,2,3,4-tetrahydro-quinolin-3-yl]acetic acid methyl ester The title compound is prepared according to the procedure of Example 78 except that [7-(2-tert-butoxycarbonylamino-ethoxy)-2-oxo-1,2,3,4-tetrahydro-quinolin-3-yl]-acetic acid methyl ester is replaced with [7-(3-tert-butoxycarbonylaminopropoxy)-1-benzyl-2-oxo-1,2,3,4-tetrahydro-quinolin-3-yl]acetic acid methyl ester.

EXAMPLE 167

[1-Benzyl-7-(2-aminoethoxy)-2-oxo-1,2,3,4-tetrahydro-quinolin-3-yl]acetic acid methyl ester The title compound is prepared according to the procedure of Example 78 except that [7-(2-tert-butoxycarbonylamino-ethoxy)-2-oxo-1,2,3,4-tetrahydro-quinolin-3-yl]-acetic acid methyl ester is replaced with [7-(2-tert-butoxycarbonylaminoethoxy)-1-benzyl-2-oxo-1,2,3,4-tetrahydro-quinolin-3-yl]acetic acid methyl ester.

EXAMPLE 168

[1-Benzyl-7-(4-aminobutoxy)-2-oxo-1,2,3,4-tetrahydro-quinolin-3-yl]acetic acid methyl ester The title compound is prepared according to the procedure of Example 78 except that [7-(2-tert-butoxycarbonylamino-ethoxy)-2-oxo-1,2,3,4-tetrahydro-quinolin-3-yl]-acetic acid methyl ester is replaced with [7-(4-tert-butoxycarbonylaminobutoxy)-1-benzyl-2-oxo-1,2,3,4-tetrahydro-quinolin-3-yl]acetic acid methyl ester.

EXAMPLE 169

[1-Benzyl-7-(3-guanidino-propoxy)-2-oxo-1,2,3,4-tetrahydro-quinolin-3-yl]-acetic acid Methyl Ester The title compound is prepared according to the procedure of Example 81 except that [1-benzyl-7-(3-aminopropoxy)-2-oxo-1,2,3,4-tetrahydro-quinolin-3-yl] acetic acid methyl ester is used in place of [7-(2-amino-ethoxy)-2-oxo-1,2,3,4-tetrahydro-quinolin-3-yl]acetic acid methyl ester trifluoroacetate.

EXAMPLE 170

[1-Benzyl-7-(2-guanidino-ethoxy)-2-oxo-1,2,3,4-tetrahydro-quinolin-3-yl]acetic acid methyl ester The title compound is prepared according to the procedure of Example 81 except that [1-benzyl-7-(2-aminoethoxy)-2-oxo-1,2,3,4-tetrahydro-quinolin-3-yl] acetic acid methyl ester is used in place of [7-(2-amino-ethoxy)-2-oxo-1,2,3,4-tetrahydro-quinolin-3-yl]acetic acid methyl ester trifluoroacetate.

EXAMPLE 171

[1-Benzyl-7-(4-guanidino-butoxy)-2-oxo-1,2,3,4-tetrahydro-quinolin-3-yl]acetic acid methyl ester The title compound is prepared according to the procedure of Example 81 except that [1-benzyl-7-(4-aminobutoxy)-2-oxo-1,2,3,4-tetrahydro-quinolin-3-yl] acetic acid methyl ester is used in place of [7-(2-amino-ethoxy)-2-oxo-1,2,3,4-tetrahydro-quinolin-3-yl]acetic acid methyl ester trifluoroacetate.

EXAMPLE 172

[1-Benzyl-7-(3-guanidino-propoxy)-2-oxo-1,2,3,4-tetrahydro-quinolin-3-yl]-acetic acid The title compound was prepared according to the procedure of Example 84 except that [7-(4-guanidino-butoxy)-2-oxo-1,2,3,4-tetrahydro-quinolin-3-yl]acetic acid methyl ester trifluoroacetate was replaced with [1-benzyl-7-(3-guanidino-propoxy)-2-oxo-1,2,3,4-tetrahydro-quinolin-3-yl]-acetic acid methyl ester.

Mp. 172–73° C.

IR (KBr): 3380 (m), 3180 (m), 1702 (s), 1672 (s), 1618 (s), 1288 (s), 1207 (s), 1188 (s), 1140 (s), 842 (m), 799 (m), 725 (m) cm$^{-1}$.

$^1$H NMR (DMSO-d$_6$, 400 MHz): δ1.83 (m, 2H, NCH$_2$C$\underline{H}_2$), 2.45 (dd, J=6 Hz, 16 Hz, 1H, ArC$\underline{H}$H), 2.74–3.00 (overlapping m, 4H, ArCH$\underline{H}$, C$\underline{H}$, C$\underline{H}$HCO$_2$), 3.19 (m, 2H, NC$\underline{H}_2$CH$_2$), 3.88 (t, J=6 Hz, 2H, OC$\underline{H}_2$), 5.09 (d, J=16 Hz, 1H, C$\underline{H}$HPh), 5.16 (d, J=16 Hz, 1H, CH$\underline{H}$Ph), 6.48 (d, J=2 Hz, 1H, Ar$\underline{H}$), 6.56 (dd, J=2 Hz, 8 Hz, 1H, Ar$\underline{H}$), 6.64–7.44 (broad, 4H, [C(N$\underline{H}_2$)$_2$]$^+$), 7.13 (d, J=8 Hz, 1H, Ar$\underline{H}$), 7.19–7.33 (overlapping m, 5H, Ar$\underline{H}$), 7.52 (t, J=6 Hz, 1H, N$\underline{H}$CH$_2$), 12.2 (broad s, 1H, CO$_2\underline{H}$).

MS (+FAB) m/e (rel. intensity): 411 (M+H, 20).

Analysis calc. for C$_{22}$H$_{26}$N$_4$O$_4$.CF$_3$COOH C, 54.96; H, 5.19; N, 10.68. Found C, 54.56; H, 4.78; N, 10.62.

EXAMPLE 173

[1-Benzyl-7-(4-guanidino-butoxy)-2-oxo-1,2,3,4-tetrahydro-quinolin-3-yl]acetic acid The title compound is prepared according to the procedure of Example 84 except that [7-(4-guanidino-butoxy-2-oxo-1,2,3,4-tetrahydro-quinolin-3-yl]acetic acid methyl ester trifluoroacetate is replaced with [1-benzyl-7-(4-guanidino-butoxy)-2-oxo-1,2,3,4-tetrahydro-quinolin-3-yl] acetic acid methyl ester.

EXAMPLE 174

[1-Benzyl-7-(2-guanidino-ethoxy)-2-oxo-1,2,3,4-tetrahydro-quinolin-3-yl]acetic acid The title compound is prepared according to the procedure of Example 84 except that [7-(4-guanidinobutoxy-2-oxo-1,2,3,4-tetrahydro-quinolin-3-yl]acetic acid methyl ester trifluoroacetate is replaced with [1-benzyl-7-(2-guanidino-ethoxy)-2-oxo-1,2,3,4-tetrahydro-quinolin-3-yl] acetic acid methyl ester.

EXAMPLE 175

[7-(2-tert-Butoxycarbonylamino-ethoxy)-2-oxo-1,2-dihydro-quinolin-3-yl]-acetic acid methyl ester The title compound is prepared according to the procedure of Example 75 except that (7-hydroxy-2-oxo-1,2- dihydro-quinolin-3-yl)-acetic acid methyl ester is used in place of (7-hydroxy-2-oxo-1,2,3,4-tetrahydro-quinolin-3-yl)-acetic acid methyl ester.

EXAMPLE 176

[7-(4-tert-Butoxycarbonylamino-butoxy)-2-oxo-1,2-dihydro-quinolin-3-yl]-acetic acid methyl ester The title compound is prepared according to the procedure of Example 75 except that (4-bromobutyl)-carbamic acid tert-butyl ester is used in place of (3-bromopropyl)-carbamic acid tert-butyl ester and that (7-hydroxy-2-oxo-1,2-dihydro-quinolin-3-yl)-acetic acid methyl ester is used in place of (7-hydroxy-2-oxo-1,2,3,4-tetrahydro-quinolin-3-yl)-acetic acid methyl ester.

EXAMPLE 177

[7-(3-tert-Butoxycarbonylamino-propoxy)-2-oxo-1,2-dihydro-quinolin-3-yl]-acetic acid methyl ester The title compound is prepared according to the procedure of Example 75 except that (3-bromopropyl)-carbamic acid tert-butyl ester is used in place of (2-bromoethyl)-carbamic acid tert-butyl ester and that (7-hydroxy-2-oxo-1,2-dihydro-quinolin-3-yl)-acetic acid methyl ester is used in place of (7-hydroxy-2-oxo-1,2,3,4-tetrahydro-quinolin-3-yl)-acetic acid methyl ester.

EXAMPLE 178

[7-(2-Amino-ethoxy)-2-oxo-1,2-dihydro-quinolin-3-yl]-acetic acid methyl ester Trifluoroacetate The title compound is prepared according to the procedure of Example 78 except that [7-(2-tert-butoxycarbonylamino-ethoxy)-2-oxo-1,2-dihydro-quinolin-3-yl]-acetic acid methyl ester is used in place of [7-(2-tert-butoxycarbonylamino-ethoxy)-2-oxo-1,2,3,4-tetrahydro-quinolin-3-yl]-acetic acid methyl ester.

EXAMPLE 179

[7-(4-Amino-butoxy)-2-oxo-1,2-dihydro-quinolin-3-yl]-acetic acid methyl ester Trifluoroacetate The title compound is prepared according to the procedure of Example 78 except that [7-(4-tert-butoxycarbonylamino-butoxy)-2-oxo-1,2-dihydro-quinolin-3-yl]-acetic acid methyl ester is used in place of [7-(2-tert-butoxycarbonylamino-ethoxy)-2-oxo-1,2,3,4-tetrahydro-quinolin-3-yl]-acetic acid methyl ester.

EXAMPLE 180

[7-(3-Amino-propoxy)-2-oxo-1,2-dihydro-quinolin-3-yl]-acetic acid methyl ester Trifluoroacetate The title compound is prepared according to the procedure of Example 78 except that [7-(3-tert-butoxycarbonylamino-propoxy)-2-oxo-1,2-dihydro-quinolin-3-yl]-acetic acid methyl ester is used in place of [7-(2-tert-butoxycarbonylamino-ethoxy)-2-oxo-1,2,3,4-tetrahydro-quinolin-3-yl]-aceticacid methyl ester.

EXAMPLE 181

[7-(2-Guanidino-ethoxy)-2-oxo-1,2-dihydro-quinolin-3-yl]-acetic acid methyl ester The title compound is prepared according to the procedure of Example 81 except that [7-(2-amino-ethoxy)-2-oxo-1,2,3,4-tetrahydro-quinolin-3-yl]-acetic acid methyl ester trifluoroacetate is replaced with [7-(4-amino-ethoxy)-2-oxo-1,2-dihydro-quinolin-3-yl]-acetic acid methyl ester trifluoroacetate.

EXAMPLE 182

[7-(4-Guanidino-butoxy)-2-oxo-1,2-dihydro-quinolin-3-yl]-acetic acid methyl ester The title compound is prepared according to the procedure of Example 81 except that [7-(2-amino-ethoxy)-2-oxo-1,2,3,4-tetrahydro-quinolin-3-yl]-acetic acid methyl ester trifluoroacetate is replaced with [7-(4-amino-butoxy)-2-oxo-1,2-dihydro-quinolin-3-yl]-acetic acid methyl ester trifluoroacetate.

EXAMPLE 183

[7-(3-Guanidino-propoxy)-2-oxo-1,2-dihydro-quinolin-3-yl]-acetic acid methyl ester The title compound is prepared according to the procedure of Example 81 except that [7-(2-amino-ethoxy)-2-oxo-1,2,3,4-tetrahydro-quinolin-3-yl]-acetic acid methyl ester trifluoroacetate is replaced with [7-(3-amino-propoxy)-2-oxo-1,2-dihydro-quinolin-3-yl]-acetic acid methyl ester trifluoroacetate.

EXAMPLE 184

[7-(4-Guanidino-butoxy)-2-oxo-1,2-dihydro-quinolin-3-yl]-acetic acid Hydrochloride The product of the example was obtained using the conditions of Example 84 and replacing [7-(4-guanidino-butoxy)-2-oxo-1,2,3,4-tetrahydro-quinolin-3-yl]-acetic acid methyl ester trifluoroacetate with [7-(4-guanidino-butoxy)-2-oxo-1,2-dihydro-quinolin-3-yl]-acetic acid methyl ester.

Mp. 216.5–19.0° C.

IR (KBr): 3400 (m), 3310 (m), 1700 (m), 1645 (s), 1408 (m), 1290 (w), 1250 (m), 1222 (m), 1172 (m), 837 (w), 773 (w) cm$^{-1}$.

$^1$H NMR (DMSO-d$_6$, 400 MHz): δ1.62 (m, 2H, NCH$_2$C$\underline{H}_2$),1.77 (m, 2H, OCH$_2$C$\underline{H}_2$), 3.17 (m, 2H, NC$\underline{H}_2$), 4.03 (t, J=6 Hz, 2H, OC$\underline{H}_2$), 6.78–6.81 (overlapping m, 2H, Ar$\underline{H}$, 6.84–7.48 (broad, 4H, [C(N$\underline{H}_2$)$_2$]$^+$), 7.53 (d, J=8.5 Hz, 1H, Ar$\underline{H}$), 7.74–7.76 (overlapping s, t, J=6 Hz, 2H, ArC$\underline{H}$=, N$\underline{H}$CH$_2$), 11.7 (s, 1H, ArN$\underline{H}$, 12.2 (broad s, 1H, CO$_2\underline{H}$).

| | |
|---|---|
| MS (+FAB) m/e (rel. intensity): 333 (M + H, 100). | |
| Analysis calc. for C$_{16}$H$_{20}$N$_4$O$_4$.HCl | C, 52.11; H, 5.74; N, 15.19 |
| Found | C, 52.05; H, 5.72; N, 15.15 |

EXAMPLE 185

[7-(2-Guanidino-ethoxy)-2-oxo-1,2-dihydro-quinolin-3-yl]-acetic acid

The product of the example was obtained using the conditions of Example 84 and [7-(2-guanidino-ethoxy)-2-oxo-1,2-dihydro-quinolin-3-yl]-acetic acid methyl ester trifluoroacetate in place of [7-(4-guanidino-butoxy)-2-oxo-1,2,3,4-tetrahydro-quinolin-3-yl]-acetic acid methyl ester trifluoroacetate.

Mp. 219–20° C.

IR (KBr): 3490 (s), 3140 (s), 1718 (s), 1685 (s), 1630 (s), 1468 (m), 1449 (m), 1290 (m), 1230 (s), 1178 (s), 1117 (s), 828 (m), 808 (w), 782 (m), 710 (m) cm$^{-1}$.

$^1$H NMR (DMSO-d$_6$, 400 MHz): δ3.41 (s, 2H, CH$_2$CO$_2$), 3.55 (m, 2H, NCH$_2$), 4.10 (t, J=5 Hz, 2H, OCH$_1$), 6.80–6.83 (overlapping m, 2H, ArH), 6.86–7.52 (broad, 4H, [C(NH$_2$)$_2$]$^+$), 7.56 (d, J=8.5 Hz, 1H, ArH), 7.71 (t, J=5.5 Hz, 1H, NHCH$_2$) 7.75 (s, 1H, ArCH=), 11.7 (s, 1H, ArNH), 12.2 (broad s, 1H, CO$_2$H).

| MS (+FAB) m/e (rel. intensity): 305 (M + H, 100). | |
|---|---|
| Analysis calc. for C$_{14}$H$_{16}$N$_4$O$_4$.CF$_3$COOH | C, 45.94; H, 4.10; N, 13.39 |
| Found | C, 45.86; H, 3.80; N, 13.24 |

EXAMPLE 186

[7-(3-Guanidino-propoxy)-2-oxo-1,2-dihydro-quinolin-3-yl]-acetic acid Trifluoroacetate The product of the example was obtained using the conditions of Example 84 and [7-(3-guanidino-propoxy)-2-oxo-1,2-dihydro-quinolin-3-yl]-acetic acid methyl ester trifluoroacetate in place of [7-(4-guanidino-butoxy)-2-oxo-1,2,3,4-tetrahydro-quinolin-3-yl]-acetic acid methyl ester trifluoroacetate.

Mp. 195–98° C. (degasses).

IR(KBr): 3440 (s), 1712(s), 1655(s), 1627 (s), 1611 (s), 1493 (m), 1419 (m), 1240 (s), 1200 (s), 1180 (s), 1122 (s), 838 (m), 810 (w), 798 (m), 723 (w) cm$^{-1}$.

$^1$H NMR (DMSO-d$_6$, 400 MHz): δ1.96 (m, 2H, NCH$_2$CH$_2$), 3.29 (m, 2H, NCH$_2$), 3.41 (s, 2H, CH$_2$CO$_2$), 4.04 (t, J=6 Hz, 2H, OCH$_2$), 6.79–6.82 (overlapping m, 2H, ArH, 6.84–7.45 (broad, 4H, [C(NH$_2$)$_2$]$^+$), 7.54 (d, J=8 Hz, 1H, ArH), 7.61 (t, J=5 Hz, 1H, NHCH$_2$), 7.74 (s, 1H, ArCH=), 11.7 (s, 1H, ArNH), 12.2 (broad s, 1H, CO$_2$H).

| MS (+FAB) m/e (rel. intensity): 319 (M + H, 100). | |
|---|---|
| Analysis calc. for C$_{15}$H$_{18}$N$_4$O$_4$.CF$_3$COOH.0.3 H$_2$O | C, 46.64; H, 4.52; N, 12.80 |
| Found | C, 46.60; H, 4.34; N, 12.57 |

EXAMPLE 187

4-Formyl-3-nitro-benzoic acid tert-butyl ester

A solution of tert-butyl 3-nitro-4-bromomethyl benzoate (Kashman, Y.; Edwards J. A. *J. Org. Chem.* 43, 1538, (1978), (20 g, 63.3 mmol) and pyridine (5.6 mL, 69.6 mmol) in ethanol (50 mL) was heated at reflux for 45 min. The solution was allowed to cool to 25° C. and the resulting precipitate was collected and washed with ethanol to give a white solid. The filtrate was concentrated to give additional precipitate. To the combined solids and ethanol (70 mL) was added p-nitrosodimethylaniline (9.5 g, 63.3 mmol) and 2.0 N aqueous sodium hydroxide (39.5 mL, 79 mmol) at 0° C. according to the procedure described in Organic Synthesis, Collective Volume V, p. 825. After 1 h a dark solid was collected and washed with water. The solid was treated with 6N aqueous sulfuric acid (100 mL). After 15 min, ice was added and the resulting beige solid filtered and washed with water. Drying in vacuo gave the title compound as a beige powder (9.08 g, 57%). NMR (dmso-d6, 200 MHz) : δ1.6 (s, 9H, C(CH3)3), 8–8.5 (m, 3H, ArH), 10.3 (s, 1 H, CHO).

EXAMPLE 188

2-(4-tert-Butoxycarbonyl-2-nitro-benzylidene)-succinic acid dimethyl ester

Triphenylphosphine (13.3 g, 50.7 mmol) and dimethyl maleate (7.31 g, 50.7 mmol) were combined in glacial acetic acid (62 mL) at 25° C. and stirred for 6 h whereupon benzene (164 mL) and 4-formyl-3-nitro-benzoic acid tert-butyl ester (8.5 g, 33.8 mmol) was added. The dark solution was heated at reflux for 18 h then cooled to 25° C. Concentration in vacuo gave a dark oil. Flash chromatography (silica gel, hexane/ethyl acetate) affords the title compound as an amber oil (11.1 g, 87%). NMR (dmso-d6, 300 MHz) : δ1.6 (s, 9H, tert-butyl), 3.3 (s, 2H, CH2), 3.6 (s, 3H, CH3), 3.8 (s, 3H, CH3), 7.5–8.6 (m, 4H, ArH, ArCH).

EXAMPLE 189

3-Methoxycarbonylmethyl-2-oxo-1,2.3,4-tetrahydro-quinolin-7-carboxylic acid tert-butyl ester A solution of 2-(4-tert-butoxycarbonyl-2-nitro-benzylidene)-succinic acid dimethyl ester (5.0 g, 13.2 mmol) in methanol (40 mL) with 10% Pd/C was hydrogenated at 50 psi and 25° C. for 20 h. The reaction mixture was filtered to afford after evaporation in vacuo the title compound as a gray solid (3.56 g, 85%). NMR (dmso-d6, 200 MHz) : δ1.5 (s, 9H, tert-butyl), 2.7–3.4 (m, 5H, CH2CHCH2), 3.6 (s, 3H, CH3), 7.2–7.5 (m, 3H, ArH), 10.3 (s, 1H, NH).

EXAMPLE 190

3-Methoxycarbonylmethyl-2-oxo-1,2,3,4-tetrahydro-quinolin-7-carboxylic acid

A suspension of 3-methoxycarbonylmethyl-2-oxo-1,2,3,4-tetrahydro-quinoline-7-carboxylic acid tert-butyl ester (3.5 g, 13.2 mmol) in dioxane (40 mL) was treated with 10 mL of 4N hydrochloric acid in dioxane and heated to 40–50° C. Evaporation of the volatiles in vacuo gave the title compound (3.35 g, 97%). NMR (dmso-d6, 200 MHz) : δ2.7–3.4 (m, 5H, CH2CHCH2), 3.6 (s, 3H, CH3), 7.2–7.5 (m, 3H, ArH), 10.3 (s, 1 H, NH).

EXAMPLE 191

[7-(3-tert-Butoxycarbonylamino-propylcarbamoyl)-2-oxo-1,2,3,4-tetrahydro-quinolin-3-yl]-acetic acid methyl ester To a solution of 3-methoxycarbonylmethyl-2-oxo-1,2,3,4-tetrahydro-quinoline-7-carboxylic acid (1.0 g, 3.8 mmol) in DMF (20 mL) at 25° C. was added 1-hydroxy-benzotriazole hydrate (HOBT) (0.565 g, 4.18 mmol). The solution was cooled to 0° C. and 1-(3-dimethylaminopropyl)-3-ethyl carbodiimide hydrochloride (DAEC) (0.801 g, 4.18 mmol) was added. After 10 min the reaction mixture was allowed to warm to 25° C. After 2 h triethylamine (1.3 mL) was added and tert-butyl-N(3-aminopropyl)carbamate (0.66 g, 3.8 mmol) added after 30 minutes. After 20 h ethyl acetate was added and the mixture washed with 0.1 N aqueous hydrochloric acid (3×), aqueous sodium bicarbonate (3×) and brine. The organic layer was dried over anhydrous magnesium sulfate and concentrated in vacuo to give the title compound as a light brown powder. NMR (dmso-d6, 200 MHz) : δ1.4 (s, 9H, tert-butyl), 1.6 (m, 2H, CH2), 2.7–3.3 (m, 9H, CH2CHCH2, NCH2, NCH2), 3.6 (s, 3H, CH3), 6.8 (t, 1H, NH), 7.2–7.4 (m, 3H, ArH), 8.3 (t, 1H, NH), 10.3 (s, 1 H. NH).

EXAMPLE 192

[7-(2-tert-Butoxycarbonylamino-ethylcarbamoyl)-2-oxo-1,2,3,4-tetrahydro-quinolin-3-yl]-acetic acid methyl ester Using the conditions of Example 191 and tert-butyl-N(2-aminoethyl)carbamate in place of tert-butyl-N(3-aminopropyl)carbamate the product of the example is obtained.

EXAMPLE 193

[7-(4-tert-Butoxycarbonylamino-butylcarbamoyl)-2-oxo-1,2,3,4-tetrahydro-quinolin-3-yl]-acetic acid methyl ester Using the conditions of Example 191 and tert-butyl-N(4-aminobutyl)carbamate in place of tert-butyl-N(3-aminopropyl)carbamate the product of the example is obtained.

EXAMPLE 194

[7-(2-Amino-ethylcarbamoyl)-2-oxo-1,2,3,4-tetrahydro-quinolin-3-yl]-acetic acid methyl ester Using the conditions of Example 78 and [7-(2-tert-butoxycarbonylamino-ethylcarbamoyl)-2-oxo-1,2,3,4-tetrahydro-quinolin-3-yl]-acetic acid methyl ester in place of [7-(2-tert-butoxycarbonylaminoethoxy)-2-oxo-1,2,3,4-tetrahydro-quinolin-3-yl]acetic acid methyl ester, the product of the example is obtained.

EXAMPLE 195

[7-(3-Amino-proylcarbamoyl)-2-oxo-1,2,3,4-tetrahydro-quinolin-3-yl]-acetic acid methyl ester Using the conditions of Example 78 and [7-(3-tert-butoxycarbonylamino-propylcarbamoyl)-2-oxo-1,2,3,4-tetrahydro-quinolin-3-yl]-acetic acid methyl ester in place of [7-(2-tert-butoxycarbonylaminoethoxy)-2-oxo-1,2,3,4-tetrahydro-quinolin-3-yl]acetic acid methyl ester, the product of the example is obtained.

EXAMPLE 196

[7-(4-Amino-butylcarbamoyl)-2-oxo-1,2,3,4-tetrahydro-quinolin-3-yl]-acetic acid methyl ester Using the conditions of Example 78 and [7-(4-tert-butoxycarbonylamino-butylcarbamoyl)-2-oxo-1,2,3,4-tetrahydro-quinolin-3-yl]-acetic acid methyl ester in place of [7-(2-tert-butoxycarbonylaminoethoxy)-2-oxo-1,2,3,4-tetrahydro-quinolin-3-yl]acetic acid methyl ester, the product of the example is obtained.

EXAMPLE 197

[7-(2-Guanidino-ethylcarbamoyl)-2-oxo-1,2,3,4-tetrahydro-quinolin-3-yl]-acetic acid methyl ester Using the conditions of Example 81 and [7-(2-amino-ethylcarbamoyl)-2-oxo-1,2,3,4-tetrahydro-quinolin-3-yl]-acetic acid methyl ester in place of [7-(2-aminoethoxy)-2-oxo-1,2,3,4-tetrahydro-quinolin-3-yl]acetic acid methyl ester, the product of the example is obtained.

EXAMPLE 198

[7-(3-Guanidino-propylcarbamoyl)-2-oxo-1,2,3,4-tetrahydro-quinolin-3-yl]-acetic acid methyl ester Using the conditions of Example 81 and [7-(3-amino-propylcarbamoyl)-2-oxo-1,2,3,4-tetrahydro-quinolin-3-yl]-acetic acid methyl ester in place of [7-(2-aminoethoxy)-2-oxo-1,2,3,4-tetrahydro-quinolin-3-yl]acetic acid methyl ester, the product of the example is obtained.

EXAMPLE 199

[7-(4-Guanidino-butylcarbamoyl)-2-oxo-1,2,3,4-tetrahydro-quinolin-3-yl]-acetic acid methyl ester Using the conditions of Example 81 and [7-(4-amino-butylcarbamoyl)-2-oxo-1,2,3,4-tetrahydro-quinolin-3-yl]-acetic acid methyl ester in place of [7-(2-aminoethoxy)-2-oxo-1,2,3,4-tetrahydro-quinolin-3-yl]acetic acid methyl ester, the product of the example is obtained.

EXAMPLE 200

[7-(2-Guanidino-ethylcarbamol)-2-oxo-1,2,3,4-tetrahydro-quinolin-3-yl]-acetic acid Hydrochloride Using the conditions of Example 85 and [7-(2-guanidino-ethylcarbamoyl)-2-oxo-1,2,3,4-tetrahydro-quinolin-3-yl]-acetic acid methyl ester in place of [7-(2-guanidino-ethoxy)-2-oxo-1,2,3,4-tetrahydro-quinolin-3-yl]acetic acid methyl ester, the product of the example was obtained as a white powder.

$^1$H NEMR (D20, 400 MHz): δ2.4–2.9 (overlapping m, 5H, ArC$\underline{HH}$—C$\underline{H}$—C$\underline{H}$HCO$_2$), 3.24 (t, 2H, J=5.7 Hz, NC$\underline{H}_2$), 3.37 (t, 2H, J=5.7 Hz, NC$\underline{H}_2$), 7.03 (d, 1H, J=1.8 Hz, Ar$\underline{H}$), 7.13 (d, 1H, J=7.9 Hz, Ar$\underline{H}$), 7.20 (dd, 1H, J=1.8, 7.9 Hz, Ar$\underline{H}$).

MS (+FAB) m/e (rel. intensity): 334 (M+H, 75).

Analysis calc. for $C_{15}H_{19}N_5O_4 \cdot HCl \cdot 1.3H_2O$ C, 45.82; H, 5.79; N, 17.81. Found C, 45.45; H, 5.85; N, 18.13.

EXAMPLE 201

[7-(3-Guanidino-propylcarbamoyl)-2-oxo-1,2,3,4-tetrahydro-quinolin-3-yl]-acetic acid Hydrochloride Using the conditions of Example 85 and [7-(3-guanidino-propylcarbamoyl)-2-oxo-1,2,3,4-tetrahydro-quinolin-3-yl]-acetic acid methyl ester in place of [7-(2-guanidino-ethoxy)-2-oxo-1,2,3,4-tetrahydro-quinolin-3-yl]acetic acid methyl ester, the product of the example was obtained as a white powder.

$^1$H NMR (D20, 400 MHz): δ1.70 (p, 2H, J=6.8 Hz, —C$\underline{H}_2$—)J=2.4–2.9 (overlapping m, 5H, ArC$\underline{HH}$—C$\underline{H}$—C$\underline{HH}$CO$_2$), 3.06 (t, 2H, J=6.8 Hz, NC$\underline{H}$), 3.25 (t, 2H, J=6.8 Hz, NC$\underline{H}_2$), 7.01 (d, 1H, J=1.8 Hz, Ar$\underline{H}$), 7.11 (d, 1H, J=7.9 Hz, Ar$\underline{H}$), 7.19 (dd, 1H, J=1.8, 7.9 Hz, Ar$\underline{H}$).

MS (+FAB) m/e (rel. intensity): 348 (M+H, 37).

Analysis calc. for $C_{16}H_{21}N_5O_4 \cdot HCl \cdot 0.4H_2O$ C, 49.15; H, 5.88; N, 17.91. Found C, 48.79; H, 5.73; N, 18.28.

EXAMPLE 202

[7-(4-Guanidino-butylcarbamoyl)-2-oxo-1,2,3,4-tetrahydro-quinolin-3-yl]-acetic acid hydrochloride Using the conditions of Example 85 and [7-(4-guanidino-butylcarbamoyl)-2-oxo-1,2,3,4-tetrahydro-quinolin-3-yl]- acetic acid methyl ester in place of [7-(2-guanidino-ethoxy)-2-oxo-1,2,3,4-tetrahydro-quinolin-3-yl]acetic acid methyl ester, the product of the example was obtained as a white powder.

IR (KBr): 3395 (s), 3350 (s), 1720 (s), 1670 (s), 1570 (s), 1410 (s), 1240 (s), 1160 (s), 875 (m), 7000 (s) cm$^{-1}$.

$^1$H NMR (D20, 400 MHz): δ1.45 (bd s, 4H, —CH2CH2—), 2.4–2.9 (overlapping m, 5H, ArC$\underline{H}$H—C$\underline{H}$—C$\underline{H}$HCO$_2$), 3.01 (bd s, 2H, NC$\underline{H}_2$), 3.19 (bd s, 2H, NC$\underline{H}_2$), 7.02 (s, 1H, Ar$\underline{H}$), 7.12 (m, 1H, ArH), 7.19 (m, 1H, ArH).

Analysis calc. for C$_{17}$H$_{23}$N$_5$O$_4$.HCl C, 51.32; H, 6.08; N, 17.60; Found C, 50.46; H, 6.07; N, 16.93.

EXAMPLE 203

[7-(4-Amino-butoxy)-2-oxo-1,2,3,4-tetrahydro-quinolin-3-yl]-acetic acid

The product of the example was obtained using the conditions of Example 84 and the product of Example 79.

Mp. 229–30 ° C.

IR (KBr): 3530 (m), 3140 (m), 1714 (s), 1692 (s), 1640 (s), 1611 (s), 1464 (m), 1240 (s), 1183 (s), 1158 (m), 1118 (s), 848 (m), 825 (m), 807 (m), 787 (m), 710 (m) cm$^{-1}$.

$^1$H NMR (DMSO-d$_6$, 400 MHz): δ1.70 (m, 2H, NCH$_2$C$\underline{H}_2$), 1.79 (m, 2H, OCH$_2$C$\underline{H}_2$), 2.86 (m, 2H, NC$\underline{H}_2$), 3.41 (s, 2H, C$\underline{H}_2$CO$_2$), 4.03 (t, J=6 Hz, 2H, OC$\underline{H}_2$), 6.78–6.80 (overlapping m, 2H, Ar$\underline{H}$), 7.54 (d, J=9 Hz, 1H, Ar$\underline{H}$), 7.58–7.82 (overlapping broad s, s, 4H, N$\underline{H}_3^+$, ArC$\underline{H}$=), 11.7 (s, 1H, ArN$\underline{H}$), 12.2 (broad s, 1H, CO$_2\underline{H}$).

MS (+FAB) m/e (rel. intensity): 291 (M+H, 30).

Analysis calc. for C$_{15}$H$_{18}$N$_2$O$_4$.CF$_3$COOH.0.25 H$_2$O C, 49.94; H, 4.81; N, 6.85. Found C, 49.67; H, 5.02; N, 7.10.

EXAMPLE 204

[7-(2-Amino-ethoxy)-2-oxo-1,2,3,4-tetrahydro-quinolin-3-yl]-acetic acid

Using the conditions of Example 84 and the product of Example 78 the title compound was obtained.

Mp. 205–08 ° C. (degasses).

IR (KBr): 3110 (m), 1678 (s), 1642 (m), 1600 (m), 1290 (s), 1238 (m), 1200 (s), 1177 (s), 1157 (s), 1130 (s), 842 (m), 822 (m), 800 (m), 722 (m) cm$^{-1}$.

$^1$H NMR (DMSO-d$_6$, 400 MHz): δ2.35 (m, 1H, ArC$\underline{H}$H), 2.67–2.88 (overlapping m, 4H, ArC$\underline{H}\underline{H}$, C$\underline{H}$, C$\underline{H}$HCO$_2$), 3.21 (t, J=5 Hz, 2H, NC$\underline{H}_2$), 4.08 (t, J=5 Hz, 2H, OC$\underline{H}_2$), 6.49 (d, J=2.5 Hz, 1H, Ar$\underline{H}$), 6.54 (dd, J=2.5 Hz, 8 Hz, 1H, Ar$\underline{H}$), 7.09 (d, J=8 Hz, 1H, Ar$\underline{H}$), 7.99 (broad s, 3H, N$\underline{H}_3^+$), 10.2 (s, 1H, ArN$\underline{H}$), 12.9 (broad s, 1H, CO$_2\underline{H}$).

MS (+DCI) m/e (rel. intensity): 265 (M+H, 100).

Analysis calc. for C$_{13}$H$_{16}$N$_2$O$_4$.CF$_3$COOH C, 47.62; H, 4.53; N, 7.40. Found C, 47.84; H, 4.48; N, 7.43.

EXAMPLE 205

[7-(3-Amino-propoxy)-2-oxo-1,2,3,4-tetrahydro-quinolin-3-yl]-acetic acid

Using the conditions of Example 84 and the product of Example 80 the title compound was obtained.

Mp. 194–96 ° C.

IR (KBr): 3410 (m), 3090 (m), 1743 (m), 1722 (s), 1672 (s), 1630 (m), 1287 (m), 1185 (s), 1130 (s), 862 (m), 832 (m), 798 (m), 778 (m), 720 (m) cm$^1$.

$^1$H NMR (DMSO-d$_6$, 400 MHz): δ1.97 (m, 2H, NCH$_2$C$\underline{H}_2$), 2.34 (m, 1H, ArC$\underline{H}$H), 2.66–2.87 (overlapping m, 4H, ArC$\underline{H}\underline{H}$, C$\underline{H}$, C$\underline{H}\underline{H}$CO$_2$), 2.94 (broad, 2H, NC$\underline{H}_2$), 3.98 (t J=6 Hz, 2H, OC$\underline{H}_2$), 6.43 (d, J=2.5 Hz, 1H, Ar$\underline{H}$), 6.50 (dd, J=2.5 Hz, 8 Hz, 1H, Ar$\underline{H}$), 7.07 (d, J=8 Hz, 1H, Ar$\underline{H}$), 7.74 (broad s, 3H, N$\underline{H}_3^+$), 10.0 (s, 1H, ArN$\underline{H}$), 12.2 (broad s, 1H, CO$_2\underline{H}$).

MS (+FAB) m/e (rel. intensity): 279 (M+H, 14).

Analysis calc. for C$_{14}$H$_{18}$N$_2$O$_4$.CF$_3$COOH C, 48.98; H, 4.88; N, 7.14. Found C, 49.09; H, 4.54; N, 7.16.

EXAMPLE 206

[7-(4-Amino-butoxy)-2-oxo-1,2,3,4-tetrahydro-quinolin-3-yl]-acetic acid

Using the conditions of Example 84 and the product of Example 79 the title compound was obtained.

Mp. 152.5–55.0° C.

IR (KBr): 3490 (m), 3225 (m), 3130 (m), 1700 (s), 1615 (s), 1622 (m), 1593 (s), 1434 (m), 1260 (m), 1188 (s), 1127 (s), 849 (m), 832 (m), 808 (m), 792 (m), 718 (m) cm$^{-1}$.

$^1$H NMR (DMSO-d$_6$, 400 MHz): δ1.63–1.78 (overlapping m, 4H, NCH$_2$C$\underline{H}_2$, OCH$_2$C$\underline{H}_2$), 2.34 (m, 1H, ArC$\underline{H}$H), 2.66–2.87 (overlapping m, 6H, ArC$\underline{H}\underline{H}$, C$\underline{H}$, C$\underline{H}\underline{H}$CO$_2$, NC$\underline{H}_2$), 3.91 (t, J=6 Hz, 2H, OC$\underline{H}_2$), 6.42 (d, J=2 Hz, 1H, Ar$\underline{H}$), 6.49 (dd, J=2 Hz, 8 Hz, 1H, Ar$\underline{H}$), 7.06 (d, J=8 Hz, 1H, Ar$\underline{H}$), 7.70 (broad s, 3H, N$\underline{H}_3^+$), 10.1 (s, 1H, ArN$\underline{H}$), 12.2 (broad s, 1H, CO$\underline{H}$).

MS (+FAB) m/e (rel. intensity): 293 (M+H, 17).

Analysis calc. for C$_{15}$H$_{20}$N$_2$O$_4$.CF$_3$COOH.0.5 H$_2$O C, 49.15; H. 5.35; N. 6.75. Found C, 48.95; H, 5.41; N, 6.60.

EXAMPLE 207

(6-Methoxy-3,4-dihydro-1H-naphthalen-2-ylidene)-acetic acid ethyl ester

A suspension of 2,6-dimethoxynaphthalene (20.0 g, Aldrich) in 200 mL of anhydrous EtOH was heated to reflux under a stream of nitrogen. Sodium spheres (18 g, Aldrich) were added gradually to the hot suspension over a period of 2 hours. Additional ETOH (50 ml) was added and the reaction was heated until all of the sodium had dissolved. The solution was cooled to room temperature and placed in an ice bath. The addition of 6 N HCl brought the solution to pH 6, and additional HCl (10 mL) was added. The solution was heated to reflux for 0.5 h. The golden mixture was cooled to room temperature, H$_2$O (200 mL) was added, and the solution was extracted with ET$_2$O. The combined ET$_2$O extracts were dried (Na$_2$SO$_4$), filtered, and concentrated to afford 6-methoxy-2-tetra-lone as a red oil (23.5 g). Triethyl phosphono-acetate (29 mL, Aldrich) was added dropwise to a suspension of hexane-washed sodium hydride (5.8 g of 60% dispersion) in benzene (80 mL) cooled in an ice bath. The phos-phonate solution was stirred at room temperature for 0.5 h, and the ice bath was replaced. A solution of 6-methoxy-2-tetralone (23.5 g) in benzene (20 mL) was added to the phosphonate solution over 10 minutes, and the reaction was allowed to stir at room temperature overnight. The reaction was poured into H$_2$O and extracted with EtOAc (3×150 mL). The combined extracts were dried (Na$_2$SO$_4$), filtered, and concentrated to afford a brown oil which was purified using silica gel chromatography. Elution with 10% EtOAc/hexane afforded the title compound (27 g) as a yellow oil. NMR (300 MHz, CDCl$_3$) δ6.98 (d, J=9.03 Hz, 1 H), 6.79–6.70 (m, 2H), 6.35 (s, 1H), 3.94 (q, J=7.11 Hz, 2H), 3.58 (s, 3H), 2.99 (s, 2H), 2.61 (t, J 8.11 Hz, 2H), 2.14 (t, J=8.07 Hz, 2H), 1.08 (t, J 7.14 Hz, 3H).

EXAMPLE 208

(6-Methoxy-1,2,3,4-tetrahydro-naphthalen-2-yl)-acetic acid ethyl ester

A mixture of 6-methoxy-3,4-dihydro-1H-naphthalen-2-ylidene)-acetic acid ethyl ester (27 g) in EtOH (200 mL) and 10% Pd/C (0.3 g) was hydrogenated at 40 psi over 5 h. The mixture was filtered through diatomaceous earth and washed with EtOH (50 mL). The filtrate was concentrated under reduced pressure to give the product of the example as a yellow oil (27 g).

NMR (300 MHz, $CDCl_3$) δ7.02 (d, J=8.34 Hz, 1H), 6.74 (dd, J=8.34, 2.67 Hz, 1H), 6.67 (d, J=2.52 Hz, 1H), 4.22 (q, J=7.12 Hz, 2H), 3.82 (s, 3H), 2.93–2.85 (m, 3H), 2.52–2.40 (m, 3H), 2.33–2.28 (m, 1H), 2.03–1.97 (m, 1H), 1.55–1.51 (m, 1H), 1.33 (t, J=7.11 Hz, 3H).

EXAMPLE 209

(6-Hydroxy-1,2,3,4-tetrahydro-nahthalen-2-yl)-acetic acid methyl ester

To a solution of (6-methoxy-1,2,3,4-tetrahydro-naphthalen-2-yl)-acetic acid ethyl ester (6.2 g) in $CH_2Cl_2$ (50 mL) cooled to −78° C. under $N_2$ was added dropwise boron tribromide in $CH_2Cl_2$ (1.0 M, 100 mL, Aldrich). The solution was stirred for 1 h at −78° C. and 2 h at 0° C., then cooled again to −78° C. Methanol (25 mL) was added and the solution was allowed to warm to room temperature overnight. The brown solution was concentrated under reduced pressure and the resulting oil was purified using silica gel chromatography. Elution with a gradient of 20% EtOAc/hexane to 60% EtOAc/hexane afforded the product of the example as a tan powder (3.4 g). MAR (300 MHz, $CDCl_3$) δ6.89 (d, J=8.15 Hz, 1H), 6.59 (d of d, J=8.10, 2.66 Hz, 1H), 6.55 (d, J=2.44 Hz, 1H), 5.37 (s, 1H), 3.71 (s, 3H), 2.79–2.74 (m, 3H), 2.41–2.36 (m, 3H), 2.28–2.17 (m, 1H), 1.94–1.88 (m, 1H), 1.49–1.35 (m, 1H).

EXAMPLE 210

{6-[3-(1,3-Dioxo-1,3-dihydro-isoindol-2-yl)-propoxy]-1,2,3,4-tetrahydro-naphthalen-2-yl}-acetic acid methyl ester To a solution of (6-hydroxy-1,2,3,4-tetrahydro-naphthalen-2-yl)-acetic acid methyl ester, (11.9 g) in DMF (45 mL) was added sodium hydride (2.2 g, 60% dispersion) in portions over 0.5 h. The solution was stirred at room temperature for 1 h, and N-(3-bromopropyl)phthalimide (14.6 g) was added in one portion. The solution was stirred at room temperature for 1h, then concentrated under reduced pressure. The resulting material was suspended in EtOAc and filtered to remove the salt. The filtrate was concentrated to a brown oil and applied to a silica gel column. Elution with 2% acetone in $CHCl_3$ afforded the product of the example also containing (6-hydroxy-1,2,3,4-tetrahydro-naphthalen-2-yl)-acetic acid methyl ester. A solution of the combined material in $CH_2Cl_2$ was washed sequentially with 1 N NaOH solution and brine. The solution was dried ($Na_2SO_4$), filtered, and concentrated to afford the product of the example as a yellow powder (17.7 g). NMR (300 MHz, $CDCl_3$) δ7.70 (dd, J=5.47, 3.03 Hz, 2H), 7.57 (dd, J=5.43, 3.05 Hz, 2H), 6.77 (d, J=8.36 Hz, 1H), 6.43 (dd, J=8.32, 2.62 Hz, 1H), 6.37 (d, J=2.45 Hz, 1H), 3.85 (t, J=6.06 Hz, 2H), 3.76 (t, J=6.89 Hz, 2H), 3.56 (s, 3H), 2.70–2.60 (m, 3H), 2.47–2.33 (m, 3H), 2.26–2.14 (m, 3H), 2.02–1.91 (m, 1H), 1.51–1.38 (m, 1H); MS (+APCI) m/z 408 (M+H) ; Calculated for $C_{24}H_{25}NO_5$: C, 70.75; H, 6.18; N, 3.44. Found: C, 70.35; H, 6.15; N, 3.25.

EXAMPLE 211

[6-(3-Amino-propoxy)-1,2,3,4-tetrahydro-naphthalen-2-yl]-acetic acid methyl ester To a suspension of {6-[3-(1,3-dioxo-1,3-dihydro-isoindol-2-yl)-propoxy]-1,2,3,4-tetrahydro-naphthalen-2-yl}-acetic acid methyl ester, (17.7 g) in isopropyl alcohol (350 mL) heated at 55° C. was added hydrazine (3 mL). The mixture was heated to reflux for 1.5 h, then the reaction mixture was allowed to stand at room temperature overnight. Concentrated HCl (7.8 mL) was added, the mixture was stirred for 10 minutes, and filtered. The white solid was washed with isopropyl alcohol. The filtrate was concentrated under reduced pressure and applied to a silica gel column. Elution with 2% $NH_4OH$/10% MeOH/$CH_2Cl_2$ afforded the product of the example as a golden oil which solidified on standing (8.0 g). NMR (300 MHz, $CDCl_3$) δ6.95 (d, J=8.34 Hz, 1H), 6.67 (dd, J=8.30, 2.55 Hz, 1H), 6.62 (d, J=2.16 Hz, 1H), 4.01 (t, J=6.07 Hz, 2H), 3.69 (s, 3H), 2.93 (broad s, 2H), 2.86–2.77 (m, 3H), 2.46–2.36 (m, 3H), 2.26–2.18 (m, 1H), 2.12–1.98 (broad s, 2H), 1.93 (m, 3H), 1.51–1.38 (m, 1H).

EXAMPLE 212

{6-[3-(Pyrimidin-2-ylamino)-propoxy]-1,2,3,4-tetrahydro-naphthalen-2-yl}-acetic acid methyl ester A solution of [6-(3-amino-propoxy)-1,2,3,4-tetrahydro-naphthalen-2-yl]-acetic acid methyl ester, (5.8 g), 2-bromopyrimidine (3.5 g), chlorotrimethyl-silane (21.5 mL), and diisopropylethyl amine (29 mL) in 1,4-dioxane (100 mL) was heated to reflux for 72 h. The reaction was cooled to room temperature and concentrated under reduced pressure. The residue was dissolved in EtOAc, washed with $H_2O$, dried ($Na_2SO_4$), filtered, and concentrated. The dark oil was purified by silica gel chromatography. Elution with a gradient of $CH_2Cl_2$ to 1% MeOH/$CH_2Cl_2$ to 2% MeOH/$CH_2Cl_2$ gave the product of the example as a slightly yellow solid (4.68 g). NMR (300 MHz, $CDCl_3$) δ8.26 (d, J=4.79 Hz, 2H), 6.95 (d, J=8.35 Hz, 1H), 6.67 (dd, J=8.29, 2.62 Hz, 1H), 6.62 (d, J=2.37 Hz, 1H), 6.50 (t, J=4.82 Hz, 1H), 5.49 (broad s, 1H), 4.04 (t, J=5.93 Hz, 2H), 3.70 (s, 3H), 3.61 (q, J=6.46 Hz, 2H), 2.86–2.77 (m, 3H), 2.46–2.36 (m, 3H), 2.27–2.20 (m, 1H), 2.08 (dt, J=12.53, 6.31 Hz, 2H), 1.96–1.89 (m, 1H), 1.51–1.40 (m, 1H); Calculated for $C_{20}H_{25}N_3O_3$·0.20 $CH_2Cl_2$: C, 65.15; H, 6.87; N, 11.28. Found: C, 65.11; H, 6.89; N, 10.81.

EXAMPLE 213

{6-[3-(Pyrimidin-2-ylamino)-propoxy]-1,2,3,4-tetrahydro- naphthalen-2-yl}-acetic acid To a solution of {6-[3-(pyrimidin-2-ylamino)-propoxy]-1,2,3,4-tetrahydro-naphthalen-2-yl}-acetic acid methyl ester (0.09 g) in 1,4-dioxane (5 mL) was added a solution of LiOH·$H_2O$ (0.04 g) in $H_2O$ (2 mL) and the reaction was heated to 100° C. for 1 h. The reaction was cooled to room temperature and concentrated under reduced pressure. Water was added to the residue and the mixture was cooled in an ice bath. The mixture was brought to pH 5 by the addition of 1N HCl. The aqueous suspension was extracted with $CH_2Cl_2$ and $CHCl_3$. The combined organic layers were washed with brine, dried ($Na_2SO_4$), filtered, and concentrated under reduced pressure. The residue was purified using silica gel chromatography. Elution with 10% MeOH/ $CH_2Cl_2$ gave the title compound as a white solid (14 mg). NMR (300 MHz, MeOH-$d_4$) δ8.24 (broad s, 2H), 7.32 (broad s, 1H), 6.82 (d, J=8.25 Hz, 1H), 6.68–6.63 (m, 2H), 6.52 (t, J=4.76 Hz, 1H), 4.08 (t, J=6.11 Hz, 2H), 3.63 (d, J=5.59 Hz, 2H), 2.83 (dd, J=15.90, 3.70 Hz, 1H), 2.71 (d, J=3.32 Hz, 2H), 2.42–2.34 (m, 3H), 2.11 (dd, J=11.82, 5.88 Hz, 3H), 1.90 (d, J=11.76 Hz, 1H), 1.46–1.32 (m, 1H); MS (+ESI) m/z 342 (M+H)$^+$; Calculated for $C_{19}H_{23}N_3O_3 \cdot 0.5 H_2O$: C, 64.94; H, 6.88; N, 11.96. Found: C, 65.43; H, 6.72; N, 11.48.

EXAMPLE 214

{6-[3-(1,4,5,6-Tetrahydro-pyrimidin-2-ylamino)-propoxy]-1,2,3,4-tetrahydro-nahthalen-2-yl}-acetic acid A mixture of {6-[3-(pyrimidin-2-ylamino)-propoxy]-1,2,3,4-tetrahydro-naphthalen-2-yl}-acetic acid methyl ester (0.29 g), 10% Pd/C (0.03 g), acetic acid (5 mL), and 1N HCl (2 mL) was stirred under $H_2$ atmosphere (balloon) for 7 days. The mixture was filtered through diatomaceous earth and washed with 1N HCl. The filtrate was concentrated under reduced pressure and azeotroped with toluene. The residue was dissolved in 1% ammonium hydroxide/10% MeOH/$CH_2Cl_2$ and eluted from a silica gel column with this solution. The product was further purified using reverse phase silica gel, eluting with 20% and 40% $CH_3CN/H_2O$, and reverse phase HPLC, eluting with 37% $CH_3CN/H_2O$, to provide the title compound as a hygroscopic ivory powder (66 mg). NMR (300 MHz, MeOH-$d_4$) δ6.93 (d, J=5.52 Hz, 1H), 6.68–6.65 (m, 2H), 4.01 (t, J=5.35 Hz, 2H), 3.33–3.32 (m, 4H), 2.80 (s, 2H), 2.42–2.31 m, 3H), 2.42–2.31 (m, 3H), 2.29–2.16 (m, 1H), 2.03–1.92 (m, 3H), 1.46–1.33 (m, 1H); MS (+ESI) m/z 346 (M+H)$^+$.

EXAMPLE 215

{6-[3-(1,4,5,6-Tetrahydro-pyrimidin-2-ylamino) propoxy]-1,2,3,4-tetrahydro-naphthalen-2-yl}-acetic acid methyl ester bis(hydrochloride)

To a solution of {6-[3-(1,4,5,6-tetrahydro-pyrimidin-2-ylamino)-propoxy]-1,2,3,4-tetrahydro-naphthalen-2-yl}-acetic acid (25 mg) in MeOH (2 mL) was added HCl in MeOH and the solution was heated to reflux for 3 h. The reaction was cooled to room temperature and concentrated under reduced pressure to afford a tan oil. Ether was added, the contents were swirled and the solvent decanted. Lyophilization of the oily residue gave the title compound as a hygroscopic, ivory solid (29 mg). NMR (300 MHz, MeOH-$d_4$) δ6.84 (d, J 8.20 Hz, 1H), 6.61–6.56 (m, 2H), 3.92 (t, J=5.75 Hz, 2H), 3.59 (s, 3H), 3.28–3.21 (m, 5H), 2.72–2.68 (m, 3H), 2.33–2.24 (m, 3H), 2.09–2.06 (m, 1H), 1.92 (t, J=7.09 Hz, 2H), 1.87–1.77 (m, 3H), 1.37–1.19 (m, 2H); MS (+ESI) m/z 360 (M+H)$^+$; Calculated for $C_{20}H_{29}N_3O_3 \cdot 2$ HCl: C, 55.56; H, 7.23; N, 9.72. Found: C, 55.15; H. 7.10; N, 9.88.

EXAMPLE 216

{6-[3-(1,4,5 6-Tetrahydro-pyrimidin-2-ylamino)-propoxy]1,2,3,4-tetrahydro-naphthalen-2-yl}-acetic acid ethyl ester, acetic acid salt To a solution of {6-[3-(pyrimidin-2-ylamino)-propoxy]-1,2,3,4-tetrahydro-naphthalen-2-yl}-acetic acid methyl ester (4.68 g) in 1,4-dioxane (170 mL) was added a solution of LiOH·$H_2O$ (1.66 g) in $H_2O$ (25 mL) and the reaction was heated to 100° C, for 0.5 h. The reaction was cooled to room temperature and concentrated under reduced pressure. Water (250 mL), EtOAc (150 mL), and $ET_2O$ (100 mL) were added to the residue and the mixture was filtered to obtain a white solid. The aqueous layer of the filtrate was combined with the collected solid and the suspension was concentrated under reduced pressure. Water (15 mL), concentrated HCl (10 mL), acetic acid (5 mL), EtOH (50 mL), and 10% Pd/C (0.04 g) were added to the residue. The mixture was stirred under $H_2$ pressure (balloon) overnight. The mixture was filtered through diatomaceous earth and washed with EtOH. The filtrate was concentrated under reduced pressure. Absolute EtOH (120 mL) and 1M HCl in $ET_2O$ (20 mL) were added to the syrup and the solution was heated to reflux for 1.5 h. The reaction was cooled to room temperature and concentrated under reduced pressure. The residue was adsorbed onto silica gel and purified by silica gel chromatography, eluting with 2% acetic acid/2% MeOH/ $CHCl_3$ and 5% acetic acid/5% MeOH/$CHCl_3$. After a pass through a second silica gel column using the same conditions, the residue was lyophilized to give the title compound as a hygroscopic, beige solid (2.56 g). NMR (300 MHz, MeOH-$d_4$) δ6.99 (d, J=10.98 Hz, 1H), 6.68–6.61 (m, 2H), 4.12 (q, J=7.12 Hz, 2H), 3.96 (t, J=5.71 Hz, 2H), 3.33–3.25 (m, 8H), 2.76–2.73 (m, 3H), 2.39–2.31 (m, 3H), 2.15–2.00 (m, 1H), 1.95 (dd, J=12.23, 6.31 Hz, 2H), 1.90–1.82 (m, 5H), 1.47–1.36 (m, 1H), 1.23 (t, J=7.13 Hz, 3H); MS (+ESI) m/z 374 (M+H)$^+$.

EXAMPLE 217

4-Methyl-N-({6-[3-(1,4,5,6-tetrahydro-pyrimidin-2-ylamino)-propoxyl]1,2,3,4-tetrahydro-naphthalen-2-yl}-acetyl)-benzenesulfonamide, trifluoroacetic acid salt To {6-[3-(1,4,5,6-tetrahydro-pyrimidin-2-ylamino)-propoxy]-1,2,3,4-tetrahydro-naphthalen-2-yl}-acetic acid (0.39 g) was added paratoluenesulfonamide (0.29 g), 1-[3-(dimethylamino)-propyl]-3-ethylcarbodiimide hydrochloride (0.33 g), dimethylaminopyridine (0.02 g), and DMF (20 mL) and the resulting solution was stirred under $N_2$ at room temperature for 48 h. The DMF was removed by vacuum distillation. Water (25 mL) was added, and saturated $NaHCO_3$ solution was used to bring the pH of the suspension to 10. The solution was washed with $CH_2Cl_2$ (25 mL). The pH of the aqueous layer was adjusted to 3.5 by the addition of 6M HCl. The acidic solution was extracted with EtOAc (3×25 mL). The combined EtOAc layers were dried ($Na_2SO_4$), filtered and concentrated. The resulting oil was adsorbed onto magnesium silicate and purified by silica gel chromatography, eluting with a gradient of 0.5% acetic acid/2% MeOH/$CH_2Cl_2$ to 5% acetic acid/10% MeOH/ $CH_2Cl_2$ to afford the title compound as a white powder (17 mg). The compound was dissolved in a solution of 5% trifluoroacetic acid/20% $CH_3CN/H_2O$ and eluted through a reverse phase C18 column with the same solution to afford the title compound (11 mg) as a beige gum.

NMR (300 MHz, DMSO-$d_6$) δ7.64 (d,J=8.05 Hz, 2H), 7.22 (d, J=8.03 Hz, 2H), 6.85 (d, J=8.35 Hz, 1H), 6.67–6.61 (m,2H), 3.96–3.92(m,2H), 3.24–3.16(m,6H), 2.76–2.61 (m,3H), 2.33(s,3H), 2.23–2.11(m,1H), 1.98–1.86(m,5H), 1.83–1.74(m,3H), 1.24(s,1H); MS(+ESI) m/z 499 (M+H)$^+$.

EXAMPLE 218

3-(2-Chloro-6-methoxy-quinolin-3-yl)-acrylic acid ethyl ester

A suspension of 2-chloro-6-methoxy-quinoline-3-carbaldehyde (22.6 g, 102 mmol) and sodium hydride (4.5 g, 113 mmol, 60% dispersion in mineral oil) in tetrahydrofuran (450 mL) was treated dropwise with triethyl phosphonoacetate (20.2 mL, 102 mmol) during 10–15 min at 0° C. After 30 min, the mixture was warmed to rt. After 15 h, the reaction was quenched with water (4.5 mL) and concentrated in vacuo. The resulting wet solid was partitioned between water (1 L) and chloroform (1 L), the phases separated, and the aqueous phase extracted once more with chloroform (1 L). The combined extracts were washed with water (1 L), dried ($K_2CO_3$) and concentrated to give a soft, pale yellow solid (30.8 g). Recrystallization from hot 5:2 ether-methylene chloride (700 mL) gave the title compound (20.2 g, 68% yield) as fluffy, pale yellow needles.

Mp. 113–14° C.

$^1$H NMR (DMSO-$d_6$, 300 MHz): δ1.27 (t, J=7 Hz, 3H, CH$_2$CH$_3$), 3.90 (s, 3H, OCH$_3$), 4.24. (q, J=7 Hz, 2H, CH$_2$), 6.82 (d, J=17 Hz, 1H, =CHCO$_2$), 7.38 (s, 1H, ArH), 7.49 (d, J=9 Hz, 1H, ArH), 7.84–7.94 (overlapping d, J=9 Hz, 17 Hz, 2H, ArH, ArCH=), 8.90 (s, 1H, ArH).

EXAMPLE 219

3-(6-Methoxy-2-oxo-1,2-dihydro-quinolin-3-yl)-acrylic acid ethyl ester

A suspension of 3-(2-chloro-6-methoxy-quinolin-3-yl)-acrylic acid ethyl ester (20.2 g, 69.2 mmol) in ethanol (175 mL) was treated with 12 N aqueous HCl and heated to reflux to form a solution. After 21 h, the resulting precipitate was cooled to 0° C. for 1 h. Vacuum filtration gave the title compound (18.0 g, 95% yield) as a yellow crystalline solid.

Mp. 209–110° C.

$^1$H NMR (DMSO-$d_6$, 300 MHz): δ1.25 (t, J=7 Hz, 3H, CH$_2$CH$_3$), 3.78 (s, 3H, OCH$_3$), 4.16 (q, J=7 Hz, 2H, CH$_2$), 7.11 (d, J=16 Hz, 1H, =CHCO$_2$), 7.18–7.28 (overlapping m, 3H, ArH), 7.64 (d, J=16 Hz, 1H, ArCH=), 8.34 (s, 1H, ArH), 12.0 (s, 1H, ArNH).

EXAMPLE 220

3-(6-Methoxy-2-oxo-1,2,3,4-tetrahydro-quinolin-3-yl)-propionic acid ethyl ester A suspension of 3-(6-methoxy-2-oxo-1,2-dihydro-quinolin-3-yl)-acrylic acid ethyl ester (9.0 g, 33 mmol) in acetic acid (900 mL) was hydrogenated over 10% Pd-C (9.0 g) at 50 psi. After 6 days, the catalyst was filtered through diatomaceous earth and washed with acetic acid (2×500 mL). Concentration of the filtrate gave a tan crystalline solid (9.5 g). Recrystallization from hot ethanol (100 mL) gave the title compound (5.0 g, 55% yield) as white needles.

Mp. 106–07° C.

$^1$H NMR (DMSO-$d_6$, 300 MHz): δ1.16 (t, J=7 Hz, 3H, CH$_2$CH$_3$), 1.57 (m, 1H, CHHCHHCO$_2$), 1.92 (m, 1H, CHHCHHCO$_2$), 2.32–2.44 (overlapping m, 3H, CH, CHHCO$_2$), 2.63 (m, 1H, ArCHH), 2.90 (m, 1H, ArCHH), 4.03 (q, J=7 Hz, 2H, CO$_2$CH$_2$), 6.68–6.78 (overlapping m, 3H, ArH), 9.94 (s, 1H, ArNH).

EXAMPLE 221

3-(6-Hydroxy-2-oxo-1,2,3,4-tetrahydro-quinolin-3-yl)-propionic acid ethyl ester Using the conditions of Example 73 and 3-(6-methoxy-2-oxo-1,2,3,4-tetrahydro-quinolin-3-yl)-propionic acid ethyl ester in place of (7-methoxy-2-oxo-1,2,3,4-tetrahydro-quinolin-3-yl)acetic acid methyl ester and in the presence of ethyl alcohol the title compound was prepared.

Mp. 138.0–38.5° C.

$^1$H NMR (DMSO-$d_6$, 300 MHz): δ1.16 (t, J=7Hz, 3H, CH$_3$), 1.57 (m, 1H, CHHCHHCO$_2$), 1.91 (m, 1H, CHHCHHCO$_2$), 2.26–2.43 (overlapping m, 3H, CH, CHHCO$_2$), 2.56 (m, 1H, ArCHH), 2.83 (m, 1H, ArCHH), 4.04 (q, J=7 Hz, 2H, CO$_2$CH$_2$), 6.50–6.64 (overlapping m, 3H, ArH), 9.01 (s, 1H, ArOH), 9.82 (s, 1H, ArNH).

EXAMPLE 222

3-[6-(2-Guanidino-ethoxy)-2-oxo-1,2,3,4-tetrahydro-quinolin-3-yl]-propionic acid Starting with 3-(6-hydroxy-2-oxo-1,2,3,4-tetrahydro-quinolin-3-yl)-propionic acid ethyl ester and using the conditions of Examples 75, 78, 81 and 84 the title compound was synthesized.

Mp. 119–22° C.

IR (KBr): 3440 (s), 3360 (s), 1692 (s), 1655 (s), 1428 (m), 1410 (m), 1247 (s), 1200 (s), 1168 (s), 1134 (s), 843 (m), 800 (m), 721 (m) cm$^{-1}$.

$^1$H NMR (DMSO-$d_6$, 400 MHz): δ1.54 (m, 1H, CHHCHHCO$_2$), 1.89 (m, 1H, CHHCHHCO$_2$), 2.32–2.41 (overlapping m, 3H, CH, CHHCO$_2$), 2.64 (dd, J=10 Hz, 16 Hz, 1H, ArCHH), 2.92 (dd, J=6 Hz, 16 Hz, 1H, ArCHH), 3.48 (m, 2H, NCH$_2$), 4.00 (t, J=5 Hz, 2H, OCH$_2$), 6.73–6.82 (overlapping m, 3H, ArH), 6.82–7.55 (broad s, 4H, [C(NH$_2$)$_2$]$^+$), 7.65 (t, J=6 Hz, 1H, NHCH$_2$), 9.96 (s, 1H, ArNH), 12.1 (s, 1H, CO$_2$H).

MS (+FAB) m/e (rel. intensity): 321 (M+H, 57).

Analysis calc. for $C_{15}H_{20}N_4O_4 \cdot CF_3COOH_{0.5} \cdot H_2O$. C, 46.05; H, 5.00; N, 12.64. Found C, 46.09; H, 4.93; N, 12.69.

EXAMPLE 223

3-[6-(3-Guanidino-propoxy)-2-oxo-1,2,3,4-tetrahydro-quinolin-3-yl]-propionic acid Starting from 3-(6-hydroxy-2-oxo-1,2,3,4-tetrahydro-quinolin-3-yl)-propionic acid ethyl ester and using the conditions of Examples 75 (except that (3-bromopropyl)-carbamic acid tert-butyl ester is used in place of (2-bromoethyl)-carbamic acid tert-butyl ester), 78, 81 and 84 the title compound was synthesized.

Mp. 168–72° C. (degasses).

IR (KBr): 3370 (m), 1695 (m), 1625 (m), 1405 (m), 1248 (m), 1197 (m), 1163 (m), 1138 (m), 842 (w), 817 (w), 800 (w), 722 (w) cm$^{-1}$.

$^1$H NMR (DMSO-$d_6$, 400 MHz): δ1.54 (m, 1H, CHHCHHCO$_2$), 1.85–1.94 (overlapping m, 3H, NCH$_2$CH$_2$, CHHCHHCO$_2$), 2.33–2.41 (overlapping m, 3H, CHHCO$_2$,CH), 2.63 (dd, J=10 Hz, 16 Hz, 1H, ArCHH), 2.91 (dd, J=6 Hz, 16 Hz, 1H, ArCHH), 3.25 (m, 2H, NCH$_2$), 3.94 (t, J=6 Hz, 2H, OCH$_2$), 6.71–6.80 (overlapping m, ArH), 6.80–7.45 (broad s, 4H, [C(NH$_2$)$_2$]$^+$), 7.56 (t, J=5 Hz, 1H, NHCH$_2$), 9.94 (s, 1H, ArNH), 12.3 (broad s, 1H, CO$_2$H). MS (+FAB) m/e (rel. intensity): 335 (M+H, 100).

Analysis calc. for $C_{16}H_{22}N_4O_4 \cdot CF_3COOH$ C, 48.21; H, 5.17; N, 12.49. Found C, 47.91; H, 5.01; N, 12.46.

EXAMPLE 224

3-[6-(4-Guanidino-butoxy)-2-oxo-1,2,3,4-tetrahydro-quinolin-3-yl]-proionic acid Starting from 3-(6-hydroxy-2-oxo-1,2,3,4-tetrahydro-quinolin-3-yl)-propionic acid ethyl ester and using the conditions of Examples 75 (except that (4-bromobutyl)-carbamic acid tert-butyl ester was used in place of (2-bromoethyl)-carbamic acid tert-butyl ester), 78, 81 and 84 the title compound was synthesized.

Mp. 152–55° C.

IR (KBr): 3370 (m), 1728 (m), 1692 (s), 1632 (s), 1400 (m), 1268 (m), 1250 (m), 1192 (s), 1158 (m), 1135 (m), 838 (m), 810 (m), 796 (m), 720 (m) cm$^{-1}$.

$^1$H NMR (DMSO-$d_6$, 400 MHz): δ1.49–1.68 (overlapping m, 3H, CH̲HCHHCO$_2$, NCH$_2$CH̲$_2$), 1.68 (m, 2H, OCH$_2$CH̲$_2$), 1.89 (m, 1H, CHH̲CHHCO$_2$), 2.32–2.40 (overlapping m, 3H, CH̲HCO$_2$, CH̲), 2.62 (dd, J=10 Hz, 16 Hz, 1H, ArCH̲H), 2.90 (dd, J=6 Hz, 16 Hz, 1H, ArCHH̲), 3.15 (m, 2H, NCH̲$_2$H), 3.91 (t, J=6 Hz, 2H, OCH̲$_2$), 6.69–6.78 (overlapping m, 3H, ArH̲), 6.80–7.50 (broad s, 4H, [C(NH̲$_2$)$_2$]$^+$), 7.56 (t, J=5.5 Hz, 1H, NH̲CH$_2$), 9.94 (s, 1H, ArNH̲), 12.1 (broad s, 1H, CO$_2$H).

MS (+FAB) m/e (rel. intensity): 349 (M+H, 100).

Analysis calc. for $C_{17}H_{24}N_4O_4 \cdot CF_3COOH$ C, 49.35; H, 5.45; N, 12.12. Found C, 49.08; H, 5.33; N, 12.05.

EXAMPLE 225

[6-(3-tert-Butoxycarbonylamino-propoxy)-2-oxo-1, 2,3,4-tetrahydro-quinolin-3-yl]-acetic acid ethyl ester A solution of (6-hydroxy-2-oxo-1,2,3,4-tetrahydro-quinolin-3-yl)-acetic acid ethyl ester (2.0 g, 8.0 mmol) in N,N-dimethylformamide (16 mL) was treated with a solution of sodium ethoxide (21 wt %) in ethanol (3.0 mL, 8.0 mmol) at rt and after 15 min, (3-bromopropyl)-carbamic acid tert-butyl ester (1.9 g, 8.0 mmol) was added. After 4 days, the solution was treated with water (75 mL) and the resulting gum was briefly heated, then cooled to 0° C. The precipitated solid was triturated for 6 h, to give the crude product (2.7 g). Flash chromatography (90 g silica; CHCl$_3$, then 1% MeOH (saturated with NH$_3$) —CHCl$_3$) gave the title compound (2.6 g, 79% yield) as a white solid.

$^1$H NMR: (DMSO-$d_6$, 300 MHz): δ1.16 (t, J=7.5 Hz, 3H, CH$_2$CH̲$_3$), 1.33 (s, 9H, C(CH̲$_3$)$_3$), 1.75 (m, 2H, NCH$_2$CH̲$_2$), 2.30–2.90 (overlapping m, 5H, ArCH̲H, CH̲, CH̲HCO$_2$), 3.03 (m, 2H, NCH̲$_2$), 3.87 (t, J=6 Hz, 2H, OCH̲$_2$), 4.05 (q, J=7.5 Hz, 2H, CH̲$_2$CH$_3$), 6.65–6.90 (overlapping m, 4H, Ar H̲, NH̲CH$_2$), 9.96 (s, 1H, ArNH̲).

EXAMPLE 226

[6-(3-Amino-propoxy)-2-oxo-1,2,3,4-tetrahydro-quinolin-3-yl]-acetic acid ethyl ester

[6-(3-tert-Butoxycarbonylamino-propoxy)-2-oxo-1,2,3,4-tetrahydro-quinolin-3-yl]-acetic acid ethyl ester (2.6 g, 6.4 mmol) and trifluoroacetic acid (5.0 mL, 65 mmol) were combined in methylene chloride (25 mL) at rt. After 18 h, the solution was concentrated in vacuo to give a sticky tan solid (2.8 g) which was triturated with 25:1 methylene chloride-methanol (50 mL) for 2 h to give the trifluoroacetate salt of the title compound (2.5 g, 93% yield) as a white powder.

$^1$H NMR: (DMSO-$d_6$, 300 MHz): δ1.17, (t, J=7.5 Hz, 3H, CH̲$_3$), 1.96 (m, 2H, NCH$_2$CH̲$_2$), 2.37–3.00 (overlapping m, 7H, ArCH̲H, CH̲, CH̲HCO$_2$, NCH̲$_2$), 3.98 (t, J=6 Hz, 2H, OCH̲$_2$), 4.05 (q, J=7.5 Hz, 2H, CO$_2$CH̲$_2$), 6.76 (overlapping m, 3H, ArH̲), 7.80 (s, 3H, NH̲$_3^+$), 10.0 (s, 1H, ArNH̲).

EXAMPLE 227

[6-(3-Guanidino-propoxy)-2-oxo-1,2,3 4-tetrahydro-quinolin-3-yl]-acetic acid ethyl ester A suspension of [6-(3-amino-propoxy)-2-oxo-1,2,3,4-tetrahydro-quinolin-3-yl]-acetic acid ethyl ester (0.80 g, 1.9 mmol), 3,5-dimethylpyrazole carboxamidine nitrate (0.42 g, 2.1 mmol) and diisopropylethylamine (0.73 mL, 4.2 mmol) in 3:1 dioxane-water (5.5 mL) was heated at reflux for 9 h. The cooled solution was concentrated in vacuo to yield a viscous oil. Purification by reverse phase HPLC gave the title compound (0.76 g, 86%) as a clear, almost colorless oil.

$^1$H NMR: (DMSO-$d_6$, 300 MHz): δ1.18 (t, J=7.5 Hz, 3H, CH$_2$CH̲$_3$), 1.94 (m, NCH$_2$CH̲$_2$), 2.37–2.90 (overlapping m, 5H, ArCH̲H, CH̲, CH̲HCO$_2$), 3.22 (m, 2H, NCH̲$_2$), 3.95 (t, J=6 Hz, 2H, OCH̲$_2$), 4.05 (q, J=7.5 Hz, 2H, CO$_2$CH̲$_2$), 6.70–6.78 (overlapping m, 3H, ArH̲), 6.80–7.50 (broad s, 4H, [C(NH̲$_2$)$_2$]$^+$), 7.65 (broad m, 1H, NH̲CH$_2$), 10.0 (s, 1H, ArNH̲).

EXAMPLE 228

[6-(3-Guanidino-propoxy)-2-oxo-1,2,3,4-tetrahydro-quinolin-3-yl]-acetic acid

A solution of [6-(3-Guanidino-propoxy)-2-oxo-1,2,3,4-tetrahydro-quinolin-3-yl]-acetic acid ethyl ester (0.76 g, 1.6 mmol) in ethanol (7 mL) was treated with 0.5 N aqueous NaOH and heated at reflux for 3 h. The resulting precipitate was cooled to room temperature, treated with trifluoroacetic acid (1.5 mL) and the solution thus formed concentrated in vacuo to yield a clear, colorless oil. Purification by reverse phase HPLC gave the title compound (0.38 g, 55% yield) as a fluffy white solid.

Mp. 178–79° C.

IR(KBr): 3400 (m), 1705 (m), 1660 (s), 1605 (s), 1245 (s), 1198 (s), 1180 (s), 1158 (s), 1125 (s), 1025 (m), 790 (m), 715 (m) cm$^{-1}$.

$^1$H NMR: (DMSO-$d_6$, 400 MHz): δ1.89 (m, 2H, NHCH$_2$CH̲$_2$), 2.33 (m, 1H, ArCH̲H), 2.68–2.97 (overlapping m, 4H, ArCHH̲, CH̲, CH̲HCO$_2$), 3.25 (m, 2H, NCH̲$_2$), 3.94 (t, J=6 Hz, 2H, OCH̲$_2$), 6.72–6.79 (overlapping m, 3H, ArH̲), 6.79–7.50 (broad s, 4H, [C(NH̲$_2$)$_2$]$^+$), 7.63 (broad m, 1H, NH̲CH$_2$), 10.0 (s, 1H, ArNH̲), 12.2 (s, 1H, CO$_2$H̲).

MS (+FAB) m/e (rel. intensity): 321 (M+H, 100).

Analysis calc. for $C_{15}H_{20}N_4O_4 \cdot CF_3COOH$ C, 47.01; H, 4.87; N, 12.99. Found C, 47.03; H, 4.75; N, 12.86.

EXAMPLE 229

[6-(4-Guanidino-butoxy)-2-oxo-1,2,3,4-tetrahydro-quinolin-3-yl]-acetic acid

The title compound was synthesized from (6-hydroxy-2-oxo-1,2,3,4-tetrahydro-quinolin-3-yl)-acetic acid ethyl ester and (4-bromo-butyl)carbamic acid tert-butyl ester in essentially the same manner as described in Example 225 and followed by steps in essentially the same manner as described in Examples 226, 227 and 228.

Mp. 170–73° C.

IR(KBr): 3420 (s), 1703 (s), 1665 (s), 1432 (m), 1409 (m), 1245 (s), 1195 (s), 1160 (s), 1134 (s), 863 (w), 800 (w), 720 (m), 679 (m) cm$^{-1}$.

$^1$H NMR: (DMSO-$d_6$, 400 MHz): δ1.60 (m, 2H, NCH$_2$CH̲$_2$), 1.69 (m, 2H, OCH$_2$CH̲$_2$), 2.31 (m, 2H, ArCH̲H), 2.68–2.91 (overlapping m, 4H, ArCHH̲, CH̲, CH̲HCO$_2$), 3.15 (m, 2H, NCH̲$_2$), 3.92 (t, J=6 Hz, 2H, OCH̲$_2$), 6.70–6.78 (overlapping m, 3H, ArH̲), 6.78–7.54 (broad s, 4H, [C(NH̲$_2$)$^+$), 7.64 (t, J=6 Hz, 1H, NH̲CH$_2$), 9.99 (s, 1H, ArNH̲), 12.2 (broad s, 1H, CO$_2$H̲).

MS (+FAB) m/e (rel. intensity): 335 (M+H, 100).

Analysis calc. for $C_{16}H_{22}N_4O_4 \cdot CF_3COOH \cdot H_2O$ C, 46.35; H, 5.40; N, 12.01. Found C, 46.09; H, 5.31; N, 12.02.

EXAMPLE 230

3-[7-(2-Guanidino-ethoxy)-2-oxo-1,2,3,4-tetrahydro-quinolin-3-yl]-propionic acid The title compound was synthesized from 3-(7-hydroxy-2-oxo-1,2,3,4-tetrahydro-quinolin-3-yl)-propionic acid ethyl ester prepared using the conditions of Examples 218, 219, 220 and 221 and (2-bromo-ethyl)carbamic acid tert-butyl ester in essentially the same manner as described in Example 225 and followed by steps in essentially the same manner as described in Examples 226, 227 and 228.

Mp. 193–96° C.

IR (KBr): 3410 (m), 3190 (m), 1695 (s), 1675 (s), 1620 (s), 1278 (m), 1205 (s), 1183 (s), 1140 (s), 870 (m), 848 (m), 800 (m), 727 cm$^{31}$ $^1$.

$^1$H NMR (DMSO-$d_6$, 400 MHz): δ1.54 (m, 1H, CHHCHHCO$_2$), 1.91 (m, 1H, CHHCHHCO$_2$), 2.32–2.42 (overlapping m, 3H, CH, CHHCO$_2$), 2.58 (dd, J=10 Hz, 16 Hz, 1H, ArCHH), 2.89 (dd, J=6 Hz, 16 Hz, 1H, ArCHH), 3.50 (m, 2H, NCH$_2$), 3.98 (t, J=5 Hz, 2H, OCH$_2$), 6.44 (d, J=2.5 Hz, 1H, ArH), 6.50 (dd, J=2.5 Hz, 8 Hz, 1H, ArH), 6.66–7.56 (broad, 4H, [C(NH$_2$)$_2$]$^+$), 7.08 (d, J=8 Hz, 1H, ArH), 7.66 (t, J=6 Hz, 1H, NHCH$_2$), 10.1 (s, 1H, ArNH), 12.1 (broad s, 1H, CO$_2$H).

MS (–FAB) m/e (rel. intensity): 319 (M–H, 22).

Analysis calc. for $C_{15}H_{20}N_4O_4 \cdot CF_3COOH$ C, 47.01; H, 4.87; N, 12.90. Found C, 47.29; H, 4.70; N, 13.11.

EXAMPLE 231

3-[7-(3-Guanidino-propoxy)-2-oxo-1,2,3,4-tetrahydro-quinolin-3-yl]-propionic acid The title compound was synthesized from 3-(7-hydroxy-2-oxo-1,2,3,4-tetrahydro-quinolin-3-yl)-propionic acid ethyl ester prepared using the conditions of Examples 218, 219, 220 and 221 and (3-bromo-propyl)carbamic acid tert-butyl ester in essentially the same manner as described in Example 225 and followed by steps in essentially the same manner as described in Examples 226, 227 and 228.

Mp. 157–59° C.

IR (KBr): 3420 (m), 3200 (m), 1718 (s), 1680 (s), 1620 (s), 1275 (m), 1202 (s), 1182 (s), 1139 (s), 868 (m), 842 (m), 798 (m), 722 (m) cm$^{-1}$.

$^1$H NMR (DMSO-$d_6$, 400 MHz): δ1.54 (m, 1H, CHHCHHCO$_2$), 1.87–1.93 (overlapping m, 3H, CHHCHHCO$_2$, NCH$_2$CH$_2$), 2.32–2.42 (overlapping m, 3H, CHHCO$_2$, CH), 2.57 (dd, J=10 Hz, 16 Hz, H, ArCHH), 2.88 (dd, J=6 Hz, 16 Hz, 1H, ArCHH), 3.25 (m, 2H, NCH$_2$), 3.93 (t, J=6 Hz, 2H, OCH$_2$), 6.42 (d, J=2.5 Hz, 1H, ArH), 6.49 (dd, J=2.5 H, 8 Hz, ArH), 6.60–7.50 (broad, 4H, [C(NH$_2$)$_2$]$^+$), 7.07 (d, J=8 Hz, 1H, ArH), 7.60 (t, J=5 Hz, NHCH$_2$), 10.0 (s, 1H, ArNH), 12.1 (broad s, 1H, CO$_2$H).

MS (–FAB) m/e (rel. intensity): 333 (M–H, 18).

Analysis calc. for $C_{16}H_{22}N_4O_4 \cdot CF_3COOH$ C, 48.21; H, 5.17; N, 12.50. Found C, 48.41; H, 4.98; N, 12.64.

EXAMPLE 232

3-[7-(4-Guanidino-butoxy)-2-oxo-1,2,3,4-tetrahydro-quinolin-3-yl]-proionic acid

The title compound was synthesized from 3-(7-hydroxy-2-oxo-1,2,3,4-tetrahydro-quinolin-3-yl)-propionic acid ethyl ester prepared using the conditions of Examples 218, 219, 220 and 221 and (4-bromo-butyl)carbamic acid tert-butyl ester in essentially the same manner as described in Example 225 and followed by steps in essentially the same manner as described in Examples 226, 227 and 228.

Mp. 176–77° C.

IR (KBr): 3380 (m), 3198 (m), 1718 (s), 1688 (s), 1662 (s), 1629 (s), 1388 (m), 1295 (m), 1286 (m), 1210 (s), 1182 (s), 1138 (s), 872 (m), 847 (m), 800 (m), 730 (m) cm$^{-1}$.

$^1$H NMR (DMSO-$d_6$, 400 MHz): δ1.49–1.63 (overlapping m, 3H, CHHCHHCO$_2$, NCH$_2$CH$_2$), 1.70 (m, 2H, OCH$_2$CH$_2$), 1.91 (m, 1H, CHHCHHCO$_2$), 2.32–2.42 (overlapping m, 3H, CH, CHHCO$_2$), 2.57 (dd, J=10 Hz, 16 Hz, 1H, ArCHH), 2.87 (dd, J=6 Hz, 16 Hz, 1H, ArCHH), 3.15 (m, 2H, NCH$_2$), 3.90 (t, J=6 Hz, 2H, OCH$_2$), 6.41 (d, J=2.5 Hz, 1H, ArH), 6.48 (dd, J=2.5 Hz, 8 Hz, 1H, ArH), 6.60–7.46 (broad, 4H, [C(NH$_2$)$_2$]$^+$), 7.05 (d, J=8 Hz, 1H, ArH), 7.55 (t, J=5 Hz, 1H, NHCH$_2$), 10.0 (s, 1H, ArNH), 12.1 (s, 1H, CO$_2$H).

MS (–FAB) m/e (rel. intensity): 347 (M–H, 15).

Analysis calc. for $C_{17}H_{24}N_4O_4 \cdot CF_3COOH$ C, 49.35; H, 5.45; N, 12.12. Found C, 49.32; H, 5.36; N, 12.45.

EXAMPLE 233

(8-Hydroxy-2-oxo-1,2,3,4-tetrahydro-quinolin-3-yl)-acetic acid ethyl ester

A solution of (8-methoxy-2-oxo-1,2,3,4-tetrahydro-quinolin-3-yl)-acetic acid ethyl ester (prepared in essentially the same manner as described for Example 72) (2.4 g, 9.1 mmol) in methylene chloride (25 mL) was treated with 1.0 M BBr$_3$—CH$_2$Cl$_2$ solution (90 mL, 90 mmol) at 0° C. in an oven-dried flask. After 3 h, the resulting mixture was concentrated in vacuo and the residue treated with ice-cold ethanol (200 mL) and concentrated. Ethanol treatment and concentration were repeated twice more to give a tan foam (3.1 g). Flash chromatography (102 g silica; 2.5% MeOH (saturated with NH$_3$)—CHCl$_3$) gave the title compound (2.1 g, 91% yield) as a pale yellow solid.

$^1$H NMR (DMSO-$d_6$, 300 MHz): δ1.18 (t, J=7 Hz, 3H, CH$_3$), 2.41–2.48 (m 1H, ArCHH), 2.70–2.88 (overlapping m, 4H, ArCHH, CH, CHHCO$_2$), 4.07 (t, J=7 Hz, 2H, CO$_2$CH$_2$), 6.60–6.78 (overlapping m, 3H, ArH), 8.94 (s, 1H, ArOH), 9.63 (s, 1H, ArNH).

EXAMPLE 234

[8-(3-Guanidino-propoxy)-2-oxo-1,2,3,4-tetrahydro-quinolin-3-yl]-acetic acid

The title compound was synthesized from (8-hydroxy-2-oxo-1,2,3,4-tetrahydro-quinolin-3-yl)-acetic acid ethyl ester prepared using the conditions of Examples 218, 219, 220 and 221 and (3-bromo-propyl)carbamic acid tert-butyl ester in essentially the same manner as described in Example 225 and followed by steps in essentially the same manner as described in Examples 226, 227 and 228.

Mp. 151–55° C.

IR (KBr): 3405 (s), 1750 (m), 1690 (s), 1660 (s), 1630 (s), 1435 (m), 1420 (m), 1400 (m), 1275 (s), 1195 (s), 1145 (s), 835 (m), 780 (m), 725 (s) cm$^{-1}$.

$^1$H NMR (DMSO-$d_6$, 400 MHz): δ1.94 (m, 2H, NCH$_2$CH$_2$), 2.37 (m, 1H, ArCHH), 2.69–2.93 (overlapping m, 4H, ArCHH, CH, CHHC$_2$), 3.36 (m, 2H, NCH$_2$), 3.99 (t, J=6 Hz, 2H, OCH$_2$), 6.77 (d, J=7 Hz, 1H, ArH), 6.84–6.91 (overlapping m, 2H, ArH), 7.00–7.50 (broad s, 4H, [C(NH$_2$)$_2$]$^+$), 7.61 (t, J=5 Hz, 1H, NHCH$_2$), 9.28 (s, 1H, ArNH), 12.2 (s, 1H, CO$_2$H). MS (+FAB) m/e (rel. intensity): 321 (M+H, 100).

Analysis calc. for $C_{15}H_{20}N_4O_4 \cdot CF_3COOH$ C, 47.01; H, 4.87; N, 12.90. Found C, 46.61; H, 4.80; N, 12.64.

EXAMPLE 235

[8-(4-Guanidino-butoxy)-2-oxo-1,2,3,4-tetrahydro-quinolin-3-yl]-acetic acid

The title compound was synthesized from (8-hydroxy-2-oxo-1,2,3,4-tetrahydro-quinolin-3-yl)-acetic acid ethyl ester prepared using the conditions of Examples 218, 219, 220 and 221 and (4-bromo-butyl)carbamic acid tert-butyl ester in essentially the same manner as described in Example 225 and followed by steps in essentially the same manner as described in Examples 226, 227 and 228.

Mp. 207–210° C.

IR (KBr): 3385 (s), 1700 (s), 1630 (s), 1440 (m), 1425 (m), 1400 (m), 1275 (m), 1205 (s), 1180 (s), 835 (w), 805 (m), 775 (m), 725 (m), 680 (m) cm$^{-1}$.

$^1$H NMR (DMSO-$d_6$, 400 MHz): δ1.67 (m, 2H, NCH$_2$CH$_2$), 1.75 (m, 2H, OCH$_2$CH$_2$), 2.37 (m, 1H, ArCHH), 2.69–2.93 (overlapping m, 4H, ArCHH,CH, CHHCO$_2$), 3.14 (m, 2H, NCH$_2$), 3.99 (t, J=6 Hz, 2H, OCH$_2$), 6.76 (d, J=7 Hz, 1H, ArH), 6.84–6.91 (overlapping m, 2H, ArH), 7.00–7.46 (broad s, 4H, [C(NH$_2$)$_2$]$^+$), 7.54 (t, J=5 Hz, 1H, NHCH$_2$), 9.09 (s, 1H, ArNH), 12.2 (broad s, 1H, CO$_2$H).

MS (DCI) m/e (rel. intensity): 335 (M + H, 38).

| | |
|---|---|
| Analysis calc. for $C_{16}H_{22}N_4O_4 \cdot CF_3COOH \cdot 0.2 \, H_2O$ | C, 47.83; H, 5.22; N, 12.40 |
| Found | C, 47.76; H, 5.00; N, 12.37 |

EXAMPLE 236

(6-Hydroxy-2-oxo-1,2-dihydro-quinolin-3-yl)-acetic acid ethyl ester

A mixture of 2-(5-hydroxy-2-nitro-benzylidene)-succinic acid diethyl ester (9.5 g, 30 mmol) and Zn (5.8 g, 89 mmol) in ethanol (125 mL) was treated with 12 N aqueous HCl at 0° C. After 5 min, the reaction was warmed to room temperature and then heated to reflux after 30 min total. After 3 h, additional Zn (0.2 g, 3 mmol) was added. After 4 h total at reflux, the cooled solution was filtered and concentrated in vacuo. The crude, dark brown residue was triturated with water (500 mL) overnight to give a brown solid (6.3 g). Recrystallization from hot acetonitrile gave the title compound (5.3 g, 73% yield) as a tan crystalline solid.

$^1$H NMR: (DMSO-$d_6$, 300 MHz): δ1.26 (t, J=7.5 Hz, 3H, CH$_3$), 3.04 (s, 2H, CH$_2$CO$_2$), 4.02 (q, J=7.5Hz, 2H, CO$_2$CH$_2$), 6.85 (overlapping m, 2H, ArH), 6.98 (d, J=9Hz, 1H, ArH), 7.67 (s, 1H, ArCH=), 9.53 (s, 1H, ArOH), 10.1 (s, 1H, ArNH).

EXAMPLE 237

[6-(3-Guanidino-propoxy)-2-oxo-1,2-dihydro-quinolin-3-yl]-acetic acid

The title compound was prepared according to the procedures of Examples 77, 80, 81 and 84 starting from (6-hydroxy-2-oxo-1,2-dihydro-quinolin-3-yl)-acetic acid ethyl ester in place of 7-hydroxy-2-oxo-1,2,3,4-tetrahydro-quinolin-3-yl)-acetic acid methyl ester.

Mp. 207–12° C. (dec).

IR (KBr): 3360 (s), 1680 (broad s), 1435 (m), 1414 (m), 1400 (m), 1263 (s), 1192 (s), 1168 (s), 1130 (s), 1081 (s), 842 (m), 798 (m), 720 (m) cm$^{-1}$.

$^1$H NMR (DMSO-$d_6$, 400 MHz): δ1.92 (m, 2H, NCH$_2$CH$_2$), 3.04 (s, 2H, CH$_2$CO$_2$), 3.27 (m, 2H, NCH$_2$), 4.02 (t, J=6 Hz, 2H, OCH$_2$), 6.60–7.60 (overlapping m, broad s, 7H, Ar H, [C(NH$_2$)$_2$]$^+$), 7.65 (t, J=5.5 Hz, 1H, NHCH$_2$), 7.75 (s, 1H, ArCH=), 10.2 (s, 1H, ArNH), 12.9 (broad s, 1H, CO$_2$H).

MS (+FAB) m/e (rel. intensity): 319 (M+H, 100).

Analysis calc. for $C_{15}H_{18}N_4O_4 \cdot CF_3COOH \cdot H_2O$ C, 45.34; H, 4.70; N, 12.44. Found C, 45.50; H, 4.58; N, 12.45.

EXAMPLE 238

[6-(4-Guanidino-butoxy)-2-oxo-1,2-dihydro-quinolin-3-yl]-acetic acid trifluoroacetic acid salt The title compound was prepared according to the procedures of Examples 76, 79, 81 and 84 starting from (6-hydroxy-2-oxo-1,2-dihydro-quinolin-3-yl)-acetic acid ethyl ester in place of 7-hydroxy-2-oxo-1,2,3,4-tetrahydro-quinolin-3-yl)-acetic acid methyl ester.

IR (KBr): 3380 (s), 1690 (s), 1654 (s), 1615 (s), 1432 (m), 1270 (s), 1250 (s), 1208 (s), 1182 (s), 1125 (s), 834 (m), 795 (m), 760 (m), 718 (m) cm$^{-1}$.

$^1$H NMR (DMSO-$d_6$, 400 MHz): δ1.61 (m, 2H, NCH$_2$CH$_2$), 1.73 (m, 2H, OCH$_2$CH$_2$), 3.04 (s, 2H, CH$_2$CO$_2$), 3.16 (m, 2H, NCH$_2$), 3.99 (t, J=6 Hz, 2H, OCH$_2$), 6.60–7.50 (overlapping m, broad, 7H, ArH, [C(NH$_2$)$_2$]$^+$), 7.59 (t, J=6 Hz, 1H, NHCH$_2$), 7.75 (s, 1H, ArCH=), 10.2 (s, 1H, ArNH), 12.9 (broad s, 1H, CO$_2$H).

MS (+FAB) m/e (rel. intensity): 333 (M+H, 26).

Analysis calc. for $C_{16}H_{20}N_4O_4 \cdot CF_3COOH \cdot H_2O$ C, 46.55; H, 4.99; N, 12.06. Found C, 46.54; H, 4.88; N, 12.10.

EXAMPLE 239

[1-Benzyl-7-(3-guanidino-propoxy)-2-oxo-1,2-dihydro-quinolin-3-yl]-acetic acid trifluoroacetic acid salt The title compound was prepared according to the procedures of Examples 81 and 84 starting from [1-benzyl-7-(3-aminopropoxy)-2-oxo-1,2-dihydro-quinolin-3-yl]acetic acid methyl ester in place of 7-hydroxy-2-oxo-1,2,3,4-tetrahydro-quinolin-3-yl)-acetic acid methyl ester.

Mp. 132–34° C.

IR (KBr): 3342 (m), 3190 (m), 1715 (s), 1670 (s), 1645 (s), 1594 (s), 1408 (m), 1199 (s) 1133 (m), 840 (m), 799 (m), 723 (m) cm$^{-1}$.

$^1$H NMR (DMSO-$d_6$, 400 MHz): δ1.88 (m, 2H, NCH$_2$CH$_2$), 3.23 (m, 2H, NCH$_2$CH$_2$), 3.52 (s, 2H, CH$_2$CO$_2$), 4.01 (t, J=6 Hz, 2H, OCH$_2$), 5.52 (broad s, 2H, CH$_2$Ph), 6.60–7.50 (broad, 4H, [C(NH$_2$)$_2$]$^+$), 6.81 (s, 1H, ArH), 6.88 (d, J=9 Hz, 1H, ArH), 7.19–7.35 (overlapping m, 5H, ArH), 7.60 (t, J=5 Hz, 1H, NHCH$_2$), 7.63 (d, J=9 Hz, 1H, ArH), 7.85 (s, 1H, ArCH=), 12.2 (broad s, 1H, CO$_2$H), MS (+FAB) m/e (rel. intensity): 409 (M+H, 100).

Analysis calc. for $C_{22}H_{24}N_4O_4 \cdot CF_3COOH$ C, 55.17; H, 4.82; N, 10.72. Found C, 55.07; H, 4.74; N, 10.80.

EXAMPLE 240

(7-Methoxy-2-oxo-1,2-dihydro-quinolin-3-yl) propionic acid methyl ester

The title compound was prepared from 7.0 g 3-(2-chloro-7-methoxy-quinolin-3-yl)propionic acid methyl ester using the conditions of Example 71 gave 4.5 g of the title compound as a white crystalline solid.

EXAMPLE 241

(7-Methoxy-2-oxo-1,2-dihydro-quinolin-3-yl)butyric acid methyl ester

The title compound was prepared from 3-(2-chloro-7-methoxy-quinolin-3-yl)butyric acid methyl ester using the conditions of Example 71.

EXAMPLE 242

(7-Hydroxy-2-oxo-1,2-dihydro-quinolin-3-yl) propionic acid methyl ester

Treatment of 4.5 g of (7-Methoxy-2-oxo-1,2-dihydro-quinolin-3-yl)propionic acid methyl ester with boron tribromide in dichloromethane using the conditions of Example 73 gave 2.5 g of the title compound as a yellow crystalline solid.

EXAMPLE 243

7-(Hydroxy-2-oxo-1,2-dihydro-quinolin-3-yl)butyric acid methyl ester

Treatment of (7-Methoxy-2-oxo-1,2-dihydro-quinolin-3-yl)butyric acid methyl ester with boron tribromide in dichloromethane using the conditions of Example 73 gives the title compound.

EXAMPLE 244

[7-(2-tert-Butoxycarbonylaminoethoxy)-2-oxo-1,2-dihydro-quinolin-3-yl]propionic acid methyl ester The title compound was prepared from 2.5 g of (7-Hydroxy-2-oxo-1,2-dihydro-quinolin-3-yl)propionic acid methyl ester using the conditions of Example 75 gave 2.2 g of a white crystalline solid.

EXAMPLE 245

[7-(2-Amino-ethoxy)-2-oxo-1,2-dihydro-quinolin-3-yl]propionic acid methyl ester

The title compound was prepared from 2.2 g of [7-(2-tert-Butoxycarbonylamino-ethoxy)-2-oxo-1,2-dihydro-quinolin-3-yl]propionic acid methyl ester using the conditions of Example 78 gave 2.3 g of the title compound as a light tan crystalline solid.

EXAMPLE 246

[7-(2-Guanidino-ethoxy)-2-oxo-1,2-dihydro-quinolin-3-yl]propionic acid methyl ester The title compound was prepared from 1.30 g of [7-(2-amino-ethoxy)-2-oxo-1,2-dihydro-quinolin-3-yl]propionic acid methyl ester using the conditions of Example 81 gave 0.79 g of the title compound as a white crystalline solid.

EXAMPLE 247

3-[7-(2-Guanidino-ethoxy)-2-oxo-1,2-dihydro-quinolin-3-yl]-propionic acid nitric acid salt The title compound was prepared from 0.79 g of [7-(2-guanidino-ethoxy)-2-oxo-1,2-dihydro-quinolin-3-yl] propionic acid methyl ester using the conditions of Example 85 gave 0.55 g of the title compound as the nitric acid salt.

Mp. 211° C. (dec).

IR (KBr): 3345 (s), 3205 (s), 1703 (s), 1645 (s), 1400 (s), 1248 (s), 1232 (s), 1197 (s), 1176 (m), 842 (m), 830 (m), 810 (m), 785 (m) cm$^{-1}$.

$^1$H NMR (DMSO-d$_6$, 400 MHz): δ2.53 (t, J=7.5 Hz, 2H, C$\underline{H}_2$CH$_2$CO$_2$), 2.70 (t, J=7.5 Hz, 2H, C$\underline{H}_2$CO$_2$), 3.55 (m, 2H, NC$\underline{H}_2$), 4.09 (t, J=5 Hz, 2H, OC$\underline{H}_2$), 6.78–6.81 (overlapping m, 2H, Ar$\underline{H}$), 6.83–7.48 (broad, 4H, [C(N $\underline{H}_2)_2$]$^+$), 7.54 (d, J=9 Hz, 1H, Ar$\underline{H}$), 7.62 (t, J=5 Hz, 1H, N $\underline{H}$CH$_2$), 7.67 (s, 1H, ArC$\underline{H}$=), 11.7 (s, 1H, ArN$\underline{H}$), 12.1 (broad s, 1H, CO$_2\underline{H}$).

MS (+FAB) m/e (rel. intensity): 319 (M+H, 100).

Analysis calc. for C$_{15}$H$_{18}$N$_4$O$_4$.HNO$_3$ C, 47.24; H, 5.02; N, 18.37. Found C, 47.21; H, 4.96; N, 18.04.

EXAMPLE 248

4-Methyl-N-{[7-(3-guanidino-propoxy)-2-oxo-1,2,3,4-tetrahydro-quinolin-3-yl]-acetyl}-benzenesulfonamide To [7-(3-guanidino-propoxy)-2-oxo-1,2,3,4-tetrahydro-quinolin-3-yl]-acetic acid hydrochloride (0.90 g) was added para-toluenesulfonamide (0.65 g), 1-[3-(dimethylamino)-propyl]-3-ethylcarbodiimide hydrochloride (0.73 g), dimethylaminopyridine (0.05 g), and DMF (40 mL) and the resulting slurry formed a solution as it was stirred under N$_2$ at room temperature for 21 days. The DMF was removed by vacuum distillation. The golden oil was triturated with CH$_2$Cl$_2$ (25 mL) followed by EtOAc (25 mL). The resulting oil was dissolved in 10 mL of 25% CH$_3$CN/H$_2$O and chromatographed on a C$_{18}$ reverse phase column, eluting with a gradient of 10% CH$_3$CN/H$_2$O to 40% CH$_3$CN/H$_2$O to afford the title compound (73 mg) as an ivory solid after lyophilization.

NMR (300 MHz, DMSO-d$_6$) δ9.96 (s,1H), 7.69(t,J=8.23 Hz, 1H), 7.61(d,J=8.07 Hz, 2H), 7.40–7.05 (broad, 4H), 7.17(d,J=8.11 Hz,2H), 6.92(d,J=8.27 Hz,1H), 6.46(dd,J= 8.23,2.25 Hz,1H), 6.41(d,J=2.19 Hz,1H), 3.92(t,J–5.82 Hz,2H), 3.24(broad m,2H), 2.74–2.62(m,2H), 2.47–2.37(m, 2H), 2.32(s,3H), 1.90–1.82(m,3H); MS(+ESI)m/z474(M+ H)$^+$; Calculated for C$_{22}$N$_{27}$N$_5$O$_5$S.1.5H$_2$O: C, 52.79; H, 6.04; N, 13.99. Found: C, 52.79; H,6.04; N,13.05.

EXAMPLE 249

(5-Bromo-pentyl)-carbamic acid tert-butyl ester

The title compound is prepared according to the procedure of Example 16 except that 5-amino-1-pentanol is used in place of 2-amino-ethan-1-ol.

EXAMPLE 250

[8-(5-Guanidino-pentoxy)-2-oxo-1,2,3,4-tetrahydro-quinolin-3-yl]-acetic acid

The title compound was synthesized from (8-hydroxy-2-oxo-1,2,3,4-tetrahydro-quinolin-3-yl)-acetic acid ethyl ester prepared using the conditions of Examples 218, 219, 220, 221 and (5-bromo-pentyl)-carbamic acid tert-butyl ester in essentially the same manner as described in Example 225 and followed by steps in essentially the same manner as described in Examples 226, 227 and 228.

m.p. 126–31° C.

IR (KBr): 3375 (s, doublet), 1720 (s), 1680 (s), 1645 (s), 1435 (m), 1270 (s), 1200 (s), 1145 (s), 845 (m), 805 (m), 725 (s) cm$^{-1}$.

¹H NMR (DMSO-d₆, 400 MHz): δ1.42–1.56 (overlapping m, 4H, NCH₂CH₂CH₂), 1.76 (m, 2H, OCH₂CH₂), 2.37 (m, 1H, ArCHH), 2.69–2.92 (overlapping m, 4H, ArCHH, CH, CHHCO₂), 3.11 (m, 2H, NCH₂), 3.97 (t, J=6.5 Hz, 1H, OCH₂), 6.76 (d, J=6.5 Hz, 1H, ArH), 6.84–6.90 (overlapping m, 2H, ArH), 6.96–7.46 (broad s, 4H, [C(NH₂)₂]⁺), 7.51 (t, J=5 Hz, 1H, NHCH₂), 9.01 (s, 1H, ArNH), 12.2 (s, 1H, CO₂H).

| | |
|---|---|
| MS (DCI) m/e (rel. intensity): 349 (M + H, 100). | |
| Analysis calc. For C₁₇H₂₄N₄O₄·CF₃COOH·0.2 H₂O | C, 48.97; H, 5.49; N, 12.02 |
| Found | C, 48.75; H, 5.29; N, 12.06 |

We claim:
1. A compound of Formula (I):

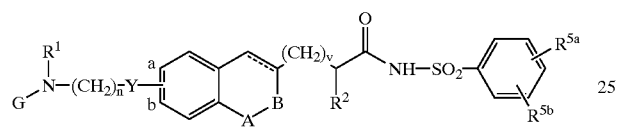

Formula (I)

wherein:
— — — represents the presence of an optional double bond;
n is an integer of 2 to 5;
v is an integer of 0 or 1;
A—B is a diradical of the formula:

Y is selected from the group consisting of —O—, —CH₂—CH₂—, —CH=CH—,

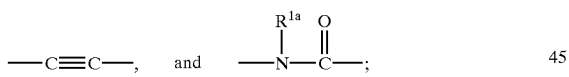

$R^1$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or more substituents which are the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl optionally substituted with one or more substituents which may be the same or different, and are selected from hydroxy, amino, halogen, straight chain alkyl of 1 to 6 carbon atoms, cyano and nitro;

$R^{1a}$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or more substituents which are the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

$R^2$ is hydrogen, —NHR¹, or —OR¹, aryl of 6 to 12 carbon atoms optionally substituted with one or more substituents selected from straight chain alkyl of 1 to 6 carbon atoms, alkoxy of 1 to 6 carbon atoms, —S-alkyl of 1 to 6 carbon atoms, cyano, nitro, halogen and phenyl; the heterocyclyl moiety is selected from 2- or 3-furyl, 2- or 3-thienyl, and 2-, 3- or 4-pyridyl optionally substituted with one or more substituents which are the same or different, and are selected from hydroxy, amino, halogen, straight chain alkyl of 1 to 6 carbon atoms, cyano and nitro; phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl optionally substituted with one or more substituents which are the same or different, and are selected from hydroxy, amino, halogen, straight chain alkyl of 1 to 6 carbon atoms, cyano and nitro;

G is

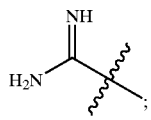

$R^5$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which are the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms and dialkylamino of 1 to 6 carbon atoms;

$R^{5a}$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which are the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

$R^{5b}$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

or a pharmaceutically acceptable salt thereof.

2. A compound as defined in claim 1 wherein:

n is an integer of 2 to 4;

the moiety

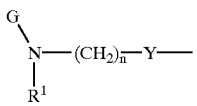

is located at the a or b position of the bicyclic nucleus;

$R^1$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or two substituents which are the same or different and are selected from halogen, straight chain alkyl of 1 to 6 carbon atoms, and nitro; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl optionally substituted with one or two substituents which are the same or different, and are selected from halogen, straight chain alkyl of 1 to 6 carbon atoms and nitro;

$R^2$ is hydrogen; aryl of 6 to 12 carbon atoms optionally substituted with one or more substituents selected from straight chain alkyl of 1 to 6 carbon atoms, alkoxy of 1 to 6 carbon atoms, nitro, and halogen; the heterocyclyl moiety is selected from 2- or 3-furyl, 2- or 3-thienyl, and 2-, 3- or 4-pyridyl; phenylalkyl wherein the alkyl moiety is a straight chain alkyl of 1 to 6 carbon atoms and the phenyl moiety is optionally substituted with one or more substituents which are the same or different and are selected from halogen, straight chain alkyl of 1 to 6 carbon atoms, and nitro; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl; the optional double bond — — — is a single bond; or a pharmaceutically acceptable salt thereof.

3. A compound as defined in claim 1 wherein:

n is an integer of 2 to 4;

the moiety

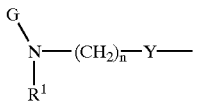

is located at the a or b position of the bicyclic nucleus;

A—B is the diradical —CH$_2$—(CH$_2$)$_m$—;

$R^1$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or two substituents which are the same or different and are selected from halogen, straight chain alkyl of 1 to 6 carbon atoms, and nitro; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl optionally substituted with one or two substituents which are the same or different, and are selected from halogen, straight chain alkyl of 1 to 6 carbon atoms and nitro;

$R^2$ is hydrogen; aryl optionally substituted with one or more substituents selected from straight chain alkyl of 1 to 6 carbon atoms, alkoxy of 1 to 6 carbon atoms, nitro, and halogen; the heterocyclyl moiety is selected from 2- or 3-furyl, 2- or 3-thienyl, and 2-, 3- or 4-pyridyl; phenylalkyl wherein the alkyl moiety is a straight chain alkyl of 1 to 6 carbon atoms and the phenyl moiety is optionally substituted with one or more substituents which are the same or different and are selected from halogen, straight chain alkyl of 1 to 6 carbon atoms, and nitro; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl;

the optional double bond — — — is a single bond;

or a pharmaceutically acceptable salt thereof.

4. A compound as defined in claim 1 wherein:

n is an integer of 2 to 4;

the moiety

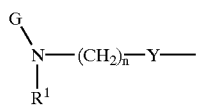

is located at the a or b position of the bicyclic nucleus;

$R^1$ is H;

$R^2$ is H;

$R^5$ is H;

the optional double bond — — — is a single bond;

or a pharmaceutically acceptable salt thereof.

5. A compound as defined in claim 1 wherein:

n is an integer of 2 to 4;

m is an integer of 1;

v is an integer of 0;

the moiety

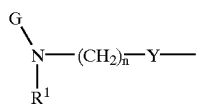

is located at the a or b position of the bicyclic nucleus;

Y is —O—;

$R^1$ is H;

$R^2$ is H;

$R^5$ is H;

the optional double bond — — — is a single bond;

or a pharmaceutically acceptable salt thereof.

6. A compound as defined in claim 1 wherein:

n is an integer of 2 to 4;

the moiety

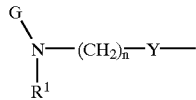

is located at the a or b position of the bicyclic nucleus;
R¹ is H;
R² is H;
R⁵ is H;
G is

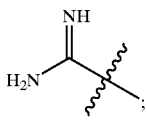

or a pharmaceutically acceptable salt thereof.

7. A compound as defined in claim 1 wherein:

n is an integer of 2 to 4;
the moiety

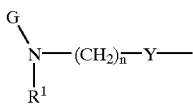

is located at the a or b-position of the bicyclic nucleus;
R¹ is H;
R² is H;
R⁵ is H;
Y is —O—;
G is

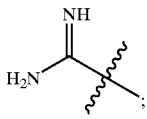

or a pharmaceutically acceptable salt thereof.

8. A compound as defined in claim 1 wherein:

n is an integer of 2 to 4;
the moiety

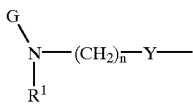

is located at the b-position of the bicyclic nucleus;
R¹ is H;
R² is H;
R⁵ is H;
G is

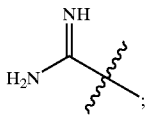

or a pharmaceutically acceptable salt thereof.

9. A compound as defined in claim 1 wherein:

n is an integer of 2 to 4;
the moiety

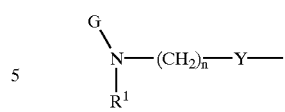

is located at the b-position of the bicyclic nucleus;
G is

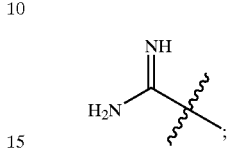

or a pharmaceutically acceptable salt thereof.

10. A compound as defined in claim 1 wherein:

n is an integer of 2 to 4;
A—B is the diradical —CH₂—(CH₂)$_m$—;
R¹ is H;
R² is H;
R⁵ is H;
the moiety

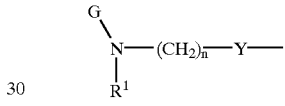

is located at the a or b-position of the bicyclic nucleus;
G is

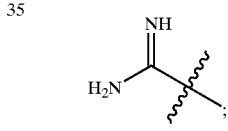

the optional double bond — — — — is a single bond;
or a pharmaceutically acceptable salt thereof.

11. The compound according to claim 1, 4-Methyl-N-{[7-(3-guanidino-propoxy)-2-oxo-1,2,3,4-tetrahydro-quinolin-3-yl]-acetyl}-benzenesulfonamide, or a pharmaceutically acceptable salt thereof.

12. A pharmaceutical composition useful for blocking or inhibiting bone resorption by antagonizing the α$_v$β$_3$ integrin receptor mediated binding of an osteoclast to a bone matrix which comprises administering to a mammal in need thereof an effective amount of a compound of general Formula (II):

Formula (II)

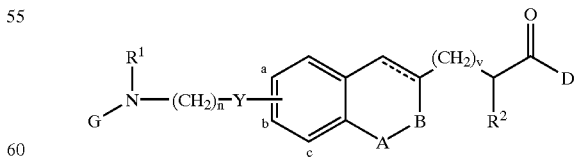

wherein:
— — — represents the presence of an optional double bond;
n is an integer of 2 to 5;
v is an integer of 0 or 1;

A—B is a diradical of the formula:

D is a moiety selected from the group consisting of:

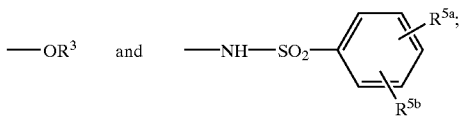

Y is selected from the group consisting of —O—, —CH$_2$—CH$_2$—, —CH=CH—,

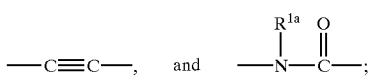

R$^1$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or more substituents which are the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl optionally substituted with one or more substituents which may be the same or different, and are selected from hydroxy, amino, halogen, straight chain alkyl of 1 to 6 carbon atoms, cyano and nitro;

R$^{1a}$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or more substituents which are the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

R$^2$ is hydrogen, —NHR$^1$, or —OR$^1$, aryl of 6 to 12 carbon atoms optionally substituted with one or more substituents selected from straight chain alkyl of 1 to 6 carbon atoms, alkoxy of 1 to 6 carbon atoms, —S-alkyl of 1 to 6 carbon atoms, cyano, nitro, halogen and phenyl; the heterocyclyl moiety is selected from 2- or 3-furyl, 2- or 3-thienyl, and 2-, 3- or 4-pyridyl optionally substituted with one or more substituents which are the same or different, and are selected from hydroxy, amino, halogen, straight chain alkyl of 1 to 6 carbon atoms, cyano and nitro; phenylalkyl wherein the alkyl moiety is a straight chain alkyl of 1 to 6 carbon atoms and the phenyl moiety is optionally substituted with one or more substituents which are the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl optionally substituted with one or more substituents which are the same or different, and are selected from hydroxy, amino, halogen, straight chain alkyl of 1 to 6 carbon atoms, cyano and nitro;

R$^3$ is H, straight chain alkyl of 1 to 6 carbon atoms optionally substituted with a group selected from amino, hydroxyl and carboxyl or branched chain alkyl of 3 to 7 carbon atoms optionally substituted with a group selected from amino, hydroxyl and carboxyl;

G is

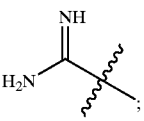

R$^5$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which are the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms and dialkylamino of 1 to 6 carbon atoms;

R$^{5a}$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which are the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

R$^{5b}$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which are the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

with the proviso that Y is not —O—; n is not 3 or 4; R$^1$, R$^2$, R$^3$ and R5 are not H; D is not —OR$^3$;

G is not

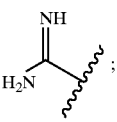

A—B is not

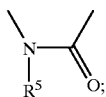

— — — is not a single bond;
a) when v is 0 and substitution is at position a;
with the additional proviso that n is not 2,3 or 4; G is not

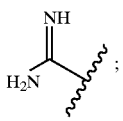

— — — is not a single bond; v is not 1; A—B is not

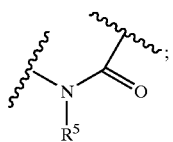

D is not —OR$^3$;
a) when Y is O; R$^1$, R$^2$, R$^3$ and R$^5$ are H; and substitution is at position a;
with the still further proviso that when A—B is the moiety

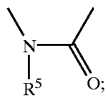

the moiety

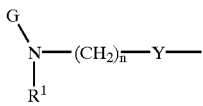

is located at the a,b or c positions of the bicyclic nucleus; or a pharmaceutically acceptable salt thereof together with a pharmaceutically acceptable carrier.

13. A pharmaceutical composition according to claim 12 wherein the disease is osteoporosis.

14. The pharmaceutical composition of claim 12 containing a compound which is selected from the group consisting of:
[7-(4-Guanidino-butoxy)-2-oxo-1,2,3,4-tetrahydro-quinolin-3-yl]-acetic acid trifluoroacetate,
[7-(2-Guanidino-ethoxy)-2-oxo-1,2,3,4-tetrahydro-quinolin-3-yl]-acetic acid Hydrochloride,
[7-(3-Guanidino-propoxy)-2-oxo-1,2,3,4-tetrahydro-quinolin-3-yl]-acetic acid Hydrochloride,
[7-(4-Guanidino-but-1-ynyl)-2-oxo-1,2,3,4-tetrahydro-quinolin-3-yl]-acetic acid Hydrochloride,
[7-(5-Guanidino-pent-1-ynyl)-2-oxo-1,2,3,4-tetrahydro-quinolin-3-yl]-acetic acid Trifluoroacetate,
[7-(4-Guanidino-but-1-enyl)-2-oxo-1,2,3,4-tetrahydro-quinolin-3-yl]-acetic acid Trifluoroacetate,
[7-(5-Guanidino-pent-1-enyl)-2-oxo-1,2,3,4-tetrahydro-quinolin-3-yl]-acetic acid Trifluoroacetate,
[7-(4-Guanidino-butyl)-2-oxo-1,2,3,4-tetrahydro-quinolin-3-yl]-acetic acid Trifluoroacetate,
[7-(5-Guanidino-pentyl)-2-oxo-1,2,3,4-tetrahydro-quinolin-3-yl]-acetic acid Trifluoroacetate,
[1-Ethyl-7-(3-guanidino-propoxy)-2-oxo-1,2-dihydro-quinolin-3-yl]-acetic acid Trifluoroacetate
[1-Benzyl-7-(3-guanidino-propoxy)-2-oxo-1,2-dihydro-quinolin-3-yl]-acetic acid
[1-Ethyl-7-(3-guanidino-propoxy)-2-oxo-1,2,3,4-tetrahydro-quinolin-3-yl]-acetic acid Trifluoroacetate,
[1-Benzyl-7-(3-guanidino-propoxy)-2-oxo-1,2,3,4-tetrahydro-quinolin-3-yl]-acetic acid,
[7-(4-Guanidino-butoxy)-2-oxo-1,2-dihydro-quinolin-3-yl]-acetic acid Hydrochloride,
[7-(2-Guanidino-ethoxy)-2-oxo-1,2-dihydro-quinolin-3-yl]-acetic acid,
[7-(3-Guanidino-propoxy)-2-oxo-1,2-dihydro-quinolin-3-yl]-acetic acid Trifluoroacetate,
[7-(2-Guanidino-ethylcarbamoyl)-2-oxo-1,2,3,4-tetrahydro-quinolin-3-yl]-acetic acid Hydrochloride,
[7-(3-Guanidino-propylcarbamoyl)-2-oxo-1,2,3,4-tetrahydro-quinolin-3-yl]-acetic acid Hydrochloride,
[6-(3-Guanidino-propoxy)-2-oxo-1,2,3,4-tetrahydro-quinolin-3-yl]-acetic acid,
[6-(4-Guanidino-butoxy)-2-oxo-1,2,3,4-tetrahydro-quinolin-3-yl]-acetic acid trifluoroacetate,
3-[7-(2-Guanidino-ethoxy)-2-oxo-1,2,3,4-tetrahydro-quinolin-3-yl]-propionic acid,
3-[7-(3-Guanidino-propoxy)-2-oxo-1,2,3,4-tetrahydro-quinolin-3-yl]-propionic acid,
[8-(3-Guanidino-propoxy)-2-oxo-1,2,3,4-tetrahydro-quinolin-3-yl]-acetic acid,
[8-(4-Guanidino-butoxy)-2-oxo-1,2,3,4-tetrahydro-quinolin-3-yl]-acetic acid,
[1-Benzyl-7-(3-guanidino-propoxy)-2-oxo-1,2,3,4-tetrahydro-quinolin-3-yl]-acetic acid Trifluoroacetate,
3-[7-(2-Guanidino-ethoxy)-2-oxo-1,2-dihydro-quinolin-3-yl]propionic acid nitric acid salt,
4-Methyl-N-{[7-(3-guanidino-propoxy)-2-oxo-1,2,3,4-tetrahydro-quinolin-3-yl]-acetyl}-benzenesulfonamide, and
[8-(5-Guanidino-pentoxy)-2-oxo-1,2,3,4-tetrahydro-quinolin-3-yl]-acetic acid
or a pharmaceutically acceptable salt thereof together with a pharmaceutically acceptable carrier.

15. A method of blocking or inhibiting bone resorption by antagonizing the $\alpha_v\beta_3$ integrin receptor mediated binding of an osteoclast to a bone matrix which comprises administering to a mammal in need thereof an effective amount of a compound of Formula (II):

Formula (II)

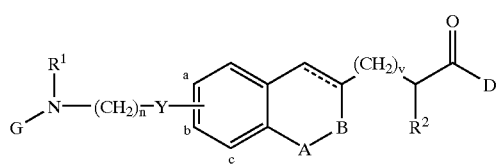

wherein:

— — — represents the presence of an optional double bond;
n is an integer of 2 to 5;
v is an integer of 0 or 1;

A—B is a diradical of the formula:

D is a moiety selected from the group consisting of:

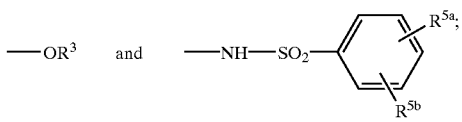

Y is selected from the group consisting of —O—, —CH₂—CH₂—, —CH=CH—,

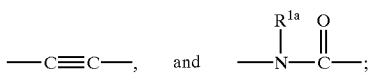

$R^1$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or more substituents which are the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl optionally substituted with one or more substituents which may be the same or different, and are selected from hydroxy, amino, halogen, straight chain alkyl of 1 to 6 carbon atoms, cyano and nitro;

$R^{1a}$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or more substituents which are the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

$R^2$ is hydrogen, —NHR¹, or —OR¹, aryl of 6 to 12 carbon atoms optionally substituted with one or more substituents selected from straight chain alkyl of 1 to 6 carbon atoms, alkoxy of 1 to 6 carbon atoms, —S-alkyl of 1 to 6 carbon atoms, cyano, nitro, halogen and phenyl; the heterocyclyl moiety is selected from 2- or 3-furyl, 2- or 3-thienyl, and 2-, 3- or 4-pyridyl optionally substituted with one or more substituents which are the same or different, and are selected from hydroxy, amino, halogen, straight chain alkyl of 1 to 6 carbon atoms, cyano and nitro; phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl optionally substituted with one or more substituents which are the same or different, and are selected from hydroxy, amino, halogen, straight chain alkyl of 1 to 6 carbon atoms, cyano and nitro;

$R^3$ is H, straight chain alkyl of 1 to 6 carbon atoms optionally substituted with a group selected from amino, hydroxyl and carboxyl or branched chain alkyl of 3 to 7 carbon atoms optionally substituted with a group selected from amino, hydroxyl and carboxyl;

$R^5$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which are the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms and dialkylamino of 1 to 6 carbon atoms;

$R^{5a}$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which are the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

$R^{5b}$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which are the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

with the proviso that Y is not —O—; n is not 3 or 4; $R^1$, $R^2$, $R^3$ and $R^5$ are not H; D is not —OR³;

G is not

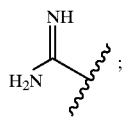

A—B is not

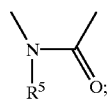

— — — is not a single bond;

a) when v is 0 and substitution is at position a;

with the additional proviso that n is not 2,3 or 4; G is not

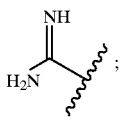

———— is not a single bond; v is not 1; A—B is not

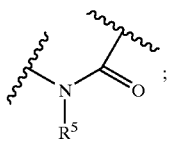

D is not —OR³;
a) when Y is O; R¹, R², R³ and R⁵ are H; and substitution is at position a;
with the still further proviso that when A—B is the moiety

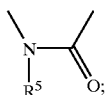

the moiety

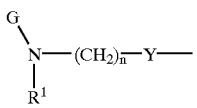

is located at the a,b or c positions of the bicyclic nucleus; or a pharmaceutically acceptable salt thereof.

16. The method of claim 15 wherein the bone resorption disease is osteoporosis.

17. The method of claim 15 in which a compound selected from the group consisting of:
[7-(4-Guanidino-butoxy)-2-oxo-1,2,3,4-tetrahydro-quinolin-3-yl]-acetic acid trifluoroacetate,
[7-(2-Guanidino-ethoxy)-2-oxo-1,2,3,4-tetrahydro-quinolin-3-yl]-acetic acid Hydrochloride,
[7-(3-Guanidino-propoxy)-2-oxo-1,2,3,4-tetrahydro-quinolin-3-yl]-acetic acid Hydrochloride,
[6-(4-Guanidino-butoxy)-2-oxo-1,2,3,4-tetrahydro-quinolin-3-yl]-acetic acid trifluoroacetate,
[7-(4-Guanidino-but-1-ynyl)-2-oxo-1,2,3,4-tetrahydro-quinolin-3-yl]-acetic acid Hydrochloride,
[7-(5-Guanidino-pent-1-ynyl)-2-oxo-1,2,3,4-tetrahydro-quinolin-3-yl]-acetic acid Trifluoroacetate,
[7-(4-Guanidino-but-1-enyl)-2-oxo-1,2,3,4-tetrahydro-quinolin-3-yl]-acetic acid Trifluoroacetate,
[7-(5-Guanidino-pent-1-enyl)-2-oxo-1,2,3,4-tetrahydro-quinolin-3-yl]-acetic acid Trifluoroacetate,
[7-(4-Guanidino-butyl)-2-oxo-1,2,3,4-tetrahydro-quinolin-3-yl]-acetic acid Trifluoroacetate,
[7-(5-Guanidino-pentyl)-2-oxo-1,2,3,4-tetrahydro-quinolin-3-yl]-acetic acid Trifluoroacetate,
[1-Ethyl-7-(3-guanidino-propoxy)-2-oxo-1,2-dihydro-quinolin-3-yl]-acetic acid Trifluoroacetate
[1-Benzyl-7-(3-guanidino-propoxy)-2-oxo-1,2-dihydro-quinolin-3-yl]-acetic acid
[1-Ethyl-7-(3-guanidino-propoxy)-2-oxo-1,2,3,4-tetrahydro-quinolin-3-yl]-acetic acid Trifluoroacetate,
[1-Benzyl-7-(3-guanidino-propoxy)-2-oxo-1,2,3,4-tetrahydro-quinolin-3-yl]-acetic acid,
[7-(4-Guanidino-butoxy)-2-oxo-1,2-dihydro-quinolin-3-yl]-acetic acid Hydrochloride,
[7-(2-Guanidino-ethoxy)-2-oxo-1,2-dihydro-quinolin-3-yl]-acetic acid,
[7-(3-Guanidino-propoxy)-2-oxo-1,2-dihydro-quinolin-3-yl]-acetic acid Trifluoroacetate,
[7-(2-Guanidino-ethylcarbamoyl)-2-oxo-1,2,3,4-tetrahydro-quinolin-3-yl]-acetic acid Hydrochloride,
[7-(3-Guanidino-propylcarbamoyl)-2-oxo-1,2,3,4-tetrahydro-quinolin-3-yl]-acetic acid Hydrochloride,
[6-(3-Guanidino-propoxy)-2-oxo-1,2,3,4-tetrahydro-quinolin-3-yl]-acetic acid,
3-[7-(2-Guanidino-ethoxy)-2-oxo-1,2,3,4-tetrahydro-quinolin-3-yl]-propionic acid,
3-[7-(3-Guanidino-propoxy)-2-oxo-1,2,3,4-tetrahydro-quinolin-3-yl]-propionic acid,
[8-(3-Guanidino-propoxy)-2-oxo-1,2,3,4-tetrahydro-quinolin-3-yl]-acetic acid,
[8-(4-Guanidino-butoxy)-2-oxo-1,2,3,4-tetrahydro-quinolin-3-yl]-acetic acid,
[1-Benzyl-7-(3-guanidino-propoxy)-2-oxo-1,2-dihydro-quinolin-3-yl]-acetic acid Trifluoroacetate,
3-[7-(2-Guanidino-ethoxy)-2-oxo-1,2-dihydro-quinolin-3-yl]propionic acid nitric acid salt,
4-Methyl-N-{[7-(3-guanidino-propoxy)-2-oxo-1,2,3,4-tetrahydro-quinolin-3-yl]-acetyl}-benzenesulfonamide, and
[8-(5-Guanidino-pentoxy)-2-oxo-1,2,3,4-tetrahydro-quinolin-3-yl]-acetic acid or a pharmaceutically acceptable salt thereof is administered.

18. A method of treating diseases having bone resorption of mineralized tissue and by bone loss, resulting from an imbalance between bone resorption and bone formation selected from the group consisting of osteoporosis, hypercalcemia of malignancy, osteopenia due to bone metastases, periodontal disease, hyperparathyroidism, periarticular erosions in rheumatoid arthritis, Paget's disease, immobilization-induced osteopenia and the result of glucocorticoid treatment, which comprises administering to a mammal in need thereof an effective amount of a compound of Formula (II):

Formula (II)

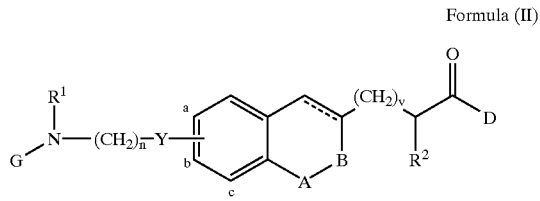

wherein:

———— represents the presence of an optional double bond;
n is an integer of 2 to 5;
v is an integer of 0 or 1;
A—B is a diradical of the formula:

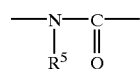

D is a moiety selected from the group consisting of:

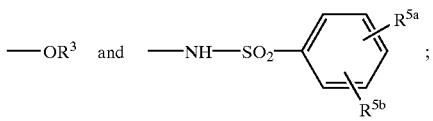 ;

Y is selected from the group consisting of —O—, —CH$_2$—CH$_2$—, —CH=CH—,

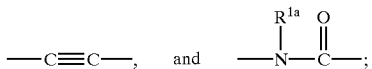 ;

R$^1$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or more substituents which are the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl optionally substituted with one or more substituents which may be the same or different, and are selected from hydroxy, amino, halogen, straight chain alkyl of 1 to 6 carbon atoms, cyano and nitro;

R$^{1a}$ is hydrogen or straight chain alkyl of 1 to 6 carbon atoms; phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

R$^2$ is hydrogen, —NHR$^1$, or —OR$^1$, aryl of 6 to 12 carbon atoms optionally substituted with one or more substituents selected from straight chain alkyl of 1 to 6 carbon atoms, alkoxy of 1 to 6 carbon atoms, —S-alkyl of 1 to 6 carbon atoms, cyano, nitro, halogen and phenyl; the heterocyclyl moiety is selected from 2- or 3-furyl, 2- or 3-thienyl, and 2-, 3- or 4-pyridyl optionally substituted with one or more substituents which may be the same or different, and are selected from hydroxy, amino, halogen, straight chain alkyl of 1 to 6 carbon atoms, cyano and nitro; phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms; heterocyclylalkyl, wherein the alkyl moiety is a straight chain alkyl of 1 to 6 carbon atoms and the heterocyclyl moiety is selected from 2- or 3-furyl, 2- or 3-thienyl, and 2-, 3- or 4-pyridyl optionally substituted with one or more substituents which may be the same or different, and are selected from hydroxy, amino, halogen, straight chain alkyl of 1 to 6 carbon atoms, cyano and nitro;

R$^3$ is H, straight chain alkyl of 1 to 6 carbon atoms optionally substituted with a group selected from amino, hydroxyl and carboxyl or branched chain alkyl of 3 to 7 carbon atoms optionally substituted with a group selected from amino, hydroxyl and carboxyl;

G is

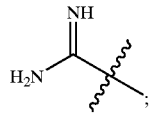 ;

R$^5$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms and dialkylamino of 1 to 6 carbon atoms;

R$^{5a}$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

R$^{5b}$ is hydrogen, straight chain alkyl of 1 to 6 carbon atoms, or phenylalkyl wherein the alkyl moiety is a straight chain alkyl of 1 to 6 carbon atoms and the phenyl moiety is optionally substituted with one or more substituents which may be the same or different and are selected from hydroxy, amino, halogen, straight chain alkyl of 1 to 6 carbon atoms, branched chain alkyl of 3 to 7 carbon atoms, cyano, nitro, alkylamino of 1 to 6 carbon atoms, and dialkylamino of 1 to 6 carbon atoms;

with the proviso that Y is not —O—; n is not 3 or 4; R$^1$, R$^2$, R$^3$ and R$^5$ are not H; D is not —OR$^3$;

G is not

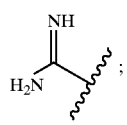 ;

A—B is not

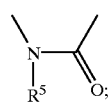

— — — is not a single bond;

a) when v is 0 and substitution is at position a;

with the additional proviso that n is not 2,3 or 4; G is not

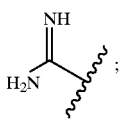

— — — is not a single bond; v is not 1; A—B is not

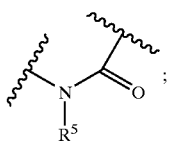

D is not —OR$^3$;
a) when Y is O; R$^1$, R$^2$, R$^3$ and R$^5$ are H; and substitution is at position a;
with the still further proviso that when A—B is the moiety

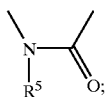

the moiety

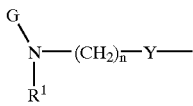

is located at the a,b or c positions of the bicyclic nucleus; or a pharmaceutically acceptable salt thereof.

19. The method of claim 18 wherein the bone loss, resulting from an imbalance between bone resorption and bone formation disease is osteoporosis.

20. The method of claim 18 in which a compound selected from the group consisting of:
[7-(4-Guanidino-butoxy)-2-oxo-1,2,3,4-tetrahydro-quinolin-3-yl]-acetic acid trifluoroacetate,
[7-(2-Guanidino-ethoxy)-2-oxo-1,2,3,4-tetrahydro-quinolin-3-yl]-acetic acid Hydrochloride,
[7-(3-Guanidino-propoxy)-2-oxo-1,2,3,4-tetrahydro-quinolin-3-yl]-acetic acid Hydrochloride,
[6-(4-Guanidino-butoxy)-2-oxo-1,2,3,4-tetrahydro-quinolin-3-yl]-acetic acid trifluoroacetate,
[7-(4-Guanidino-but-1-ynyl)-2-oxo-1,2,3,4-tetrahydro-quinolin-3-yl]-acetic acid Hydrochloride,
[7-(5-Guanidino-pent-1-ynyl)-2-oxo-1,2,3,4-tetrahydro-quinolin-3-yl]-acetic acid Trifluoroacetate,
[7-(4-Guanidino-but-1-enyl)-2-oxo-1,2,3,4-tetrahydro-quinolin-3-yl]-acetic acid Trifluoroacetate,
[7-(5-Guanidino-pent-1-enyl)-2-oxo-1,2,3,4-tetrahydro-quinolin-3-yl]-acetic acid Trifluoroacetate,
[7-(4-Guanidino-butyl)-2-oxo-1,2,3,4-tetrahydro-quinolin-3-yl]-acetic acid Trifluoroacetate,
[7-(5-Guanidino-pentyl)-2-oxo-1,2,3,4-tetrahydro-quinolin-3-yl]-acetic acid Trifluoroacetate,
[1-Ethyl-7-(3-guanidino-propoxy)-2-oxo-1,2-dihydro-quinolin-3-yl]-acetic acid Trifluoroacetate
[1-Benzyl-7-(3-guanidino-propoxy)-2-oxo-1,2-dihydro-quinolin-3-yl]-acetic acid
[1-Ethyl-7-(3-guanidino-propoxy)-2-oxo-1,2,3,4-tetrahydro-quinolin-3-yl]-acetic acid Trifluoroacetate,
[1-Benzyl-7-(3-guanidino-propoxy)-2-oxo-1,2,3,4-tetrahydro-quinolin-3-yl]-acetic acid,
[7-(4-Guanidino-butoxy)-2-oxo-1,2-dihydro-quinolin-3-yl]-acetic acid Hydrochloride,
[7-(2-Guanidino-ethoxy)-2-oxo-1,2-dihydro-quinolin-3-yl]-acetic acid,
[7-(3-Guanidino-propoxy)-2-oxo-1,2-dihydro-quinolin-3-yl]-acetic acid Trifluoroacetate,
[7-(2-Guanidino-ethylcarbamoyl)-2-oxo-1,2,3,4-tetrahydro-quinolin-3-yl]-acetic acid Hydrochloride,
[7-(3-Guanidino-propylcarbamoyl)-2-oxo-1,2,3,4-tetrahydro-quinolin-3-yl]-acetic acid Hydrochloride,
[6-(3-Guanidino-propoxy)-2-oxo-1,2,3,4-tetrahydro-quinolin-3-yl]-acetic acid,
3-[7-(2-Guanidino-ethoxy)-2-oxo-1,2,3,4-tetrahydro-quinolin-3-yl]-propionic acid,
3-[7-(3-Guanidino-propoxy)-2-oxo-1,2,3,4-tetrahydro-quinolin-3-yl]-propionic acid,
[8-(3-Guanidino-propoxy)-2-oxo-1,2,3,4-tetrahydro-quinolin-3-yl]-acetic acid,
[8-(4-Guanidino-butoxy)-2-oxo-1,2,3,4-tetrahydro-quinolin-3-yl]-acetic acid,
[1-Benzyl-7-(3-guanidino-propoxy)-2-oxo-1,2-dihydro-quinolin-3-yl]-acetic acid Trifluoroacetate,
3-[7-(2-Guanidino-ethoxy)-2-oxo-1,2-dihydro-quinolin-3-yl]propionic acid nitric acid salt,
4-Methyl-N-{[7-(3-guanidino-propoxy)-2-oxo-1,2,3,4-tetrahydro-quinolin-3-yl]-acetyl}-benzenesulfonamide, and
[8-(5-Guanidino-pentoxy)-2-oxo-1,2,3,4-tetrahydro-quinolin-3-yl]-acetic acid
or a pharmaceutically acceptable salt thereof is administered.

* * * * *